(12) United States Patent
Rawson et al.

(10) Patent No.: US 7,749,994 B2
(45) Date of Patent: Jul. 6, 2010

(54) PENTACYCLIC KINASE INHIBITORS

(75) Inventors: Thomas E. Rawson, Mountain View, CA (US); Brian Safina, Redwood City, CA (US); Jennafer Dotson, Belmont, CA (US); Aihe Zhou, San Jose, CA (US); Ignacio Aliagas-Martin, San Francisco, CA (US); Jason Halladay, Los Gatos, CA (US); Jun Liang, Palo Alto, CA (US); Matthias Rueth, Penzberg (DE); Bing-Yan Zhu, Palo Alto, CA (US); Frederick Brookfield, Abington (GB); Michael Prime, Abington (GB); Birong Zhang, Union City, CA (US); Jun M. Li, Burlingame, CA (US)

(73) Assignees: Genentech, Inc., South San Francisco, CA (US); Hoffman-LaRoche, Inc. (US Only), Nutley, NJ (US); F. Hoffman-LaRoche, AG (EX-US), Basel (CH)

( * ) Notice: Subject to any disclaimer, the term of this patent is extended or adjusted under 35 U.S.C. 154(b) by 845 days.

(21) Appl. No.: 11/503,405

(22) Filed: Aug. 14, 2006

(65) Prior Publication Data

US 2007/0037791 A1 Feb. 15, 2007

Related U.S. Application Data

(60) Provisional application No. 60/707,902, filed on Aug. 12, 2005.

(51) Int. Cl.
*A61K 31/55* (2006.01)
*A61K 31/538* (2006.01)
*A61K 31/424* (2006.01)
*A61K 31/4188* (2006.01)
*C07D 498/22* (2006.01)

(52) U.S. Cl. .............. 514/215; 514/229.5; 514/366; 514/375; 514/393; 540/577; 544/99; 544/332; 548/148; 548/218; 548/301.7

(58) Field of Classification Search .............. None
See application file for complete search history.

(56) References Cited

FOREIGN PATENT DOCUMENTS

WO WO 2005/005414 A2 1/2005
WO WO 2006/133885 A1 12/2006

OTHER PUBLICATIONS

Sausville et al ( Cancer Research, 2006, vol. 66, pp. 3351-3354).*

* cited by examiner

*Primary Examiner*—Kamal A Saeed
(74) *Attorney, Agent, or Firm*—Millen, White, Zelano & Branigan, P.C.

(57) ABSTRACT

The invention provides novel kinase inhibitors that are useful as therapeutic agents for example in the treatment malignancies where the compounds have the general formula I

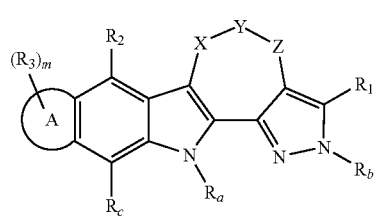

wherein A, X, Y, Z, Ra, Rb, Rc, $R_1$, $R_2$, $R_3$ and m are defined herein.

17 Claims, No Drawings

PENTACYCLIC KINASE INHIBITORS

This application claims priority to provisional U.S. patent application No. 60/707,902 filed Aug. 12, 2005, the entirety of which is incorporated herein by reference.

FIELD OF THE INVENTION

The present invention relates to organic compounds useful for therapy and/or prophylaxis in a mammal, and in particular to inhibitors of kinases useful for treating cancers.

BACKGROUND OF THE INVENTION

An important class of enzymes that has been the subject of extensive study is protein kinases which are involved in a majority of cellular signaling pathways affecting cell proliferation, migration, differentiation, and metabolism. Kinases function by removing a phosphate group from ATP and phosphorylating hydroxyl groups on serine, threonine and tyrosine amino acid residues of proteins in response to a stimulus such as environmental and chemical stress signals (e.g. osmotic shock, heat shock, ultraviolet radiation, bacterial endotoxin), cytokines (e.g., interleukin-1 and tumor necrosis factor alpha), and growth factors (e.g. granulocyte macrophage-colony-stimulating factor, transforming growth factor, fibroblast growth factor). Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find inhibitors of protein kinase that are effective as therapeutic agents.

Aurora kinase is a family serine/threonine kinases that are essential for cell proliferation. The three known mammalian family members, Aurora-A (also referred to as Aurora-2, Aur-2, STK-15), Aurora-B (also referred to as Aurora-1, Aur-1 and STK-12) and Aurora-C (also referred to as STK-13), are highly homologous proteins responsible for chromosome segregation, mitotic spindle function and cytokinesis. (Bischoff, J. R. & Plowman, G. D., Trends in Cell Biology 9:454, 1999; Giet R. and Prigent, C. Journal of Cell Science 112:3591, 1999; Nigg, E. A., Nat. Rev. Mol. Cell Biol. 2:21, 2001; Adams, R. R. Carmena, M. and Earnshaw, W. C., Trends in Cell Biology 11:49, 2001). Aurora kinase expression is low or undetectable in resting cells, with expression and activity peaking during the G2 and mitotic phases in cycling cells. In mammalian cells, proposed substrates for Aurora kinase include histone H3, a protein involved in chromosome condensation, and CENP-A, myosin II regulatory light chain, I protein phosphatase 1, TPX2, all of which are required for cell division. Aurora-A plays a role in the cell cycle by controlling the accurate segregation of chromosomes during mitosis and misregulation thereof can lead to cellular proliferation and other abnormalities.

Since its discovery in 1997 the mammalian Aurora kinase family has been closely linked to tumorigenesis due to its effect on genetic stability. Cells with elevated levels of this kinase contain multiple centrosomes and multipolar spindles, and rapidly become aneuploid. Indeed, a correlation between amplification of the Aurora-A locus and chromosomal instability in mammary and gastric tumours has been observed. (Miyoshi, Y., Iwao, K., Egawa, C., and Noguchi, S. Int. J. Cancer 92:370, 2001; Sakakura, C. et al. British Journal of Cancer 84:824, 2001). Moreover, Aurora-A overexpression has been shown to transforms rodent fibroblasts (Bischoff, J. R., et al. EMBO J. 17:3052, 1998).

The Aurora kinases have been reported to be overexpressed in a wide range of human tumours. Elevated expression of Aurora-A has been detected in over 50% of colorectal, ovarian and gastric cancers, and in 94% of invasive duct adenocarcinomas of the breast. Amplification and/or overexpression of Aurora-A have also been reported in renal, cervical, neuroblastoma, melanoma, lymphoma, bladder, pancreatic and prostate tumours and is associated with aggressive clinical behaviour. For example, amplification of the aurora-A locus (20q13) correlates with poor prognosis for patients with node-negative breast cancer (Isola, J. J., et al. American Journal of Pathology 147:905, 1995). Aurora-B is highly expressed in multiple human tumour cell lines, including colon, breast, lung, melanoma, kidney, ovary, pancreas, CNS, gastric tract and leukemias (Tatsuka et al 1998 58, 4811-4816; Katayama et al., Gene 244:1). Also, levels of Aurora-B enzyme have been shown to increase as a function of Duke's stage in primary colorectal cancers (Katayama, H. et al. Journal of the National Cancer Institute 91:1160, 1999). Aurora-C, which is normally only found in testis, is also overexpressed in a high percentage of primary colorectal cancers and in a variety of tumour cell lines including cervical adenocarinoma and breast carcinoma cells (Kimura, M., et al., Journal of Biological Chemistry 274:7334, 1999; Takahashi, T., et al., Jpn. J. Cancer Res. 91:1007-1014, 2000).

Based on the known function of the Aurora kinases, inhibition of their activity will disrupt mitosis leading to cell cycle arrest halting cellular proliferation and therefore will slow tumour growth in a wide range of cancers.

SUMMARY OF THE INVENTION

In one aspect of the present invention there is provided novel inhibitors of Auora kinases having the general formula (I)

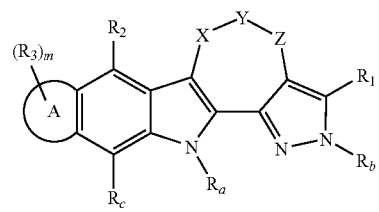

wherein ring A is a 5, 6 or 7 member ring carbocycle or heterocycle;

X, Y and Z are independently absent, $CR_4R_{4'}$, $NR_5$, S, SO, $SO_2$ or O; wherein at least one of X, Y and Z is not absent; or X and Y together are $CR_4=CR_4$; or Y and Z together are $CR_4=CR_4$;

$R_a$ and $R_b$ are independently H or a protecting group;

$R_c$ is H, hydroxyl, halogen, alkyl, haloalkyl;

$R_1$ is H, hydroxyl, halogen, amino, or is alkyl, acyl, alkoxy or alkylthio optionally substituted with hydroxyl, halogen, carbonyl, thiocarbonyl, amino, carboxyl and alkoxy;

$R_2$ is H, halogen, hydroxyl, mercapto, amino, alkyl, a carbocycle or a heterocycle, wherein said alkyl, carbocycle and heterocycle are optionally substituted with halogen, hydroxyl, mercapto, amino, carboxyl, alkyl, a carbocycle or a heterocycle and wherein one or more $CH_2$ groups of an alkyl group is optionally replaced with —O—, —S—, —S(O)—, —S(O)$_2$—, —N(R$_5$)—, —C(O)—, —C(S)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—;

R$_3$ is hydroxyl, mercapto, halogen, amino, nitro, cyano, carbonyl, thiocarbonyl, alkyl, a carbocycle or a heterocycle, or two R$_3$ groups together form a carbocycle or a heterocycle; wherein said alkyl, carbocycles and heterocycles are optionally substituted with halogen, hydroxyl, mercapto, carboxyl, carbonyl, thiocarbonyl, amino, nitro, cyano, alkyl, haloalkyl, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—;

R$_4$ and R$_4$' are independently H, hydroxyl, halogen, amino, carbonyl, thiocarbonyl, alkyl, a carbocycle or a heterocycle, or R$_4$ and R$_4$, together form a carbocycle or heterocycle, wherein said alkyl, carbocycles and heterocycles are optionally substituted with halogen, hydroxyl, carboxyl, amino, alkyl, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—;

R$_5$ is H, alkyl, a carbocycle or a heterocycle wherein one or more CH$_2$ or CH groups of said alkyl is optionally replaced with —O—, —S—, —S(O)—, —S(O)$_2$—, —N—H—, or —C(O)—; and said alkyl, carbocycle and heterocycle is optionally substituted with hydroxyl, alkoxy, acyl, halogen, mercapto, carbonyl, carboxyl, acyl, halo-substituted alkyl, amino, cyano nitro, amidino, guanidino an optionally substituted carbocycle or an optionally substituted heterocycle;

m is 0 to 10;

and salts and solvates thereof.

In another aspect of the invention, there are provided compositions comprising compounds of formula I and a carrier, diluent or excipient.

In another aspect of the invention, there is provided a method for inhibiting the signalling of Aurora kinases in a cell comprising contacting said Aurora protein with a compound of formula I.

In another aspect of the invention, there is provided a method for treating a disease or condition in a mammal associated with the signalling of Aurora kinasaes, comprising administering to said mammal an effective amount of a compound of formula I.

DETAILED DESCRIPTION OF THE PREFERRED EMBODIMENTS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion may be a saturated hydrocarbon chain, however also includes unsaturated hydrocarbon chains such as "alkenylamino" and "alkynylamino". Examples of particular alkyl groups are methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "C$_1$-C$_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one, for example two, three or four substituents which may be the same or different. Examples of substituents are, unless otherwise defined, halogen, amino, hydroxyl, protected hydroxyl, mercapto, carboxyl, alkoxy, nitro, cyano, amidino, guanidino, urea, sulfonyl, sulfinyl, aminosulfonyl, alkylsulfonylamino, arylsulfonylamino, aminocarbonyl, acylamino, alkoxy, acyl, acyloxy, a carbocycle, a heterocycle. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Substituted alkyls include substituted methyls e.g. a methyl group substituted by the same substituents as the "substituted C$_n$-C$_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" means the group —C(NH)—NHR wherein R is H, alkyl (e.g. methyl, ethyl, propyl), a carbocycle (e.g. cyclohexyl, phenyl), a heterocycle (e.g. piperidinyl, piperizinyl, pyridinyl) or aralkyl (e.g. benzyl). A particular amidine is the group —NH—C(NH)—NH$_2$.

"Amino" means primary (i.e. —NH$_2$), secondary (i.e. —NRH) and tertiary (i.e. —NRR) amines wherein R is H, alkyl (e.g. methyl, ethyl, propyl), a carbocycle (e.g. cyclohexyl, phenyl), a heterocycle (e.g. piperidinyl, piperizinyl, pyridinyl) or aralkyl (e.g. benzyl) or two R groups together with the nitrogen atom from which they depend form a heterocycle. Particular secondary and tertiary amines are alkylamine, dialkylamine, arylamine, diarylamine, aralkylamine and diaralkylamine wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and disopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Particular amino protecting groups are Boc, Fmoc and Cbz. Further examples of these groups are found in T. W. Greene and P. G. M. Wuts, "Protective Groups in Organic Synthesis", 2$^{nd}$ ed., John Wiley & Sons, Inc., New York, N.Y., 1991, chapter 7; E.

Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Particular aryl groups are phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]). A particular aryl is phenyl. Substituted phenyl or substituted aryl denotes a phenyl group or aryl group substituted with one, two, three, four or five, for example 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxyl, protected carboxyl, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonyl-aminoalkyl, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or protected carboxyphenyl group such as 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl) phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetra-substituted phenyl groups where the substituents are different such as 3-methoxy-4-benzyloxy-5-methyl-6-phenyl sulfonylamino. Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl) benzyloxy-6-methyl sulfonyl aminophenyl groups. Fused aryl rings may also be substituted with any, for example 1, 2 or 3, of the substituents specified herein in the same manner as substituted alkyl groups.

"Carbamoyl" means an aminocarbonyl containing substituent represented by the formula —C(O)N(R)$_2$ in which R is H, hydroxyl, alkoxy, alkyl, a carbocycle, a heterocycle, carbocycle-substituted alkyl or alkoxy, or heterocycle-substituted alkyl or alkoxy wherein the alkyl, alkoxy, carbocycle and heterocycle are as herein defined. Alternatively, two R groups together with the nitrogen atom from which they depend may form a heterocycle. Carbamoyl groups include alkylaminocarbonyl (e.g. ethylaminocarbonyl, Et-NH—CO—), arylaminocarbonyl (e.g. phenylaminocarbonyl), aralkylaminocarbonyl (e.g. benzoylaminocarbonyl) a heterocycleaminocarbonyl (e.g. piperizinylaminocarbonyl), and in particular a heteroarylaminocarbonyl (e.g. pyridylaminocarbonyl).

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms, for example 3 to 7 carbon atoms, which may be saturated or unsaturated, aromatic or non-aromatic. Particular saturated carbocyclic groups are cyclopropyl, cyclobutyl, cyclopentyl and cyclohexyl groups. A particular saturated carbocycle is cyclopropyl. Another particular saturated carbocycle is cyclohexyl. Particular unsaturated carbocycles are aromatic e.g. aryl groups as previously defined, for example phenyl. The terms "substituted carbocyclyl", "carbocycle" and "carbocyclo" mean these groups substituted by the same substituents as the "substituted alkyl" group.

"Carboxy-protecting group", also referred to as a "carboxyl-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as LiAlH$_4$. (Such harsh removal conditions are also to be avoided when removing amino-protecting groups and hydroxy-protecting groups, discussed below.) Particular carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", 2$^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" denotes the group —NH—C(NH)—NHR wherein R is H, alkyl (e.g. methyl, ethyl, propyl), a carbocycle (e.g. cyclohexyl, phenyl), a heterocycle (e.g. piperidinyl, piperizinyl, pyridinyl) or aralkyl (e.g. benzyl). A particular guanidine is the group —NH—C(NH)—NH$_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", 2$^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen), for example 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, SO$_2$), and any nitrogen heteroatom may optionally be quaternized. Particular non-aromatic heterocycles are morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Substituents for "optionally substituted heterocycles", and further examples of the 5- and 6-membered ring systems discussed above can be found in W. Druckheimer et al., U.S. Pat. No. 4,278,793. In a particular embodiment, such optionally substituted heterocycle groups are substituted with hydroxyl, alkyl, alkoxy, acyl, halogen, mercapto, carbonyl, carboxyl, acyl, halo-substituted alkyl, amino, cyano, nitro, amidino and guanidino. It will be understood that by "optionally substituted" is meant that the heterocycle may be substituted with one or more of the same or different substituents specified. Similarly other groups defined herein that are "optionally substituted" may be substituted with one or more of the specified substituents that may be the same or different. Similarly, a group substituted with a substituents referred to in the alternative (e.g. a group substituted with (or by) substituents x, y or z) means the group may be substituted with one or more of the same or different substituent).

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and in a particular embodiment at least one heteroatom is nitrogen (*Lang's Handbook of Chemistry*, supra). Included in the definition are any bicyclic groups where any of the above heteroaryl rings are fused to a benzene ring. Particular heteroaryls incorporate a nitrogen or oxygen heteroatom. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particular "heteroaryl" is: 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxoas-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl. Heteroaryl groups are optionally substituted as described for heterocycles.

"Inhibitor" means a compound which reduces or prevents the phosphorylation of Aurora kinases or which reduces or prevents the signalling of Aurora kinase. Alternatively, "inhibitor" means a compound which arrests cells in the G2 phase of the cell cycle.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

"Sulfinyl" means a —SO—R group wherein R is alkyl, carbocycle, heterocycle, carbocycloalkyl or heterocycloalkyl. Particular sulfinyl groups are alkylsulfinyl (i.e. —SO-alkyl), for example methylsulfinyl; arylsulfinyl (i.e. —SO-aryl) for example phenylsulfinyl; aralkylsulfinyl, for example benzylsulfinyl.

"Sulfonyl" means a —SO$_2$—R group wherein R is alkyl, carbocycle, heterocycle, carbocycloalkyl or heterocycloalkyl. Particular sulfonyl groups are alkylsulfonyl (i.e. —SO$_2$-alkyl), for example methylsulfonyl; arylsulfonyl, for example phenylsulfonyl; aralkylsulfonyl, for example benzylsulfonyl.

The present invention provides novel compounds having the general formula I:

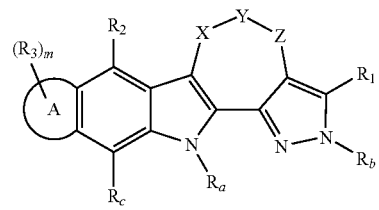

wherein ring A, and X, Y, Z, $R_a$, $R_b$, $R_1$, $R_2$, $R_3$, m and n are as described herein.

Ring A is a 5, 6 or 7 member ring carbocycle or heterocycle which is substituted with 0 to 10 $R_3$ substituents. It will be understood that substitutions on ring A and any other group herein are as permitted by valency. In a particular embodiment ring A is a 5-7 member carbocycle. In a particular embodiment ring A is a 5-7 member heterocycle. In a particular embodiment the ring A heterocycle contains 1 to 4 heteroatoms selected from N, O, S, SO and SO$_2$. In an embodiment ring A is substituted with 0 to 5 $R_3$ substituents. In an embodiment ring A is substituted with 1 to 3 $R_3$ substituents. In a particular embodiment ring A is a nitrogen containing 5-member ring. In a particular embodiment ring A is a pyrrolidine, oxazolidine, dioxolane, dioxane, imidazolidine, pyrrazole, thiazole, thiazolidine, isothiazole or isothiazolidine ring.

In a particular embodiment ring A is selected from the group consisting of:

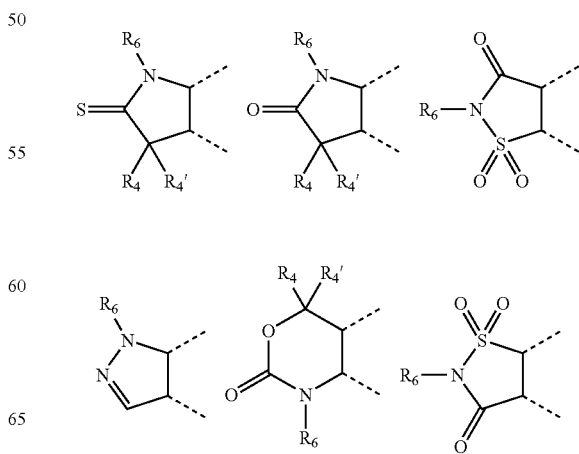

-continued

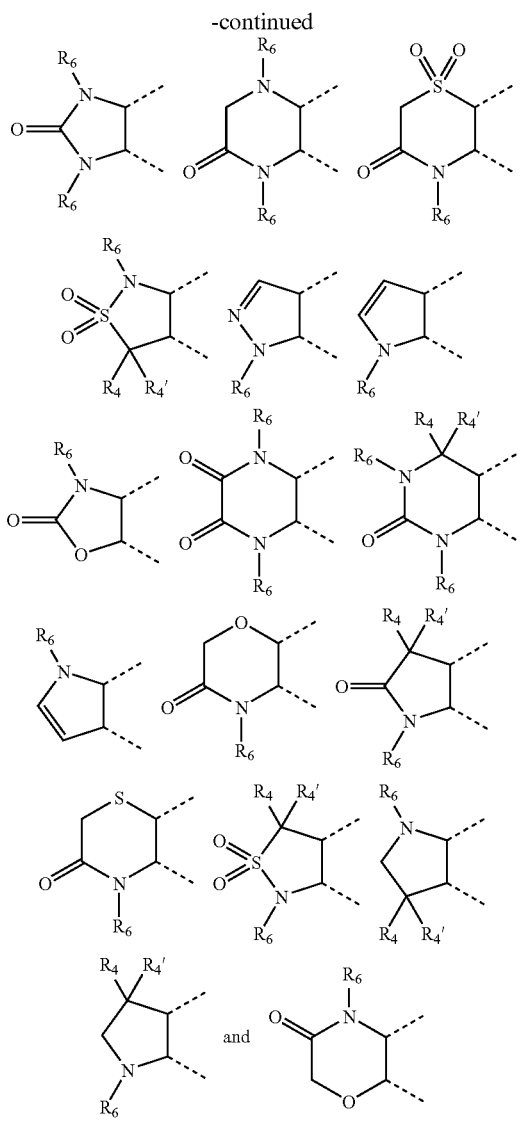

wherein $R_4$, $R_{4'}$ and $R_6$ are defined herein. The dashed lines represent bonds from the benzene ring to which ring A is fused.

In an embodiment, ring A is selected from the group consisting of:

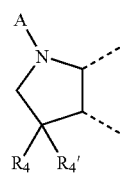

wherein $R_4$, $R_{4'}$ and $R_6$ are defined herein. The dashed lines represent bonds from the benzene ring to which ring A is fused.

In an embodiment, ring A is selected from the group consisting of:

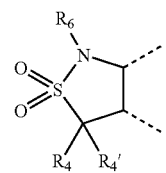

wherein $R_4$, $R_{4'}$ and $R_6$ are defined herein. The dashed lines represent bonds from the benzene ring to which ring A is fused.

In an embodiment, ring A is selected from the group consisting of:

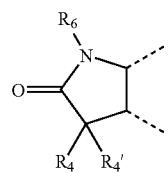

wherein $R_4$, $R_{4'}$ and $R_6$ are defined herein. The dashed lines represent bonds from the benzene ring to which ring A is fused.

In a particular embodiment ring A is selected from the group consisting of:

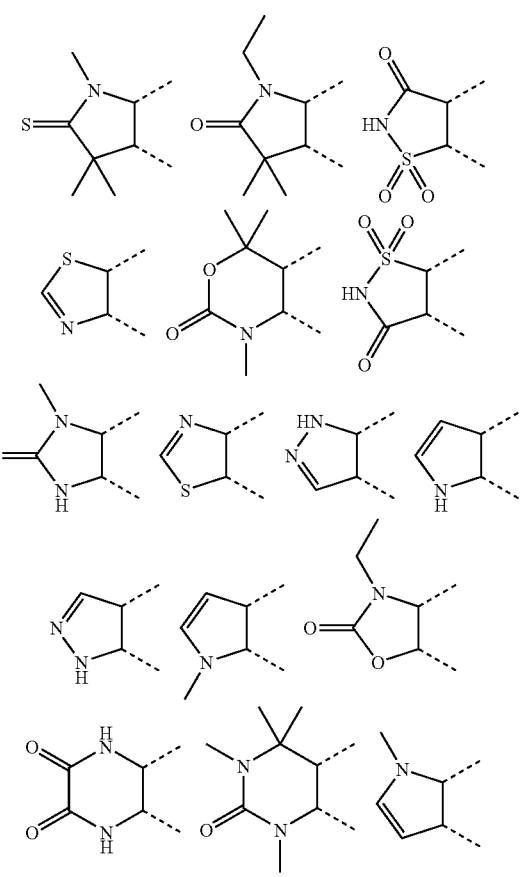

-continued

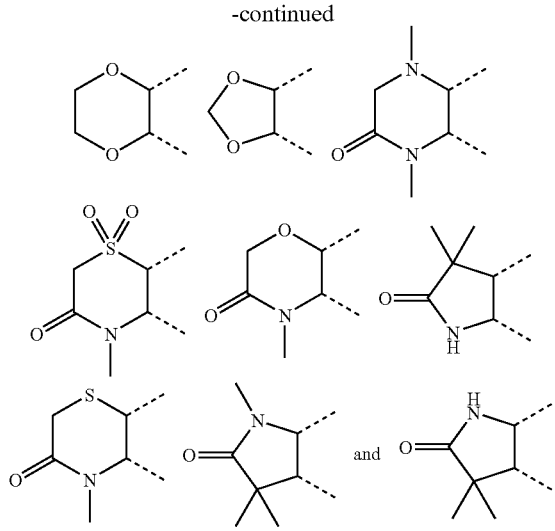

X, Y and Z are independently absent, CR$_4$R$_4'$, NR$_5$, S, SO, SO$_2$ or O; wherein at least one of X, Y and Z is not absent; or X and Y together are CR$_4$=CR$_4$; or Y and Z together are CR$_4$=CR$_4$; In a particular embodiment X is CR$_4$R$_4'$, Y is S and Z is CR$_4$R$_4'$. In a particular embodiment X is CR$_4$R$_4'$, Y is NR$_5$, and Z is CR$_4$R$_4'$. In a particular embodiment X is S, Y is CR$_4$R$_4'$, and Z is CR$_4$R$_4'$. In a particular embodiment X, Y and Z are each CR$_4$R$_4'$.

Ra and Rb are independently H or a protecting group. In a particular embodiment Ra and Rb are both the same or different acid labile amino protecting group. In a particular embodiment Ra and Rb are the same or different acyloxy group, for example —OC(O)R wherein R is alkyl, aryl or aralkyl. In a particular embodiment R is alkyl, for example, methyl, ethyl, propyl, butyl, t-butyl (i.e. forming a t-Boc group). In a particular embodiment Ra and Rb are both t-Boc). In a particular embodiment Ra and Rb are both H.

R$_c$ is H, hydroxyl, halogen, alkyl, haloalkyl. In an embodiment R$_c$ is methyl. In an embodiment R$_c$ is F. In an embodiment R$_c$ is CF$_3$. In a particular embodiment R$_c$ is H.

R$_1$ is H, hydroxyl, halogen, amino, or is alkyl, acyl, alkoxy or alkylthio optionally substituted with hydroxyl, halogen, carbonyl, thiocarbonyl, amino, carboxyl and alkoxy. The terms "carbonyl" and "thiocarbonyl" as used in R$_1$ and other groups as a separate substituent will be understood to mean the groups =O and =S respectively whereas used in conjunction with another group means —C(O)— (e.g. alkoxycarbonyl means —C(O)—O-alkyl). The term "alkylthio" means the thioether group —S-alkyl. The term "carboxy" and "carboxyl" are used herein interchangeably to mean —COOH. In a particular embodiment R$_1$ is hydroxyalkyl, alkylthio, alkoxycarbonyl or aminocarbonyl. In a particular embodiment, R$_1$ is H. In a particular embodiment R$_1$ is alkyl. In a particular embodiment R$_1$ is methyl.

R$_2$ is H, halogen, hydroxyl, mercapto, amino, alkyl, a carbocycle or a heterocycle, wherein said alkyl, carbocycle and heterocycle are optionally substituted with halogen, hydroxyl, mercapto, amino, carboxyl, alkyl, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(S)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. It will be understood that a CH$_2$ group may be replaced at any position along an alkyl chain (or a CH group of an alkenyl chain) including a terminal CH$_2$ group in which case the replacing group is attached to the preceding carbon atom and a following hydrogen. By way of example, CH$_2$ groups in a propyl substituent may be replaced with —O— in the following different ways: —O—CH$_2$—CH$_3$, —CH$_2$—O—CH$_3$ or —CH$_2$—CH$_2$—O—H. It will be understood that replacement of a CH$_2$ group in R$_2$ and any other group herein will be as permitted by valency. It is also understood that "an alkyl group" refers to any alkyl group in the definition of R$_2$. In a particular embodiment R$_2$ is H, or an optionally substituted alkyl, carbocycle or heterocycle wherein the substituents are halogen, hydroxyl, amino and mercapto and wherein one or more CH$_2$ groups of said alkyl group is optionally replaced with —O—, —S—, —S(O)—, —S(O)$_2$—, —N(R$_5$)—, —C(O)—, —C(S)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. In a particular embodiment R$_2$ is an optionally substituted carbocycle or heterocycle. In a particular embodiment R$_2$ is an optionally substituted aryl or heteroaryl ring. In a particular embodiment R$_2$ is H or alkyl wherein one more CH$_2$ groups of said alkyl moiety is optionally replaced with —O—, —S—, —S(O)—, —S(O)$_2$—, —N(R$_5$)—, —C(O)—, —C(S)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. In a particular embodiment R$_2$ is an optionally substituted aryl such as phenyl. In a particular embodiment R$_2$ is H.

R$_3$ is hydroxyl, mercapto, halogen, amino, nitro, cyano, carbonyl, thiocarbonyl, alkyl, a carbocycle or a heterocycle, or two R$_3$ groups together form a carbocycle or a heterocycle; wherein said alkyl, carbocycles and heterocycles are optionally substituted with halogen, hydroxyl, mercapto, carboxyl, carbonyl, thiocarbonyl, amino, nitro, cyano, alkyl, haloalkyl, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. In an embodiment, R$_3$ is hydroxyl, halogen, amino, carbonyl, thiocarbonyl, alkyl, a carbocycle or a heterocycle, or two R$_3$ groups together form a carbocycle or a heterocycle; wherein said alkyl, carbocycles and heterocycles are optionally substituted with halogen, hydroxyl, carboxyl, amino, alkyl, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. It will be understood that a CH$_2$ group may be replaced at any position along an alkyl chain including a terminal CH$_2$ group in which case the replacing group is attached to the preceding carbon atom and a following hydrogen. By way of example, CH$_2$ groups in a propyl substituent may be replaced with —O— in the following different ways: —O—CH$_2$—CH$_3$, —CH$_2$—O—CH$_3$ or —CH$_2$—CH$_2$—O—H. It is also understood that "an alkyl group" refers to any alkyl group in the definition of R$_3$. In a particular embodiment R$_3$ is alkyl, carbonyl or thiocarbonyl wherein said alkyl is optionally substituted with halogen, hydroxyl, amino, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. In a particular embodiment R$_3$ is alkyl wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. In an embodiment, R$_3$ is alkyl optionally substituted with carbonyl, thiocarbonyl, amino, hydroxyl, carboxyl or aminocarbonyl. In a particular embodiment R$_3$ is carbonyl. In a particular embodiment R$_3$ is thiocarbonyl. In a particular embodiment R$_3$ is methyl. In a particular embodiment R$_3$ is ethyl. In a particular embodiment R$_3$ is allyl. In a particular embodiment R$_3$ is isopropyl. In a particular embodiment R$_3$ is propyl. In a particular embodiment R$_3$ is ethyloxycarbonylmethyl. In a particular embodiment R$_3$ is carboxymethyl. In another particular embodiment two R$_3$ groups together form a carbocycle or a heterocycle. In another particular embodiment two R$_3$ groups form a spiro carbocycle or heterocycle.

R$_4$ and R$_4$' are independently H, hydroxyl, halogen, amino, carbonyl, thiocarbonyl, alkyl, a carbocycle or a heterocycle, or R$_4$ and R$_4$' together form a carbocycle or heterocycle, wherein said alkyl, carbocycles and heterocycles are optionally substituted with halogen, hydroxyl, carboxyl, amino, alkyl, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. It will be understood that a CH$_2$ group may be replaced at any position along an alkyl chain including a terminal CH$_2$ group in which case the replacing group is attached to the preceding carbon atom and a following hydrogen. By way of example, CH$_2$ groups in a propyl substitutent may be replaced with —O— in the following different ways: —O—CH$_2$—CH$_3$, —CH$_2$—O—CH$_3$ or —CH$_2$—CH$_2$—O—H. It is also understood that "an alkyl group" refers to any alkyl group in the definition of R$_4$. In a particular embodiment R$_4$ and R$_4$' are independently H, or an optionally substituted alkyl, carbocycle or heterocycle wherein the substituents are halogen, hydroxyl, amino and mercapto and wherein one or more CH$_2$ groups of said alkyl group is optionally replaced with —O—, —S—, —S(O)—, —S(O)$_2$—, —N(R$_5$)—, —C(O)—, —C(S)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. In a particular embodiment R$_4$ and R$_4$' are independently an optionally substituted carbocycle or heterocycle. In a particular embodiment R$_4$ and R$_4$' are independently an optionally substituted aryl or heteroaryl ring. In a particular embodiment R$_4$ and R$_4$' are independently H or alkyl wherein one more CH$_2$ groups of said alkyl moiety is optionally replaced with —O—, —S—, —S(O)—, —S(O)$_2$—, —N(R$_5$)—, —C(O)—, —C(S)—, —C(O)—NR$_5$—, —NR$_5$—C(O)—, —SO$_2$—, —NR$_5$—, —NR$_5$—SO$_2$—, —NR$_5$—C(O)—NR$_5$—, —C(O)—O— or —O—C(O)—. In a particular embodiment R$_4$ and R$_4$' are independently alkyl such as methyl. In a particular embodiment R$_4$ and R$_4$' are both H.

R$_5$ is H, alkyl, a carbocycle or a heterocycle wherein one or more CH$_2$ or CH groups of said alkyl is optionally replaced with —O—, —S—, —S(O)—, —S(O)$_2$—, —NH—, or —C(O)—; and said alkyl, carbocycle and heterocycle is optionally substituted with hydroxyl, alkoxy, acyl, halogen, mercapto, carbonyl, carboxyl, acyl, halo-substituted alkyl, amino, cyano nitro, amidino, guanidino an optionally substituted carbocycle or an optionally substituted heterocycle. In a particular embodiment R$_5$ is H or alkyl. In a particular embodiment R$_5$ is H. In a particular embodiment R$_5$ is alkyl, for example methyl, ethyl or propyl.

R$_6$ is alkyl, a carbocycle or a heterocycle, wherein said alkyl, carbocycle and heterocycle are optionally substituted with halogen, hydroxyl, mercapto, carboxyl, carbonyl, thiocarbonyl, amino, nitro, cyano, substituted or unsubstituted alkyl, a substituted or unsubstituted carbocycle or heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. Substituents for said substituted alkyl, carbocycle and heterocycle are halogen, hydroxyl, mercapto, carboxyl, carbonyl, thiocarbonyl, amino, nitro, cyano, alkyl and haloalkyl. In an embodiment, R$_6$ is R$_3$. In an embodiment, R$_6$ is alkyl, a carbocycle or a heterocycle, wherein said alkyl, carbocycle and heterocycle are optionally substituted with halogen, hydroxyl, carboxyl, amino, alkyl, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. In a particular embodiment R$_6$ is alkyl optionally substituted with halogen, hydroxyl, amino, a carbocycle or a heterocycle and wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. It will be understood that a CH$_2$ group may be replaced at any position along an alkyl chain including a terminal CH$_2$ group in which case the replacing group is attached to the preceding carbon atom and a following hydrogen. For example, the terminal CH$_2$ group of an ethyl —CH$_2$—CH$_3$ alkyl chain may be replaced with —C(O)—O— to give the group —CH$_2$—C(O)—O—H. In a particular embodiment R$_6$ is alkyl wherein one or more CH$_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—. For example, R$_6$ is alkyl optionally substituted with carbonyl, thiocarbonyl, amino, hydroxyl, carboxyl or aminocarbonyl.

In an embodiment, R$_6$ is alkyl; allyl substituted with hydroxyl, carboxyl, sulfinyl, sulfonyl, carbamoyl, cycloalkylcarboxamide, aminocarboxamide, a carbocycle or a heterocycle wherein said carbocycle and heterocycle is optionally substituted with carbonyl, carbamoyl, aryl, aryl substituted with carboxyl or alkoxycarbonyl; heteroaryl; heteroaryl substituted with acylamino; a non-aromatic heterocycle, a non-aromatic heterocycle substituted with sulfonyl; an ester of the formula -alkylene-C(O)—O—R$_7$ wherein R$_7$ is H, amino, alkyl, a carbocycle or aryl. In a particular embodiment the carbamoyl group or substituent of R$_6$ has the formula —C(O)N(R$_8$)$_2$ wherein R$_8$ is H, amino, alkyl, a carbocycle, a heterocycle or both R$_8$ groups together form a heterocycle with the nitrogen atom from with they depend. In a particular embodiment R$_6$ is methyl. In a particular embodiment R$_6$ is ethyl. In a particular embodiment R$_6$ is allyl. In a particular embodiment R$_6$ is isopropyl. In a particular embodiment R$_6$ is propyl. In a particular embodiment R$_6$ is ethyloxycarbonylmethyl. In a particular embodiment R$_6$ is carboxymethyl. In a particular embodiment R$_6$ is H.

m is 0 to 10. In an embodiment 0 to 5. In an embodiment m is 1 to 5. In an embodiment m is 2 to 5. In an embodiment m is 3 to 5.

In a particular embodiment, compounds of the invention have the general formula II:

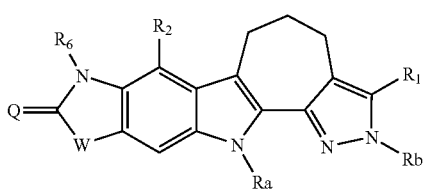

wherein $R_a$, $R_b$, $R_1$, $R_2$, $R_6$ and n are as described herein and Q is $H_2$, $NR_6$, O or S; W is $CR_4R_{4'}$, $NR_6$, O, S, SO or $SO_2$.

In an embodiment Q is $NR_6$, O or S. In an embodiment Q is O or S. In a particular embodiment Q is O. In another embodiment Q is S. In another particular embodiment Q is $H_2$ (i.e. two hydrogen atoms attached to the carbon atom). In a particular embodiment Q is $NR_6$ in which $R_6$ is defined herein. In a particular embodiment Q is $NR_6$ and $R_6$ is H. In another embodiment $R_6$ is alkyl. In a particular embodiment $R_6$ is methyl.

W is $CR_4R_{4'}$, $NR_5$, O, S, SO or $SO_2$. In a particular embodiment W is O. In a particular embodiment W is S. In a particular embodiment W is $NR_6$. In a particular embodiment $R_6$ is H or alkyl. In a particular embodiment $R_6$ is H. In a particular embodiment $R_6$ is methyl. In a particular embodiment $R_6$ is ethyl. In a particular embodiment W is $CR_4R_{4'}$ and $R_4$ and $R_{4'}$ are as herein defined. In a particular embodiment $R_4$ and $R_{4'}$ are both H. In a particular embodiment $R_4$ and $R_{4'}$ are both alkyl. In a particular embodiment $R_4$ and $R_{4'}$ are both methyl. In a particular embodiment $R_4$ and $R_{4'}$ together form a carbocycle or heterocycle (spiro) that is optionally substituted with alkyl.

In particular embodiments in which compounds of the invention have the general formula II, Q is O or $H_2$; $R_a$ and $R_b$ are both H; $R_1$ is H or alkyl; $R_2$ is H; W is $CR_4R_{4'}$ wherein $R_4$ and $R_{4'}$ are both alkyl optionally substituted with hydroxy, alkoxyl or alkoxycarbonyl; or $R_4$ and $R_{4'}$ together form a carbocycle or a heterocycle optionally substituted with cycloalkyl aralkyl; $R_6$ is selected from the group consisting of H; alkyl optionally substituted with halogen, hydroxyl, amino, cyano, carboxyl, alkoxy, alkoxyalkoxy, alkylthio, sulfinyl, sulfonyl, acylamino, carbamoyl, aminocarbamoyl, alkoxycarbonyl, a heterocycle, aryl (optionally substituted with halogen, carboxyl, alkoxy, alkoxycarbonyl, acylamino or sulfonyl), aryloxy, aralkoxy, a heterocycle (optionally substituted with alkyl, alkoxy, alkoxycarbonyl, carbonyl, nitro or cyano); aryl substituted with acylamino; and a heterocycle optionally substituted with sulfonyl.

In particular embodiments in which compounds of the invention have the general formula II, Q is O; $R_a$ and $R_b$ are both H; $R_2$ is H; $R_1$ is H; W is $CR_4R_{4'}$ and $R_4$ and $R_{4'}$ are both methyl; $R_6$ is selected from the group consisting of H; alkyl optionally substituted with halogen, hydroxyl, amino, carboxyl, alkoxy, alkoxyalkoxy, alkylthio, sulfinyl, sulfonyl, acylamino, carbamoyl, aminocarbamoyl, alkoxycarbonyl, a heterocycle, aryl (optionally substituted with halogen, carboxyl, alkoxy, alkoxycarbonyl, acylamino or sulfonyl), heteroaryl (substituted with alkyl, alkoxy, alkoxycarbonyl, carbonyl, nitro or cyano); and a heterocycle substituted with sulfonyl.

In particular embodiments in which compounds of the invention have the general formula II, Q is O; $R_a$ and $R_b$ are both H; $R_2$ is H; $R_1$ is Me; W is $CR_4R_{4'}$ and $R_4$ and $R_{4'}$ are both methyl; $R_6$ is selected from the group consisting of H; alkyl optionally substituted with hydroxyl, amino, carboxyl, alkoxycarbonyl, carbamoyl, alkoxyalkoxy, cyano, aryl (optionally substituted with halogen); and aryl substituted with acylamino.

In particular embodiments in which compounds of the invention have the general formula II, Q is O; $R_a$ and $R_b$ are both H; $R_2$ is H; $R_1$ is H; W is $CR_4R_{4'}$ and $R_4$ and $R_{4'}$ are both ethyl; $R_6$ is selected from the group consisting of alkyl (optionally substituted with hydroxyl, alkoxy, alkoxyalkoxy, aryloxy, aralkoxy, carbamoyl, sulfinyl or a heterocycle); and heteroaryl.

In particular embodiments in which compounds of the invention have the general formula II, Q is O; $R_a$ and $R_b$ are both H; $R_2$ is H; $R_1$ is Me; W is $CR_4R_{4'}$ and $R_4$ and $R_{4'}$ are both ethyl; $R_6$ is selected from the group consisting of alkyl optionally substituted with a heterocycle.

In particular embodiments in which compounds of the invention have the general formula II, Q is O; $R_a$ and $R_b$ are both H; $R_2$ is H; $R_1$ is H; W is $CR_4R_{4'}$ and $R_4$ and $R_{4'}$ are both propyl; $R_6$ is selected from the group consisting of H; alkyl optionally substituted with hydroxyl, carboxyl, alkoxy, alkoxyalkoxy, alkoxycarbonyl, carbamoyl, sulfinyl or a heterocycle; and a heterocycle.

In particular embodiments in which compounds of the invention have the general formula II, Q is O; $R_a$ and $R_b$ are both H; $R_2$ is H; $R_1$ is H; W is $CR_4R_{4'}$ and $R_4$ and $R_{4'}$ are both methoxymethyl; $R_6$ is selected from the group consisting of alkyl optionally substituted with hydroxyl, alkoxy, alkoxyalkoxy, carbamoyl or a heterocycle; and a heterocycle.

In particular embodiments in which compounds of the invention have the general formula II, Q is O; $R_a$ and $R_b$ are both H; $R_2$ is H; $R_1$ is H; W is $CR_4R_{4'}$ and $R_4$ and $R_{4'}$ are both methoxyethyl; $R_6$ is selected from the group consisting of alkyl optionally substituted with hydroxy, carbamoyl or a heterocycle; and a heterocycle.

In particular embodiments in which compounds of the invention have the general formula II, Q is O; $R_a$ and $R_b$ are both H; $R_2$ is H; $R_1$ is H; W is $CR_4R_{4'}$ and $R_4$ and $R_{4'}$ together for a cyclopentyl ring; $R_6$ is selected from the group consisting of alkyl optionally substituted with hydroxyl, alkoxy or carbamoyl; and a heterocycle.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

The invention also encompasses prodrugs of the compounds described herein. Suitable prodrugs where applicable include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. In a particular embodiment, the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc.

Particular compounds of formula I include the following:

1
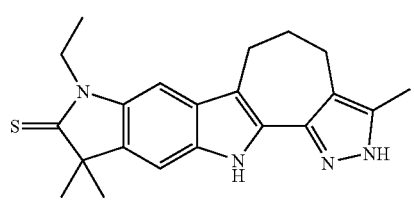

2
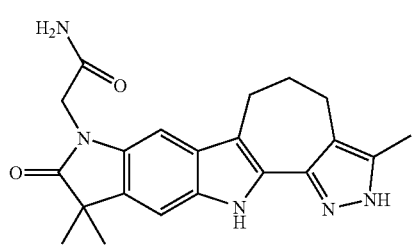

3
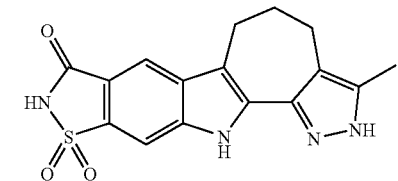

4
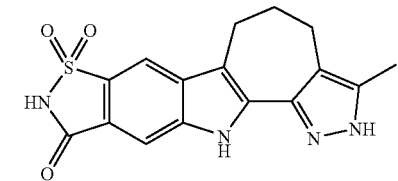

5
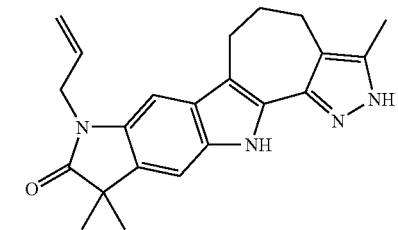

-continued

6
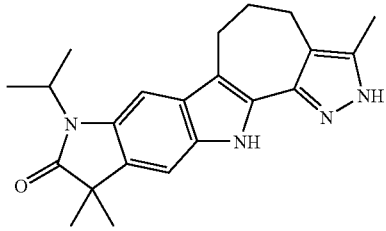

7
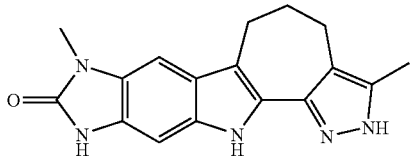

8
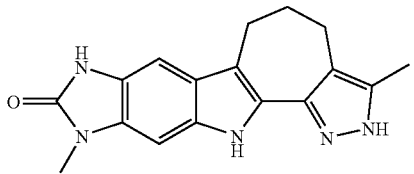

9
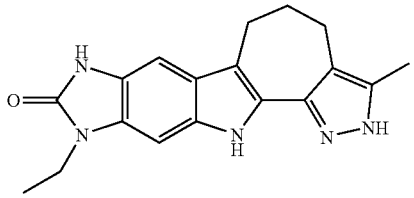

10
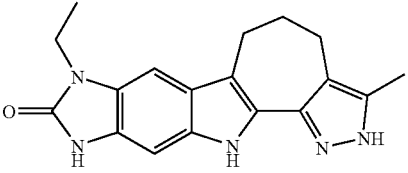

11
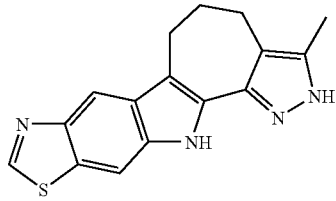

12
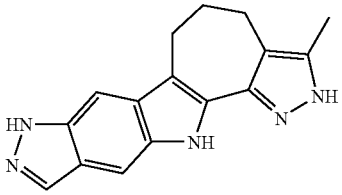

-continued
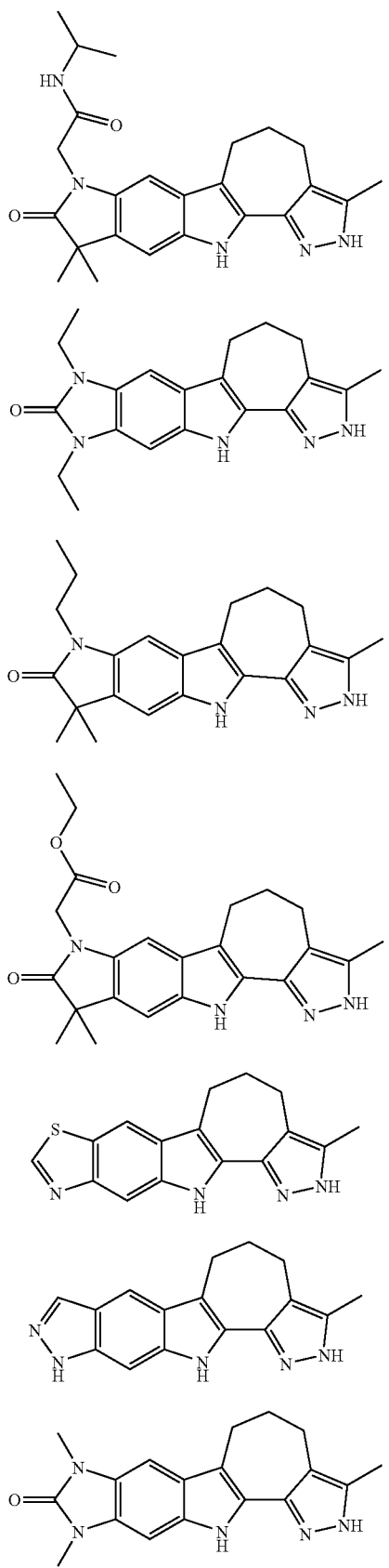
-continued
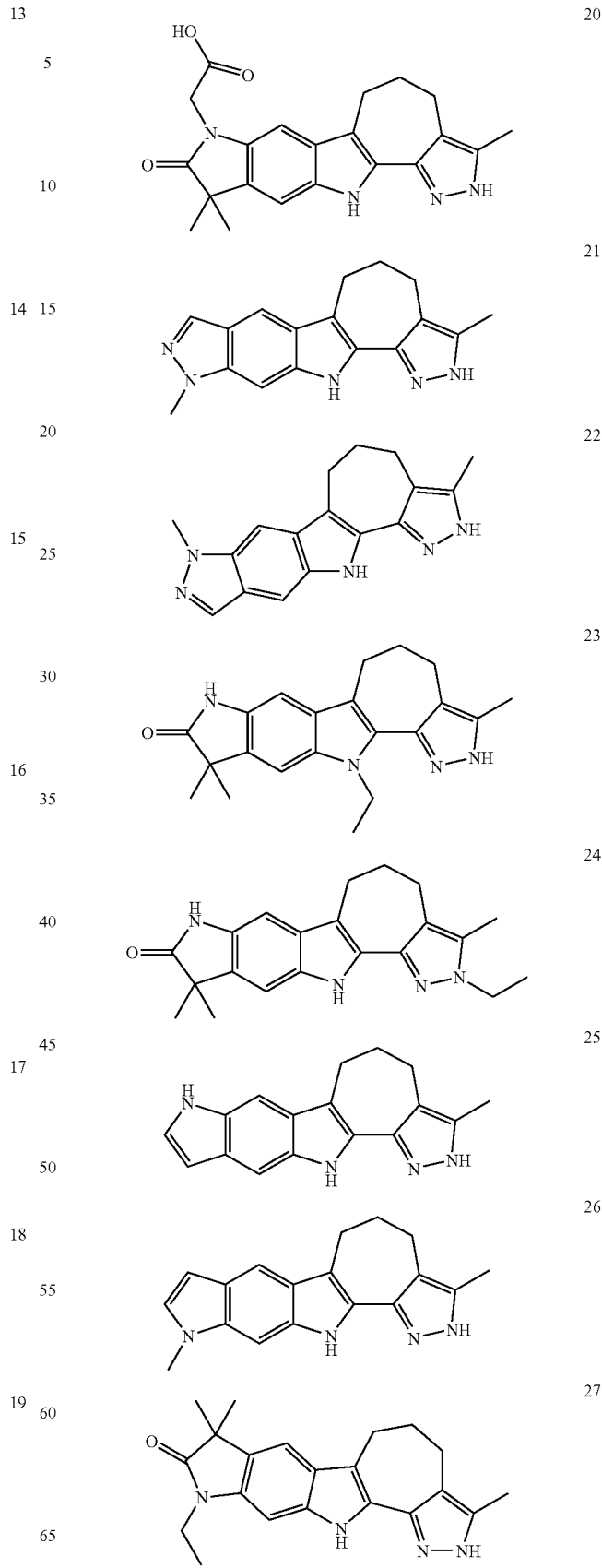

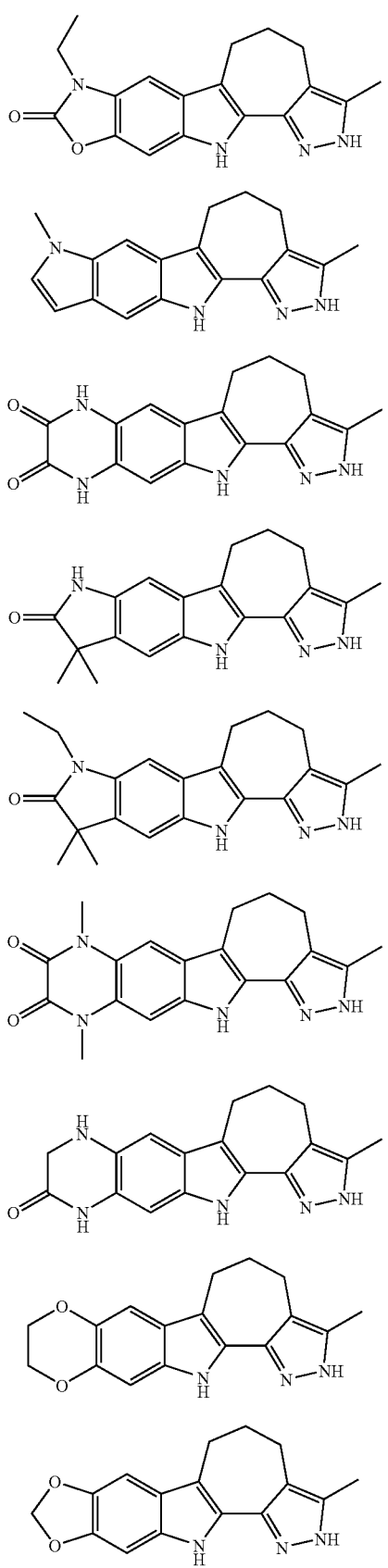
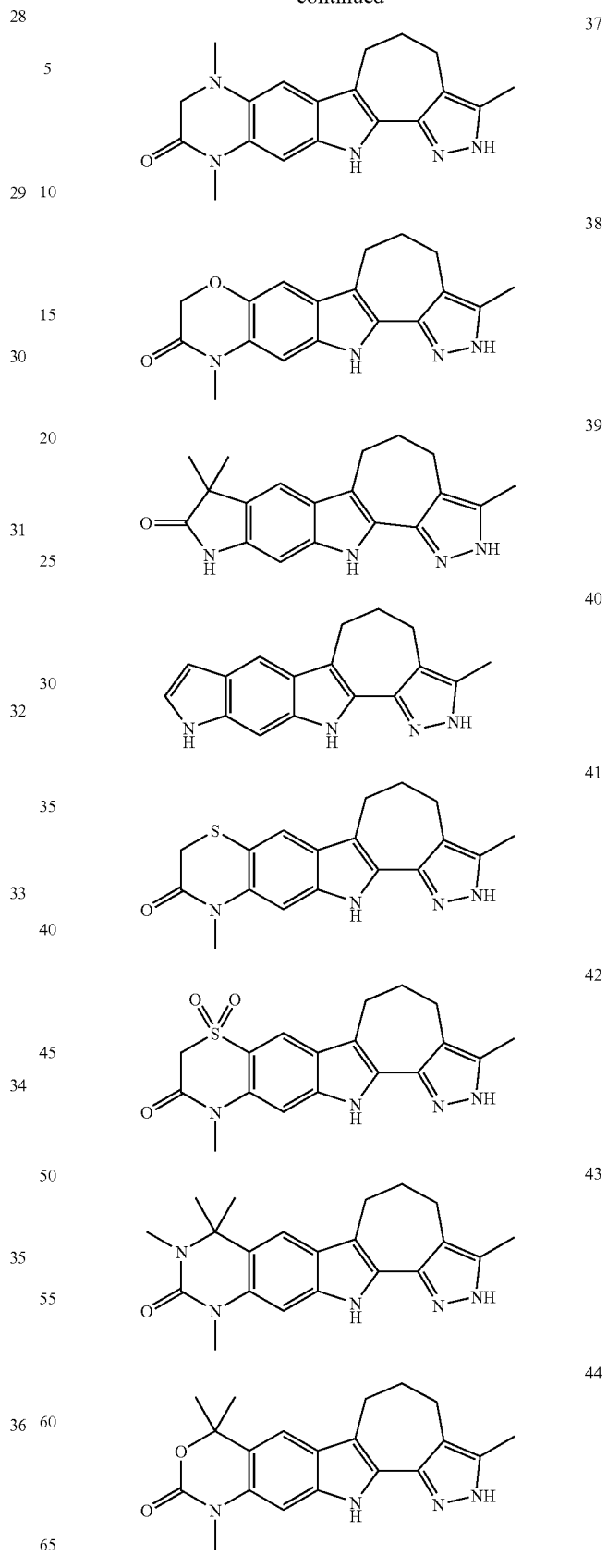

45
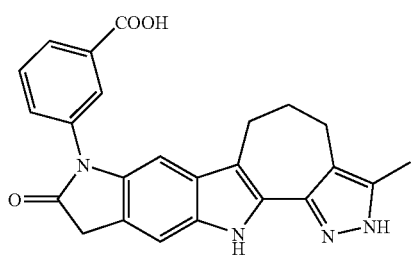
46
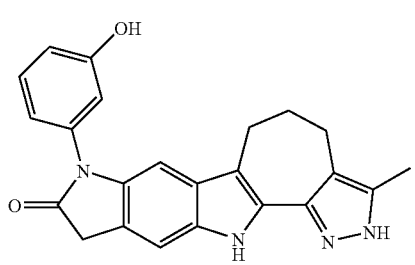
47
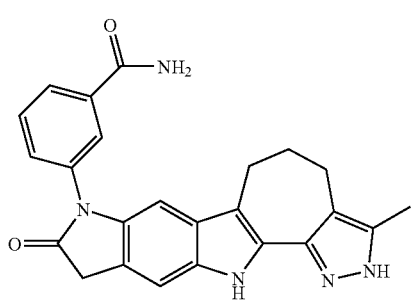
48
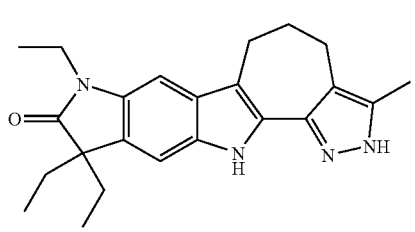
49
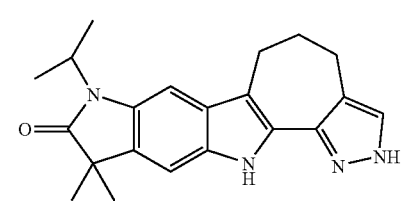
50
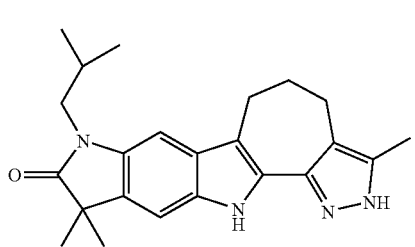
51
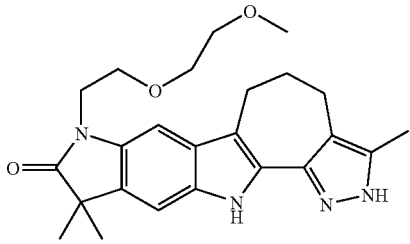
52
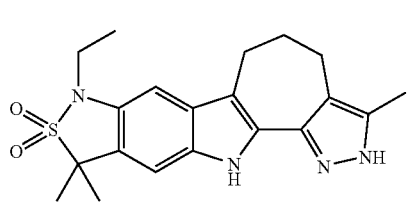
53
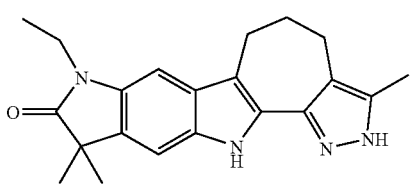
54
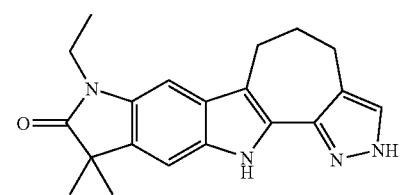
55
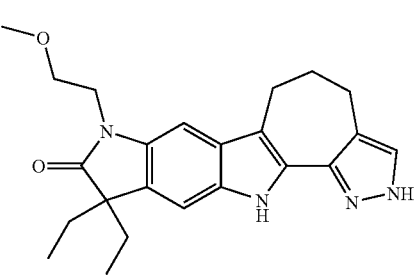
56
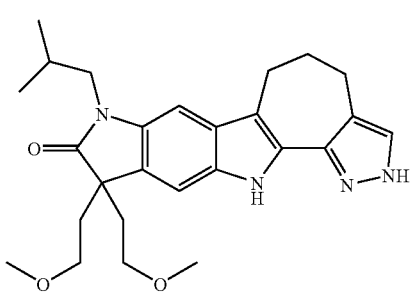

57
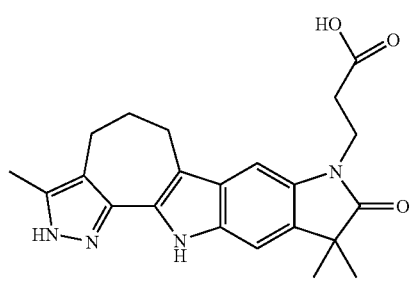
58
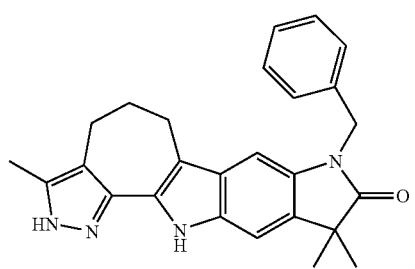
59
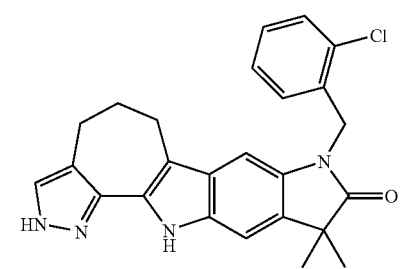
60
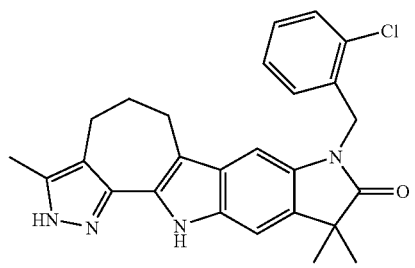
61
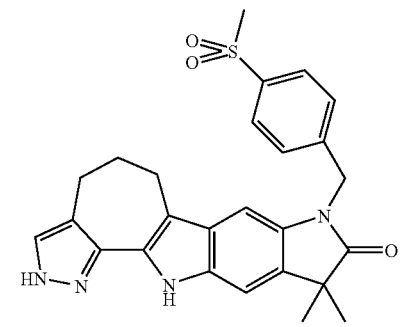
62
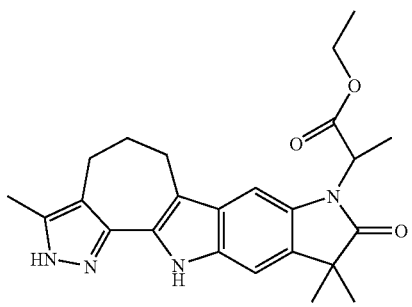
63
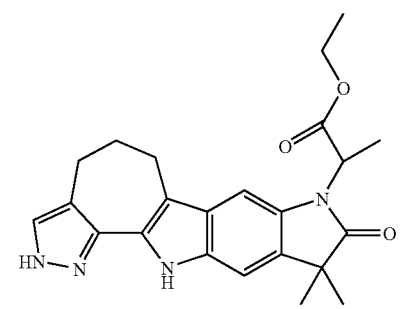
64
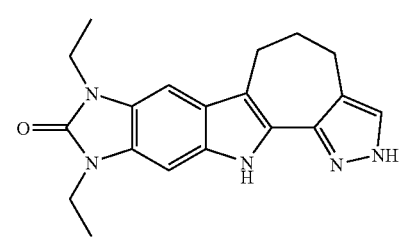
65
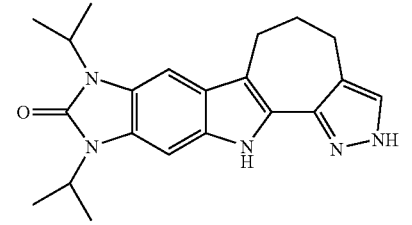
66
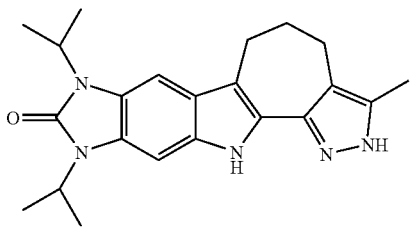
67
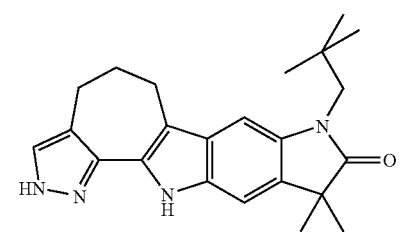

68
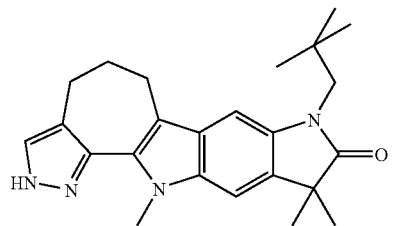
69
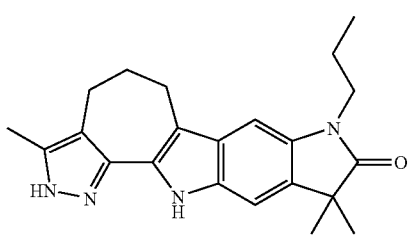
70
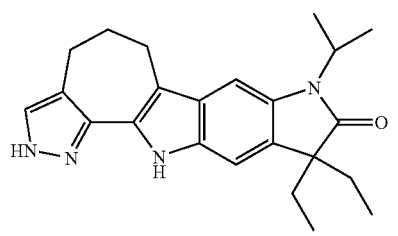
71
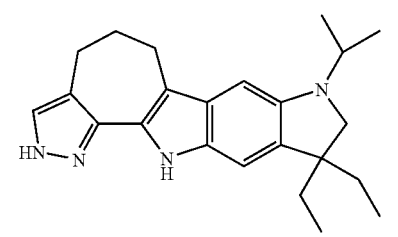
72
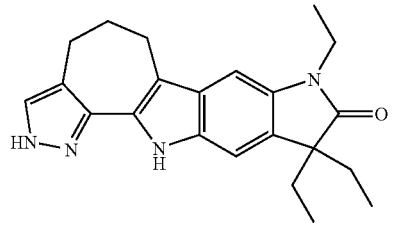
73
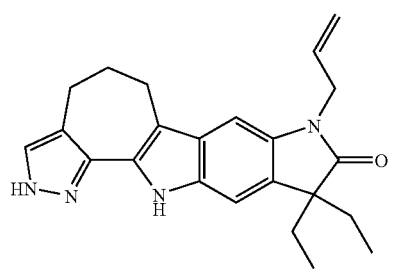
74
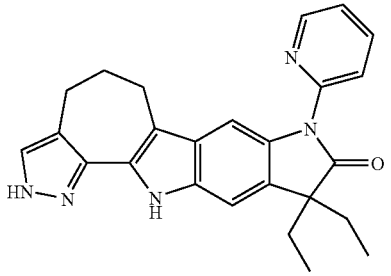
75
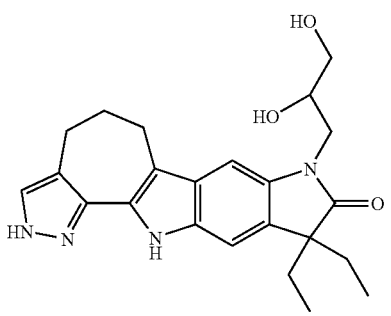
76
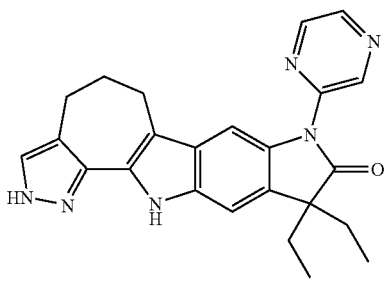
77
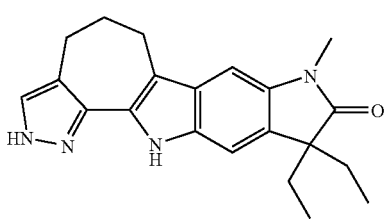
78
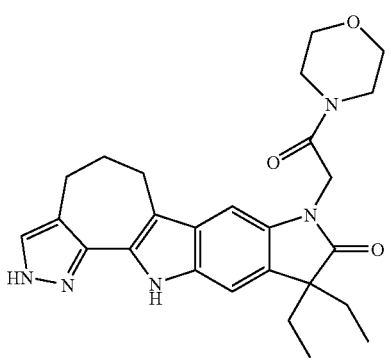

79 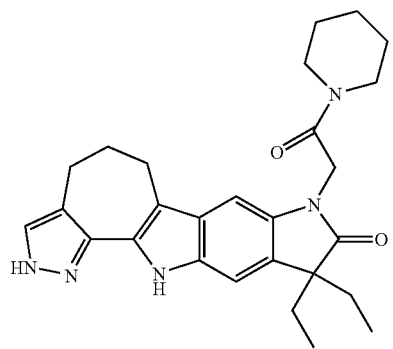
80 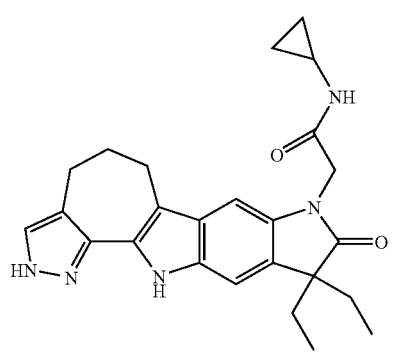
81 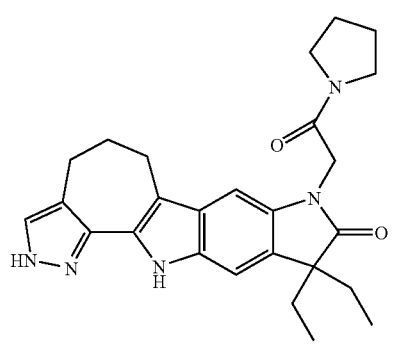
82 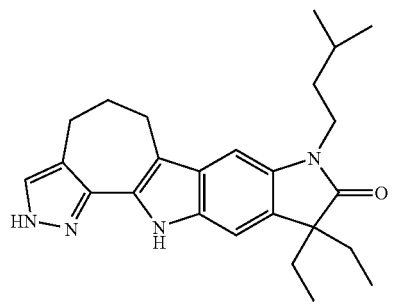
83 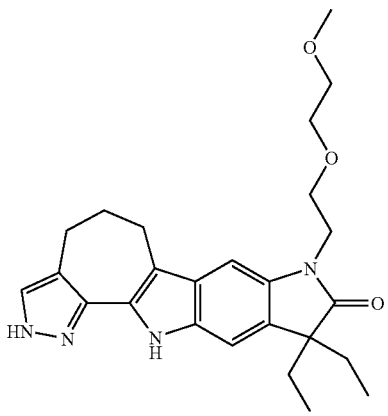
84 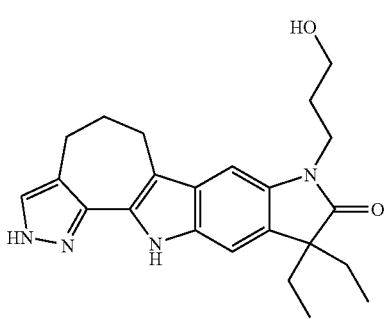
85 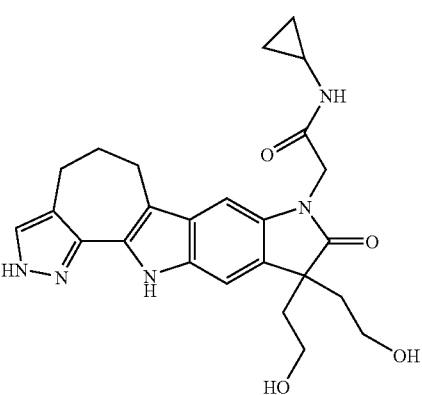
86 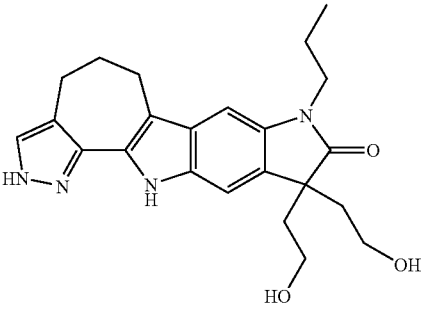

87
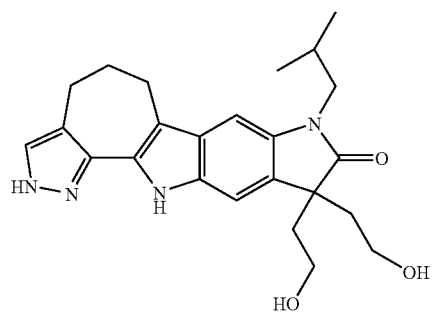
88
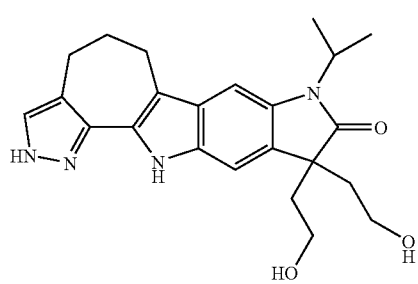
89
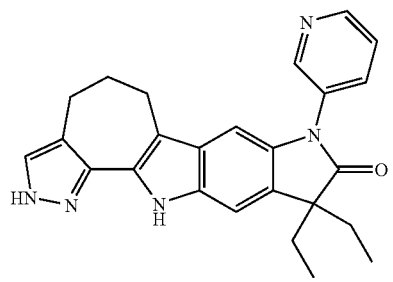
90
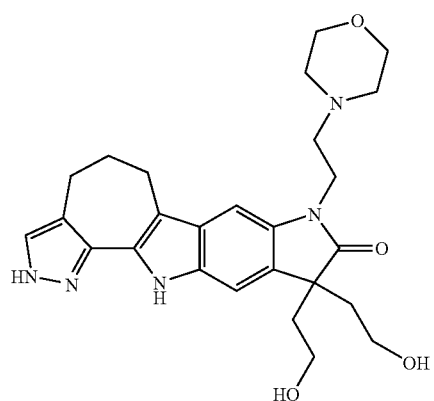
91
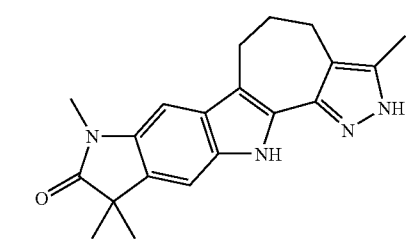
92
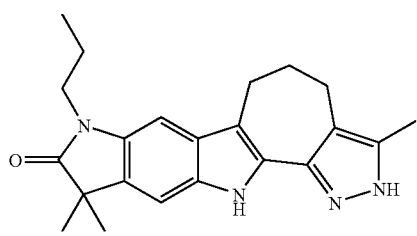
93
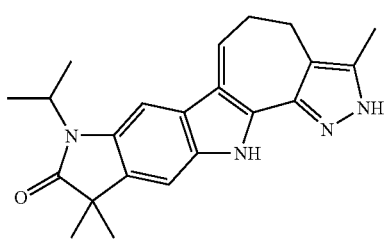
94
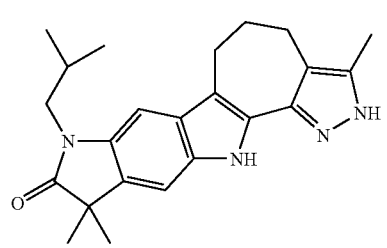
95
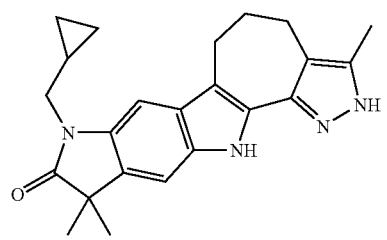
96
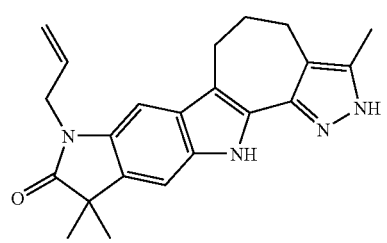
97
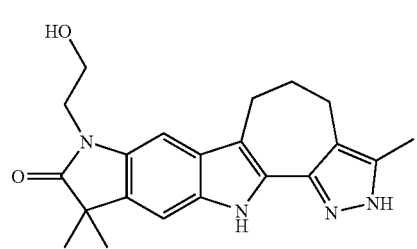

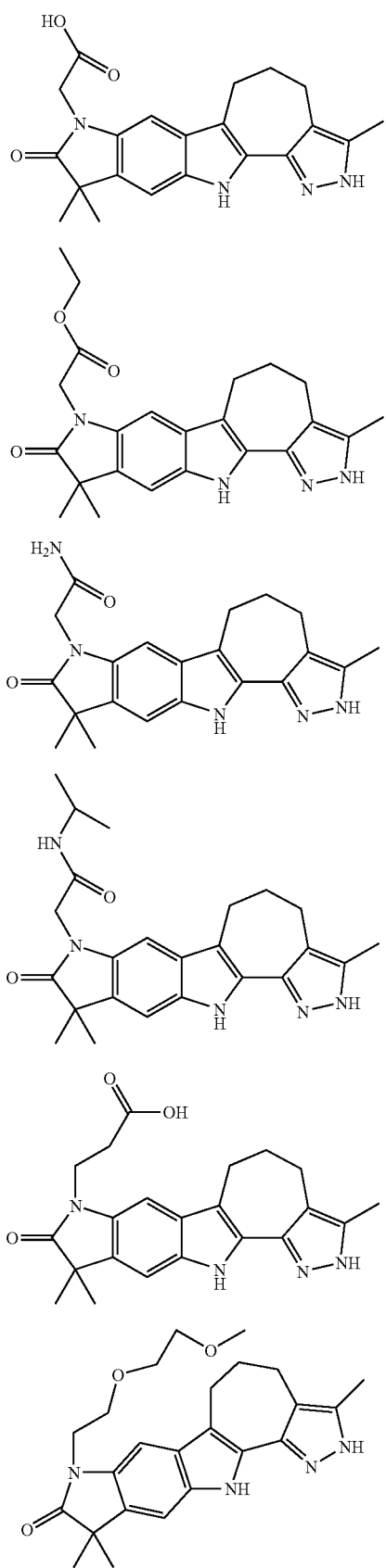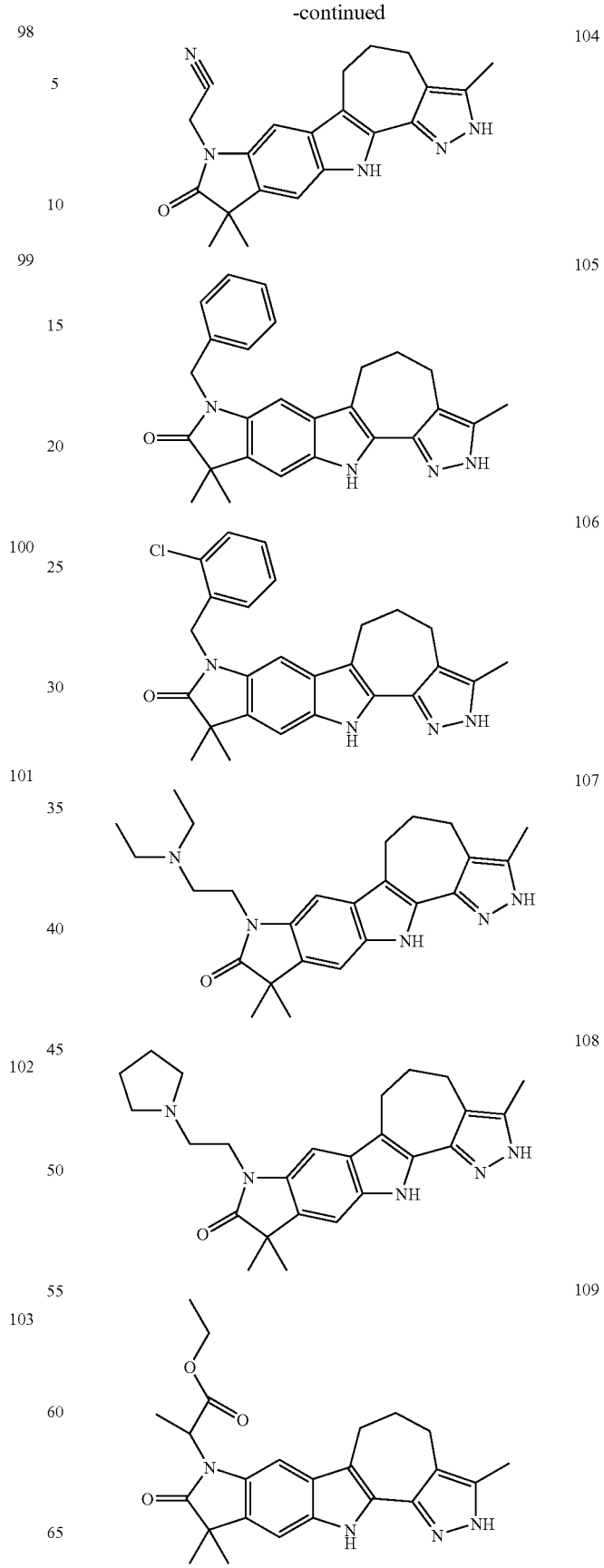

-continued
110
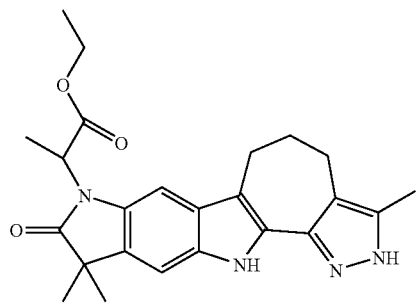
111
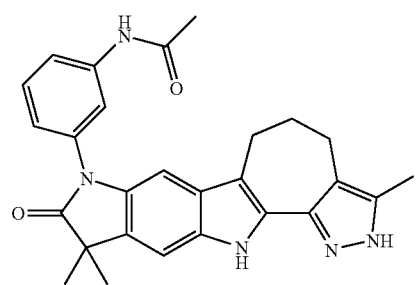
112
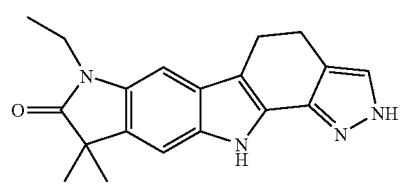
113
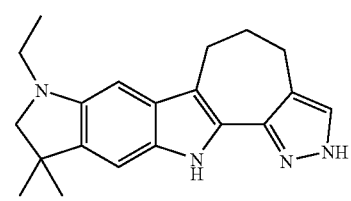
114
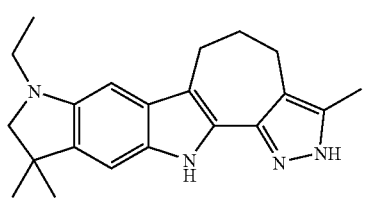
115
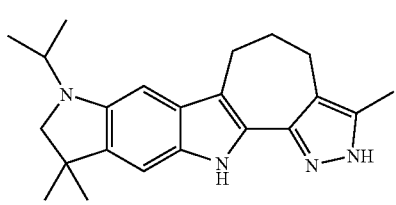
-continued
116
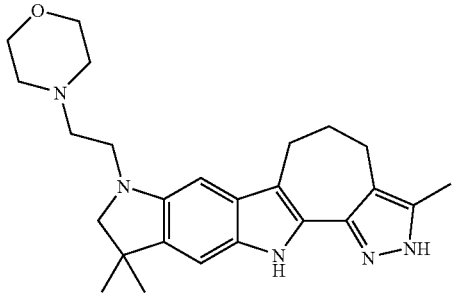
117
118
119
120
121
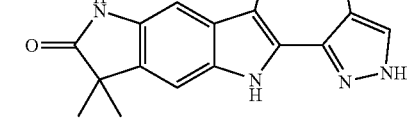
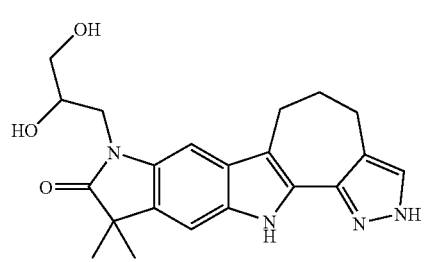

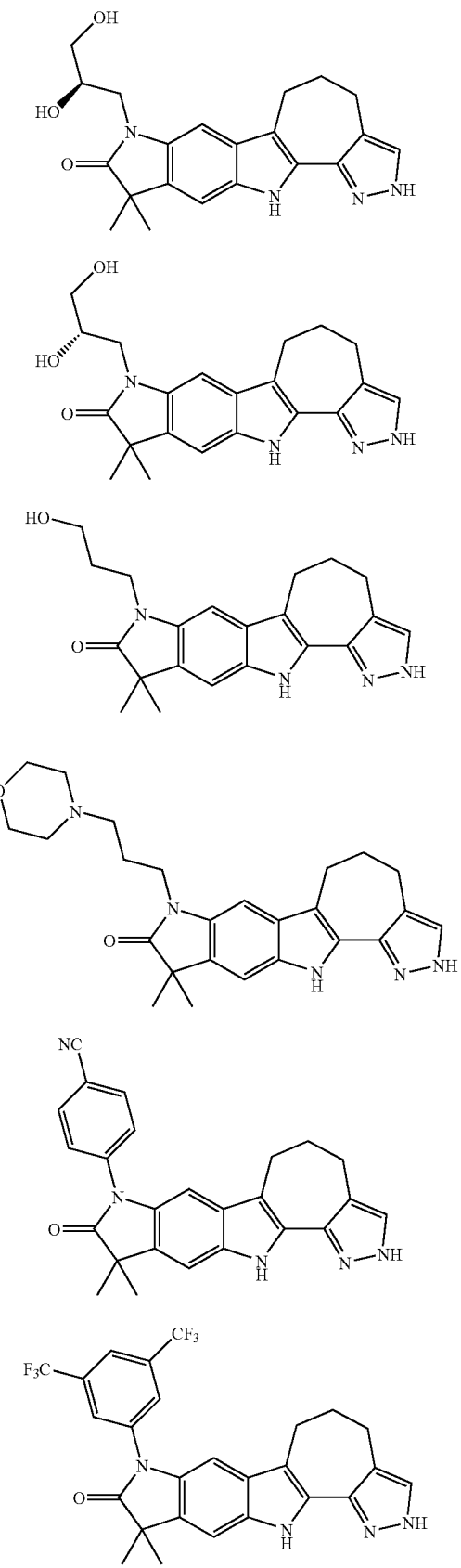
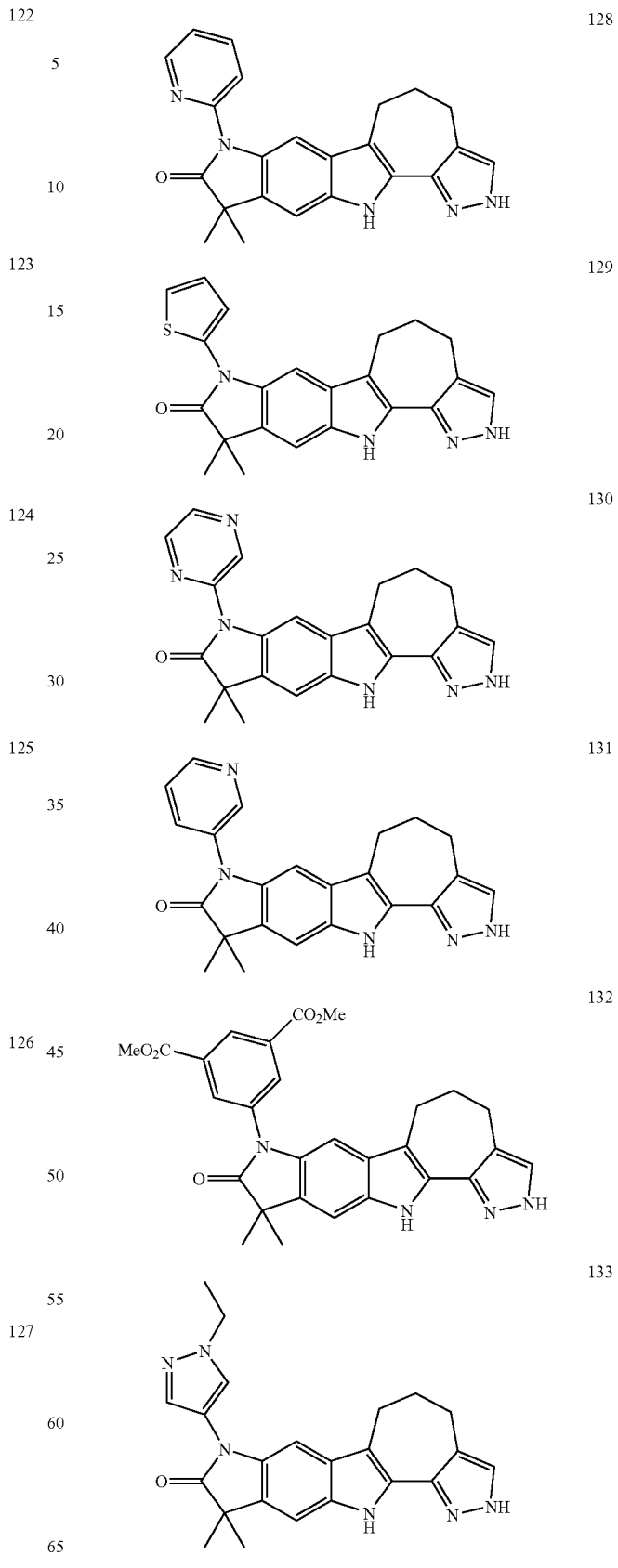

-continued
| | |
|---|---|
| 134 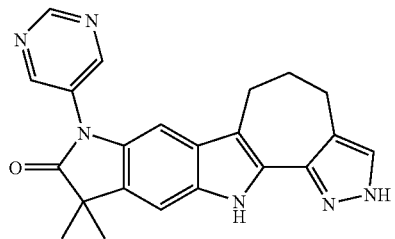 | 139 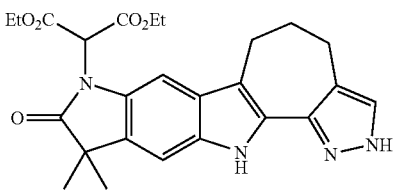 |
| 135 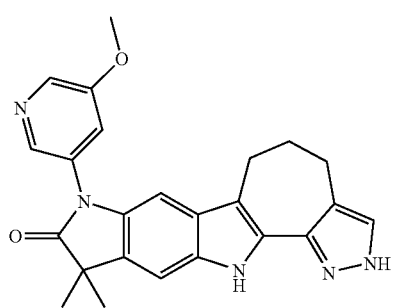 | 140 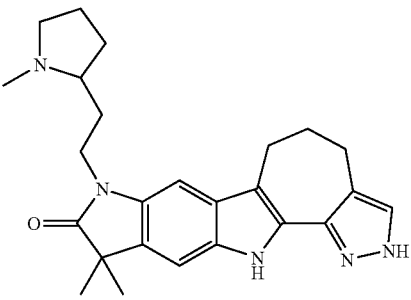 |
| 136 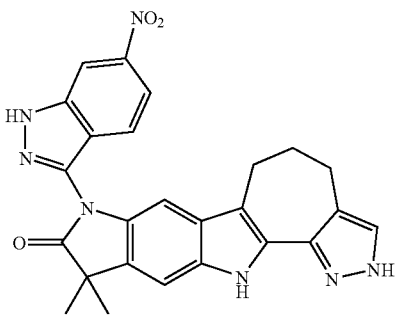 | 141 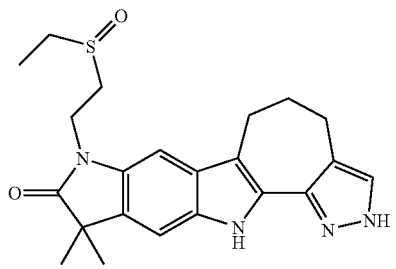 |
| 137 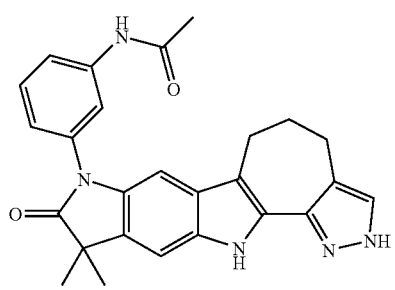 | 142 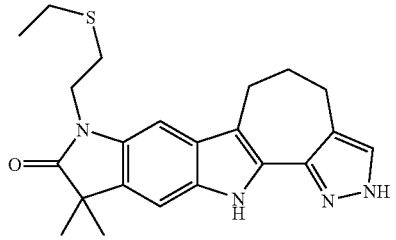 |
| 138 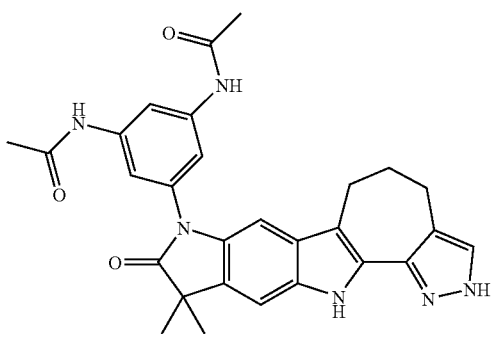 | 143 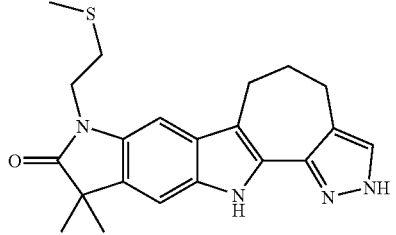 |
| | 144 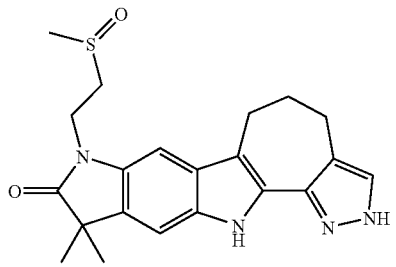 |

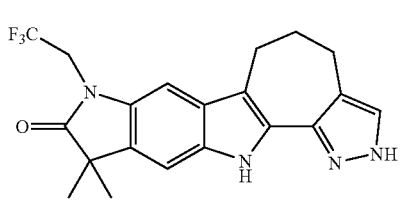
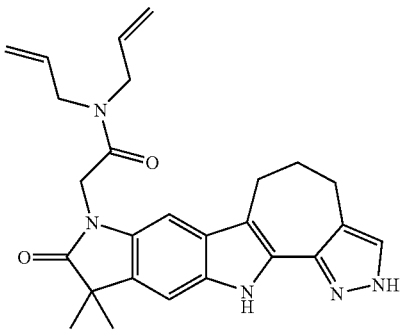
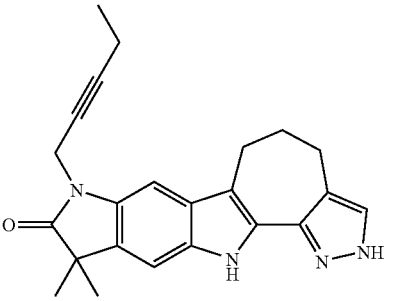
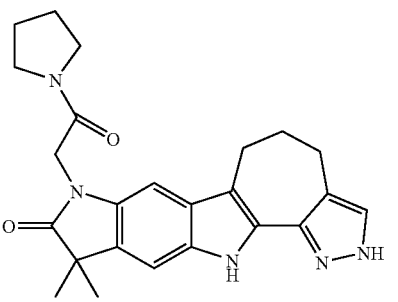
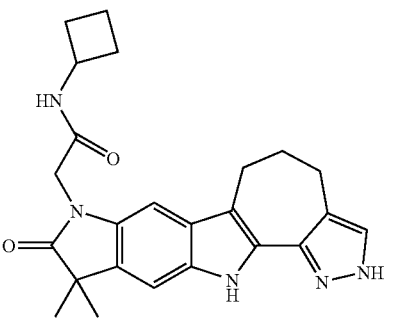

156 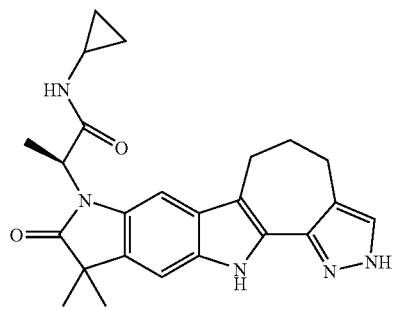
157 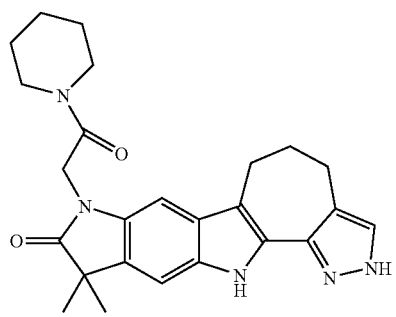
158 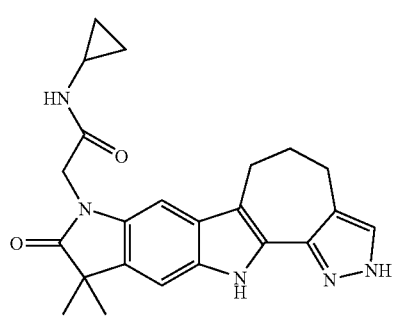
159 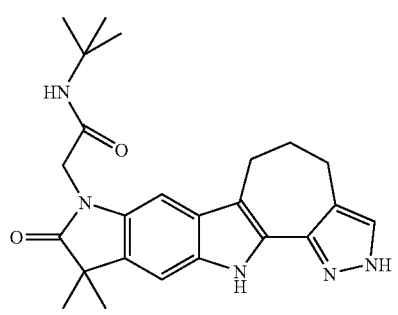
160 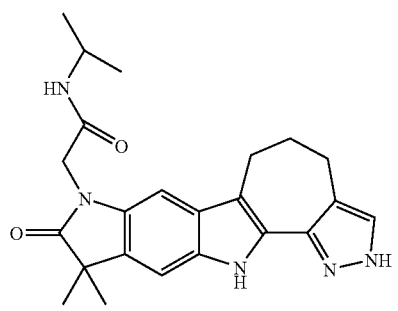
161 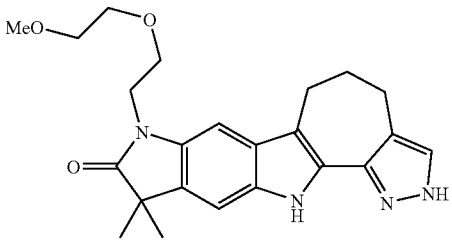
162 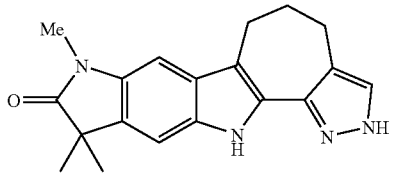
163 
164 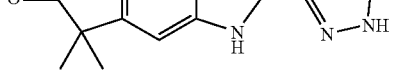
165 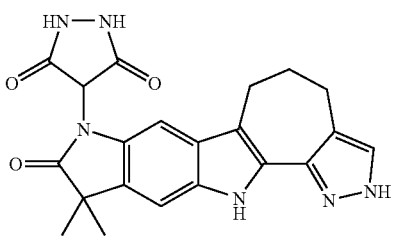
166 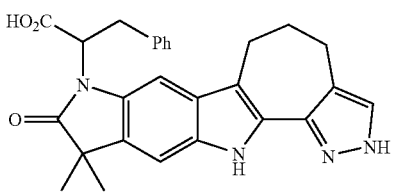
167 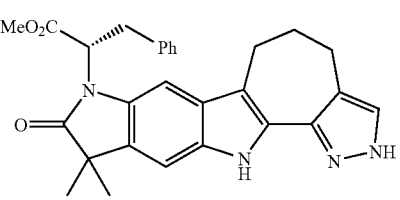

-continued
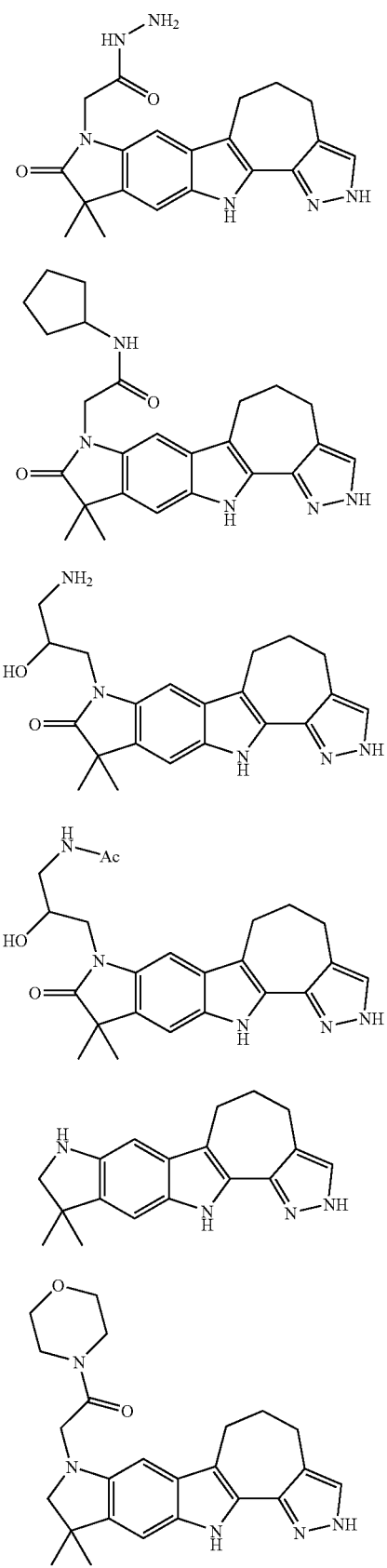
168
169
170
171
172
173
-continued
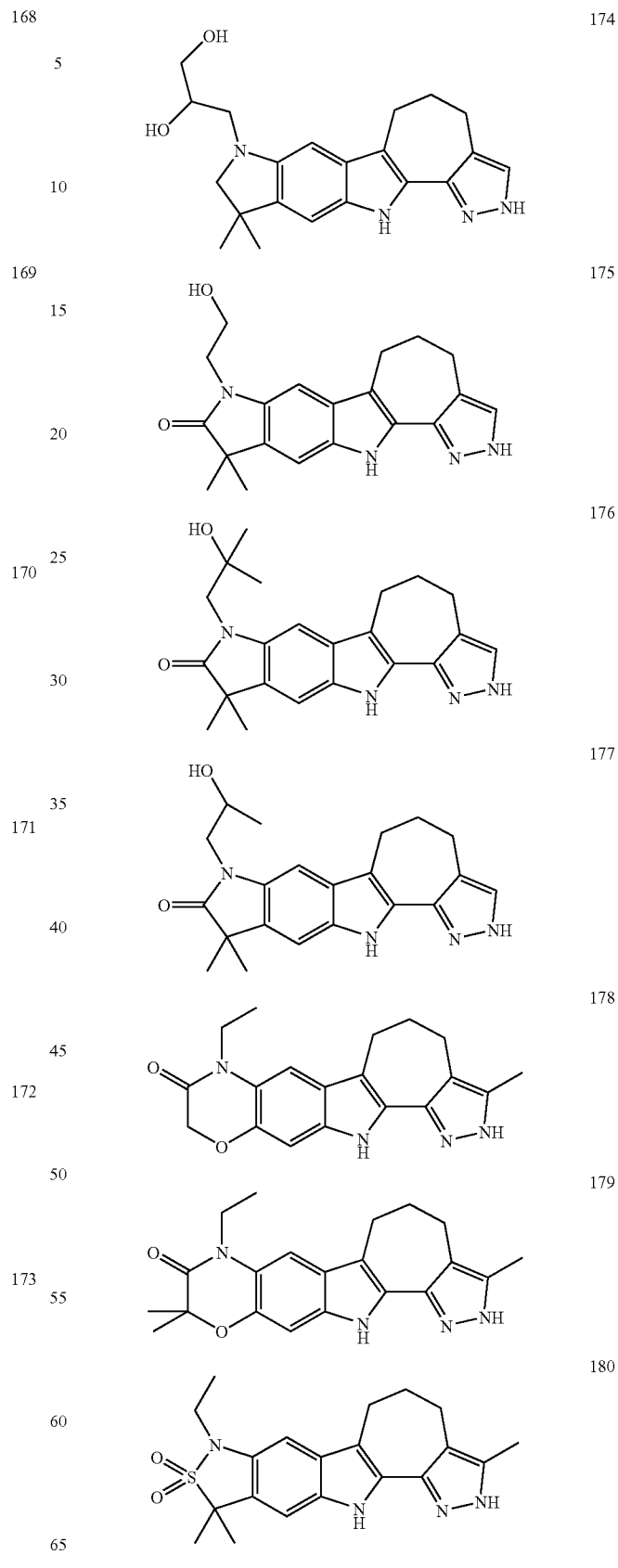
174
175
176
177
178
179
180

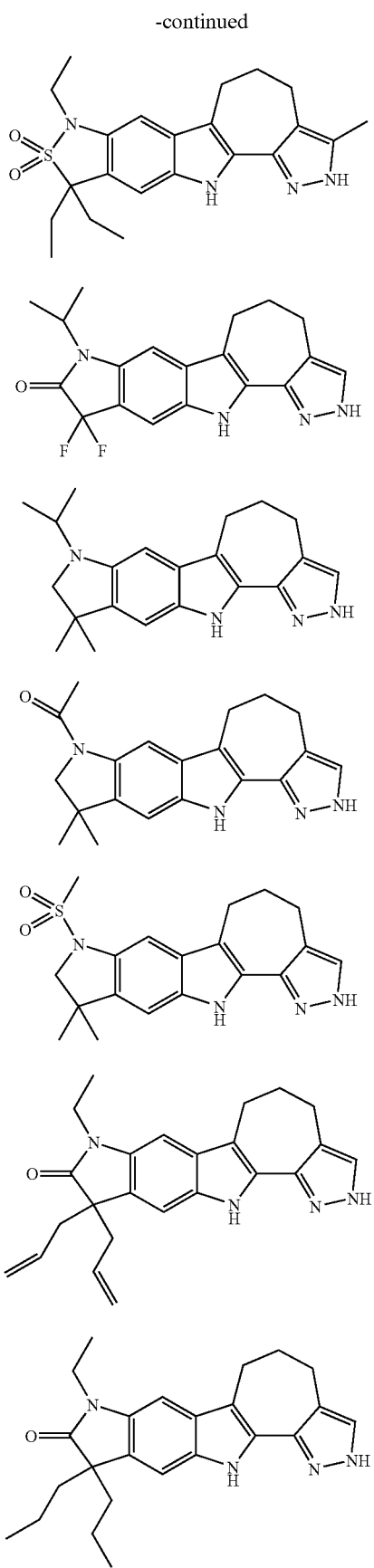
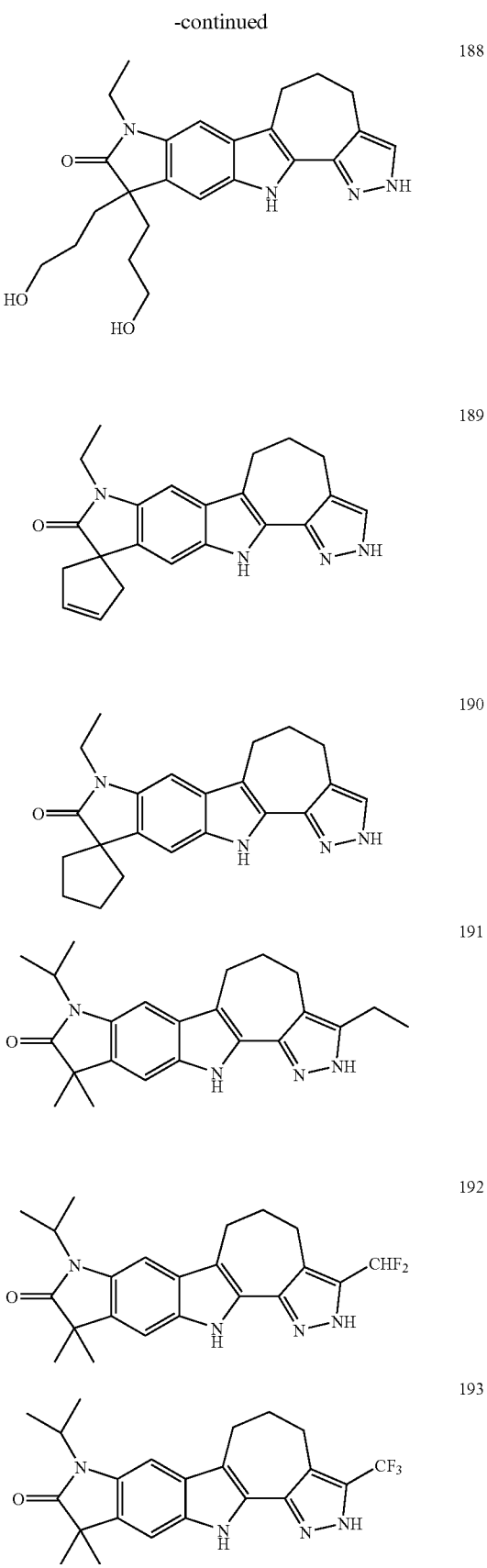

194 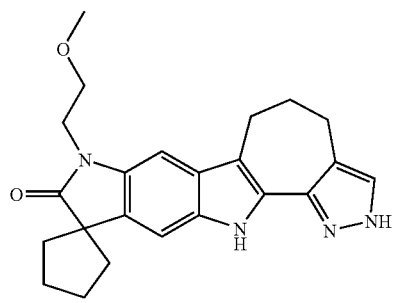
195 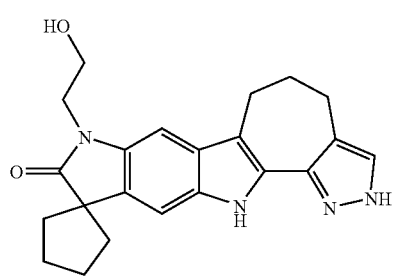
196 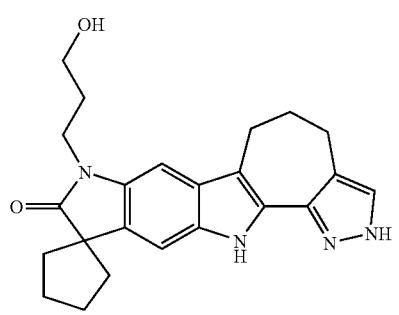
197 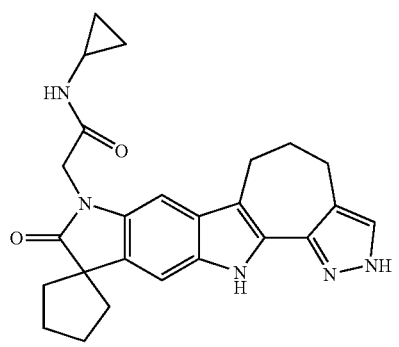
198 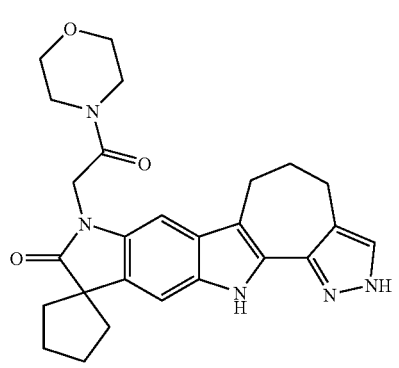
199 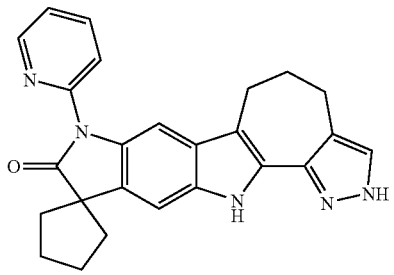
200 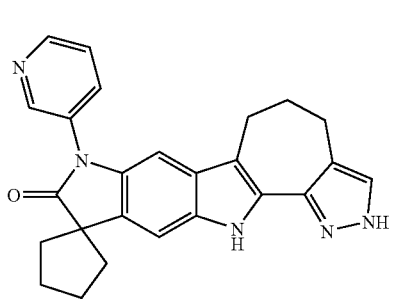
201 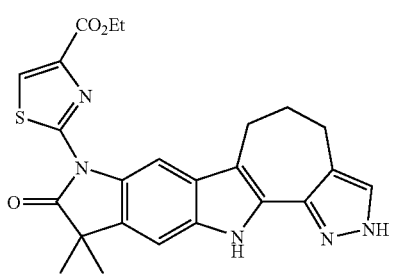
202 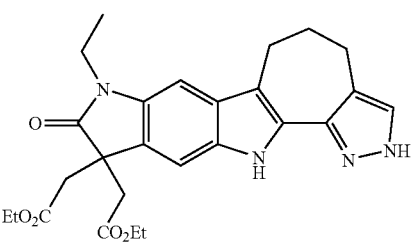
203 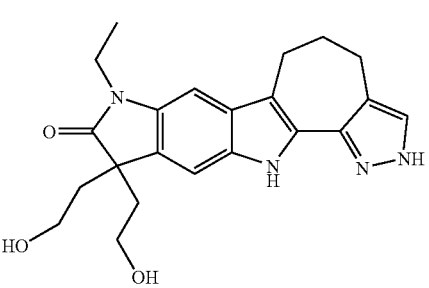

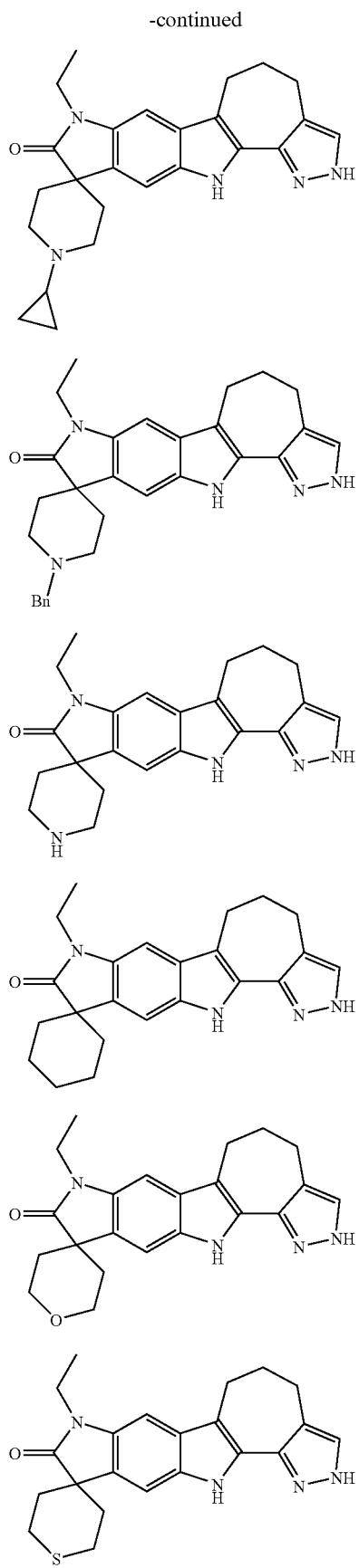
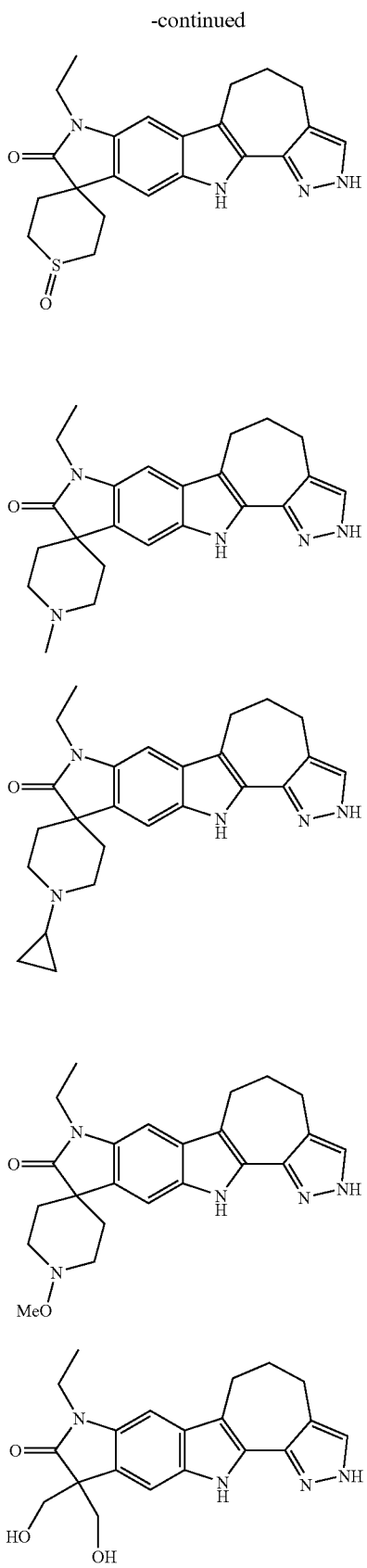

215
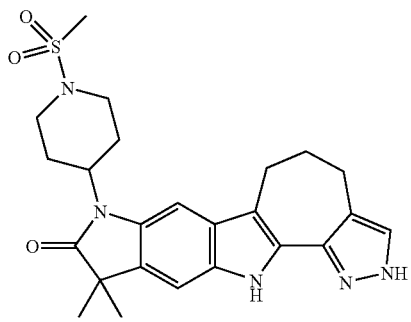
216
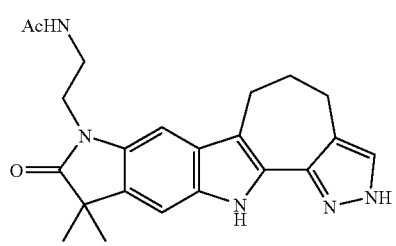
217
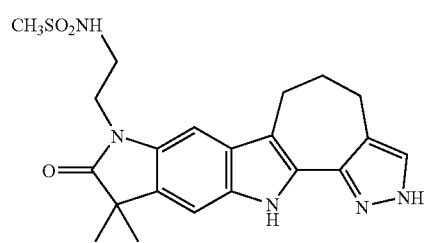
218
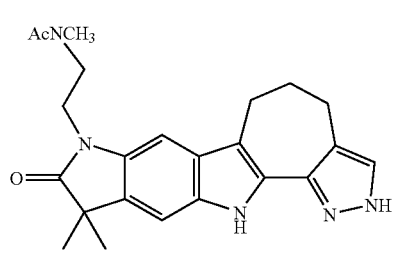
219
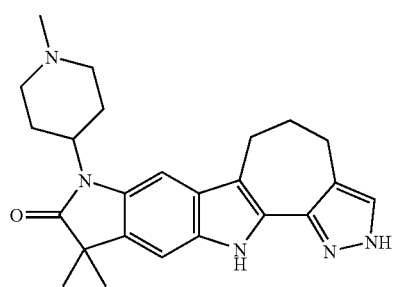
220
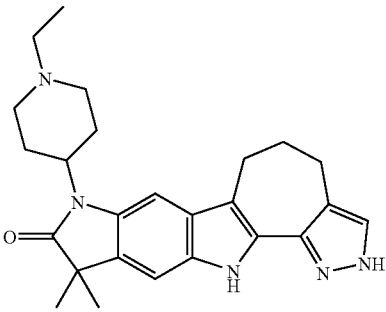
221
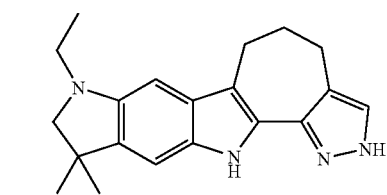
222
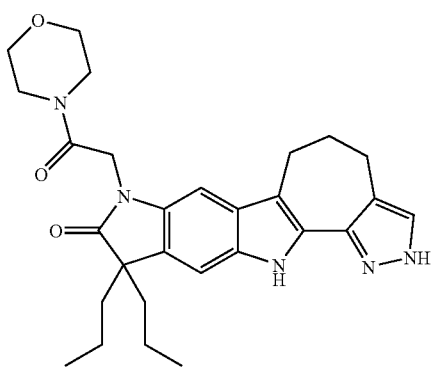
223
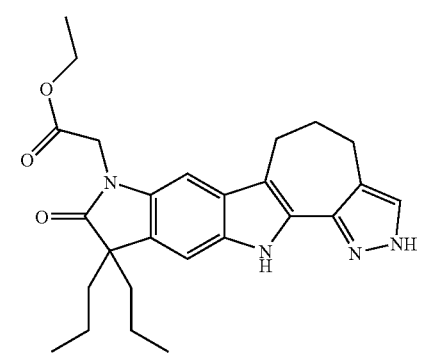
224
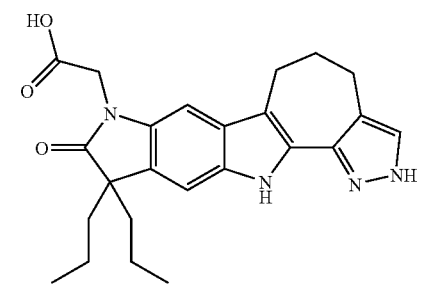

225 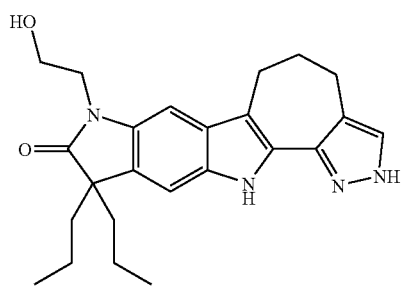
226 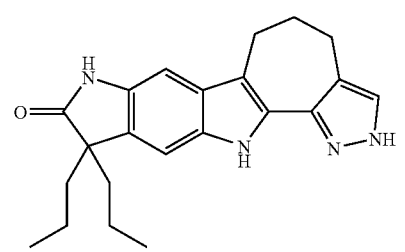
227 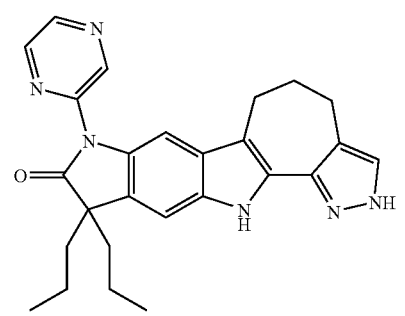
228 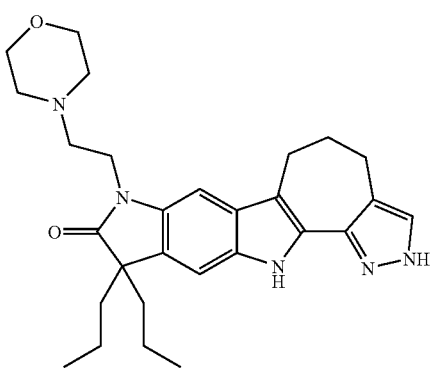
229 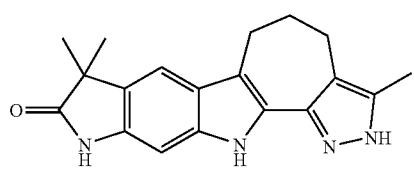
230 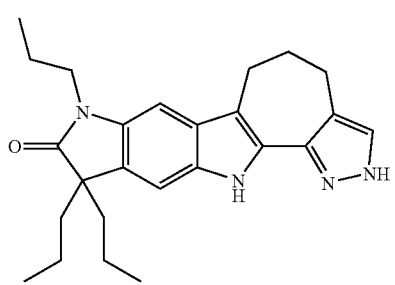
231 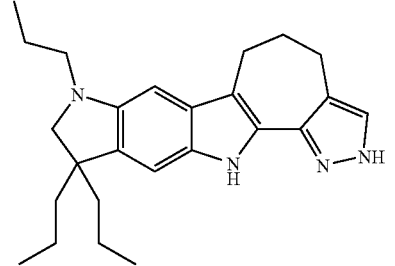
232 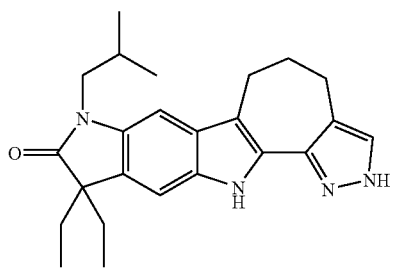
233 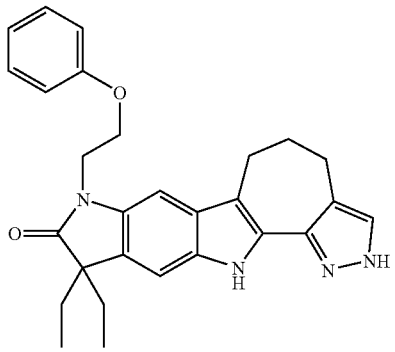
234 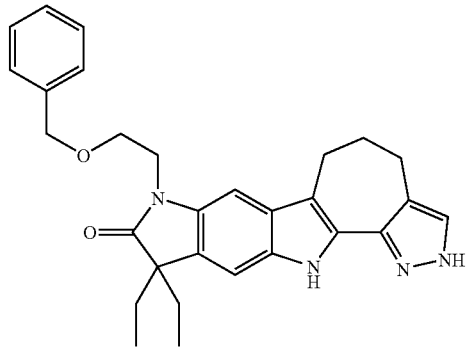

235 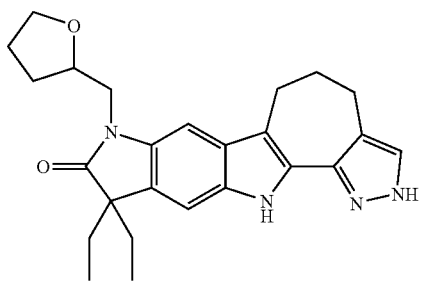
236 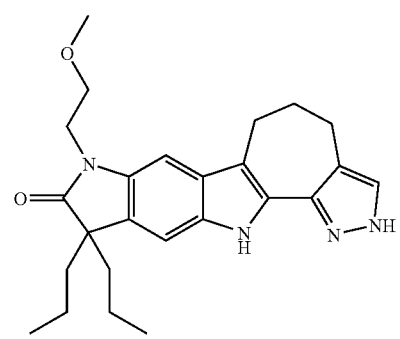
237 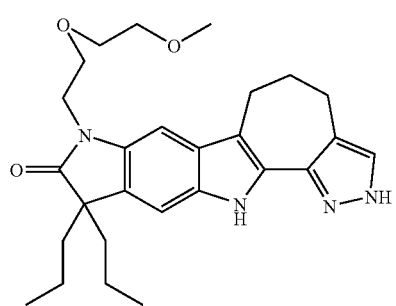
238 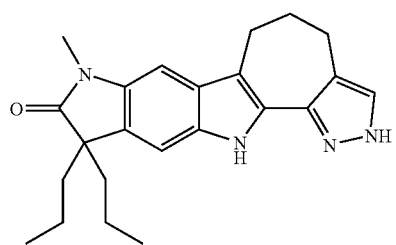
239 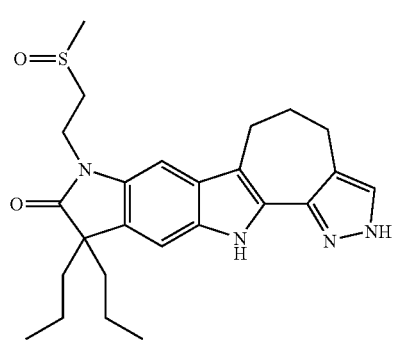
240 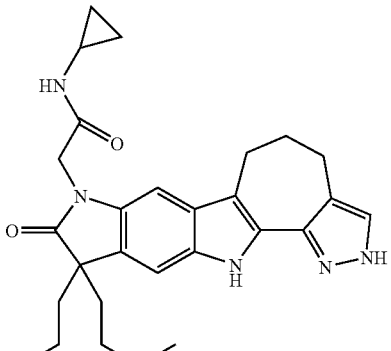
241 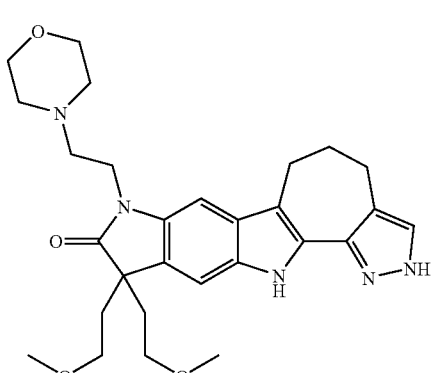
242 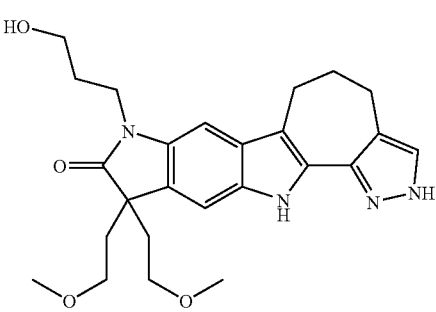
243 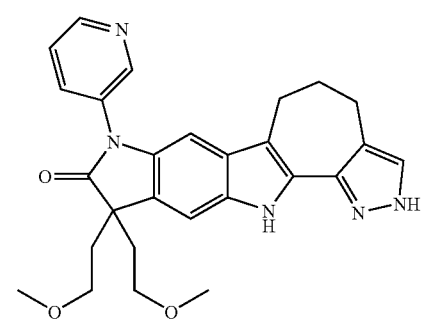
244 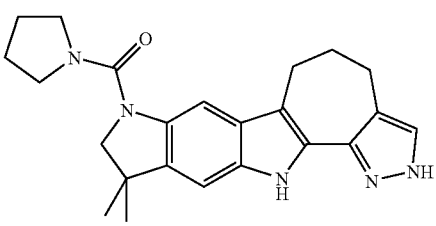

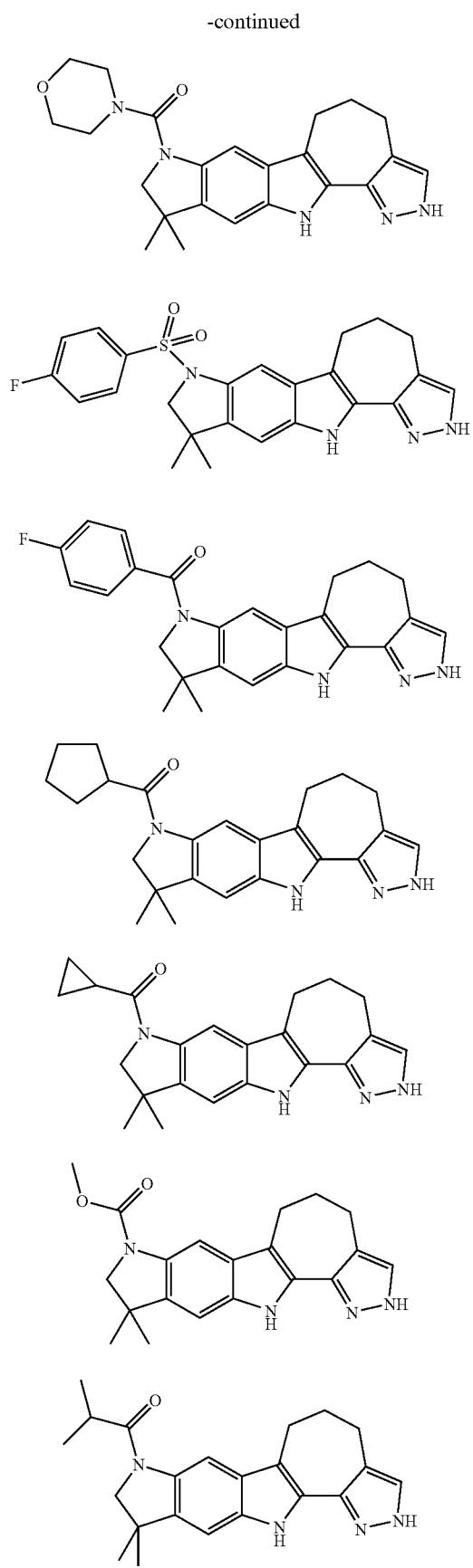
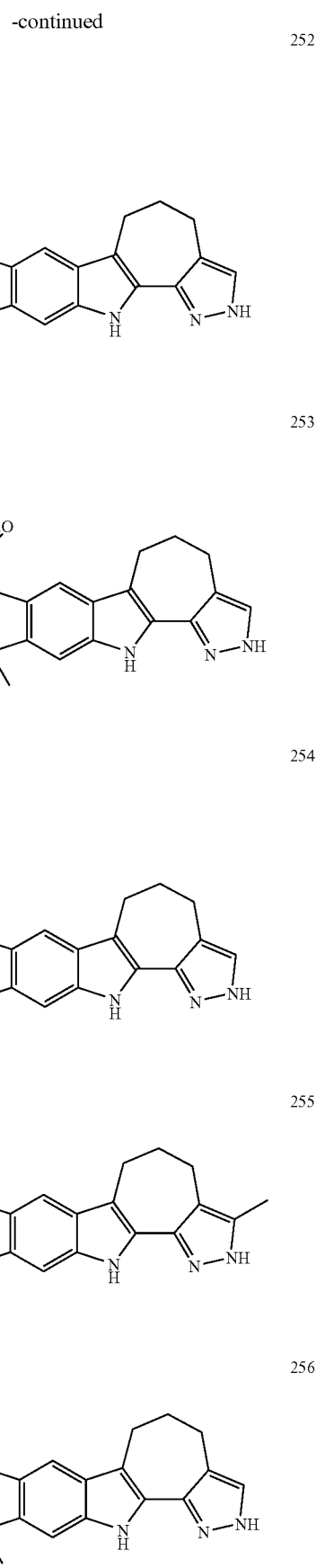

-continued

257

258

259

260

261

-continued

262

263

264

265

-continued

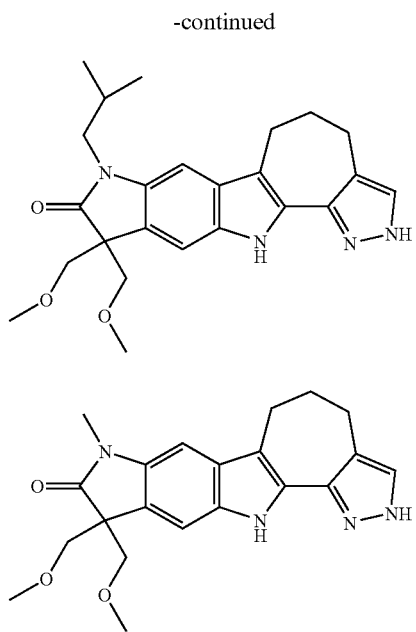

266

267

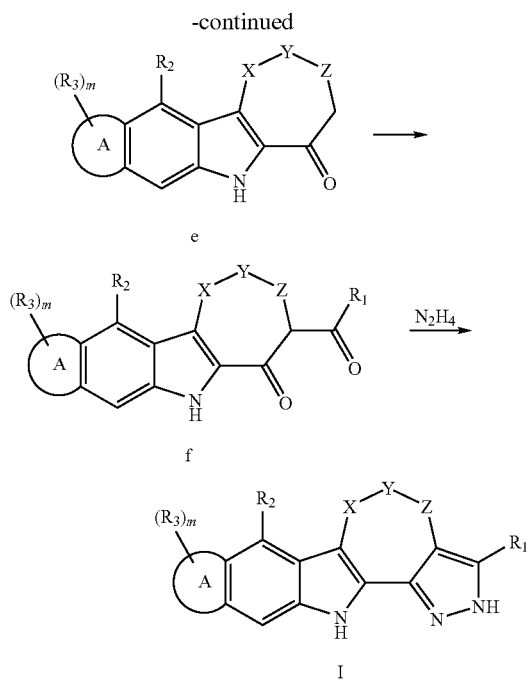

e f

I

Synthesis

Compounds of the invention are prepared using standard organic synthetic techniques from commercially available starting materials and reagents. It will be appreciated that synthetic procedures employed will depend on the particular substituents present and that various protection and deprotection steps that are standard in organic synthesis may be required but may not be illustrated in the following general schemes. In a particular embodiment compounds of the invention are prepared according to the general synthetic scheme 1.

In scheme 1, diazonium salt b is formed by reacting aromatic amine a with sodium nitrite under acidic conditions. The diazonium salt is then coupled to enol c via a Japp-Klingemann reaction to give hydrazone d which undergoes Fischer indole cyclization under acidic conditions to form compound e. Compound e is subsequently reacted with base and the desired $R_1$-containing electrophile to form beta-ketone compound f which is reacted with hydrazine to form the pyrazole-containing final compound of formula I. Suitable $R_1$-containing electrophiles are anhydrides ($R_1$—CO)$_2$O), nitrites $R_1$—CO—CN and acid halides $R_1$—CO—X.

Compounds of formula I in which X is S and Y and Z are independently $CR_4R_4'$, a bond or together $CR_4$=$CR_4$, may be prepared according to the general scheme 2.

Scheme 1

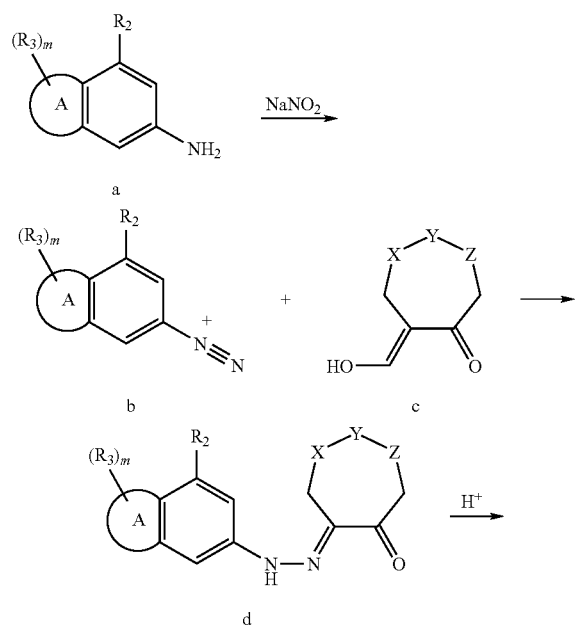

Scheme 2

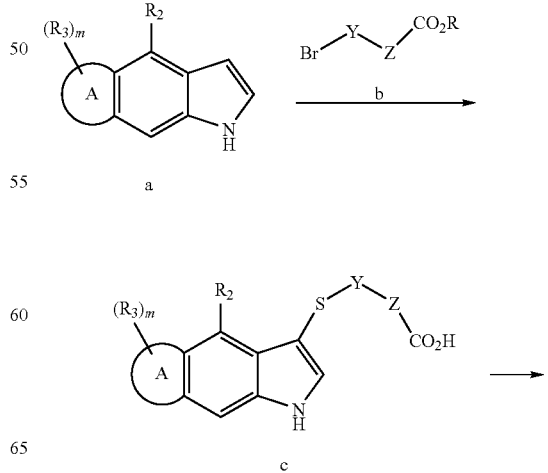

-continued

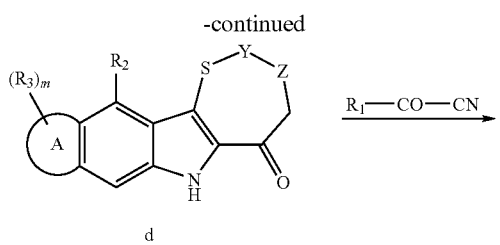

d

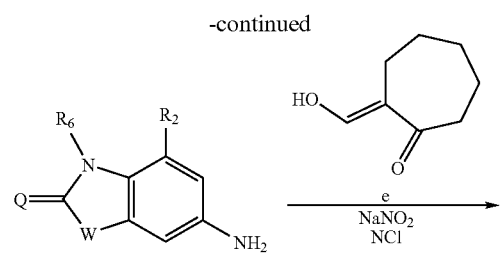

d

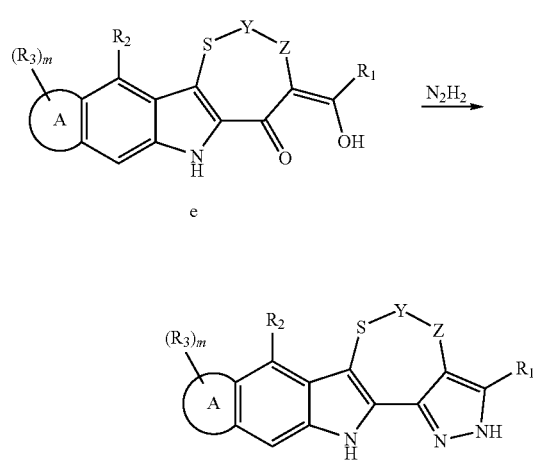

Starting compound a is reacted with thiourea and potassium triiodide followed by then addition of the desired bromo compound b to give intermediate c. Intermediate c is then reacted with polyphosphate ester to give indole-ketone d which is reacted with the desired $R_1$-containing electrophile $R_1$—CO—CN to give the enol e. Final pyrazole formation is achieved by reacting enol e with hydrazine.

Compounds of formula II may be prepared following scheme 3

Scheme 3

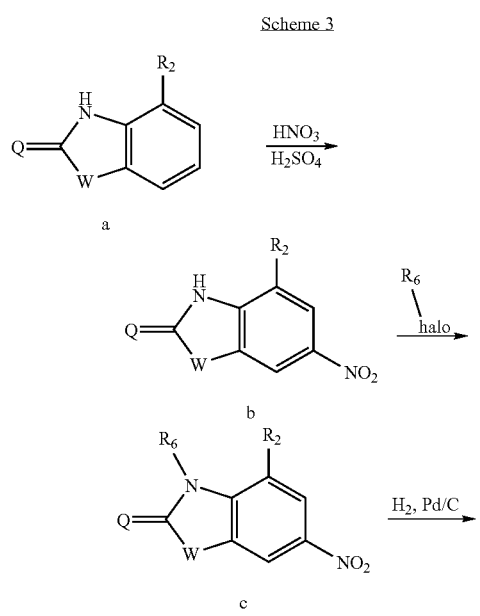

wherein Q, W, $R_1$, $R_2$, and $R_6$ are as defined herein. Starting compound a is nitrated by reacting with nitric acid and sulfuric acid to give b. The $R_3$ substituent is introduced by reacting b with halo-substituted $R_6$ and NaH to give c which is subsequently reduced, for example with palladium catalyst to give amine d. Amine d is then coupled is then coupled to enol e via a Japp-Klingemann reaction to give hydrazone f which undergoes Fischer indole cyclization under acidic conditions to form compound g. Compound g is then reacted with the desired anhydride or formate for $R_1$ in weak base such as LHMDS (lithium hexamethyldisylazide) to give compound h which is subsequently reacted with hydrazine to give the final compound.

Compounds of formula II in which ring A is a lactam (e.g. Q is O) may be reduced with a suitable reducing agent such as lithium aluminum hydroxide to give compounds in which Q is $H_2$ (e.g. two hydrogens). Alternatively, compounds of formula II in which Q is $H_2$ may be prepared according to scheme 3 in which compound a is reduced for example with $BH_3$.THF complex prior to introducing $R_6$ by coupling with a halo-substituted & group.

When compounds of the formula II have H at $R_1$, an alternative pyrazole formation procedure can be followed as illustrated in scheme 4.

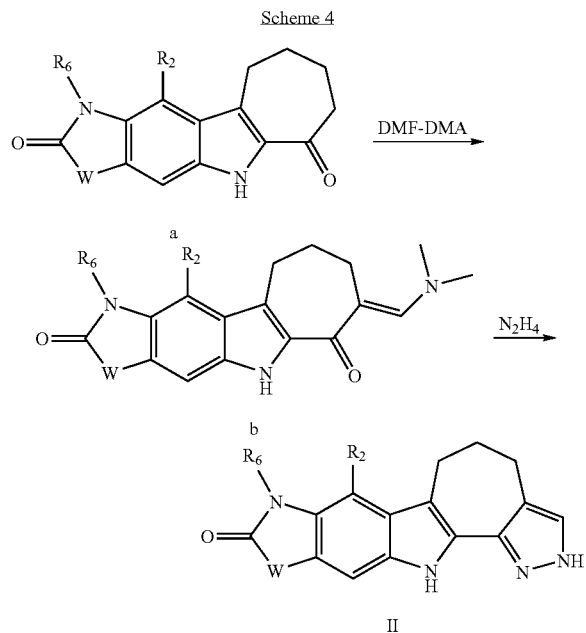

Scheme 4

Intermediate a is reacted with N,N-dimethylformamide dimethylacetal (DMF-DMA) to give enamine b which is reacted with hydrazine to give the final compound of formula II.

Utility

The compounds of the invention inhibit Aurora kinase signalling, in particular the phosphorylation of Aurora kinases. Accordingly, the compounds of the invention are useful for inhibiting all diseases associated with the abherant signalling, overexpression and/or amplification of Aurora kinases. Alternatively, compounds of the invention are useful for arresting cells in the G2 phase of the cell cycle. More specifically, the compounds can be used for the treatment of cancers associated with abherant signalling, amplification and/or overexpression of Aurora kinases. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma. In particular, compounds of the invention are useful ofr treating colorectal, ovarian, gastric, breast (such as invasive duct adenocarcinomas thereof), renal, cervical, melanoma, lymphoma, bladder, pancreatic, prostate, lung, CNS (such as neuroblastoma), cervical and leukemic cancers.

The compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered with a cytostatic compound selected from the group consisting of cisplatin, doxorubicin, taxol, taxotere and mitomycin C. In a particular embodiment, the cytostatic compound is doxorubicin.

Compounds of the invention may be coadministered with other compounds that induce apoptosis such as ligands to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. In an embodiment, the death receptor ligand is TNF-α. In a particular embodiment, the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

The compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

The invention also provides pharmaceutical compositions or medicaments containing the compounds of the invention and a therapeutically inert carrier, diluent or excipient, as well as methods of using the compounds of the invention to prepare such compositions and medicaments. Typically, the compounds of formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range anywhere from about 3 to about 8. Formulation in an acetate buffer at pH 5 is a suitable embodiment. In an embodiment, the inhibitory compound for use herein is sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit Aurora kinase signalling. Such amount may be below the amount that is toxic to normal cells, or the mammal as a whole. Alternatively, "effective amount" of a compound of the invention may be the amount necessary to inhibit the proliferation of cancer cells or the amount required to inhibit the growth of tumours. Generally, the initial pharmaceutically effective amount of the compound of the invention administered parenterally per dose will be in the range of about 0.01-1000 mg/kg, for example about 0.1 to 100 mg/kg of patient body weight per day, with the typical initial range of compound used being 0.3 to 50 mg/kg/day. Oral unit dosage forms, such as tablets and capsules, may contain from about 0.5 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

EXAMPLES

The invention will be more fully understood by reference to the following examples. They should not, however, be construed as limiting the scope of the invention. Reagents and solvents were obtained from commercial sources and used as received. ISCO chromatography refers to use of a pre-packed silica gel columns on a Companion system by Teledyne-Isco, Inc. Lincoln, Nebr. The identity and purity of all compounds were checked by LCMS and $^1$H NMR analysis.

Abbreviations used herein are as follows:
ACN: acetonitrile;
9-BBN: 9-borabicyclo[3.3.1]nonane;
Chg: cyclohexylglycine;
DCM: dichloromethane;
DEAD: diethylazodicarboxylate;
DIBAH: diisobutyl aluminum hydride;
DIPEA: diisopropylethylamine;
DMAP: 4-dimethylaminopyridine;
DME: 1,2-dimethoxyethane;
DMF: dimethylformamide;
DMSO: dimethylsulfoxide;
EDC: 1-ethyl-3-(3-dimethylaminopropyl)carbodiimide;
EEDQ: 2-ethoxy-1-ethoxycarbonyl-1,2-dihydroquinoline;
LCMS: liquid chromatography mass spectrometry;
LHMDS: lithium hexamethyldisylazide;
HATU: O-(7-Azobenzotriazol-1-yl)-1,1,3,3-tetramethyluronium hexafluorophosphate;
HOBt: N-Hydroxybenzotriazole;
HBTU: 2-(1H-Benzotriazol-1-yl)-1,1,3,3-tetramethyluronium hexafluorophosphate;
HPLC: high performance liquid chromatography;
NBS: N-bromosuccinamide;
NMO: N-methylmorpholine N-oxide;
SEM-Cl: 2-(trimethylsilyl)ethoxymethyl chloride;

TASF: tris(dimethylamino)sulfonium difluorotrimethylsilicate;
TBAF: tetrabutylammonium fluoride;
TEBA: triethylbenzylammonium chloride;
TEA: triethylamine;
TFA: trifluoroacetate;
THF: tetrahydrofuran;
TMS-Cl: chlorotrimethylsilane;

Example 1

5-amino-1-ethyl-3,3-dimethylindolin-2-one

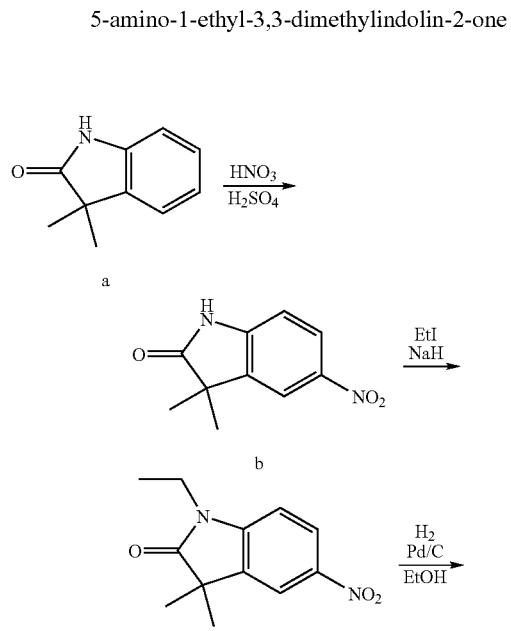

Compound a (38.4 g), prepared according to the procedures described in Robertson et. al. (J. Med. Chem. 29(10) 1832-1840 (1986)), was dissolved in 300 ml of conc. sulfuric acid using mechanical stirring and cooled using a −40° C. bath until the reaction became very thick. A solution of 10.1 ml of fuming nitric acid and 50 ml of conc. sulfuric acid was added dropwiseover 30 min. The reaction was allowed to warm to ambient temperature with stirring for 12 hours. The reaction mixture was poured into ice water and compound b was collected by filtration and dried (yield: 31 g).

Compound b (9.38 g) was dissolved in 100 ml of DMF and added dropwise to a stirred suspension of sodium hydride (2 g) in 25 ml of DMF. When hydrogen evolution ceased, 4 ml of ethyl iodide was added and the reaction mixture stirred until reaction was complete by tlc. The reaction was partitioned between ethyl acetate and water. The organic extract was concentrated and the crude compound c was recrystallized from ether/hexane (yield: 8.52 g).

Compound c (8.25 g) was reduced under 1 atmosphere of hydrogen in a suspension of 1 g of 10% Pd/C catalyst in 100 ml of methanol with stirring for 18 hours. The catalyst was removed by filtration and evaporation of the solvent gave 5.8 g of compound d.

Example 2

Synthesis of Compound 32

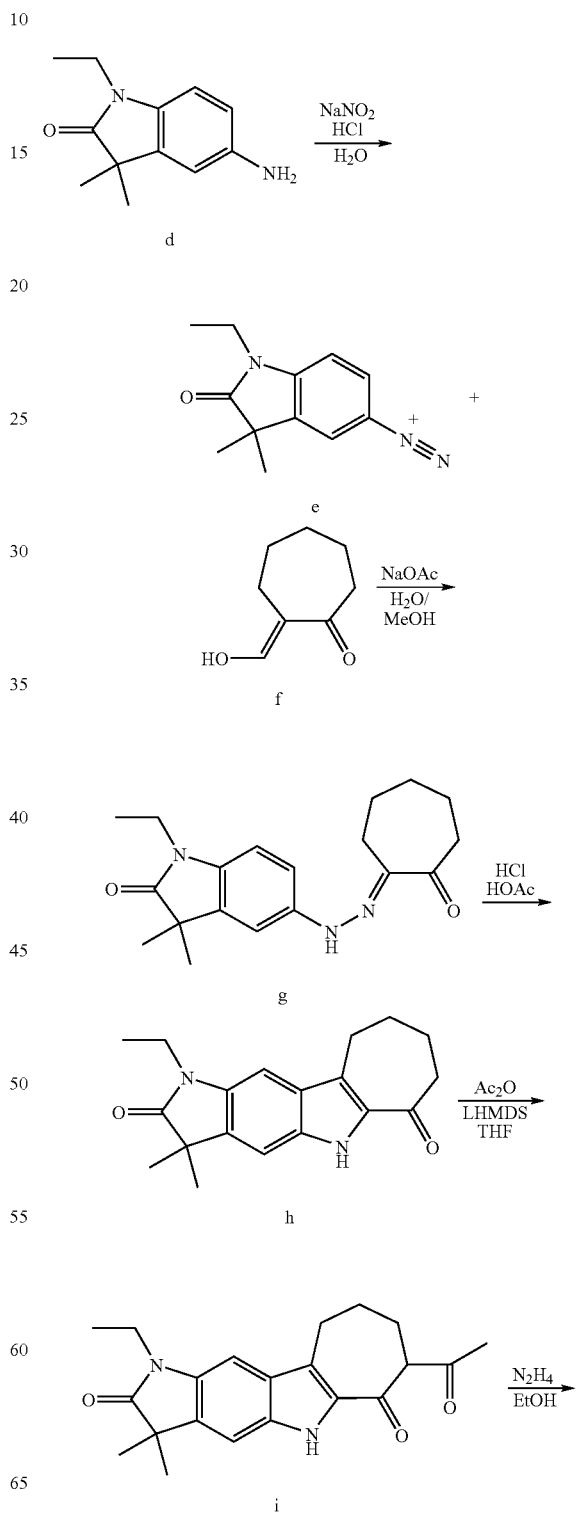

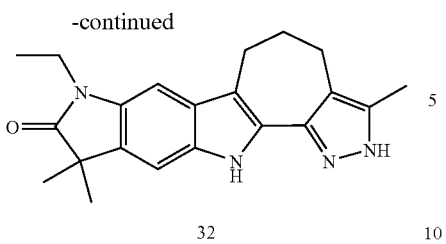

32

Compound f (2-(hydroxymethylene)cycloheptanone) was prepared by the following procedure. To a cold (0° C.) solution of 20 ml of cycloheptanone and 50 ml of dry THF was added 190 ml of lithium bis-trimethylsilyl amide solution (1M in THF) over 5 minutes. Ethyl formate (13.8 g) was then added dropwise over 15 minutes and stirring continued at 0° C. for 3 hours by which time the reaction had solidified. The reaction mixture was partitioned between water and hexane to remove unreacted cyclohepatnone. The aqueous phase was acidified with 10% aqueous citric acid and the product extracted into ethyl acetate, washed with water, brine, dried over sodium sulfate and concentrated to give 23.37 g of f as an orange oil used in the preparation of compound g.

Compound d (3.5 g) was suspended in 75 ml of water and 2.33 ml of conc. HCl added. The resulting solution was cooled to 5° C. and a solution of sodium nitrite (1.55 g) in 20 ml of water added dropwise over 10 minutes with stirring. This diazonium (e) solution was added slowly to a cold (0° C.) dispersion of compound f (2.89 g) and sodium acetate (6.9 g) in 200 ml of water and 50 ml of methanol. The initial redish oil crystallized after stirring for 2 hours at 0° C. to give g as a yellow solid which was collected by filtration. Yield: 4.68 g.

To a solution of g (4.68 g) in 300 ml of conc. acetic acid was added 20 ml of conc. HCl and the reaction mixture heated to 70° C. for 20 minutes. The reaction was cooled and 80% of the solvent removed by rotary evaporation under vacuum. The mixture was partitioned between 9:1 ethyl acetate:hexane and water. The organic phase was washed with water, saturated sodium bicarbonate, and brine then dried over sodium sulfate, filtered and concentrated to give 3.9 g of crude product which was recrystallized from ethyl acetate to give 2.25 g of h.

Compound h (2.9 g) was dissolved in 300 ml of dry THF and stirred mechanically. Lithium bis-trimethylsilylamide (75 ml of 1M sol in THF) was added in one shot and the mixture stirred for 15 minutes. Acetic anhydride (10 ml) was added and the viscous mixture stirred for 15 minutes. This solution of crude i was added to a solution of 25 ml of hydrazine in 400 ml of dry ethanol and the solution stirred overnight. The reaction was concentrated then partitioned between ethyl acetate and water. The organic phase was washed with water and brine, dried with sodium sulfate, filtered and concentrated. The product was purified by flash chromatography to give 2.01 g of final compound 32.

Example 3

Synthesis of Compound 19

DMF (10 ml) was added to 0.6 g of 60% NaH (15.12 mM) in a 100 mL round bottom flask under N₂. Added to the flask was 1.29 g of 5-nitro-2-benzimidazolinone (7.20 mM) in 10 mL DMF and rinsed with 10 mL more DMF. The solution was stirred 25 minutes and 10.22 g MeI (72 mM) was added and then stirred a further 3 hours. HCl (200 mL, 1 M) was added to the solution and then was extracted with EtOAc, washed with brine, and dried over MgSO₄ and then concentrated in vacuo and flashed 0 to 100% EtOAc in hexanes to give 1.4 g of 1,3-dimethyl-5-nitro-1H-benzo[d]imidazol-2(3H)-one (93% yield).

1.4 g of 1,3-dimethyl-5-nitro-1H-benzo[d]imidazol-2(3H)-one was suspended in 100 mL EtOH and 100 uL conc. HCl and 2 scoops of 10% Pd/C was added and an H₂ balloon was attached and stirred overnight. The solution was then filtered through celite and concentrated in vacuo to give 1.27 g of the amine 5-amino-1,3-dimethyl-1H-benzo[d]imidazol-2(3H)-one (106% yield).

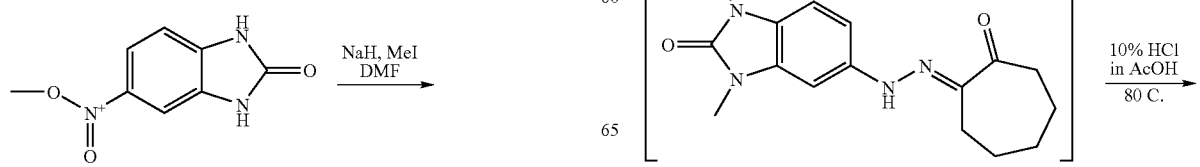

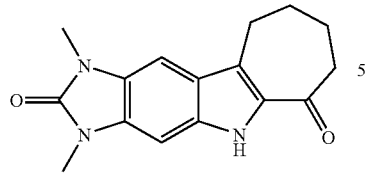

1.26 g of 5-amino-1,3-dimethyl-1H-benzo[d]imidazol-2 (3H)-one (7.11 mM) was dissolved in 50 mL H$_2$O and 0.95 mL conc. HCl, cooled to 0 C and 0.59 g of NaNO$_2$ (8.53 mM) in 3 mL H$_2$O was added and stirred 30 minutes. 1.19 g of (Z)-2-(hydroxymethylene)cycloheptanone (8.53 mM) and 2.62 g of NaOAc (32 mM) was dissolved in 50 mL MeOH and 50 mL H$_2$O and cooled to 0 C. The diazotized solution was added to the cycloheptanone mixture and let stir 4 hours followed by addition of 350 mL 1 M HCl to the solution which was then extracted with EtOAc, washed with EtOAc with brine, dried over MgSO$_4$ and concentrated in vacuo and flashed using 0 to 100% EtOAc in Hexanes. The purified hydrazone was dissolved in 50 mL of 10% conc. HCl in AcOH and heated to 80 C and let stir ON. Solvents were removed in vacuo and flashed 0 to 100% in EtOAc in Hexanes to give 0.28 g of the tetracycle (14% yield).

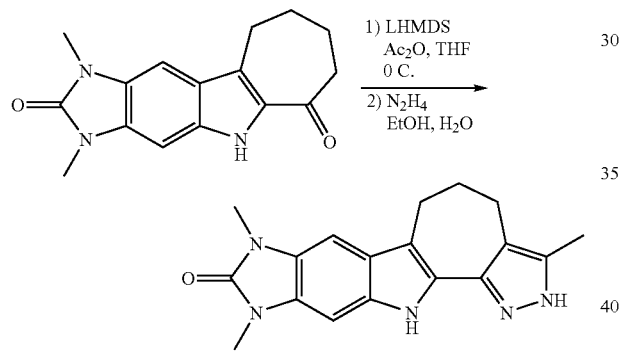

0.28 g of the tetracycle (0.99 mM) was dissolved in THF and cooled to 0 C and 3.96 mL of 1 M LHMDS (3.96 mM) was added and let stir 1 hour. 0.4 g of AC$_{20}$ (3.96 mM) was added and let stir 4 hours at RT. 2 mL of N$_2$H$_4$ in 5 mL H$_2$O and 10 mL EtOH was added and let stir for 2 days. Solvent was then removed in vacuo followed by HPLC purification to give 17.7 mg of final compound 19 (5% yield).

Example 4

Synthesis of Compound 16

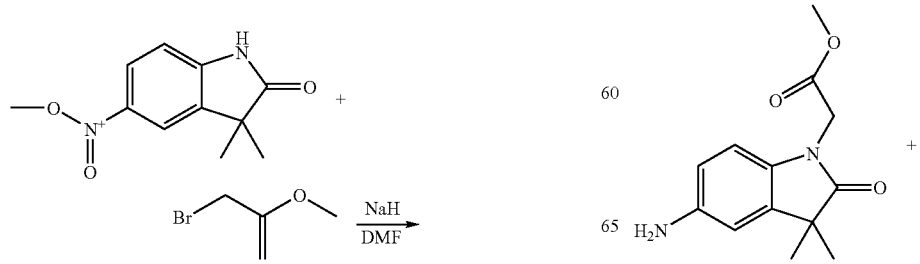

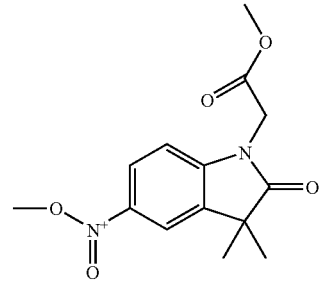

20 mL of DMF to was added 0.87 g of 95% NaH (34.47 mM) in a 250 mL round bottom flask under N$_2$. 6.46 g of the oxindole (31.34 mM) in 30 mL DMF was then added. The solution was stirred 20 minutes and to it was added 5.27 g methylbromoacetate (34.47 mM) and let stir over night. After concentration in vacuo was added 200 mL 1 M HCl and then extracted with EtOAc, washed with brine, dried over MgSO4, concentrated in vacuo and flashed 0 to 50% with EtOAc in Hexanes to yield 8.14 g of methyl 2-(3,3-dimethyl-5-nitro-2-oxoindolin-1-yl)acetate (93% yield)

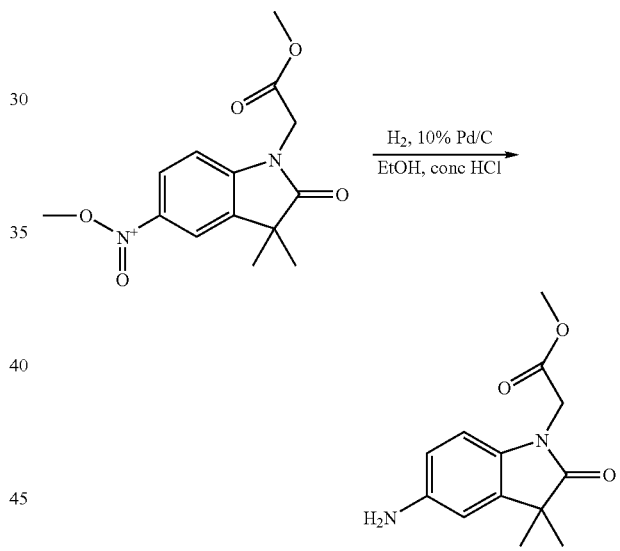

2.3 g of methyl 2-(3,3-dimethyl-5-nitro-2-oxoindolin-1-yl)acetate (8.3 mM) was suspended in 100 mL EtOH, 0.2 mL conc. HCl and approximately 100 mg of 10% Pd/C added, a H$_2$ balloon was attached and the reaction stirred over night. The solution was then filtered through celite and concentrated in vacuo to give the aminoindolone intermediate (98% yield).

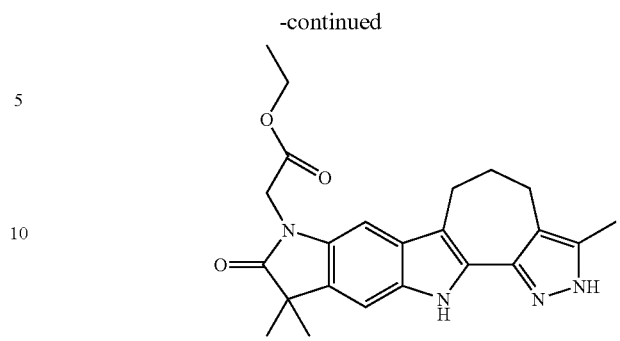

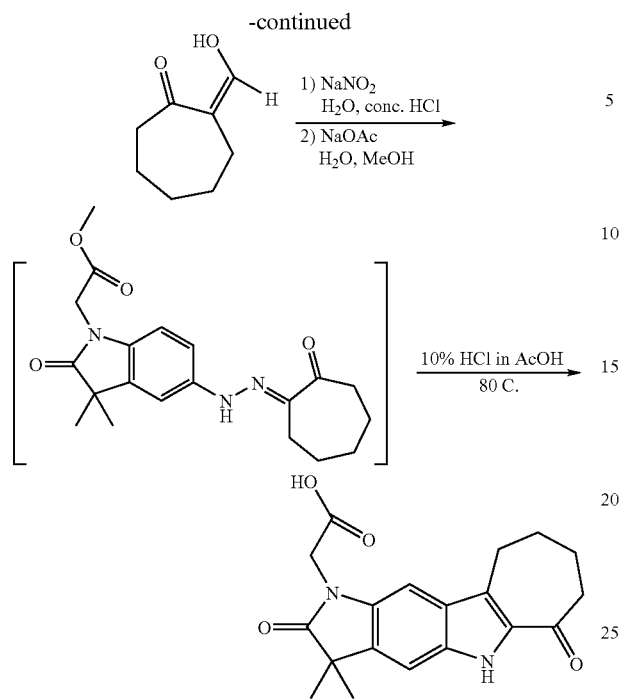

2.0 g of the aminoindolone intermediate (8.05 mM) was dissolved in 50 mL H₂O and 1.15 mL conc. HCl and cooled to 0 C. 0.67 g of NaNO₂ (9.67 mM) in 5 mL H₂O was then added and the reaction stirred for 45 minutes. 1.24 g of the 2-(hydroxymethylene)cycloheptanone (8.86 mM) and 2.97 g NaOAc (36.25 mM) was dissolved in 100 mL MeOH and 250 mL H₂O and cooled to 0 C as well. The diazotized indolone was added to the 2-(hydroxymethylene)cycloheptanone mixture and stirred for 2 hours. 350 mL of 1 M HCl was added and the mixture extracted with EtOAc, washed EtOAc. The EtOAc phase was washed with brine, dried over MgSO₄, concentrated in vacuo and flashed 0 to 50% EtOAc in Hexanes. The resulting hydrazone was dissolved in 100 mL of 10% conc. HCl in AcOH and heated to 80 C with stirring for 2 hours. Solvents were removed in vacuo and flashed 0 to 50% EtOAc in Hexanes to give 0.76 g of the tetracycle compound (28% yield).

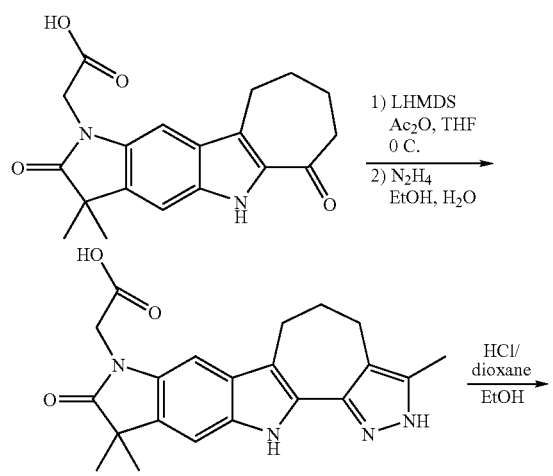

0.40 g of the tetracycle (1.18 mM) was dissolved in THF and cooled to 0 C and 4.52 mL of 1 M LHMDS (4.52 mM) was added and the reaction stirred for 1.5 hours. 0.46 g of Ac₂O (4.52 mM) was added and the solution stirred for 3.5 hours at RT followed by addition of 1 mL N₂H₄ in 5 mL H₂O and 5 mL EtOH and stirred overnight. Solvents were removed in vacuo and half of the product was dissolved in 20 mL EtOH and 10 mL 4N HCl/dioxane and stirred for 6 hours. Solvents were then removed in vacuo followed by HPLC purification to give 35.9 mg of compound 16 (15% yield). The remaining half of the product was purified by HPLC to give compound 20.

Example 5

Synthesis of Compound 2

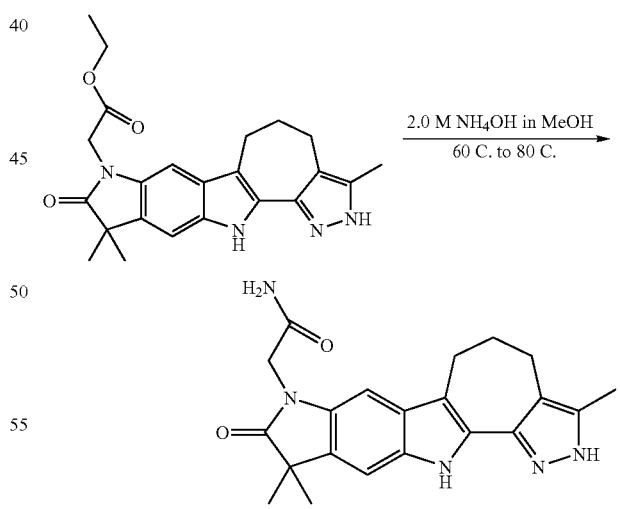

20.1 mg of compound 16 (0.049) was dissolved in 2.0 M N₄OH in MeOH (anh) in a sealed vial under N₂ and stirred at 60 C for 1.5 hours then heated to 80 C and stirred overnight. Solvent was removed solvent in vacuo and fresh NH₄OH in MeOH was added and stirred five days at 80 C. Solvent was removed in vacuo followed by HPLC purification to give 5.3 mg of compound 2 (19% yield).

Example 6

Synthesis of Compound 13

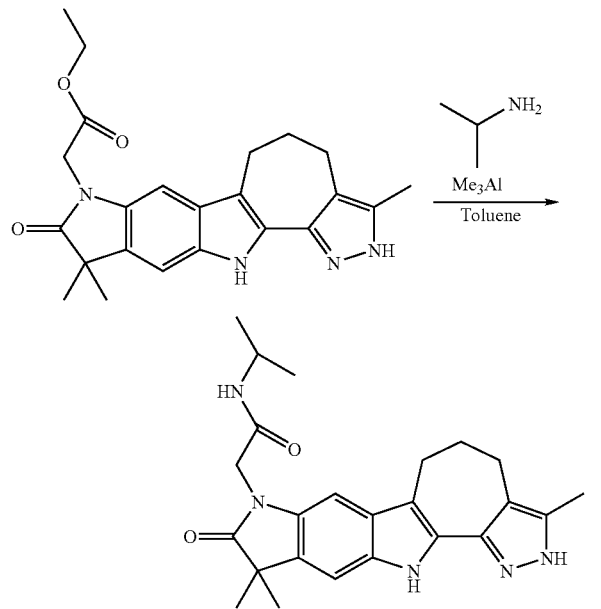

29.6 mg of isopropylamine (0.5 mM) was dissolved in 5 mL toluene and 1.0 mL Me₃Al (1.0 mM) was added and let stir 20 minutes followed by addition of 40 mg of compound 16 (0.1 mM) and let stir 2 days (48 hrs). The solution was diluted with citric acid and extracted with EtOAc, dried over MgSO₄ and solvent was removed in vacuo to give 4.3 mg of compound 13 (10% yield).

Example 7

Synthesis of Compound 31

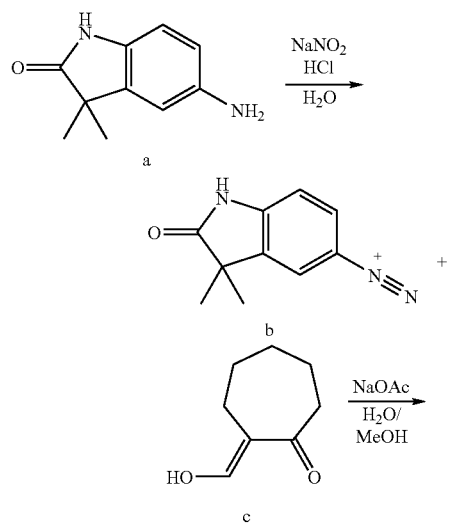

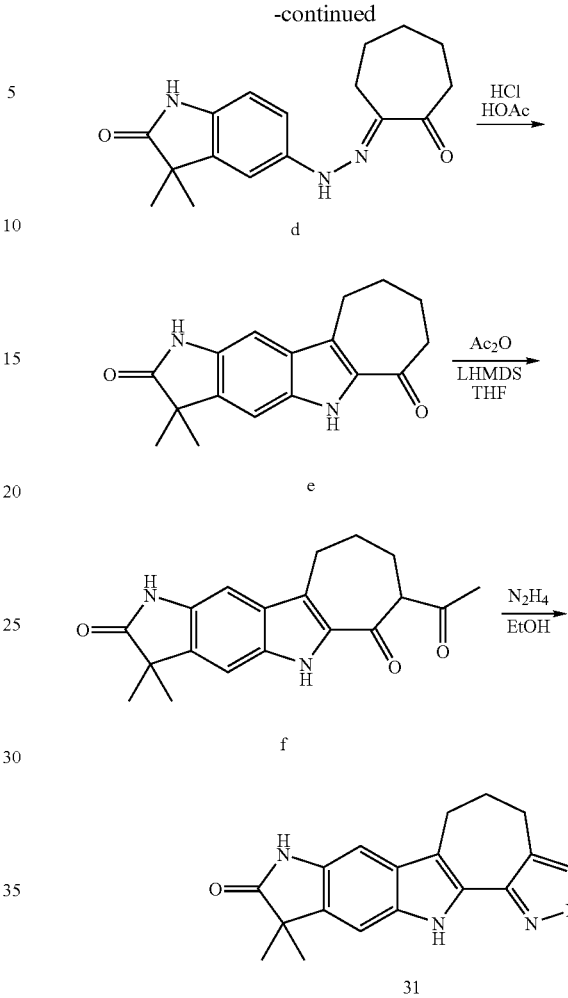

Compound 31 was prepared using similar procedures as those for preparing compound 32 (example 2). Starting amine a (460 mg) was prepared by reducing the corresponding nitro compound with Pd catalyst and was then treated with sodium nitrate to give diazonium compound b which in turn was coupled to 2-(hydroxymethylene)cycloheptanone c to give 690 mg of the hydrazone d. Fischer indole synthesis with hydrazone d in acid gave 510 mg of indole e which was reacted with acetic anhydride and then hydrazine to give 130 mg of compound 31.

Example 8

Synthesis of Compound 48

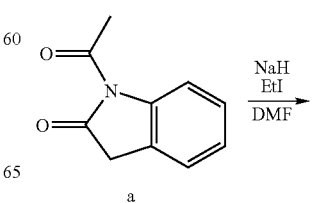

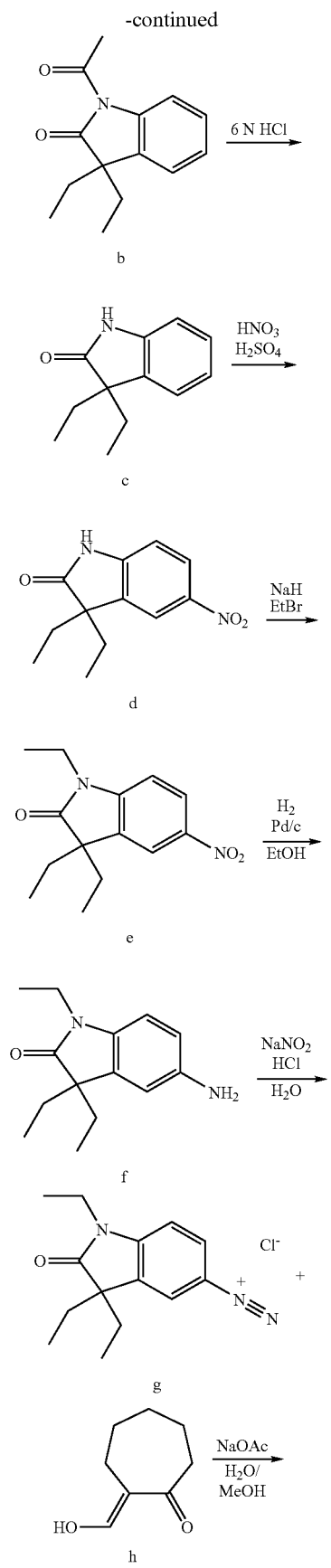

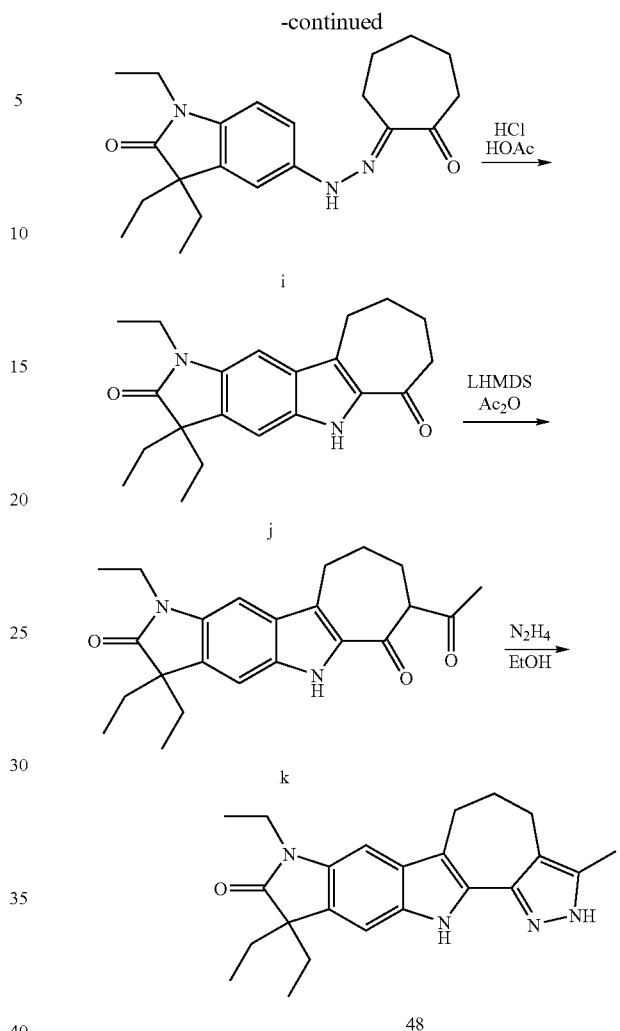

Sodium Hydride (60% dispersion in oil, 4.8 g) was triturated with hexane and decanted twice to remove the oil then suspended in 30 ml of dry DMF with stirring and cooled to 0° C. A solution of 10 g of N-acetyloxindole a in 148 ml of dry DMF was added dropwise over one hour. When hydrogen evolution ceased, 11.4 ml of iodoethane was added over 10 minutes. The reaction mixture was allowed to warm to room temperature and when complete by tlc was poured into ice water and the product extracted with ethyl acetate. The ethyl acetate solution was dried over sodium sulfate, filtered and concentrated and the product purified by automated flash chromatography on silica to give 13.2 g of compound b as a colorless oil.

Compound b (8.43 g) was refluxed in 6N HCl for 2 hrs. at which time a white precipitate had formed and tlc showed the reaction to be complete. The reaction mixture was cooled and the precipitate collected by vacuum filtration, washed with water and dried to give 6.39 g of compound c as a white solid.

Compound c (6.37 g) was suspended in 52 ml of sulfuric acid and cooled to −40° C. with mechanical stirring on a dry ice/acetonitrile bath. A solution of 1.43 ml of fuming nitric acid in 10.5 ml of sulfuric acid was added over 10 minutes. The reaction was allowed to warm to room temperature. After 6 hrs., the reaction mixture was poured into ice and the precipitated product collected by vacuum filtration. The product was washed with water 2× and vacuum dried to give 7.58 g of compound d.

Compound d (3.46 g) was combined with 9.64 g of cesium carbonate and 1.78 ml of iodoethane in 41 ml of DMF and stirred at 80° C. for 6 hrs. An additional 1.0 ml of iodoethane was added and the reaction mixture maintained at 80° C. with stirring overnight. The reaction was cooled and filtered then partitioned between ethyl acetate and water, washed with brine, dried over magnesium sulfate, filtered and concentrated to give 1.76 g of compound e as a yellow solid.

Compound e (1.2 g) was reduced in an atmosphere of hydrogen (balloon) over 10% Pd/C in methanol (12 ml) for 16 hrs. The catalyst was removed by filtration and the concentrated product recrystallized from hexane and ethyl acetate to give 0.325 g of compound f as a tan solid.

Compound f (372 mg) was dissolved in 5.8 ml of water and 218 microliters of 37% HCl. This solution was cooled to 0° C. and stirred while a solution of sodium nitrite (133 mg) in 3 ml of water was added over 5 min. This cold diazonium salt g solution was then added to a stirred suspension of compound h (246 mg) in 29 ml of water, 5.8 ml of methanol and 591 mg of sodium acetate. After one hour, the red oily product i was allowed to settle and the yellow supernatant decanted off. The red oil was triturated twice with water and twice decanted. The red oil was dissolved in 27 ml of acetic acid and 3 ml of 37% HCl and warmed to 70° C. for 20 min. The reaction mixture was cooled and partitioned between ethyl acetate and water. The organic phase was washed with sat. sodium bicarbonate, brine, dried over magnesium sulfate and concentrated. Purification by flash chromatography on silica gave 73.8 mg of compound i.

Compound j (100 mg) was dissolved in 16 ml of dry THF and cooled to 0° C. Lithium bis trimethylsilylamide (622 microliters of 1M sol. in THF) was added and the reaction stirred for 2 hrs. 66 microliters of pyruvonitrile was added and the reaction stirred for 2 hrs. This reaction mixture was then added to a solution of hydrazine (717 microliters) in 9.5 ml of ethanol and stirred for 2 hrs. The mixture was concentrated under vacuum and the product was purified by HPLC to give 3.1 mg of compound 48.

Example 9

Synthesis of Compound 6

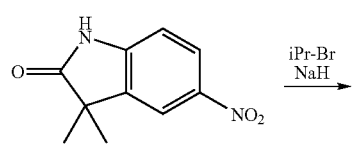

a

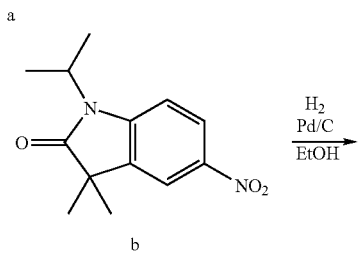

b

-continued

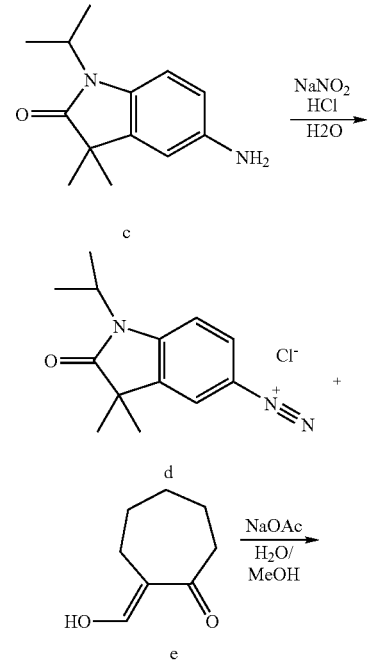

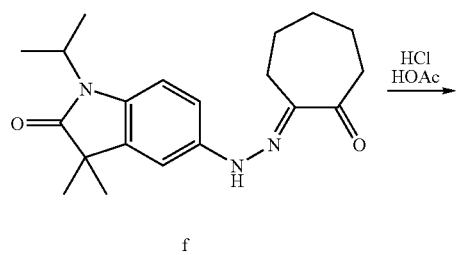

f

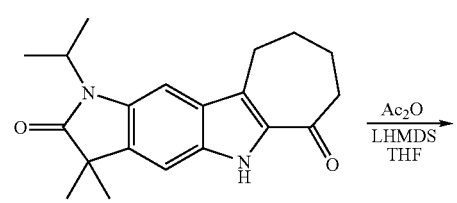

g

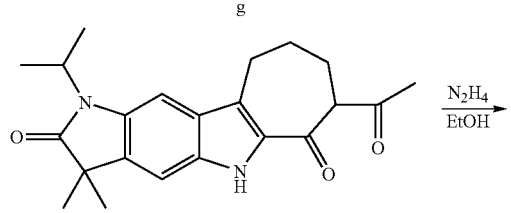

h

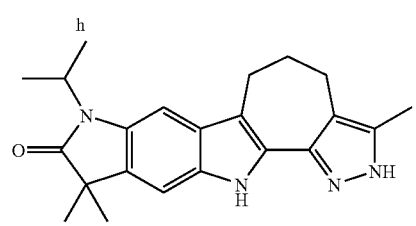

6

Compound a (1.37 g) was dissolved in 20 ml of DMF and cooled with stirring to 0° C. under nitrogen. Sodium Hydride (239 mg) was added followed 20 min later by 4.1 ml of 2-bromopropane. The reaction mixture was warmed to 60° C. for 4 hrs then concentrated and partitioned between ethyl acetate and 10% citric acid. The organic phase was washed with brine, dried, filtered and concentrated. The crude product was purified by automated flash chromatography on silica to give 1.8 g of compound b.

Compound b (1.8 g) was reduced with hydrogen (balloon) in 50 ml of methanol and 10 ml of acetic acid over 10% palladium on carbon for 2 hrs. The catalyst was removed by filtration through celite. Evaporation of the solvents gave 1.8 g of compound c.

Compound c (1.6 g) was dissolved in 60 ml of water and 1.5 ml of 37% HCl and cooled to 0° C. with stirring. A solution of sodium nitrite (500 mg) in 10 ml of water was added over 10 minutes. This diazonium salt solution d was added to a suspension of e (1.02 g) in 100 ml of water, 10 ml of methanol and 2.67 g of sodium acetate with stirring at 0° C. After 3 hours, the reaction mixture was partitioned between ethyl acetate and water. The organic phase was dried and concentrated to give 2.4 g of crude compound f.

Compound f (2.4 g, crude) was dissolved in 40 ml of acetic acid and 10 ml of 37% HCl added. The reaction mixture was heated to 100° C. for 2 hours, cooled and poured into 300 ml of water. The mixture was extracted with ethyl acetate and the separated organic phase filtered through a plug of silica and concentrated. Purification by automated flash chromatography on silica gave 722 mg of compound g.

Compound g (512 mg) was dissolved in 45 ml of THF and cooled to 0° C. 12.64 ml of lithium bis trimethylsilylamide (1M in THF) was added and reaction mixture stirred for 10 minutes. Acetic anhydride (1.49 ml) was added and the mixture stirred for 40 minutes then poured into a stirred solution of hydrazine (3.9 ml) in 200 ml of ethanol. The reaction was stirred for 22 hours then concentrated and partitioned between ethyl acetate and water. The organic phase was washed with brine and concentrated. Purification by automated flash chromatography on silica gave 132 mg of compound 6.

Example 10

Synthesis of Compound 49

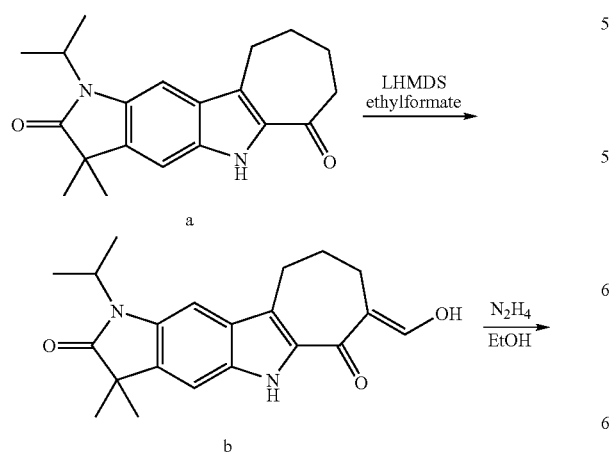

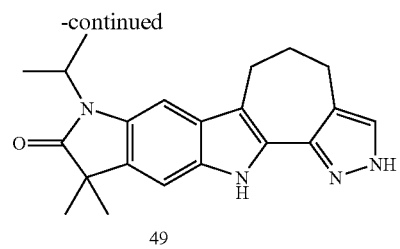

49

Compound a (98 mg) was dissolved in 10 ml of dry THF and lithium bis-trimethylsilylamide (1.2 ml of 1M in THF) added and the reaction mixture stirred for 10 min. Ethyl formate (89.5 mg) was added and the reaction mixture stirred for 4.5 hrs. The reaction was poured into 10% citric acid and extracted with ethyl acetate. The organic phase was washed with brine, dried, filtered and concentrated to give compound b as a brown solid which was used as is.

Crude compound b from step 1 was suspended in 35 ml of ethanol and 6 drops of hydrazine hydrate added. The reaction was stirred for 2.5 hours then concentrated and partitioned between water and methylene chloride. The methylene chloride phase was concentrated and the product purified by automated flash chromatography on silica to give 71 mg of compound 49.

Example 11

Synthesis of Compound 50

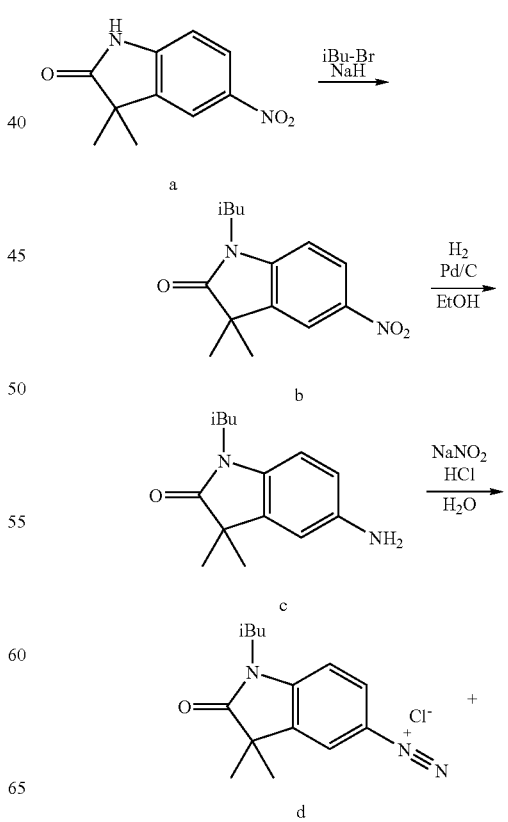

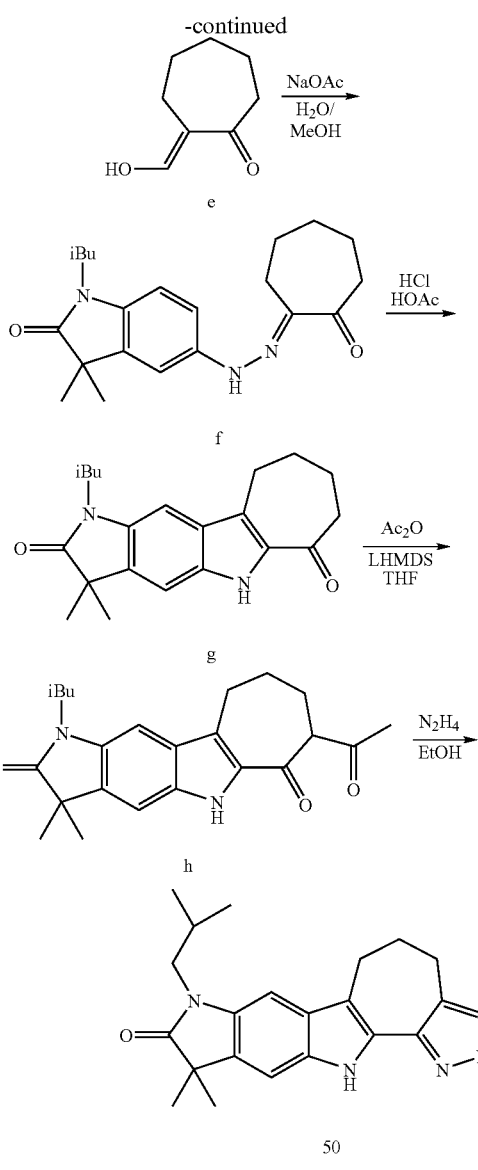

orange crystalline precipitate was filtered off and recrystallized from ethyl acetate and hexane to give 0.92 g of compound f.

Compound f (855 mg) was dissolved in 80 ml of acetic acid and warmed to 50° C. and stirred while 10 ml of 37% HCl was added followed by an additional 20 ml of acetic acid. The reaction was warmed to 60° C. for 40 minutes than cooled and concentrated. The concentrate was partitioned between ethyl acetate and dilute sodium hydroxide. The organic phase was washed twice with water, brine, dried and concentrated. The crude product was purified by flash chromatography on silica to give 462 mg of compound g.

Compound g (460 mg) was dissolved in 50 ml of dry THF and lithium LHMDS (11 ml of 1M sol in THF) added. The red solution was stirred for 15 minutes then acetic anhydride (1.28 ml) added and stirring continued for another 15 minutes. This reaction mixture was then added slowly to a stirred solution of hydrazine hydrate (3.3 ml) in 100 ml of ethanol and stirred for 1 hour. The reaction solution was concentrated and partitioned between ethyl acetate/hexane and water. The organic phase was washed with water, brine, dried and concentrated and the crude product purified by automated flash chromatography on silica to give 113 mg of compound 50.

Example 12

Synthesis of Compound 51

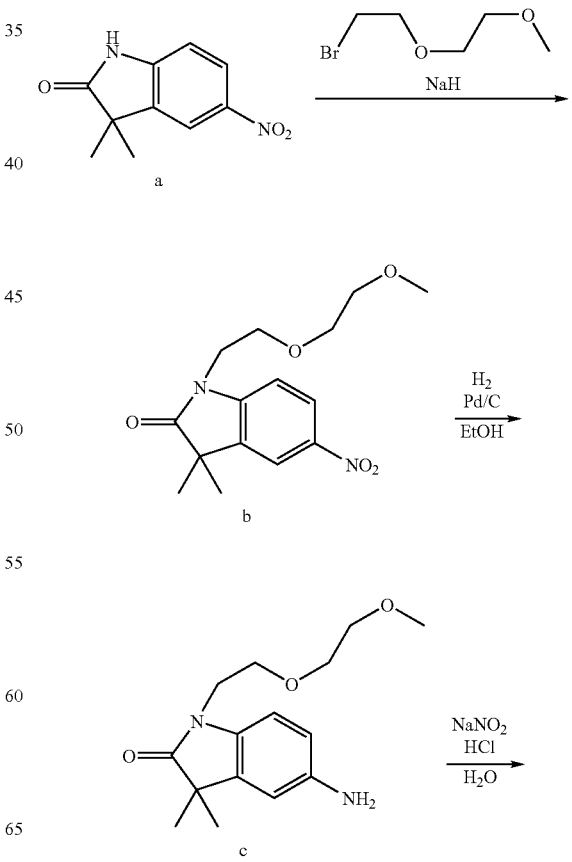

Compound a (1.0 g) was dissolved in 25 ml of dry DMF, cooled to 0°, degassed and blanketed with nitrogen. Sodium hydride (175 mg) was added and the reaction mixture stirred for 30 minutes. Isobultylbromide (3.99 g) was added and the reaction mixture allowed to warm to ambient temperature with stirring overnight. TLC showed reaction complete and the mixture was concentrated and partitioned between 10% citric acid and ethyl acetate. The organic phase was washed with water, brine, dried over sodium sulfate, filtered and concentrated to give 1.19 g of compound b as a brown oil.

Compound b (1.19 g) was reduced under one atmosphere of hydrogen with 10% Pd/C in methanol and 5% acetic acid. The catalyst was filtered off and the solvents evaporated to give 0.99 g of compound c as a brown oil.

Compound c (1.22 g) was dissolved with heating in 120 ml of water and 0.7 ml of 37% HCl. The solution was cooled on an ice water bath and a solution of sodium nitrite (1.01 g) in 5 ml of water added. This diazonium salt d solution was added to a stirred suspension of compound e (0.812 g) and sodium acetate (1.95 g) in 9/1 water/methanol at 0° C. The resultant

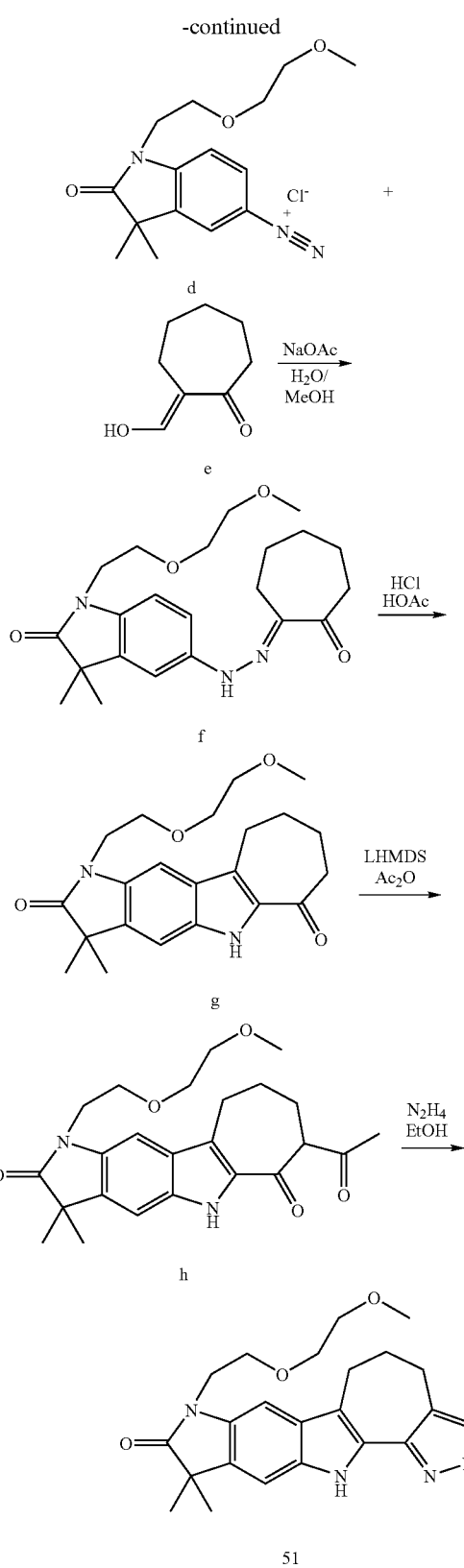

methoxyethoxy)ethane (3.26 ml) was added and the reaction stirred for 3 hours. The reaction mixture was poured into 10% citric acid and extracted with ethyl acetate. The organic layer was washed with water, brine, dried, filtered and concentrated to give 1.52 g of crude b which was used without purification.

Compound b (1.52 g) was reduced under one atmosphere of hydrogen with 10% Pd/C in 10/1 methanol/acetic acid for 2.5 hours. The catalyst was removed by filtration and the filtrate concentrated to give 1.72 g of compound c which was used without purification.

Compound c (1.72 g) was dissolved in 50 ml of water and 0.6 ml of 37% HCl and cooled to 0° C. Sodium nitrite (0.402 g) in 10 ml of water was added and the reaction stirred for 10 minutes. This diazonium d solution was added to a suspension of compound e (815 mg) and sodium acetate (1.79 g) in 100 ml of water and 10 ml of methanol at 0° C. The reaction was stirred for 3 hours then poured into water and the dark oily product extracted into ethyl acetate. The organic phase was washed with water, brine, dried, filtered and concentrated to give crude compound f which was dissolved in 30 ml of acetic acid. Four ml of 37% HCl was added and the reaction heated to 95° C. for 1 hr then cooled and poured into water. The separated oil was extracted with ethyl acetate and the organic phase washed with water, brine, dried, filtered and concentrated. The product was purified by automated flash chromatography on silica to give 690 mg of compound g.

Compound g (690 mg) was dissolved in dry THF (25 ml) and lithium-bis-trimethylsilylamide (14.37 ml of 1M sol in THF) added. The reaction was stirred for 15 minutes then 1.7 ml of acetic anhydride was added. This reaction was stirred for 15 minutes then poured into a solution of hydrazine hydrate (4.4 ml) in 120 ml of ethanol and stirred at room temperature overnight. The solvents were evaporated and the product partitioned between ethyl acetate/hexane and water. The organic phase was washed with water, brine, dried, filtered and concentrated. The crude product was purified by automated flash chromatography on silica to give 296 mg of compound 51.

Example 13

Synthesis of Compound 11

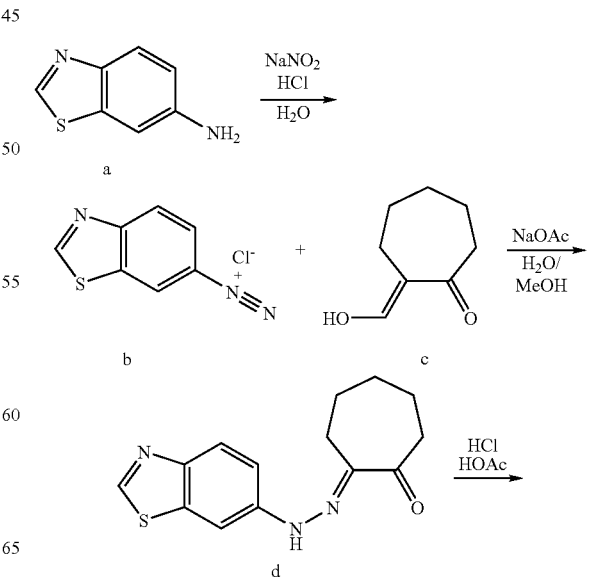

Compound a (1.0 g) was dissolved in 25 ml of dry DMF, degassed and cooled to 0° C. Sodium hydride (175 mg) was added and the reaction stirred for 30 minutes. 1-bromo-2-(2-

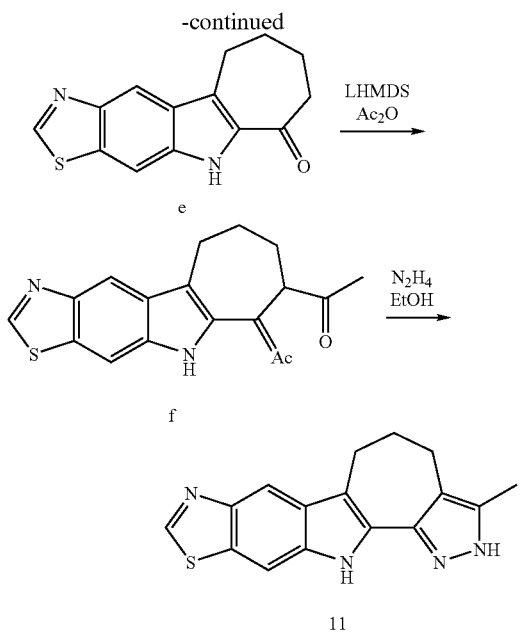

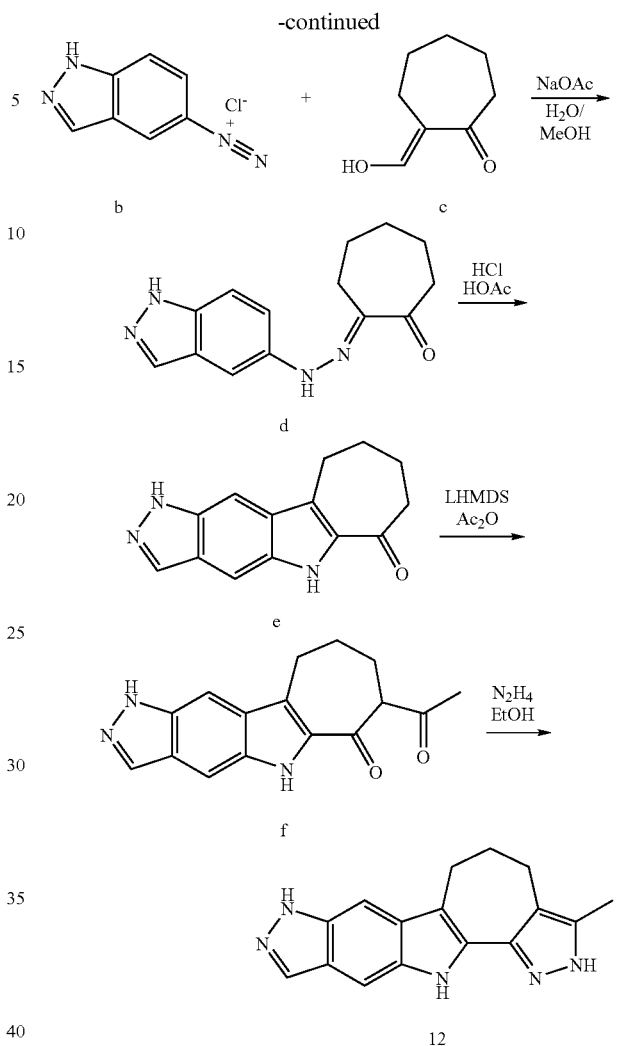

6-aminobenzothiazole a (2.25 g) was dissolved in 40 ml of water and 3.13 ml of 37% HCl then cooled on an ice water bath. A solution of sodium nitrite (1.04 g) in 10 ml of water was added over 5 minutes. This diazonium salt b solution was then added to a suspension of compound c (2.1 g) and sodium acetate (5.5 g) in 80 ml of water and 20 ml of methanol. The resultant yellow precipitate was stirred for 1.5 hours then partitioned between ethyl acetate and water. The organic phase was washed with water, brine, dried, filtered and concentrated to give 4.47 g of compound d which was used without purification.

Compound d (4.47 g) was dissolved in 40 ml of acetic acid and 4 ml of 37% HCl and heated to 90° C. for 2.5 hrs. The reaction was cooled and partitioned between ethyl acetate and water. The organic phase was washed with brine, dried, filtered and concentrated. Purification by automated flash chromatography on silica gave 480 mg of compound e.

Compound e (480 mg) was dissolved in THF and 15 ml of 1M lithium-bis-trimethylsilylamide in THF added. After stirring for 5 minutes, acetic anhydride (1.77 ml) was added and the reaction stirred for 30 minutes then poured into a solution of hydrazine hydrate (4.6 ml) in ethanol and stirred at room temperature overnight. Concentration and purification by automated flash chromatography on silica gave 75.1 mg of compound 11.

Example 14

Synthesis of Compound 12

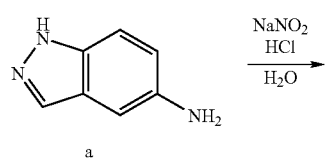

5-Aminoindazole a (2.0 g) was dissolved in 30 ml of water and 1.9 ml of 37% HCl and cooled on an ice water bath. A solution of sodium nitrite (1.04 g) in 10 ml of water was added dropwise over 5 min and the reaction stirred an additional 10 minutes. This diazonium b solution was then added to a stirred suspension of compound c (2.10 g) and sodium acetate (5.54 g) in 100 ml of water. The resultant yellow suspension was stirred for 2 hours then partitioned between ethyl acetate and brine. The organic phase was filtered through a small amount of silica and concentrated to give 1.84 g of crude d. This crude d was dissolved in 32 ml of acetic acid and 8 ml of 37% HCl and heated to 95° C. for 20 minutes. The reaction was cooled and partitioned between ethyl acetate and brine. The brine phase was again extracted with ethyl acetate and the combined organic phased evaporated. Purification by automated flash chromatography on silica gave 1.01 g of compound e.

Compound e (700 mg) was dissolved in 20 ml of THF and lithium bis-trimethylsilylamide (23.4 ml of 1M sol in THF) added. After 10 minutes, 2.76 ml of acetic anhydride was added. The thick reaction mixture stirred for 40 minutes then poured into a solution of hydrazine hydrate (8 ml) in 100 ml of ethanol. The reaction mixture was stirred for 2 days then concentrated and partitioned between ethyl acetate and water. The organic phase was washed with brine, dried, filtered and concentrated. The crude product was purified by crystallization from methanol to give 115 mg of compound 12.

Example 15

Synthesis of Compound 28

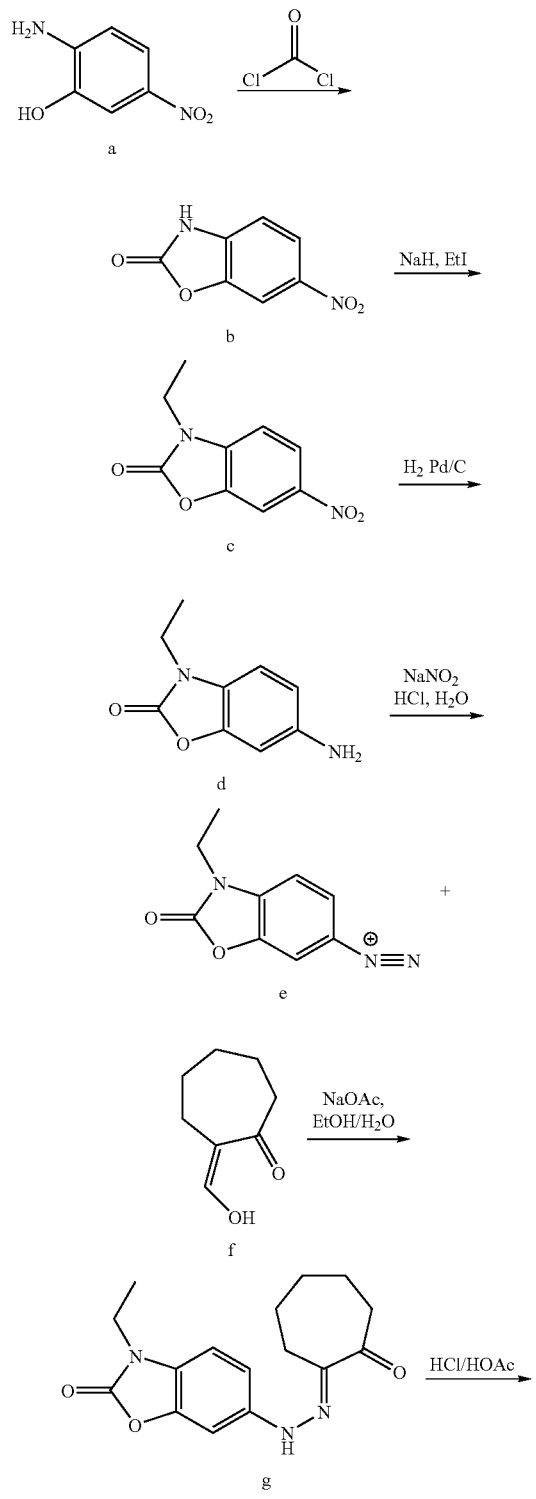

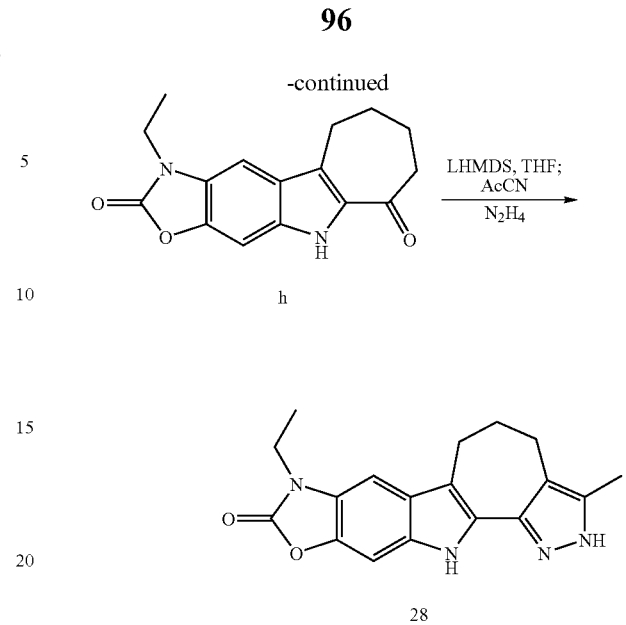

Compound b was prepared following the procedures described in John H. Musser, et. al. (*J. Med. Chem.* 1985, 28, 1255-1259).

Carbamate b (1.29 g, 7.17 mmol) was dissolved in DMF (18 ml) and added dropwise to a cold suspension of sodium hydride (0.60 g) in DMF (18 ml). When hydrogen evolution ceased, ethyl iodide (1.7 ml, 21.5 mmol) was added and the reaction mixture was allowed to stir overnight at room temperature. The reaction mixture was quenched with $H_2O$ and extracted with EtOAc, washed with brine and dried over $Na_2SO_4$. The solvent was removed in vacuo, and the residue subjected to flash chromatography (silica gel, 0→50% EtOAc in hexanes, gradient elution) to afford c (661 mg, 44%).

Nitro compound c (661 mg, 3.18 mmol) was reduced under 1 atmosphere of hydrogen in a suspension of 10% Pd/C catalyst (1 g) in methanol (7 ml) with stirring for 18 hours. The catalyst was removed by filtration and evaporation of the solvent gave amine d (530 mg) which was used directly in the next reaction. To a cold (0° C.) solution of d and hydrochloric acid (0.4 ml) in $H_2O$ (10 ml) was added an aqueous solution of sodium nitrite (0.25 g, 3.6 mmol, 0.6 M), dropwise over 5 minutes. The resulting mixture of the diazonium salt e, was slowly added to a separate reaction flask containing 2-(hydroxymethylene)cycloheptanone f (3.3 mmol) in $H_2O$ (48 ml), MeOH (10 ml) and basified with NaOAc (1.82 g, 13.4 mmol) at 0° C. The product was then filtered and washed with $H_2O$ to give hydrazone g (530 mg, 59%) as a white solid.

A solution of hydrazone g (0.53 g, 1.7 mmol) in acetic acid (100 ml) and hydrochloric acid (10 ml) was heated to 80° C. for 1.5 hours. Upon cooling to room temperature, the reaction mixture was diluted with $H_2O$ (100 ml) and extracted with EtOAc (2×100 ml). The organic layer was washed with brine (40 ml) and dried over $Na_2SO_4$. The solvent was removed in vacuo and the residue was subjected to flash chromatography (silica gel, 0→50% EtOAc in hexanes, gradient elution) to afford indole-ketone h, (0.588 g, 31%). Compound h (135 mg) was treated in a manner similar to compound h in example 2 to give 50 mg of compound 28.

Example 16

Synthesis of Compound 36

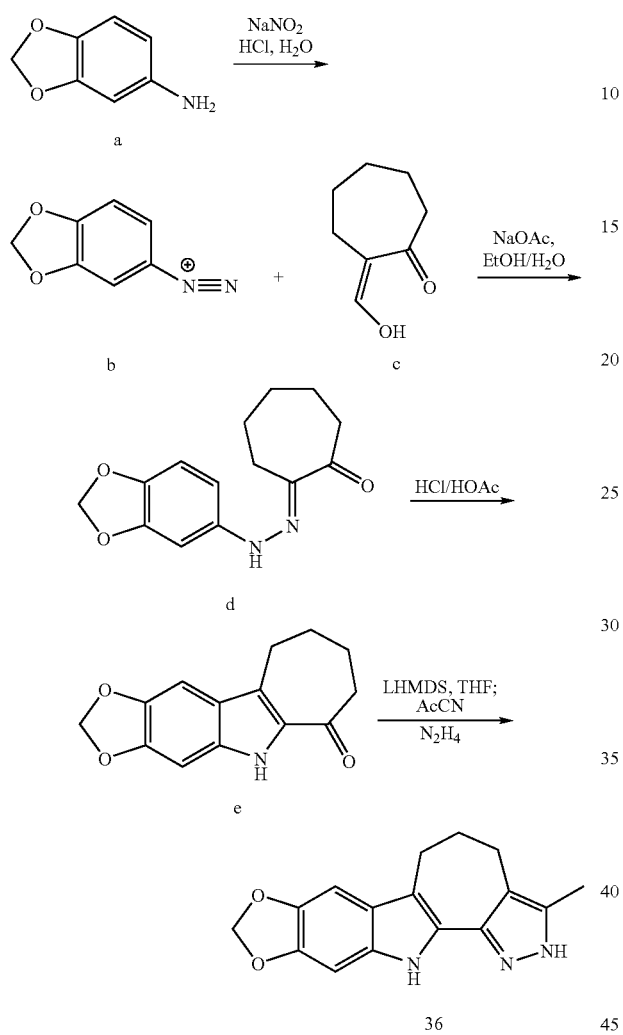

Compound 36 was prepared according to procedures analogous to those in example 15.

To a cold (0° C.) solution of a (5 g) and hydrochloric acid in H$_2$O was added an aqueous solution of sodium nitrite dropwise over 5 minutes. The resulting mixture of the diazonium salt b, was slowly added to a separate reaction flask containing 2-(hydroxymethylene)cycloheptanone c in H$_2$O, MeOH and basified with NaOAc at 0° C. The product was then filtered and washed with H$_2$O to give hydrazone 3.6 g of d.

A solution of hydrazone d (3.6 g) in acetic acid and hydrochloric acid was heated to 80° C. for 1.5 hours. Upon cooling to room temperature, the reaction mixture was diluted with H$_2$O and extracted with EtOAc (2×). The organic layer was washed with brine and dried over Na$_2$SO$_4$. The solvent was removed in vacuo and the residue was subjected to flash chromatography (silica gel, 0→50% EtOAc in hexanes, gradient elution) to afford 1.7 g of indole-ketone e.

Compound e (1.7 g) was treated in a manner similar to compound h in example 2 to give 0.6 g of compound 36.

Example 17

Synthesis of Compound 35

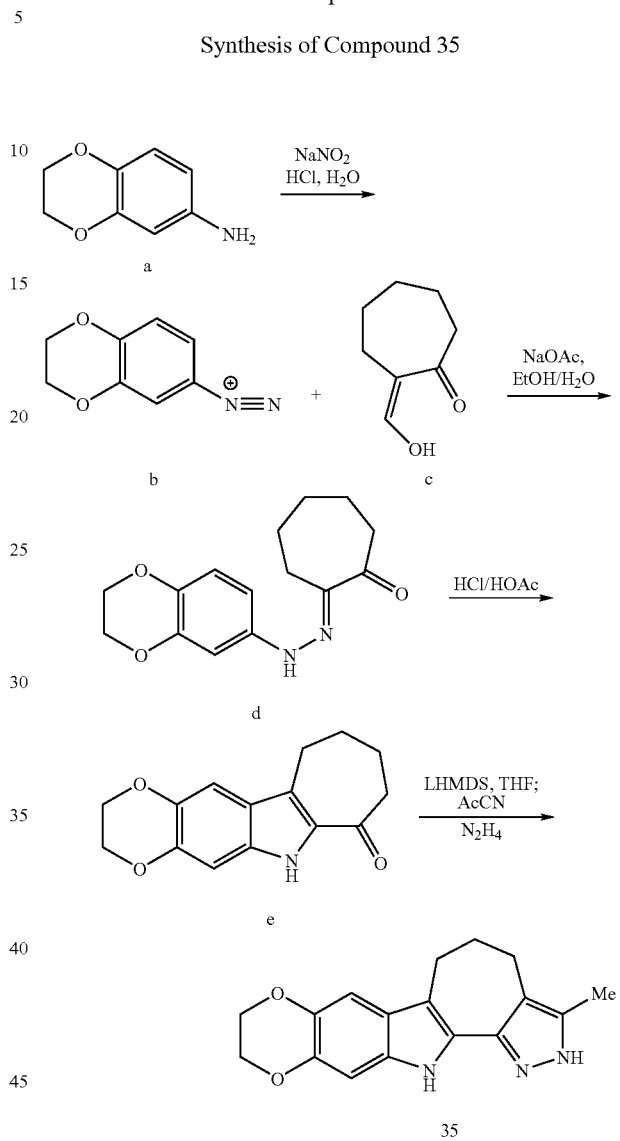

Compound 35 was prepared using analogous procedures as in example 15.

To a cold (0° C.) solution of a (5 g) and hydrochloric acid in H$_2$O was added an aqueous solution of sodium nitrite dropwise over 5 minutes. The resulting mixture of the diazonium salt b, was slowly added to a separate reaction flask containing 2-(hydroxymethylene)cycloheptanone c in H$_2$O, MeOH (10 ml) and basified with NaOAc at 0° C. The product was then filtered and washed with H$_2$O to give hydrazone 5.8 g of d.

A solution of hydrazone d (5.8 g) in acetic acid and hydrochloric acid was heated to 80° C. for 1.5 hours. Upon cooling to room temperature, the reaction mixture was diluted with H$_2$O and extracted with EtOAc (2×). The organic layer was washed with brine and dried over Na$_2$SO$_4$. The solvent was removed in vacuo and the residue was subjected to flash chromatography (silica gel, 0→50% EtOAc in hexanes, gradient elution) to afford 2.9 g of indole-ketone e.

Compound e (2.9 g) was treated in a manner similar to compound h in example 2 to give 1.1 g of compound 35.

Example 18

Synthesis of Compound 1

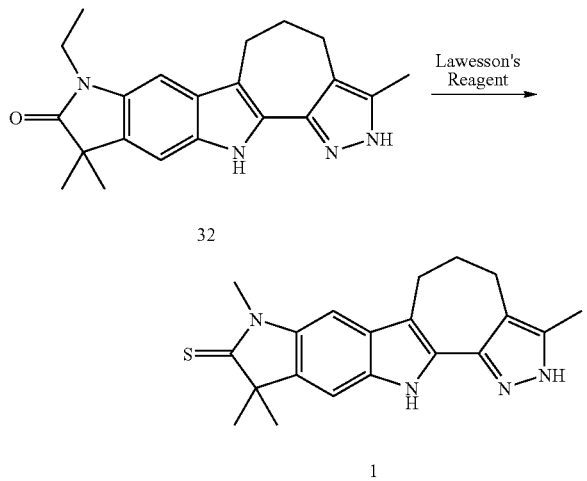

Compound 32 (65 mg, 0.19 mmol) was dissolved in toluene (1 ml) and Lawesson's reagent (0.1 mmol) was added to the solution and heated to 110° C. for 1 hour. The solvent was removed in vacuo and the residue was subjected to flash chromatography (silica gel, 0→5% MeOH in DCM, gradient elution) to afford 45 mg of compound 1.

Example 19

Synthesis of ethyl 5-oxothiepane-4-carboxylate intermediate

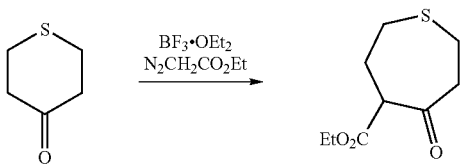

To a cold solution (−30° C.) of tetrahydrothiopyran-4-one (5.0 g, 43.0 mmol) in anhydrous ether, were simultaneously added a solution of boron trifluoride etherate (5.4 ml, 43.0 mmol) in diethyl ether (4.6 ml) and a solution of ethyl diazodicarboxylate (5.8 ml, 55.9 mmol) in diethyl ether (4.6 ml) over 1.5 hours via a syringe pump. Upon completion of additions, the reaction mixture was allowed to stir for an additional hour at −30° C. and then warmed to room temperature. The reaction mixture was washed with 30% potassium carbonate and the organic phase was dried over $Na_2SO_4$ and concentrated in vacuo to give ethyl 5-oxothiepane-4-carboxylate as a white solid.

Example 20

Synthesis of diethyl 5-oxoazepane-1,4-dicarboxylate intermediate

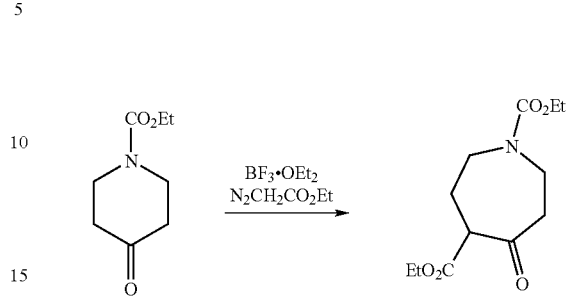

To a cold solution (−30° C.) of 1-carbethoxypiperidin-4-one (3.0 ml, 26.5 mmol) in anhydrous ether, were simultaneously added a solution of boron trifluoride etherate (3.4 ml, 26.5 mmol) in diethyl ether (2.8 ml) and a solution of ethyl diazodicarboxylate (3.6 ml, 34.5 mmol) in diethyl ether (2.8 ml) over 1.5 hours via a syringe-pump. Upon completion of additions, the reaction mixture was allowed to stir for an additional hour at −30° C. and then warmed to room temperature. The reaction mixture was washed with 30% potassium carbonate and the organic phase was dried over $Na_2SO_4$ and concentrated in vacuo to give diethyl 5-oxoazepane-1,4-dicarboxylate as a crude yellow oil.

Example 21

Synthesis of Compound 54

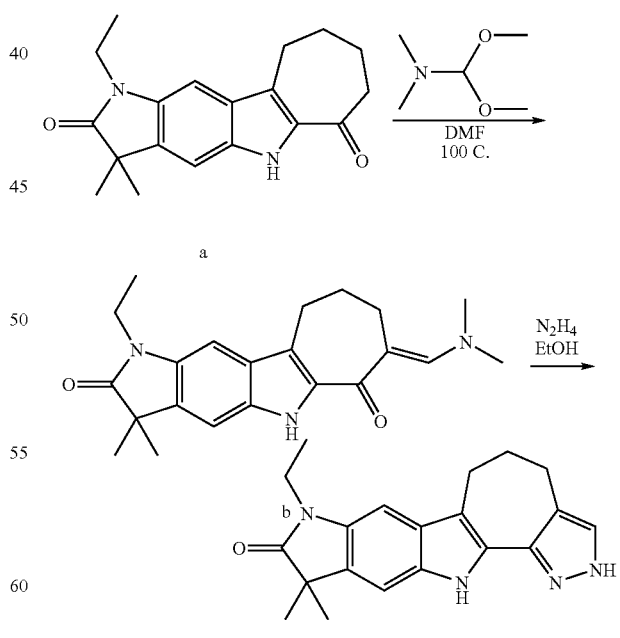

Compound a from example 2 (16.14 g) was dissolved in 200 ml of DMF, degassed and blanketed with nitrogen. DMF dimethylacetal (55 ml) was added and the mixture heated to 100° C. with stirring for 5 hours by which time tlc indicated completed reaction. The reaction mixture was cooled and concentrated under vacuum. The resulting yellow solid b was slurried in 100 ml of ethanol and collected by filtration. It was then dissolved in a mixture of 200 ml of methylene chloride and 20 ml of methanol and added drop wise to a stirred solution of 2 L of ethanol containing 125 ml of hydrazine hydrate. After 18 hours, the reaction was concentrated under vacuum and partitioned between 9:1 ethyl acetate:hexane and water. The organic phase was washed with water, brine, dried over sodium sulfate, filtered and concentrated whereupon the product crystallized and was filtered off giving 15.6 g of compound 54.

Example 22

Synthesis of Compound 55

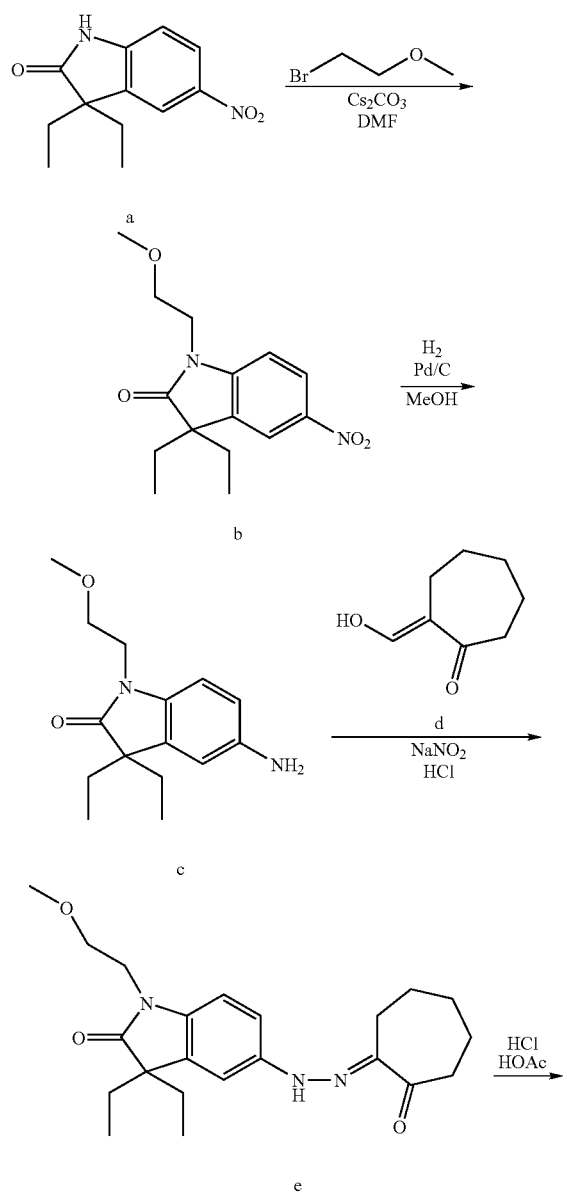

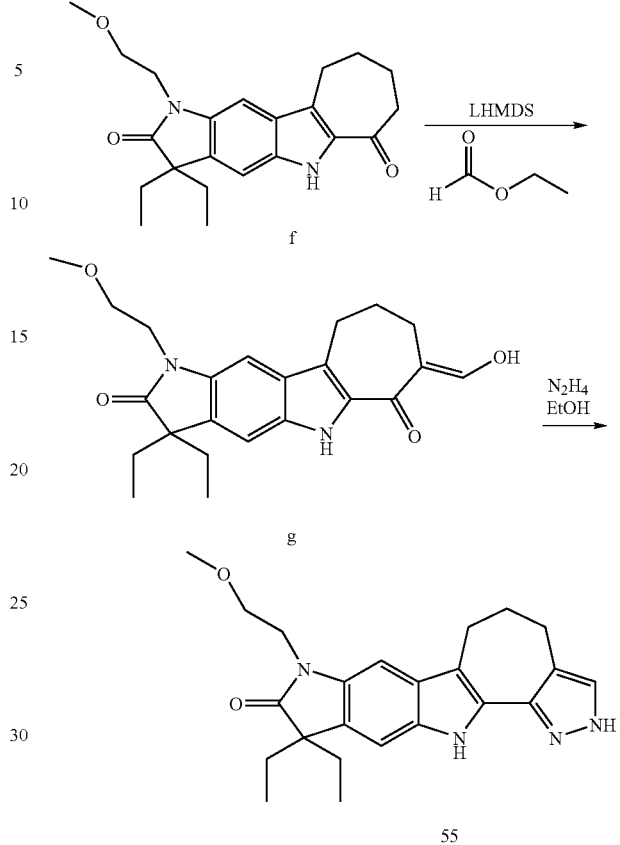

A mixture of compound a from example 8 (1.0 g), cesium carbonate (2.78 g), 1-bromo-2-methoxyethane (890 mg) and DMF (30 ml) was heated with stirring to 90° C. After 20 min, the reaction was cooled, filtered through celite and partitioned between ethyl acetate and water. The organic phase was washed with brine, dried over sodium sulfate, filtered and concentrated under vacuum. Purification by automated silica gel chromatography gave 1.35 g of compound b as a yellow oil.

Compound b (1.35 g) was reduced under a balloon of hydrogen in a solution of methanol (100 ml) and HOAc (5 ml) containing 100 mg of 10% palladium on carbon for 30 min. TLC indicated completed conversion and the reaction was filtered through celite and concentrated to give 1.21 g of compound c.

Compound c (1.0 g) was dissolved in 50 ml of water containing 0.82 ml of 12N HCl and cooled on an ice water bath. A solution of sodium nitrite (0.316 g) in 10 ml of water was added drop wise over 5 min. The reaction mixture was stirred an additional 5 minutes then added slowly to a rapidly stirred cold suspension of compound d in 100 ml of water, 15 ml of methanol and 1.41 g of sodium acetate. After stirring for 2 hours, the reaction mixture was partitioned between ethyl acetate and water. The organic phase was washed with water, brine, dried over sodium sulfate, filtered and concentrated under vacuum to give 2.26 g of crude compound e, which was used without further purification.

A solution of compound e (2.26 g) in 100 ml of acetic acid containing 10 ml of 12N HCl was heated to 60° C. for 25 minutes. The reaction was cooled and concentrated under vacuum to about 85% original volume then basified to pH 14 with 25% sodium hydroxide. This mixture was partitioned between ethyl acetate and water. The aqueous phase was extracted again with ethyl acetate and the combined organic extracts washed with brine, dried over sodium sulfate and concentrated under vacuum. The crude brown product was purified by automated silica gel chromatography to give 607 mg of compound f.

Compound f (607 mg) was dissolved in 15 ml of dry THF and stirred while 6.6 ml of 1M LHMDS in THF was added. After 15 minutes, 2.65 ml of ethyl formate was added and the reaction stirred for 55 minutes. The reaction was poured into 100 ml of 10% citric acid and extracted with ethyl acetate. The organic phase was washed with water, brine, dried over sodium sulfate, filtered and concentrated under vacuum. Purification of the crude product by automated silica gel chromatography gave 196 mg of compound g.

Compound g (196 mg) was dissolved in 50 ml of ethanol and 1.2 ml of hydrazine hydrate added. After stirring for 20 minutes, the reaction was concentrated under vacuum. Purification by automated silica gel chromatography gave 117 mg of compound 55 as yellow crystals.

Example 23

Synthesis of Compound 56

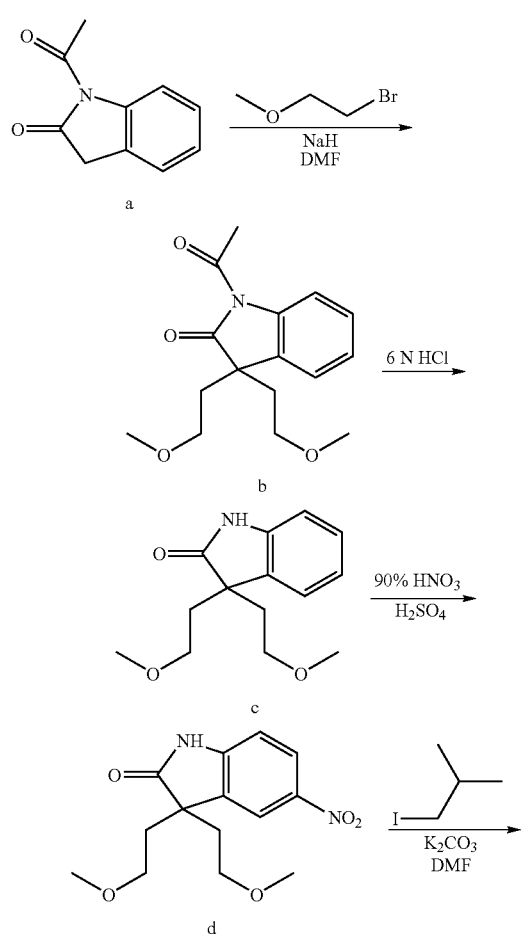

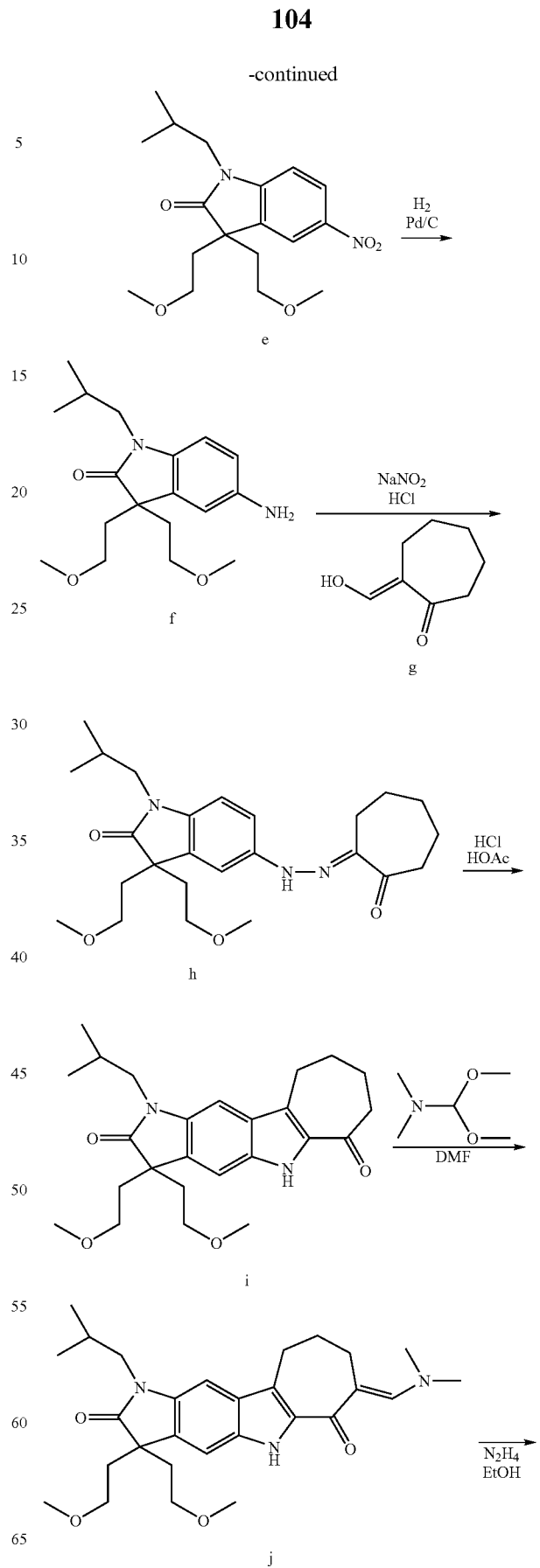

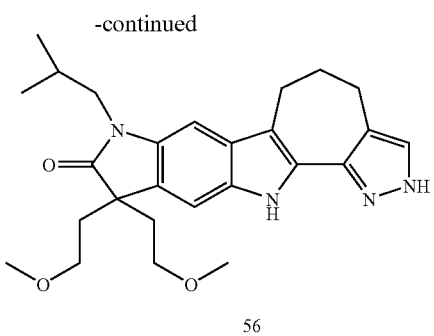

56

A mixture of sodium hydride (2.86 g) and 100 ml of DMF was stirred and cooled on an ice bath. A solution of N-acetyloxindole a (10.44 g) in 100 ml of DMF was added by addition funnel over one hour followed by addition of 1-bromo-2-methoxyethane (11.2 ml) over 15 minutes. The reaction was stirred for 1.5 hr then poured into ice and extracted with ethyl acetate. The organic phase was washed with water, brine, dried over sodium sulfate, filtered and concentrated under vacuum. Purification by automated silica gel chromatography gave 3.66 g of compound b.

Compound b (3.66 g) was heated to 60° C. in 6N HCl for 25 min then poured into 150 ml of water and extracted with ethyl acetate. The organic phase was washed with water, brine, dried over sodium sulfate, filtered and concentrated to give 4.59 g of crude c which was used without further purification.

A mechanically stirred solution of c (4.49 g crude) in 100 ml of conc. sulfuric acid was cooled on an ice/brine bath. A mixture of fuming nitric acid (1.16 g) and in 50 ml of conc. sulfuric acid was added over 10 minutes. The reaction mixture was stirred for 2 hrs then poured into ice and extracted with ethyl acetate. The organic phase was washed with water, brine, dried over sodium sulfate, filtered and concentrated. The crude product was purified by automated silica gel chromatography to give 2.44 g of compound d.

A mixture of compound d (0.65 g), 1-iodo-2 methylpropane (1.22 g), potassium carbonate (1.2 g) and 20 ml of dry DMF was heated to 100° C. for 1 hour with stirring. The reaction was cooled and solids filtered off. The filtrate was concentrated under vacuum and partitioned between ethyl acetate and 10% citric acid. The organic phase was washed with water, brine, dried over sodium sulfate, filtered and concentrated to give 0.97 g of compound e which was used without further purification.

Compound e (0.97 g) was reduced under a balloon of hydrogen in a slurry of 10% palladium on carbon (0.1 g) in 30 ml of methanol and 2 ml of HOAc for 4 hours. The catalyst was filtered off and the filtrate concentrated under vacuum to give 0.89 g of compound f as a red oil which was used without further purification.

Compound f (0.89 g) was dissolved in 30 ml of water and 0.35 ml of 12N HCl. This solution was cooled on ice and a solution of sodium nitrate (0.23 g) in 5 ml of water was slowly added. After stirring for 15 minutes, this diazonium salt solution was added slowly to a vigorously stirred mixture of compound g (0.43 g) and sodium acetate (1.03 g) in 100 ml of water and 20 ml of methanol at 0° C. After stirring for 2 hrs, the crystalline product was filtered off to give 0.8 g of compound h.

Compound h (0.8 g) was heated to 100° C. for 40 minutes in 200 ml of HOAc and 4 ml of 12N HCl. After cooling, the reaction was concentrated under vacuum and partitioned between ethyl acetate and water. The organic phase was washed with brine, dried over sodium sulfate, filtered and concentrated whereupon product i crystallized and was filtered off. Yield=380 mg. An additional 210 mg of product was recovered by silica gel chromatography of the mother liquors.

Compound i (300 mg) was heated to 100° C. in a mixture of 10 ml of DMF and 467 microliters of DMF-dimethylacetal overnight. The reaction mixture was concentrated under vacuum then partitioned between ethyl acetate and water. The organic phase was washed with water, brine, dried over sodium sulfate, filtered and concentrated. This residue (compound j) was taken up in 100 ml of ethanol, 10 ml of hydrazine hydrate added and the reaction stirred for 3 hours. The reaction was concentrated under vacuum then partitioned between ethyl acetate and water. The organic phase was washed with water, brine, dried over sodium sulfate, filtered and concentrated under vacuum. Purification of the residue by flash chromatography on silica gave 158 mg of 56 as a yellow solid.

Example 24

Synthesis of Compound 57

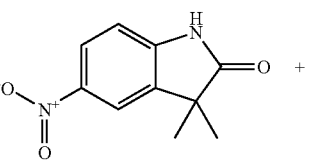

a

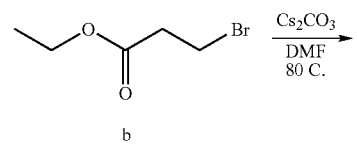

b

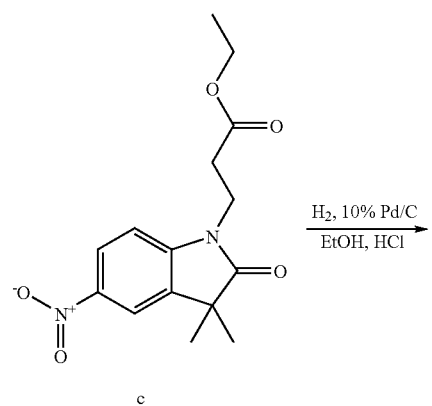

c

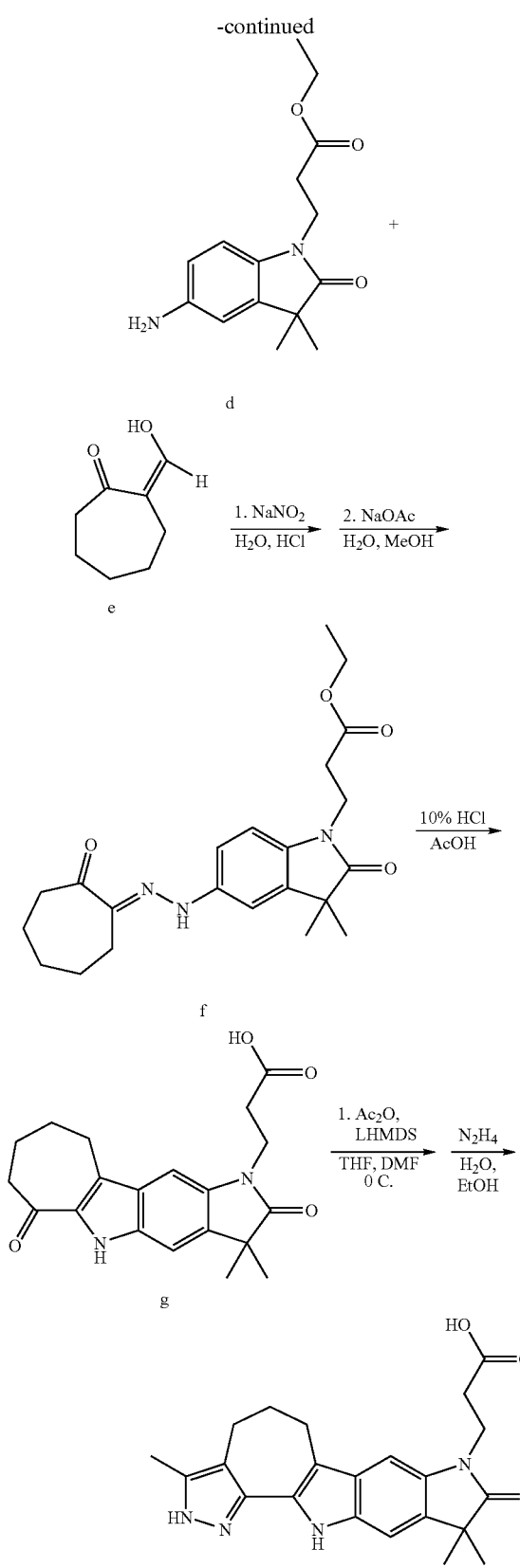

Compound a from example 1 (5.45 g) was dissolved in 100 ml of DMF. To this solution was added 21.54 g $Cs_2CO_3$ and 11.97 g of ethyl-3-bromoproprionate b and the mixture was heated at 80° C. under $N_2$ with stirring for 24 hours by which time the reaction was completed by TLC. The reaction mixture was cooled and diluted with 1 M HCl, extracted with EtOAc, washed with brine, dried over $MgSO_4$, and concentrated under vacuum to give 3.67 g (45% yield) of compound c. Compound c (3.67 g) was dissolved in 150 ml EtOH and 200 uL of concentrated HCl and bubbled under $N_2$ for 10 minutes at which time 2 scoops of 10% Pd/C was added, an $H_2$ balloon attached and the reaction stirred at room temperature for 12 hours. When completed by LCMS the reaction mixture was filtered over celite and concentrated under vacuum to give 3.31 g compound d (89% yield).

Compound d (3.31 g) was dissolved in 100 ml $H_2O$ and 1.92 ml concentrated HCl and cooled to 0° C. To this solution was added 0.99 g $NaNO_2$ in 10 ml $H_2O$ and the mixture was stirred 30 minutes. This was added to 2.01 g compound e from example 2 and 4.42 g NaOAc in 60 ml $H_2O$ and 60 ml MeOH at 0° C. The solution was allowed to warm up to room temperature and stir overnight. When completed by LCMS the reaction mixture was diluted with sat. $NaHCO_3$, extracted with EtOAc, dried over $MgSO_4$, confirmed to be compound f by LCMS and dried under vacuum. Compound f was dissolved in 50 ml of 10% HCl in AcOH and heated to 70° C. for 12 hours. The reaction was completed by LCMS, diluted with $H_2O$, extracted with EtOAC and MeOH, dried over $MgSO_4$ and concentrated under vacuum to give 2.1 g (50% yield) of compound g. Compound g was dissolved in 100 ml THF and cooled to 0° C. and then 23.72 ml 1M LHMDS in THF was added slowly under $N_2$ and the reaction stirred for 1 hr 15 min at 0° C. To this mixture was added 2.42 g $Ac_2O$ and 1 ml DMF. The reaction was allowed to warm up to room temperature and stir 4 hr 15 min. To this was added 10 ml EtOH followed by 5 ml hydrazine and the reaction was stirred overnight. Completed reaction was confirmed by LCMS and the reaction mixture concentrated under vacuum to give 9 g crude, of which 1.0 g was purified by HPLC to give 15.7 mg of the TFA salt of the final compound 57.

Example 25

Synthesis of Compound 58

-continued

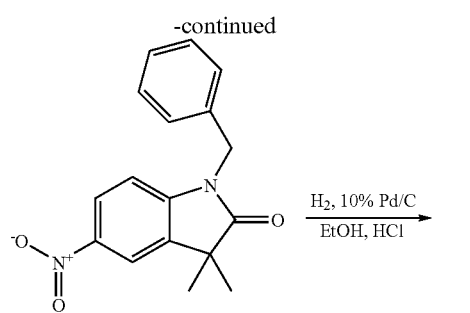
c

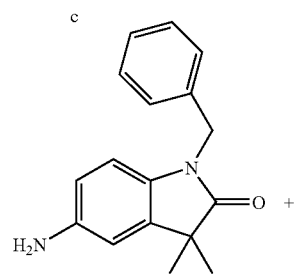
d

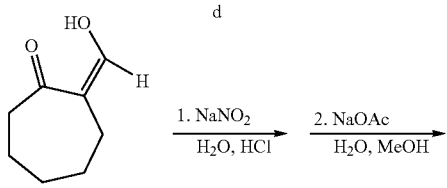
e

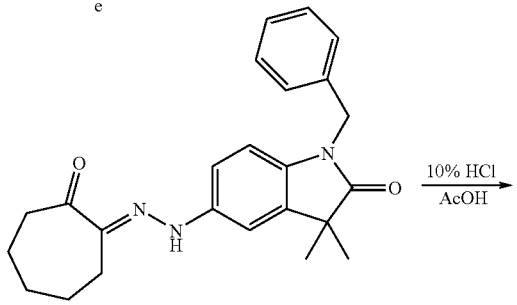
f

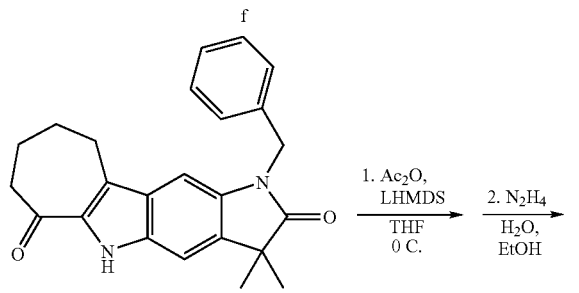
g

58

Compound a from example 1 (2.04 g) was dissolved in 50 ml of DMF in a round bottom flask with a vigreux condensation column attached. To this solution was added 8.06 g $Cs_2CO_3$ and 4.23 g of benzyl bromide b and the mixture was placed under $N_2$ in an oil bath heated to 100° C. for 4 hrs 35 min. The reaction was completed by TLC, cooled to room temp, diluted with 1 M HCl and extracted with EtOAc, washed with brine, dried over $MgSO_4$, and concentrated under vacuum to give 2.93 g (100% yield) of compound c. Compound c was dissolved in 100 ml EtOH and 200 uL of concentrated HCl and bubbled under $N_2$ for 10 minutes at which time 1 scoop of 10% Pd/C was added and an $H_2$ balloon attached. This was stirred for 12 hours. Reaction was completed by LCMS, filtered over celite and concentrated under vacuum to give 2.34 g compound d (89% yield).

Compound d was dissolved in 70 ml $H_2O$ and 1.17 ml concentrated HCl and cooled to 0° C. To this mixture was added 0.73 g $NaNO_2$ in 10 ml $H_2O$ and the mixture was stirred for 30 minutes at 0° C. This was then added to 1.48 g compound e and 3.25 g NaOAc in 20 ml $H_2O$ and 20 ml MeOH. The solution was allowed to warm up to room temperature and was stirred overnight. When completed by LCMS the precipitate formed was filtered off and confirmed to be intermediate f, which was dried under vacuum and dissolved in 50 ml 10% HCl in AcOH and heated to 80° C. for 2 hours and stirred at room temperature overnight. The reaction was completed by LCMS and the solvent was removed under vacuum to give compound g which was flashed by ISCO (EtOAc/Hexanes) and rotovapped to give 1.39 g compound g (43% yield). Compound g was dissolved in 100 ml THF and cooled to 0° C. before adding 19.04 ml 1M LHMDS in THF under $N_2$. The reaction was stirred for 3.5 hrs at 0° C. followed by addition of 1.94 g $Ac_2O$ and let warm up to room temperature and stir another 2 hrs. To this reaction mixture was then added 15 ml each of $H_2O$ and EtOH followed by 3 ml hydrazine and was stirred overnight at room temperature. Completed reaction was confirmed by LCMS and the reaction was diluted with 0.1 N $H_2SO_4$, extracted with EtOAc, washed with brine, dried over $MgSO_4$, rotovapped, and then purified by ISCO (EtOAc/Hexanes) to give 0.75 g of the final compound 58 in a 38.5% yield.

Example 26

Synthesis of Compound 59

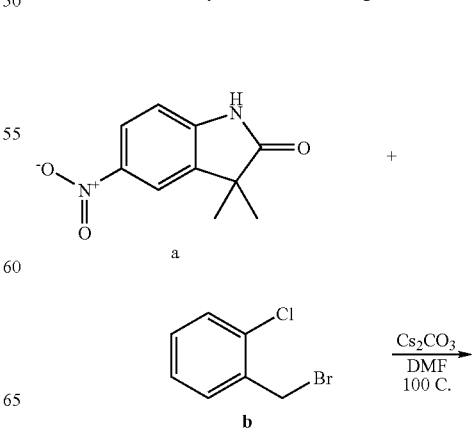

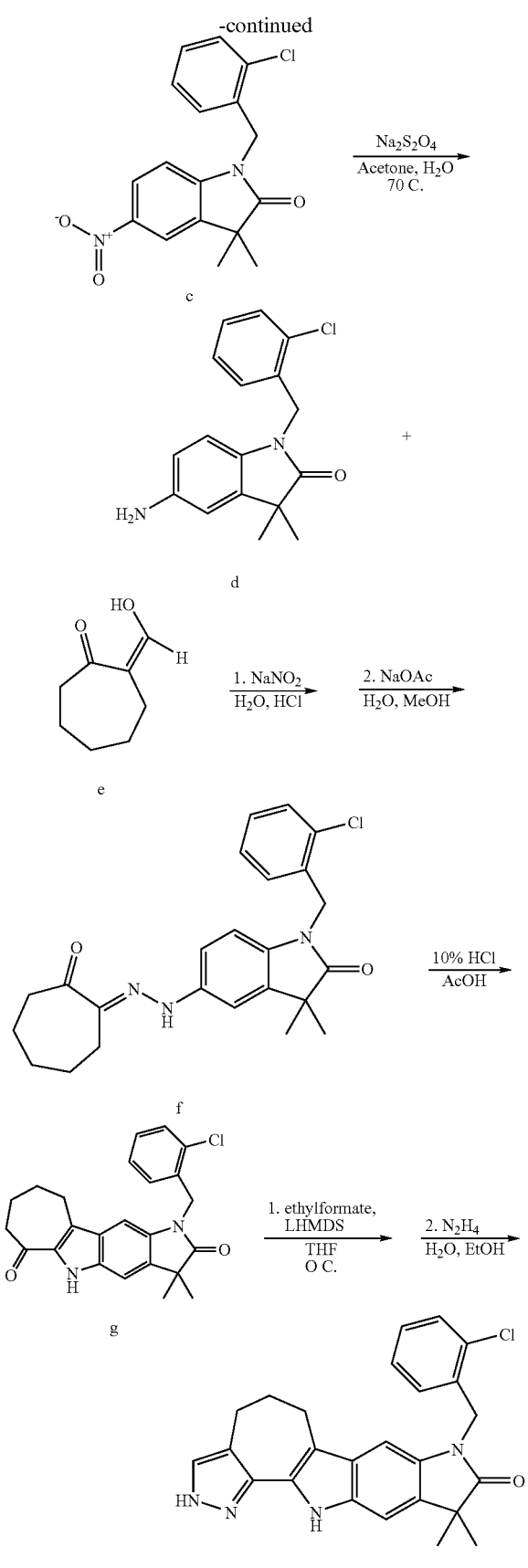

Compound a from example 1 (3.13 g) was dissolved in 50 ml of DMF. To this solution was added 9.89 g $Cs_2CO_3$ and 3.74 g of 2-clorobenzyl bromide b and the mixture was heated at 80° C. under $N_2$ with stirring for 12 hrs by which time the reaction was completed by TLC. The reaction mixture was cooled to room temperature, diluted with 1 M HCl, extracted with EtOAc, washed with Brine, dried over $MgSO_4$, and concentrated under vacuum to give 5.0 g (100% yield) of compound c. Compound c was dissolved in 200 ml acetone and 100 ml of $H_2O$ and heated to 70° C. at which point sodium hydrosulfite (52.65 g) was added and the reaction mixture stirred overnight at 70° C. The reaction was completed by LCMS so the acetone was removed under vacuum and the mixture diluted with $H_2O$, extracted with EtOAc, partitioned with saturated $NaHCO_3$, washed EtOAc with brine, dried over $MgSO_4$ and concentrated under vacuum to give 2.01 g compound d (44% yield).

Compound d was dissolved in 70 ml $H_2O$ and 1.17 ml concentrated HCl and cooled to 0° C. To this mixture was added 0.73 g $NaNO_2$ in 10 ml $H_2O$ and the mixture was stirred for 30 minutes at 0° C. This was then added to 1.48 g compound e from example 2 and 3.25 g NaOAc in 20 ml $H_2O$ and 20 ml MeOH. The solution was allowed to warm up to room temperature and was stirred overnight. When completed by LCMS the precipitate formed was filtered off and confirmed by LCMS to be intermediate f which was dried under vacuum and dissolved in 50 ml 10% HCl in AcOH and heated to 80° C. for 2 hours and stirred at room temperature overnight. The reaction was completed by LCMS and the solvent removed under vacuum to give compound g which was flashed by ISCO (EtOAc/Hexanes) and rotovapped to give 1.39 g compound g (43% yield). Compound g (0.94 g) was dissolved in 15 ml THF and cooled to 0° C. before adding 9.24 ml 1M LHMDS in THF under $N_2$. The reaction was stirred for 2 hrs 20 min at room temperature followed by the addition of 0.68 g ethylformate and was allowed to stir for four days.

To this reaction mixture was added 5 ml EtOH and 1 ml $H_2O$ followed by 1 ml hydrazine and the solution was stirred at room temperature 2 hrs 20 min. There was no reaction so the mixture was diluted with saturated $NaHCO_3$, extracted with EtOAc, washed with brine, dried over $MgSO_4$, and concentrated in vacuo. This crude intermediate was then dissolved in 30 ml EtOH and 1 ml $H_2O$ followed by 2 ml hydrazine and stirred overnight. Completed reaction was confirmed by LCMS and the reaction mixture was concentrated under vacuum and purified by HPLC to give 176.8 mg of the TFA salt of the final compound 59 in an 18% yield.

Example 27

Synthesis of Compound 60

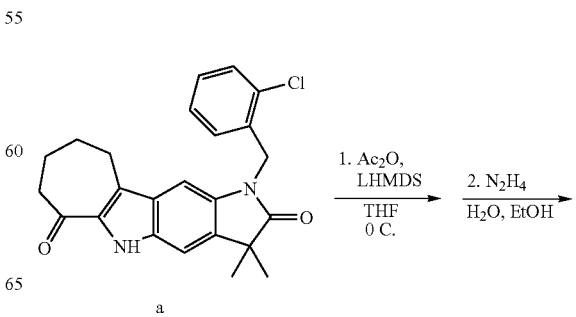

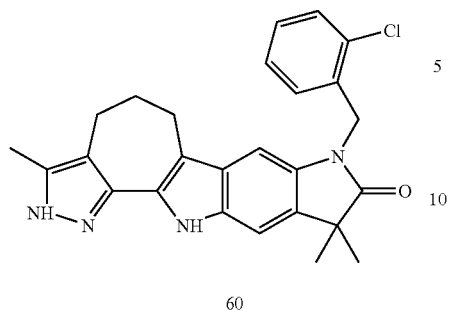

60

Compound a from example 26 (0.85 g) was dissolved in 15 ml THF and cooled to 0° C. before adding 8.36 ml 1M LHMDS in THF under N$_2$. The reaction was stirred for 3 hrs 20 min at room temperature followed by the addition of 0.85 g Ac$_2$O and allowed to stir for four days. To this reaction mixture was then added 5 ml of EtOH and 1 ml H$_2$O followed by 1 ml hydrazine and the solution was stirred overnight at room temperature. Completed reaction was confirmed by LCMS and the reaction was rotovapped, diluted with saturated NaHCO$_3$, extracted with EtOAc, washed with brine, dried over MgSO$_4$, concentrated under vacuum and purified by HPLC to give 0.18 g of the TFA salt of the final compound 60 in a 19.5% yield.

Example 28

Synthesis of Compound 61

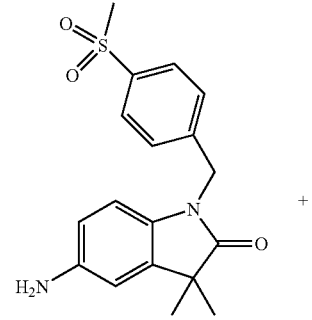

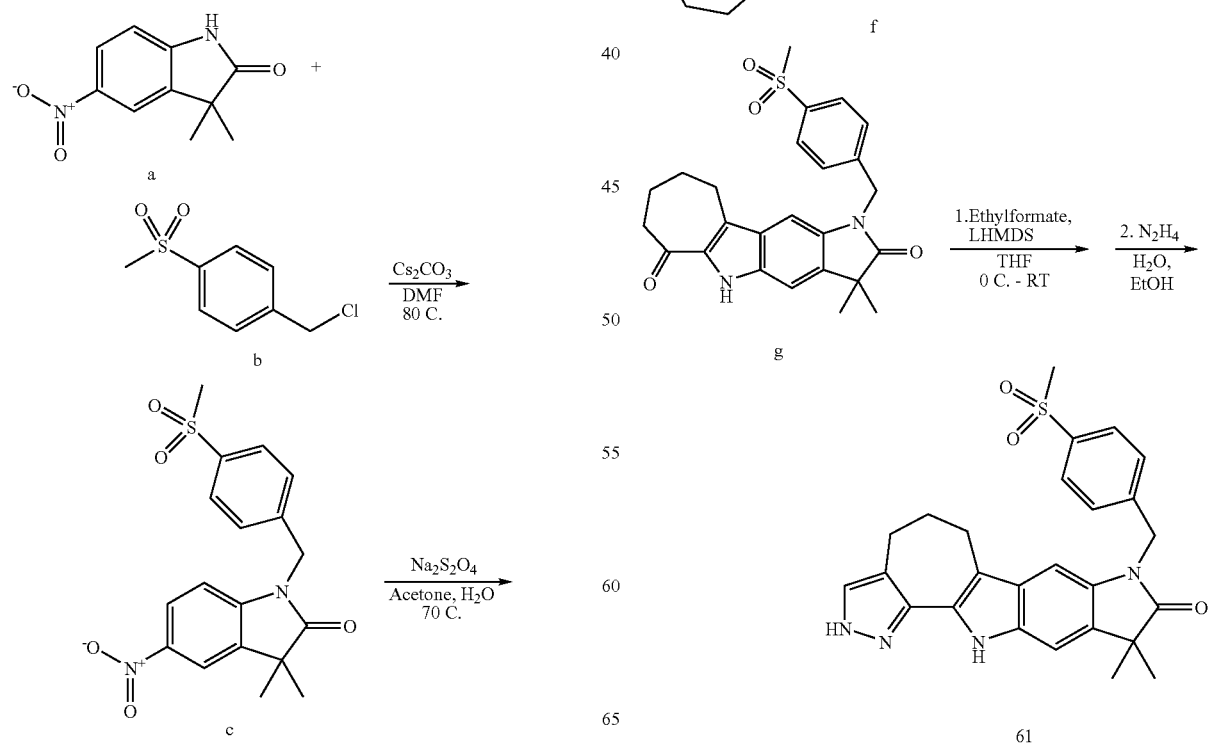

Compound a from example 1 (3.13 g) was dissolved in 50 ml of DMF. To this solution was added 11.87 g Cs₂CO₃ and 4.54 g of p-(methylsulfonyl)benzyl chloride b and the mixture was heated at 80° C. under N₂ with stirring for 12 hrs by which time the reaction was completed by TLC. The reaction mixture was cooled to room temperature, diluted with 1 M HCl, extracted with EtOAc, washed with brine, dried over MgSO₄, and concentrated under vacuum to give 5.6 g (99% yield) of compound c. Compound c was dissolved in 200 ml acetone and 100 ml of H₂O and heated to 70° C. at which point sodium hydrosulfite (52.1 g) was added and the reaction mixture was stirred overnight at 70° C. The reaction was completed by LCMS so the acetone was removed under vacuum and the mixture diluted with H₂O, extracted with EtOAc, partitioned with saturated NaHCO₃, washed EtOAc with brine, dried over MgSO₄ and concentrated under vacuum to give 2.2 g compound d (43% yield).

Compound d was dissolved in 50 ml H₂O and 0.83 ml concentrated HCl and cooled to 0° C. To this mixture was added 0.52 g NaNO₂ in 10 ml H₂O and the mixture was stirred for 30 minutes at 0° C. This was then added to 1.05 g compound e from example 2 and 2.30 g NaOAc in 20 ml H₂O and 20 ml MeOH. The solution was allowed to warm up to room temperature and stir overnight. The reaction was completed by LCMS and the precipitate formed was filtered off and confirmed to be intermediate f which was dried under vacuum and dissolved in 50 ml 10% HCl in AcOH and heated to 80° C. for 2 hours. The reaction was completed by LCMS and the solvent removed under vacuum to give compound g which was flashed by ISCO (EtOAc/Hexanes) and concentrated in vacuo to give 0.95 g compound g (34% yield).

Compound g (0.95 g) was dissolved in 15 ml THF and cooled to 0° C. before adding 10.55 ml 1M LHMDS in THF under N₂. The reaction was stirred for 2 hrs 30 min at room temperature followed by the addition of 0.78 g ethylformate and was allowed to stir overnight, the reaction was not completed so 1.66 g more ethylformate was added and the reaction mixture was stirred for two more days at room temperature. Reaction never went to completion by LCMS and was stopped. The reaction was diluted with sat. NaHCO₃, extracted with EtOAc, washed with brine and concentrated in vacuo. To this crude intermediate was added 5 ml EtOH and 1 ml H₂O followed by 1 ml hydrazine and the reaction mixture was stirred at room temperature overnight. Completed reaction was confirmed by LCMS and the reaction mixture was concentrated under vacuum and purified by HPLC to give the TFA salt of the final compound 61.

Example 29

Synthesis of Compound 62

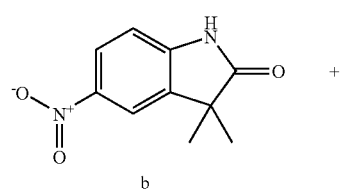

-continued

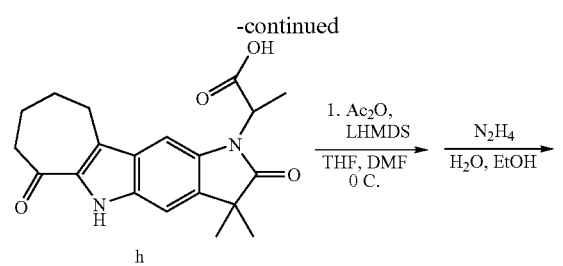

h

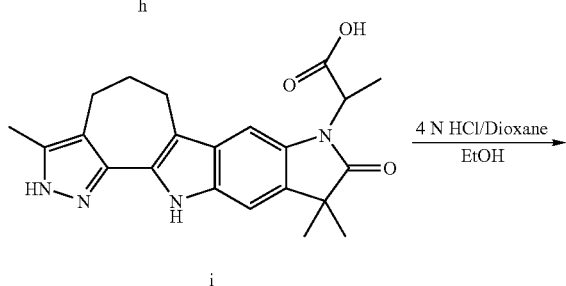

i

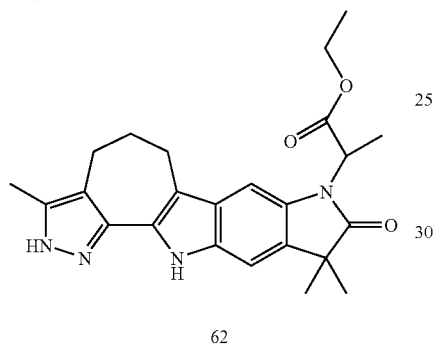

62

Compound b from example 1 (3.12 g) was dissolved in 100 ml of DMF. To this solution was added 9.87 g Cs$_2$CO$_3$ and 3.03 g of methyl-3-bromoproprionate a. The mixture was heated at 80° C. under N$_2$ with stirring for 24 hours at which time the reaction was completed by TLC. The reaction mixture was cooled to room temperature and diluted with 1 M HCl, extracted with EtOAc, washed with brine, dried over MgSO$_4$, and concentrated under vacuum to give 2.96 g (67% yield) of compound c. Compound c was dissolved in 100 ml EtOH and 200 uL of concentrated HCl and bubbled under N$_2$ for 5 minutes at which time 2 scoops of 10% Pd/C was added, an H$_2$ balloon attached and the reaction stirred at room temp 12 hours. The reaction was completed by LCMS, filtered over celite and concentrated under vacuum to give 2.6 g compound d (98% yield).

Compound d (2.6 g) was dissolved in 60 ml H$_2$O and 1.32 ml concentrated HCl and cooled to 0° C. To this mixture was added 0.82 g NaNO$_2$ in 10 ml H$_2$O and the mixture was stirred for 30 minutes. This was added to 1.66 g compound e (compound f from example 2) and 3.66 g NaOAc in 40 ml H$_2$O and 40 ml MeOH at 0° C. The solution was allowed to warm up to room temperature and stir overnight. The reaction was completed by LCMS and the precipitate formed was filtered off. This was confirmed by LCMS to be intermediate f which was dried under vacuum and dissolved in 50 ml 10% HCl in AcOH and heated to 80° C. overnight with stirring. The reaction was completed by LCMS and the solvent removed under vacuum to give compound g which was flashed by ISCO (EtOAc/hexanes) and concentrated in vacuo to give 1.51 g compound gi (41% yield). Compound g (1.5 g) was dissolved 30 ml H$_2$O and 30 ml THF and 12.21 ml 1 M LiOH was added and the reaction was allowed to stir overnight. The reaction was not complete by LCMS so 12.21 ml more 1M LiOH was added and the solution stirred overnight again. The reaction was now complete by LCMS and the THF was removed under vacuum and the remaining aqueous solution acidified with concentrated HCl, extracted with EtOAc, washed with brine, dried over MgSO$_4$ and concentrated under vacuum to give 1.76 g crude compound h (not further purified)

Compound h (0.80 g) was dissolved in 50 ml THF and cooled to 0° C. before adding 9.04 ml 1M LHMDS in THF under N$_2$. The reaction was stirred for 12 hrs at room temperature followed by the addition of 0.92 g acetic anhydride and was allowed to stir overnight at room temperature. To this reaction mixture was added 10 ml EtOH and 1 ml H$_2$O followed by 1 ml hydrazine and the mixture was stirred at room temperature overnight. The reaction was completed by LCMS, concentrated in vacuo and purified by HPLC to give compound i. Compound i (140 mg) was dissolved in 50 EtOH and 10 ml 4N HCl/Dioxane and stirred for 4 days. The reaction was completed by LCMS, concentrated in vacuo and purified by HPLC to give the TFA salt of the final compound 62 in a 28% yield.

Example 30

Synthesis of Compound 63

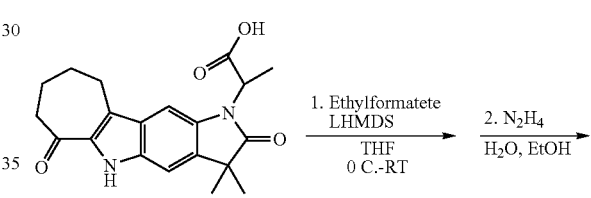

a

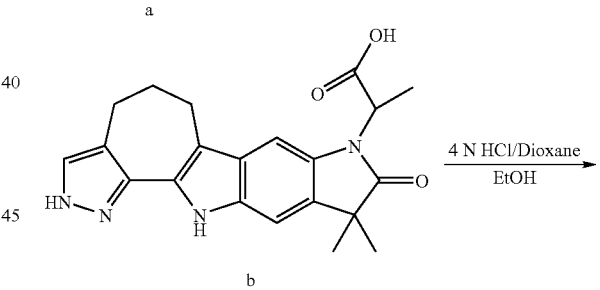

b

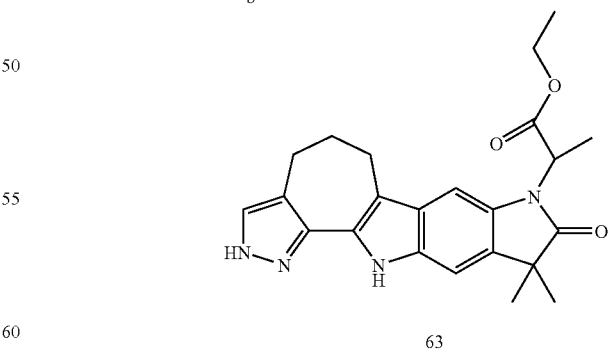

63

Compound a from the synthesis in example 29 (0.96 g) was dissolved in 50 ml THF and cooled to 0° C. before adding 10.84 ml of 1M LHMDS in THF under N$_2$. The reaction was stirred for 12 hrs at room temperature followed by the addition of 0.80 g ethylformate and was allowed to stir for three days at room temperature. To this reaction mixture was added 10 ml EtOH and 1 ml H₂O followed by 1 ml hydrazine and the mixture was stirred at room temperature overnight. The reaction was completed by LCMS, concentrated under vacuum and purified by HPLC to give compound b. Compound b (150 mg) was dissolved in 50 ml EtOH and 10 ml 4N HCl/dioxane and was stirred overnight at room temperature. The reaction was completed by LCMS, concentrated in vacuo and purified by HPLC to give the TFA salt of the final compound 63.

Example 31

Synthesis of Compound 64

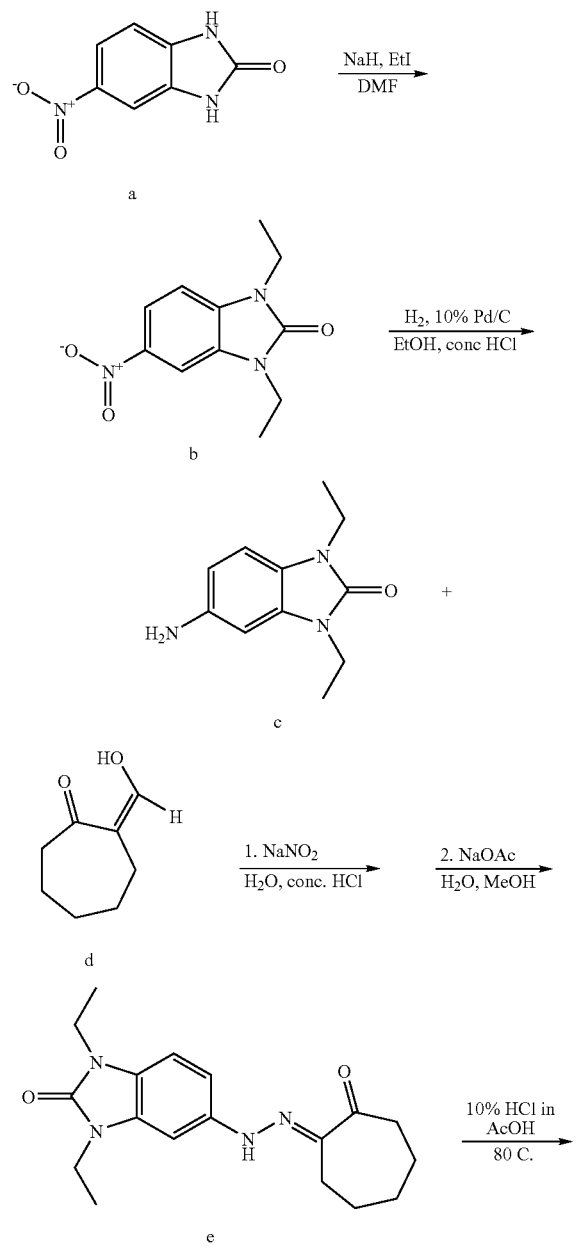

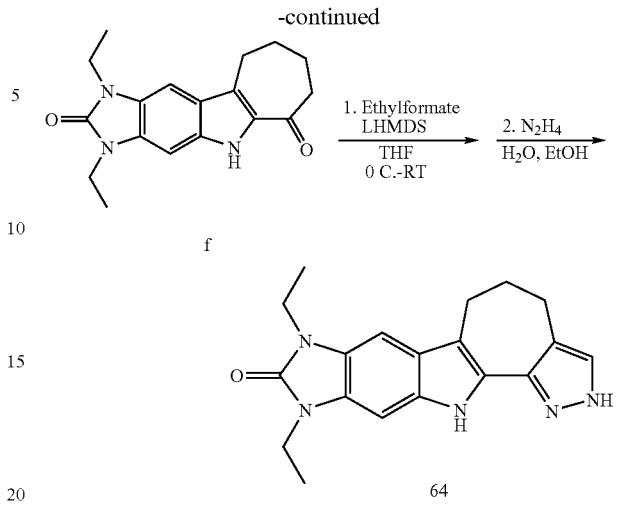

Commercially available 5-nitro-2-benzimidazolinone a was dissolved in 70 ml of DMF in a round bottom flask with a vigreux condensation column attached. To this solution was added 9.22 g Cs₂CO₃ and 4.41 g of ethyl iodide and the mixture was placed under N₂ in an oil bath heated to 80° C. for 12 hours. The reaction was almost complete by TLC, so it was cooled to room temp, diluted with 1 M HCl, extracted with EtOAc, washed with brine, dried over MgSO₄, concentrated under vacuum, and flashed by ISCO (EtOAc/hexanes) to give compound b. Compound b was dissolved in 200 ml EtOH and 200 uL of concentrated HCl and bubbled under N₂ for 10 minutes at which time 2 scoops of 10% Pd/C was added and an H₂ balloon attached. This was stirred 12 hours. The reaction was completed by LCMS, filtered over celite and concentrated under vacuum to give compound c.

Compound c was dissolved in 50 ml H₂O and 1.27 ml concentrated HCl and cooled to 0° C. To this mixture was added 0.79 g NaNO₂ in 10 ml H₂O and the mixture was stirred 2 hrs 25 minutes at 0° C. This was then added to 1.60 g compound d from example 2 and 3.51 g NaOAc in 100 ml H₂O and 100 ml MeOH. The solution was allowed to warm up to room temperature and stir overnight. When complete by LCMS the precipitate formed was filtered off and confirmed to be intermediate e, which was dried under vacuum and dissolved in 50 ml 10% HCl in AcOH and heated to 80° C. for 2 hours and stirred at room temperature overnight. The reaction was completed by LCMS and the solvent was removed under vacuum to give compound i which was flashed by ISCO (EtOAc/hexanes) and concentrated in vacuo to give 1.12 g compound f (38% yield). Compound f was dissolved in 35 ml THF and cooled to 0° C. before adding 18.0 ml 1M LHMDS in THF under N₂. The reaction was stirred for 3 hrs 20 min at 0° C. followed by addition of 1.33 g ethylformate and let warm up to room temperature and stir overnight. To this reaction mixture was then added 10 ml of EtOH and 1 ml H₂O followed by 1 ml hydrazine and was stirred overnight at room temperature. Completed reaction was confirmed by LCMS and the reaction was diluted with sat. NaHCO₃, extracted with EtOAc, washed with brine, dried over MgSO₄, concentrated in vacuo, and purified by HPLC to give 370 mg impure product and 46.8 mg of the final compound 64.

Example 32

Synthesis of Compound 65

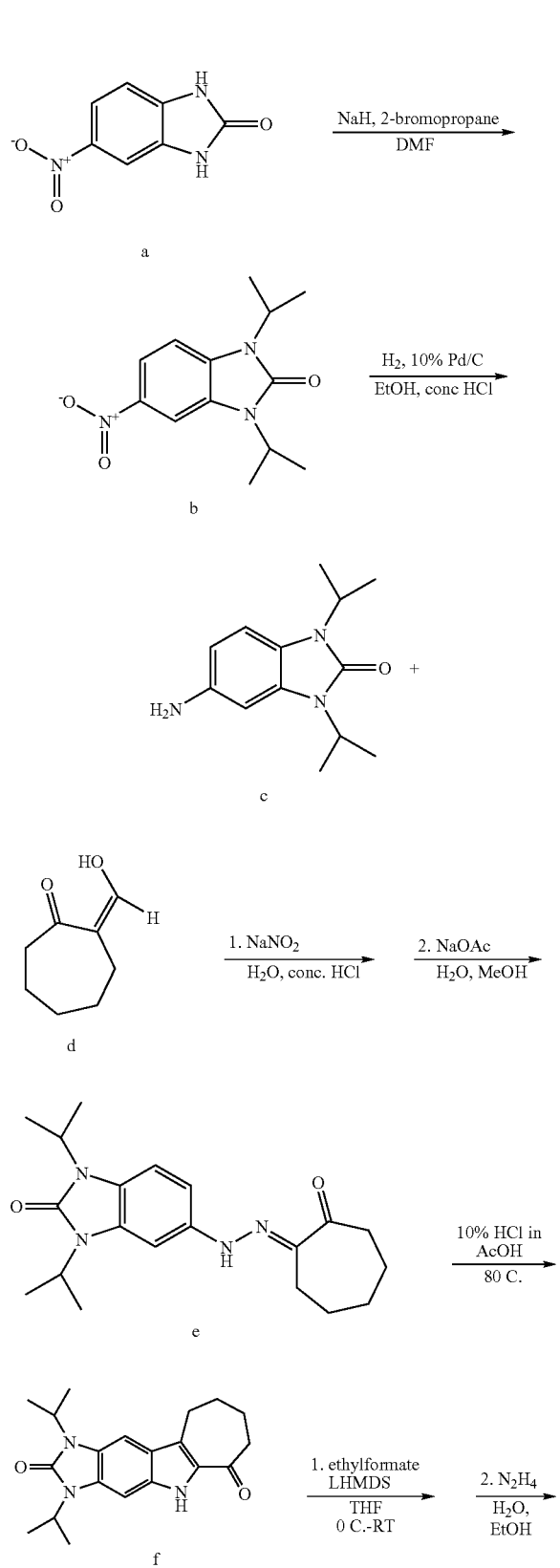
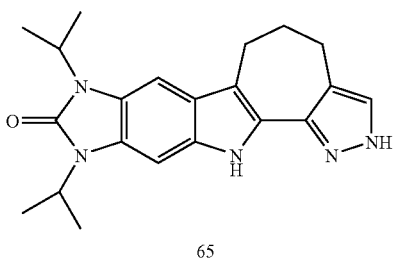

Commercially available 5-Nitro-2benzimidazolinone a was dissolved in 50 ml of DMF in a round bottom flask with a vigreux condensation column attached. To this solution was added 23.65 g $Cs_2CO_3$ and 8.93 g of 2-bromopropane and the mixture was placed under $N_2$ in an oil bath heated to 80° C. for 12 hours. The reaction was almost complete by TLC, so it was cooled to room temp, diluted with 1 M HCl, extracted with EtOAc, washed with brine, dried over $MgSO_4$, concentrated under vacuum, and flashed on silica (EtOAc/hexanes) to give 7.64 g compound b. Compound b (6.35 g) was dissolved in 200 ml EtOH and 200 uL of concentrated HCl and bubbled under $N_2$ for 10 minutes at which time 2 scoops of 10% Pd/C was added and an $H_2$ balloon attached. This was stirred for 48 hours. The reaction was completed by LCMS, filtered over celite and concentrated under vacuum to give compound c (5.6 g) in a 99% yield.

Compound c was dissolved in 50 ml $H_2O$ and 3.2 ml concentrated HCl and cooled to 0° C. To this mixture was added 1.99 g $NaNO_2$ in 10 ml $H_2O$ and the mixture was stirred for 30 minutes at 0° C. This was then added to 4.03 g compound d from example 2 and 8.86 g NaOAc in 50 ml $H_2O$ and 50 ml MeOH. The solution was allowed to warm up to room temperature and stir overnight. When complete by LCMS the precipitate formed was filtered off and confirmed to be intermediate e which was dried under vacuum, dissolved in 50 ml 10% HCl in AcOH and heated to 80° C. for 2 hours and stirred at room temperature overnight. The reaction was completed by LCMS and the solvent was removed under vacuum to give compound f which was flashed by ISCO (EtOAc/hexanes) and concentrated in vacuo. Compound f (0.91 g) was dissolved in 20 ml THF and cooled to 0° C. before adding 10.72 ml 1 M LHMDS in THF under $N_2$. The reaction was stirred for 2.5 hrs at 0° C. followed by addition of 0.79 g ethylformate and allowed to warm up to room temperature and stir overnight. The reaction was about half complete and was worked up by diluting with sat. $NAHCO_3$, extracting with ethyl acetate, washing with brine, and concentrated under vacuum. To this reaction mixture was then added 50 ml of EtOH and 1 ml $H_2O$ followed by 2 ml hydrazine and the solution was stirred overnight at room temperature. Completed reaction was confirmed by LCMS and the reaction was diluted with sat. $NaHCO_3$, extracted with EtOAc, washed with brine, dried over $MgSO_4$, concentrated in vacuo, and purified by HPLC to give 278.1 mg of the final compound 65 (29% yield).

Example 33

Synthesis of Compound 66

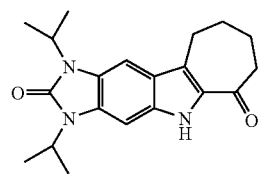

a

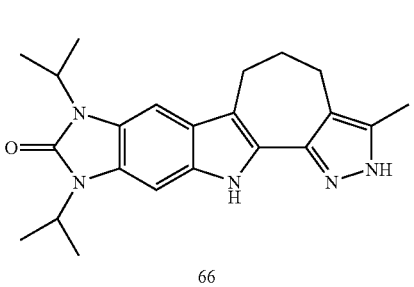

66

Compound a from example 32 (0.91 g) was dissolved in 40 ml THF and cooled to 0° C. before adding 13.4 ml 1M LHMDS in THF under N$_2$. The reaction was stirred for 2.5 at room temperature followed by the addition of 1.37 g Ac$_2$O and was allowed to overnight at room temperature. To this reaction mixture was then added 20 ml of EtOH and 10 ml H$_2$O followed by 2 ml hydrazine and the reaction mixture was stirred overnight at room temperature. Completed reaction was confirmed by LCMS and the reaction was concentrated in vacuo, diluted with saturated NaHCO$_3$, extracted with EtOAc, washed with brine, dried over MgSO$_4$, concentrated under vacuum and purified by HPLC to give 0.12 g of the TFA salt of the final compound 66 in a 12% yield.

Example 34

Synthesis of Compound 67 and 68

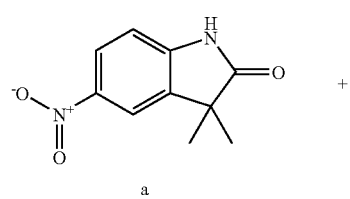

a

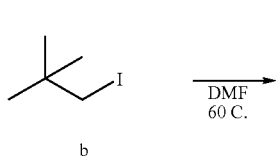

b

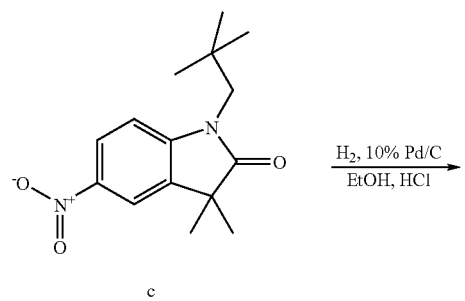

c

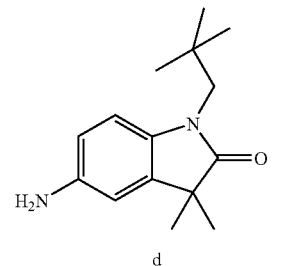

d

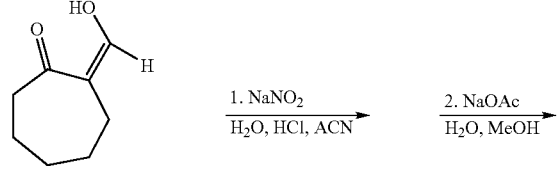

e

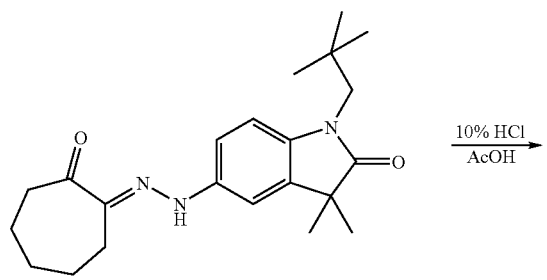

f

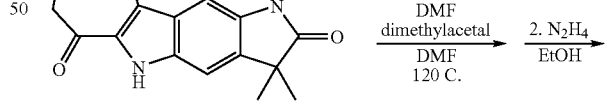

g

67

Example 35

Synthesis of Compound 69

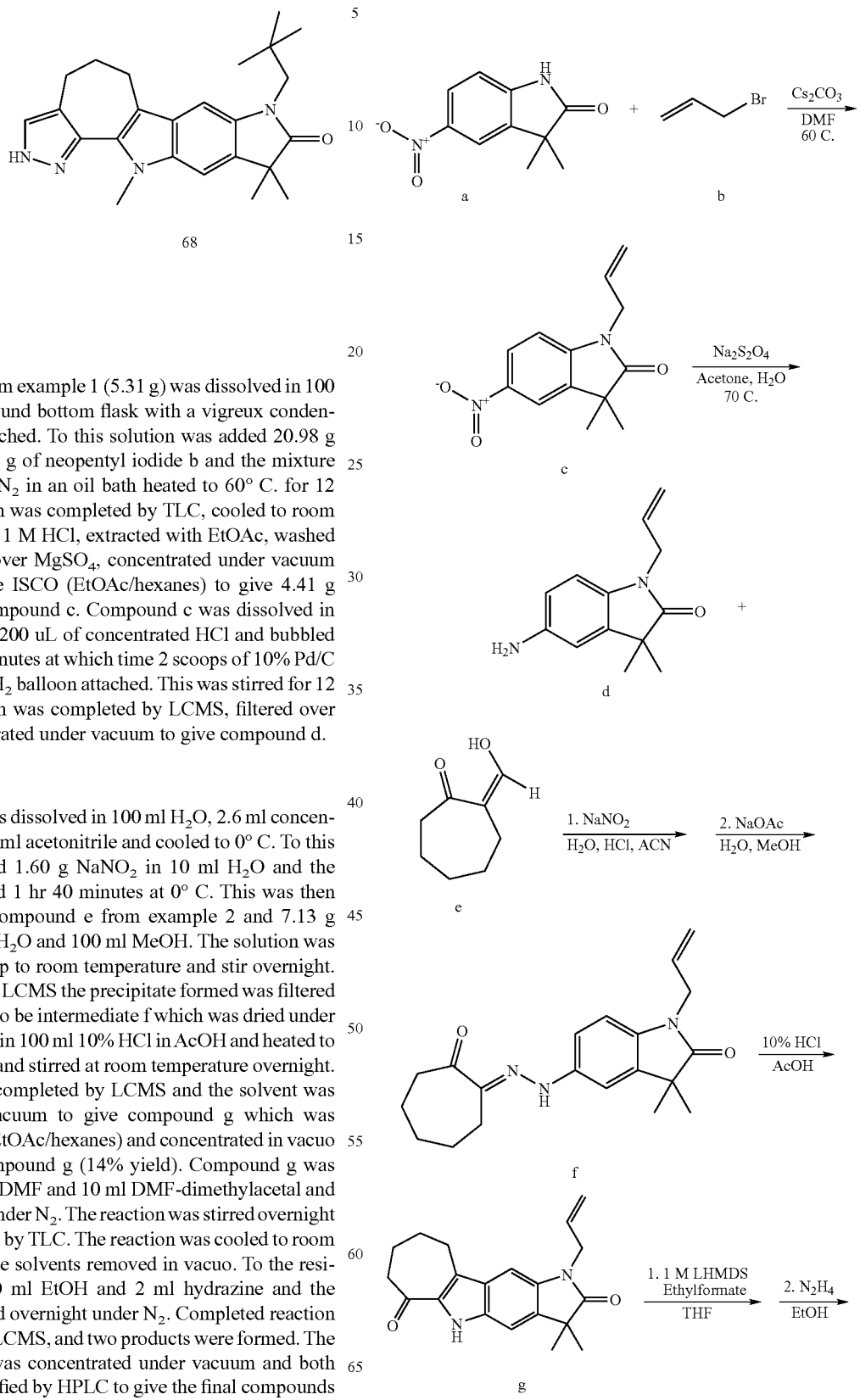

Compound a from example 1 (5.31 g) was dissolved in 100 ml of DMF in a round bottom flask with a vigreux condensation column attached. To this solution was added 20.98 g Cs$_2$CO$_3$ and 12.75 g of neopentyl iodide b and the mixture was placed under N$_2$ in an oil bath heated to 60° C. for 12 hours. The reaction was completed by TLC, cooled to room temp, diluted with 1 M HCl, extracted with EtOAc, washed with brine, dried over MgSO$_4$, concentrated under vacuum and flashed on the ISCO (EtOAc/hexanes) to give 4.41 g (62% yield) of compound c. Compound c was dissolved in 200 ml EtOH and 200 uL of concentrated HCl and bubbled under N$_2$ for 10 minutes at which time 2 scoops of 10% Pd/C was added and an H$_2$ balloon attached. This was stirred for 12 hours. The reaction was completed by LCMS, filtered over celite and concentrated under vacuum to give compound d.

Compound d was dissolved in 100 ml H$_2$O, 2.6 ml concentrated HCl, and 70 ml acetonitrile and cooled to 0° C. To this mixture was added 1.60 g NaNO$_2$ in 10 ml H$_2$O and the mixture was stirred 1 hr 40 minutes at 0° C. This was then added to 3.25 g compound e from example 2 and 7.13 g NaOAc in 100 ml H$_2$O and 100 ml MeOH. The solution was allowed to warm up to room temperature and stir overnight. When complete by LCMS the precipitate formed was filtered off and confirmed to be intermediate f which was dried under vacuum, dissolved in 100 ml 10% HCl in AcOH and heated to 80° C. for 3 hours and stirred at room temperature overnight. The reaction was completed by LCMS and the solvent was removed under vacuum to give compound g which was flashed by ISCO (EtOAc/hexanes) and concentrated in vacuo to give 0.98 g compound g (14% yield). Compound g was dissolved in 10 ml DMF and 10 ml DMF-dimethylacetal and heated to 120° C. under N$_2$. The reaction was stirred overnight and was completed by TLC. The reaction was cooled to room temperature and the solvents removed in vacuo. To the residue was added 20 ml EtOH and 2 ml hydrazine and the reaction was stirred overnight under N$_2$. Completed reaction was confirmed by LCMS, and two products were formed. The reaction mixture was concentrated under vacuum and both products were purified by HPLC to give the final compounds 67 and 68.

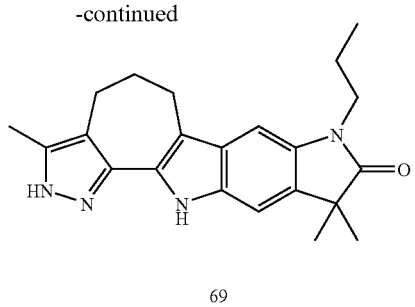

69

Compound a from example 1 (15.34 g) was dissolved in 50 ml of DMF. To this solution was added 60.62 g Cs₂CO₃ and 22.51 g of allyl bromide b and the mixture was heated at 65° C. under N₂ with stirring for 12 hrs by which time the reaction was completed by TLC. The reaction mixture was cooled to room temperature, diluted with 1 M HCl, extracted with EtOAc, washed with brine, dried over MgSO₄, and concentrated under vacuum to give 11.8 g (64% yield) of compound c. Compound c was dissolved in 150 ml acetone and 75 ml of H₂O and heated to 70° C. at which point sodium hydrosulfite (166.87 g) was added and the reaction mixture stirred four days at 70° C. The reaction was completed by LCMS so the acetone was removed under vacuum and the mixture diluted with H₂O, extracted with EtOAc, partitioned with saturated NaHCO₃, washed with brine, dried over MgSO₄ and concentrated under vacuum to give 4.08 g compound d (39% yield).

Compound d was dissolved in 50 ml H₂O and 2.52 ml concentrated HCl and cooled to 0° C. To this mixture was added 1.56 g NaNO₂ in 10 ml H₂O and the mixture was stirred for 60 minutes at 0° C. This was then added to 3.17 g compound e from example 2 and 6.97 g NaOAc in 100 ml H₂O and 100 ml MeOH. The solution was allowed to warm up to room temperature and stir overnight. When complete by LCMS the precipitate formed was filtered off and confirmed by LCMS to be intermediate f which was dried under vacuum, dissolved in 100 ml 10% HCl in AcOH and heated to 80° C. for 3 hours and stirred at room temperature overnight. The reaction was completed by LCMS and the solvent removed under vacuum to give compound g which was flashed by ISCO (EtOAc/hexanes) and concentrated in vacuo to give 2.97 g compound g (49% yield).

Compound g (2.97 g) was dissolved in 100 ml THF and cooled to 0° C. before adding 46.05 ml 1M LHMDS in THF under N₂. The reaction was stirred for 3 hrs at room temperature followed by addition of 3.41 g ethylformate and was allowed to stir overnight. The reaction was half complete by LCMS. The reaction was worked up by diluting the mixture with sat NaHCO₃, extracting with brine, drying over MgSO₄, and concentrating in vacuo. To this crude intermediate was added 10 ml EtOH and 2 ml H₂O followed by 4 ml hydrazine and the reaction was stirred at room temperature overnight. Completed reaction was confirmed by LCMS and the reaction mixture was diluted with sat. NaHCO₃, extracted with DCM, dried over MgSO₄, concentrated under vacuum and purified by HPLC to give 139 mg of the TFA salt of the final compound 69.

Example 36

Synthesis of Compound 70

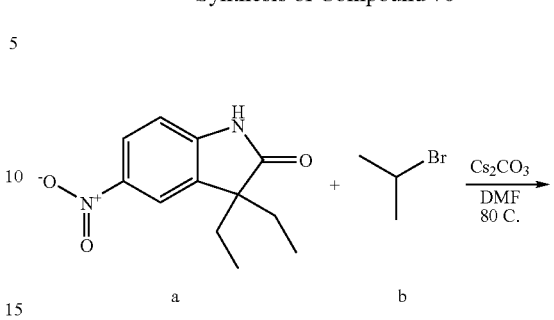

a
b

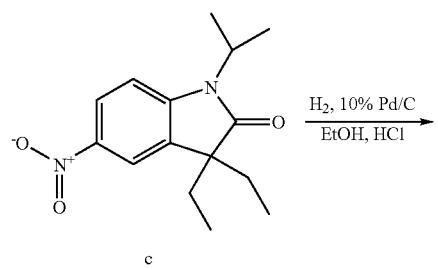

c

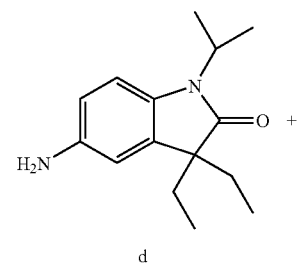

d

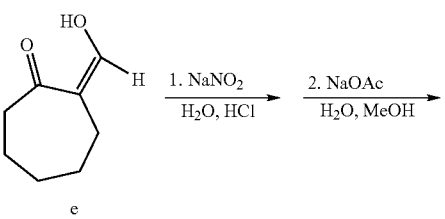

e

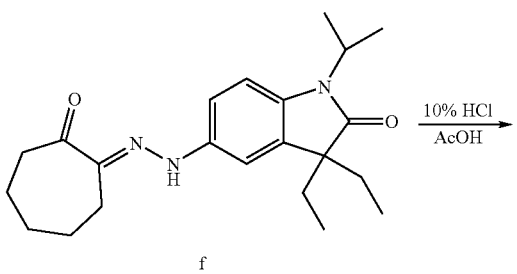

f

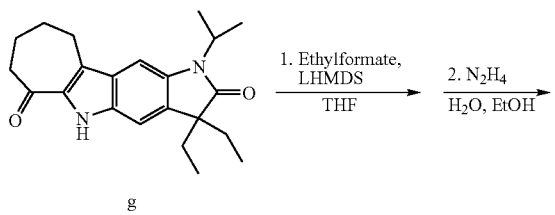

g

-continued

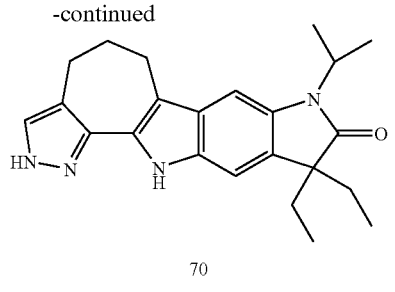

70

Compound a from example 8 (8.56 g) was dissolved in 100 ml of DMF. To this solution was added 29.76 g $Cs_2CO_3$ and 11.24 g of 2-bromopropane b and the mixture was heated at 80° C. under $N_2$ with stirring for 24 hours by which time the reaction was completed by TLC. The reaction mixture was cooled and diluted with 1 M HCl, extracted with EtOAc, washed with brine, dried over $MgSO_4$, concentrated under vacuum, and flashed on the ISCO to give 8.57 g (85% yield) of compound c. Compound c (8.57 g) was dissolved in 150 ml EtOH and 500 uL of concentrated HCl and bubbled under $N_2$ for 10 minutes at which time 2.5 scoops of 10% Pd/C was added, an $H_2$ balloon attached and the reaction stirred at room temp 12 hours. When complete by LCMS the reaction mixture was filtered over celite and concentrated under vacuum to give 7.67 g compound d (89% yield).

Compound d (7.67 g) was dissolved in 100 ml $H_2O$ and 3.1 ml concentrated HCl and cooled to 0° C. To this mixture was added 2.57 g $NaNO_2$ in 10 ml $H_2O$ and the mixture was stirred 60 minutes. This was added to 5.21 g compound e from example 2 and 11.45 g NaOAc in 50 ml $H_2O$ and 50 ml MeOH at 0° C. The solution was allowed to warm up to room temperature and stir overnight. When complete by LCMS the reaction mixture was diluted with sat. $NaHCO_3$, extracted with EtOAc, dried over $MgSO_4$, confirmed to be compound f by LCMS and dried under vacuum. Compound f was dissolved in 100 ml of 10% HCl in AcOH and heated to 80° C. for 3 hours. The reaction was completed by LCMS, concentrated under vacuum and flashed by ISCO to give 2.69 g (25% yield) of compound g.

Compound g was dissolved in 100 ml THF, cooled to 0° C. and 38.15 ml 1M LHMDS in THF was added slowly under $N_2$ and the reaction was stirred for 1 hr at 0° C. To this mixture was added 2.83 g ethylformate. The reaction was allowed to warm up to room temperature and stir overnight. The reaction was completed by LCMS and diluted with sat. $NaHCO_3$, extracted with EtOAc, washed with brine, and concentrated in vacuo. This intermediate was flashed by ISCO and dissolved in 50 ml EtOH and 1 ml $H_2O$ followed by the addition of 3 ml hydrazine and the reaction was stirred overnight. Completed reaction was confirmed by LCMS and the reaction mixture concentrated under vacuum and purified by HPLC to give 232 mg of the TFA salt of the final compound 70.

Example 37

Synthesis of Compound 71

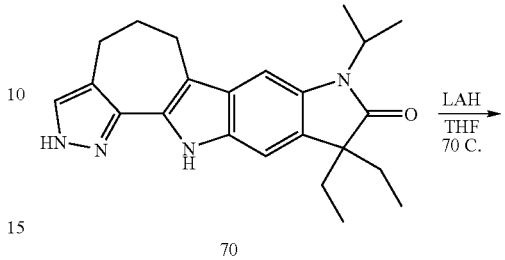

70

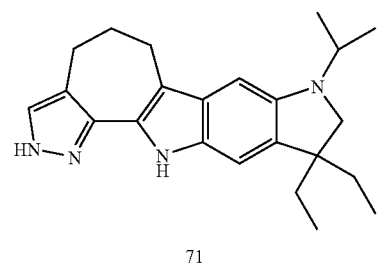

71

Compound 70 (109.5 mg) was dissolved in 40 ml THF and cooled to 0° C. under $N_2$. To this was added 2.32 ml 1 M LAH and the reaction heated to 70° C. overnight. The reaction was half complete by TLC and was quenched with 4 ml $H_2O$ and 1 ml 10% NaOH and allowed to stir overnight. Diluted reaction mixture with sat. $NaHCO_3$, extracted with EtOAc, dried over $mgSO_4$, concentrated by vacuum, and purified by HPLC to give the final compound 71.

Example 38

Synthesis of Compound 72

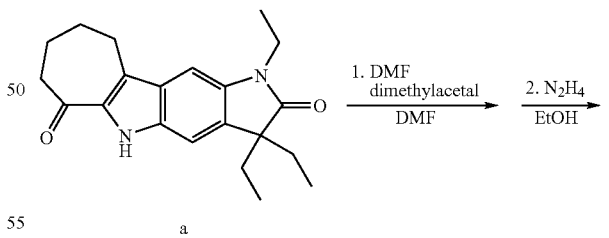

a

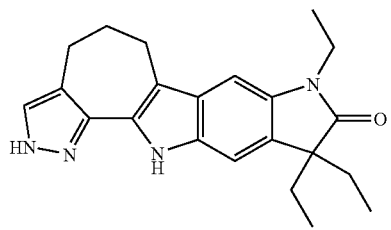

72

Compound a from example 8 was dissolved in 10 ml DMF and 20 ml DMF-dimethylacetal and was heated to 120° C. under $N_2$. The reaction was stirred overnight and was completed by TLC. The reaction was cooled to room temperature and the solvents removed in vacuo. To the residue was added 20 ml EtOH and 3 ml hydrazine and the reaction was stirred overnight under $N_2$. Completed reaction was confirmed by LCMS. The reaction mixture was concentrated under vacuum and purified by HPLC to give the final compound 72.

Example 39

Synthesis of Compound 73

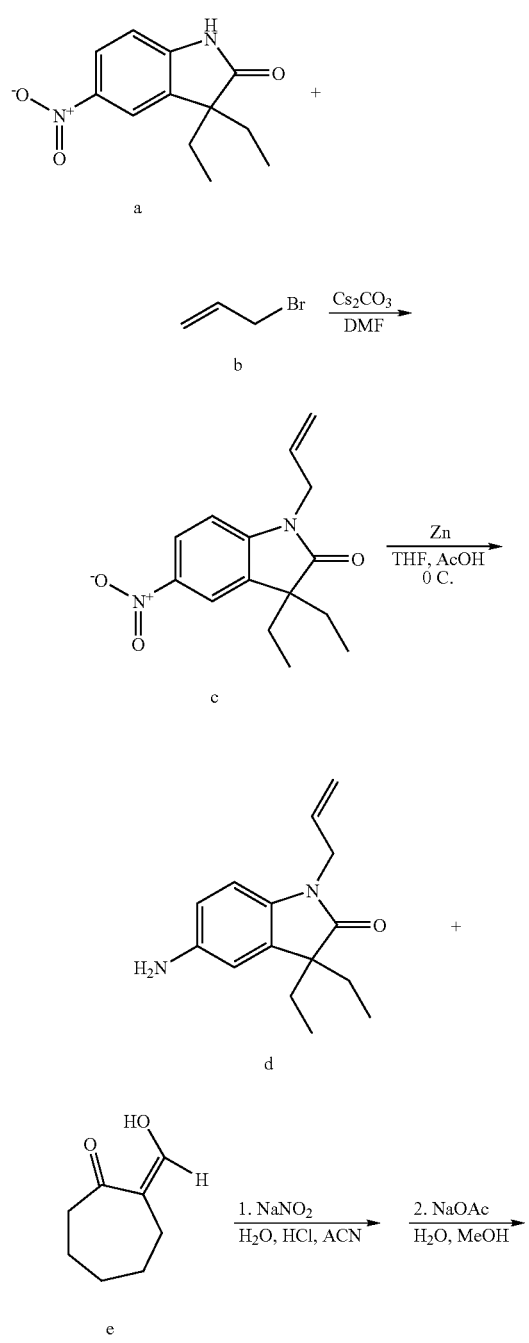

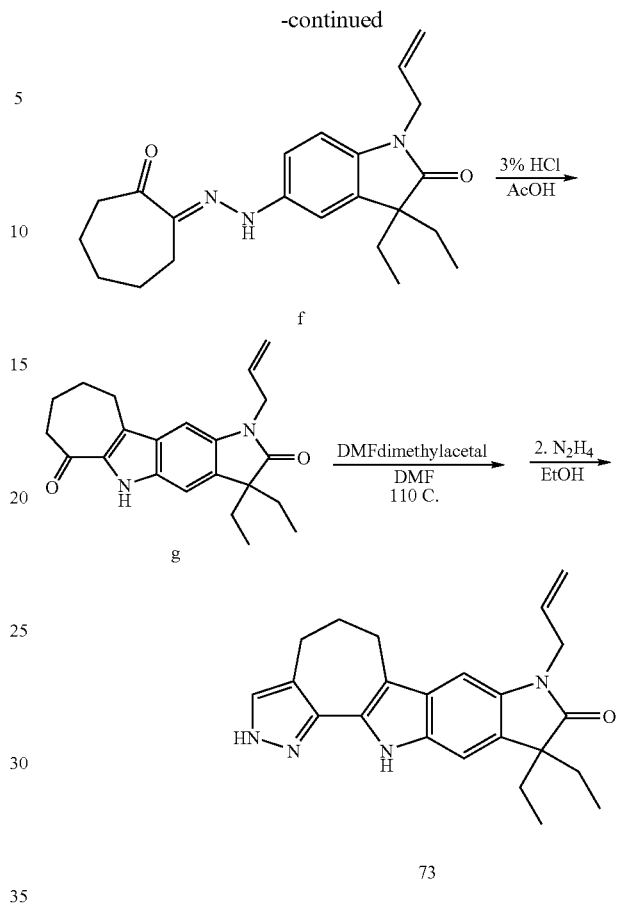

Compound a from example 8 (11.82 g) was dissolved in 100 ml of DMF. To this solution was added 19.73 g $Cs_2CO_3$ and 6.72 g of allyl bromide b and the mixture was stirred under $N_2$ at room temperature for 24 hours by which time the reaction was completed by TLC. The reaction mixture was cooled and diluted with 1 M HCl, extracted with EtOAc, washed with brine, dried over $MgSO_4$, concentrated under vacuum, and flashed on the ISCO (EtOAc/hexanes) to give 11.71 g (85% yield) of compound c. Compound c (11.71 g) was dissolved in 80 ml EtOH and 80 ml Acetic acid under $N_2$, cooled to 0° C. and 13.95 g zinc dust was added. The reaction was stirred at 0° C. 5 hrs 40 minutes under $N_2$. The reaction was completed by LCMS and the reaction mixture was filtered over celite and concentrated under vacuum to give 10.40 g compound d (100% crude yield).

Compound d (10.40 g) was dissolved in 150 ml $H_2O$, 50 ml ACN and 5.7 ml concentrated HCl and cooled to 0° C. To this mixture was added 3.52 g $NaNO_2$ in 10 ml $H_2O$ and the mixture was stirred for 20 minutes. This was added to 7.15 g compound e from example 2 and 15.71 g NaOAc in 100 ml $H_2O$ and 100 ml MeOH at 0° C. The solution was allowed to warm up to room temperature and stir overnight. The reaction was completed by LCMS and was diluted with sat. $NaHCO_3$, extracted with EtOAc, dried over $MgSO_4$, confirmed to be compound f by LCMS and dried under vacuum.

Compound f was dissolved in 100 ml of 3% HCl in AcOH and heated to 80° C. for 3 hours and room temperature overnight. The reaction was completed by LCMS, concentrated under vacuum and flashed by ISCO (EtOAc/hexanes) to give 6.24 g (42% yield) of compound g. Compound g was dissolved in 50 ml DMF-dimethylacetal and 50 ml DMF under N₂ and the reaction was heated to 110° C. with stirring for 4 hrs 40 min. The reaction was completed by TLC, cooled to room temperature and concentrated under vacuum. This intermediate was dissolved in 100 ml EtOH and 10 ml hydrazine and stirred at room temperature for 48 hrs. Completed reaction was confirmed by LCMS and the reaction mixture was concentrated under vacuum and purified by flash on the ISCO (EtOAc/hexanes) to give 5.05 g of the final compound 73 in a 76% yield.

Example 40

Synthesis of Compound 74

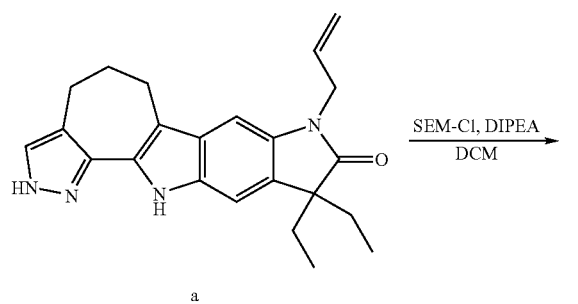

a

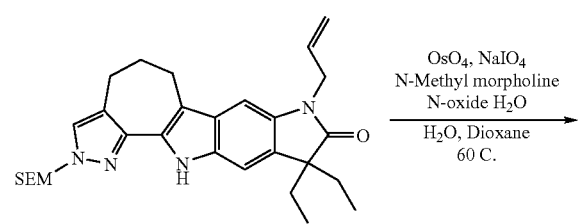

b

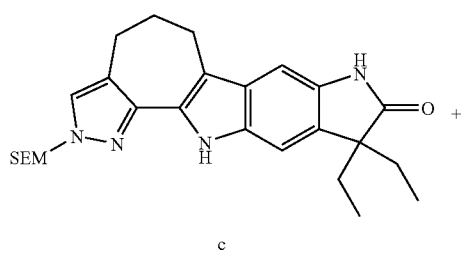

c

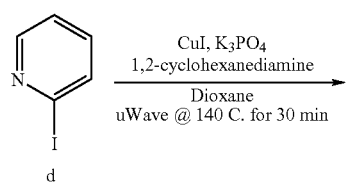

d

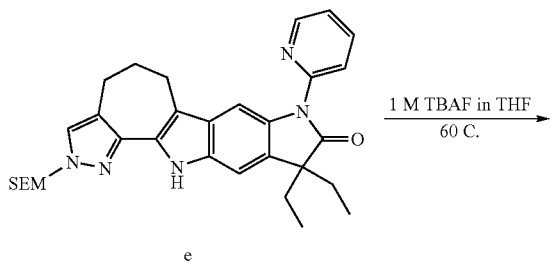

e

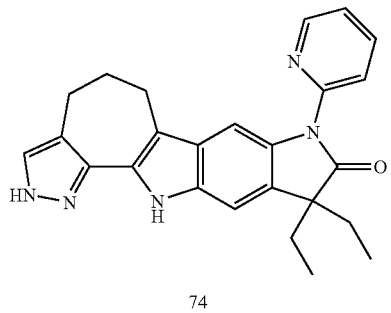

74

Compound a made in the same manner as the compound 73 (5.05 g) was suspended in 120 ml of DCM and cooled to 0° C. in an ice bath. To this suspension was added 3.37 g SEM-Cl and DIPEA and the reaction vessel was capped. The reaction was warmed to room temperature and stirred overnight by which time the reaction was completed by TLC. The reaction mixture was diluted with 0.1 N H₂SO₄ and extracted into the DCM layer, washed with brine, dried over MgSO₄, concentrated under vacuum, and flashed on the ISCO (EtOAc/hexanes) to give 6.48 g of a mixture of compound b and an inseparable side product. Compound b (5.45 g) was dissolved in 11 ml H₂O and 50 ml dioxane and N-methyl morpholine N-oxide H₂O was added and the reaction stirred until everything was in solution. To this reaction mixture was added OsO₄ (0.27 g) in a 100 mg/ml butanol solution followed by the drop wise addition of a slurry of sodium periodate in H₂O and subsequent heating at 60° C. in a capped vessel for 3 hrs 45 min. The reaction was completed by LCMS and the mixture was diluted with brine, extracted with DCM, dried over MgSO₄, concentrated under vacuum, and flashed by ISCO (EtOAc/hexanes) to give compound c.

Compound c (239 mg) was placed in an oven dried microwave reaction vial with CuI (49.5 mg) and K₃PO₄ (216.5 mg) and purged with N₂. To this mixture was added 2-iodopyridine d and the vial was purged again with N₂ followed by addition of 1,2-cyclohexanediamine (58.2 mg) in 2.6 ml dioxane and N₂ was bubbled into the solution for 10 min and the vial crimped. The reaction vial was placed in the microwave for 30 min. at 140° C. The reaction went to half completion and was worked up by filtering off the non-product solids, concentrating under vacuum, and purifying by flash to give 160 mg compound e (60% yield). Compound e was dissolved in 3 ml 1.0 M TBAF in THF and heated to 60° C. overnight. Reaction was completed by LCMS, diluted with H₂O, extracted with EtOAc, washed with brine, dried over MgSO₄, concentrated under vacuum and purified by HPLC to give 78.8 mg of the final compound 74 (64% yield).

Example 41

Synthesis of Compound 75

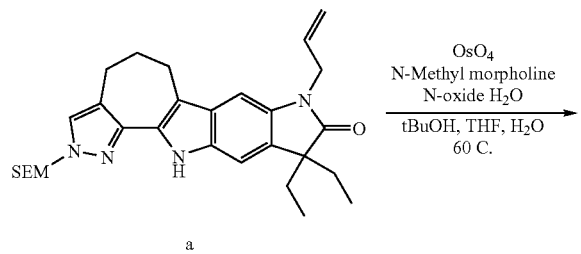

a

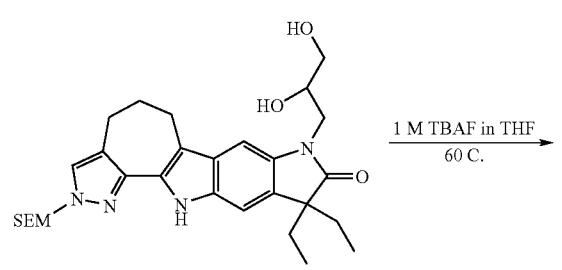

b

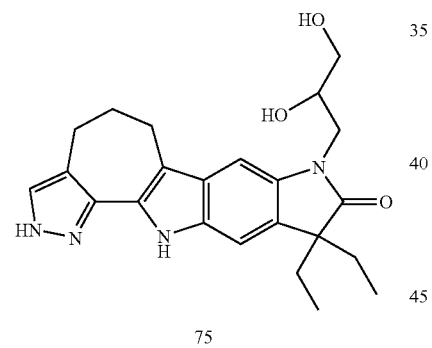

75

Compound a from the synthesis of compound 74 (276 mg) was dissolved in 2 ml tBuOH, 600 uL THF and 200 uL H$_2$O followed by addition of 77.3 mg N-methyl morpholine N-oxide.H$_2$O and 4.2 mg OsO$_4$. The reaction vial was capped and stirred overnight at 60° C. The reaction was completed by TLC. The reaction mixture was diluted with H$_2$O and sat. Na$_2$SO$_3$, extracted with EtOAc, dried over MgSO$_4$, concentrated under vacuum, and flashed on the ISCO (EtOAc/hexanes) to give compound b. Compound b was dissolved in 6 ml 1 M TBAF in THF and heated at 60° C. in a capped vessel overnight. The reaction was completed by LCMS and the mixture was diluted with H$_2$O, extracted with EtOAc, washed with brine, dried over MgSO$_4$, concentrated under vacuum, and purified by HPLC to give then final compound 75.

Example 42

Synthesis of Compound 76

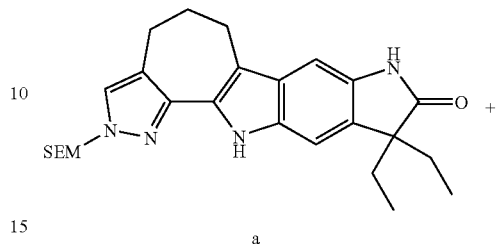

a

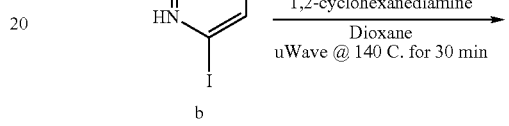

b

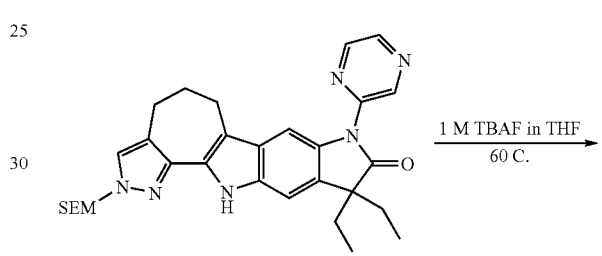

c

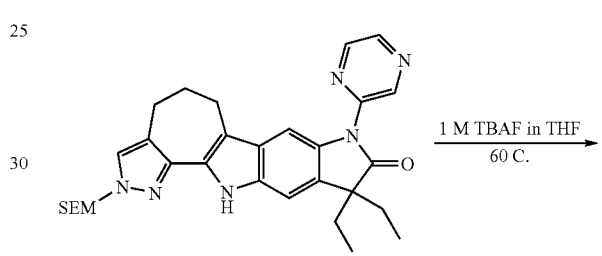

76

Compound a from the synthesis of compound 74 (255 mg) was placed in an oven dried microwave reaction vial with CuI (53.3 mg) and K$_3$PO$_4$ (233.4 mg) and purged with N$_2$. To this mixture was added iodopyrazine b and the vial purged again with N$_2$ followed by addition of 1,2-cyclohexanediamine (62.8 mg) in 2.6 ml dioxane and N$_2$ was bubbled into the solution for 10 min and the vial crimped. The reaction vial was placed in the microwave for 30 min. at 140° C. The reaction went to half completion and was worked up by filtering off the non-product solids, concentrating under vacuum, and purifying by flash to give 139 mg compound c (47% yield). Compound c was dissolved in 3 ml 1.0 M TBAF in THF and heated to 60° C. overnight. The reaction was completed by LCMS and was diluted with H$_2$O, extracted with EtOAc, washed with brine, dried over MgSO$_4$, concentrated under vacuum and purified by SFC to give the final compound 76.

Example 43

Synthesis of Compound 77

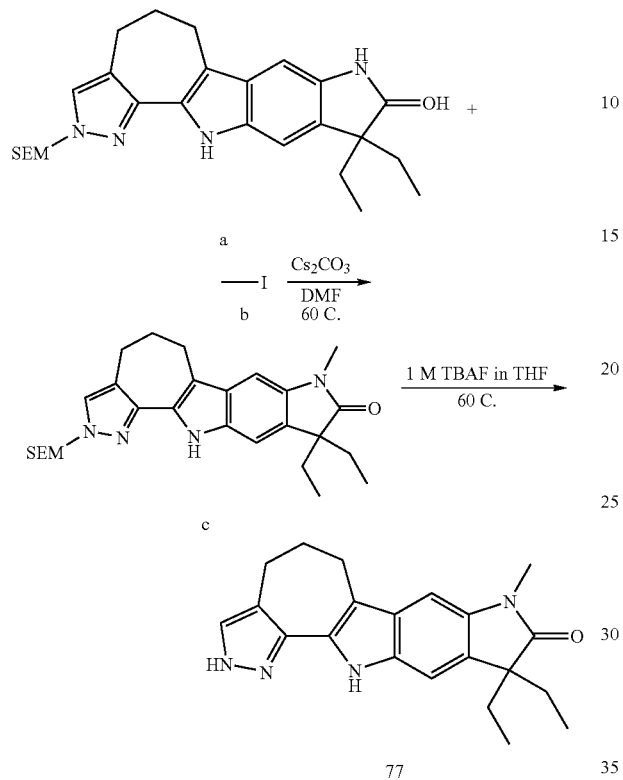

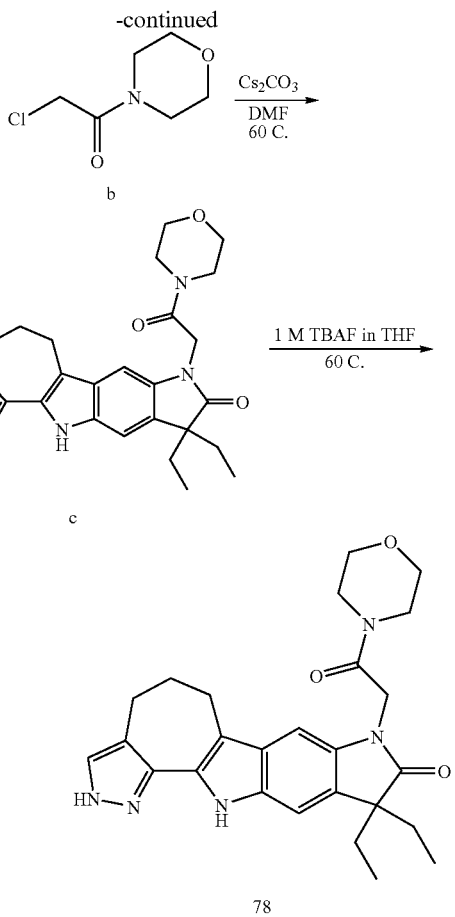

Compound a from the synthesis of compound 74 (129 mg) was dissolved in 1.4 ml DMF and was added to a vial containing $Cs_2CO_3$ (460 mg) followed by the addition of methyl iodide b (200 mg). The vial was capped and the reaction was heated to 60° C. in a heat block overnight. The reaction was completed by TLC. Diluted the reaction with $H_2O$, extracted with EtOAc, dried over $MgSO_4$, and concentrated by vacuum to give compound c. Compound c was dissolved in 3 ml 1.0 M TBAF in THF and heated to 60° C. overnight. The reaction was completed by LCMS and diluted with $H_2O$, extracted with EtOAc, washed with brine, dried over $MgSO_4$, concentrated under vacuum and purified by HPLC to give the final compound 77.

Example 44

Synthesis of Compound 78

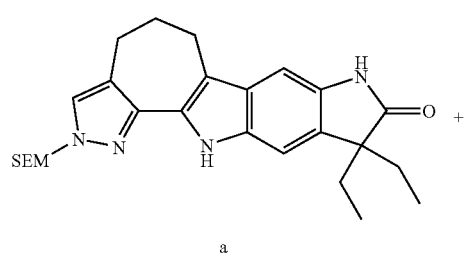

Compound a from the synthesis of compound 74 (129 mg) was dissolved in 1.4 ml DMF and added to a vial containing $Cs_2CO_3$ (460 mg) followed by addition of N-(chloroacetyl) morpholine b (229 mg). The vial was capped and the reaction was heated to 60° C. in a heat block overnight. The reaction was completed by TLC. The reaction was diluted with $H_2O$, extracted with EtOAc, dried over $MgSO_4$, and concentrated by vacuum to give compound c. Compound c was dissolved in 3 ml 1.0 M TBAF in THF and heated to 60° C. overnight. The reaction was completed by LCMS and diluted with $H_2O$, extracted with EtOAc, washed with brine, dried over $MgSO_4$, concentrated under vacuum and purified by HPLC to give the final compound 78.

Example 45

Synthesis of Compound 79

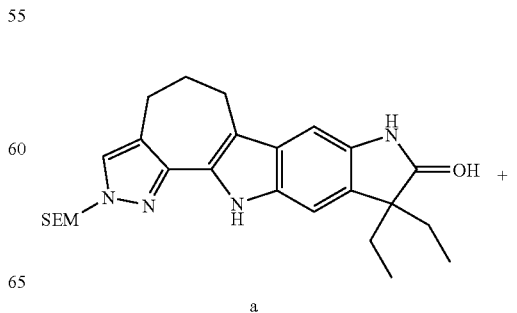

Example 46

Synthesis of Compound 80

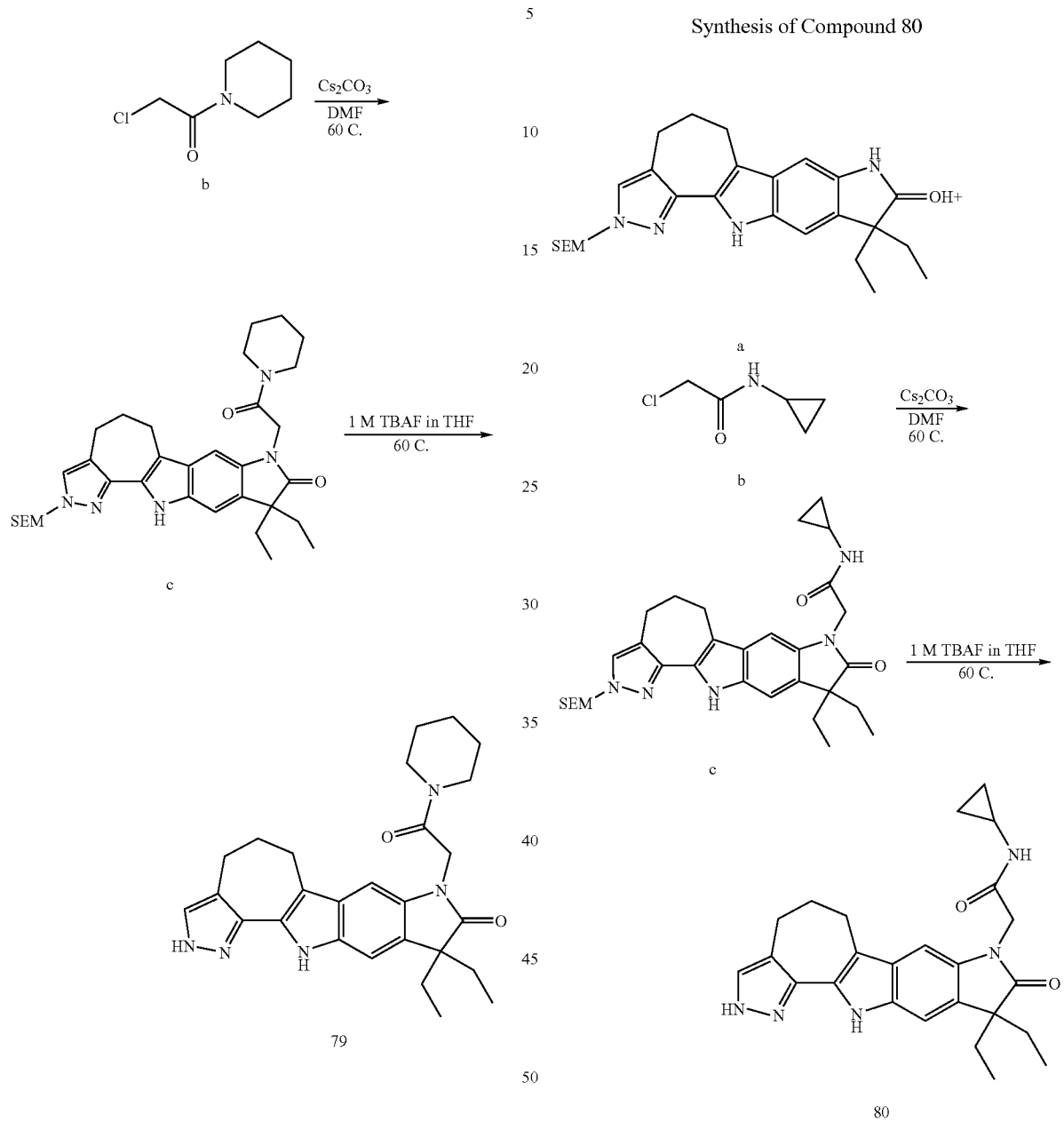

Compound a from the synthesis of compound 74 (210 mg) was dissolved in 5.0 ml DMF and Cs$_2$CO$_3$ (730 mg) was added followed by addition of N-(chloroacetyl) piperidine b (400 mg). The vial was capped and the reaction was heated to 60° C. in a heat block for four hrs. The reaction was completed by LCMS. The reaction was diluted with H$_2$O, extracted with EtOAc, dried over MgSO$_4$, and concentrated by vacuum to give compound c. Compound c was dissolved in 3 ml 1.0 M TBAF in THF and heated to 60° C. overnight. The reaction was completed by LCMS and diluted with H$_2$O and 0.1 N H$_2$SO$_4$, extracted with EtOAc, washed with brine, dried over MgSO$_4$, concentrated under vacuum and purified by HPLC to give the final compound 79.

Compound a from the synthesis of compound 74 (210 mg) was dissolved in 5.0 ml DMF and Cs$_2$CO$_3$ (730 mg) was added followed by the addition of N1-cyclopropyl-2-chloro-acetamide b (300 mg). The vial was capped and the reaction was heated to 60° C. in a heat block for four hrs. The reaction was completed by LCMS. The reaction was diluted with H$_2$O, extracted with EtOAc, dried over MgSO$_4$, and concentrated by vacuum to give compound c. Compound c was dissolved in 3 ml 1.0 M TBAF in THF and heated to 60° C. overnight. The reaction was completed by LCMS and diluted with H$_2$O and 0.1 N H$_2$SO$_4$, extracted with EtOAc, washed with brine, dried over MgSO$_4$, concentrated under vacuum and purified by HPLC to give the final compound 80.

Example 47

Synthesis of Compound 81

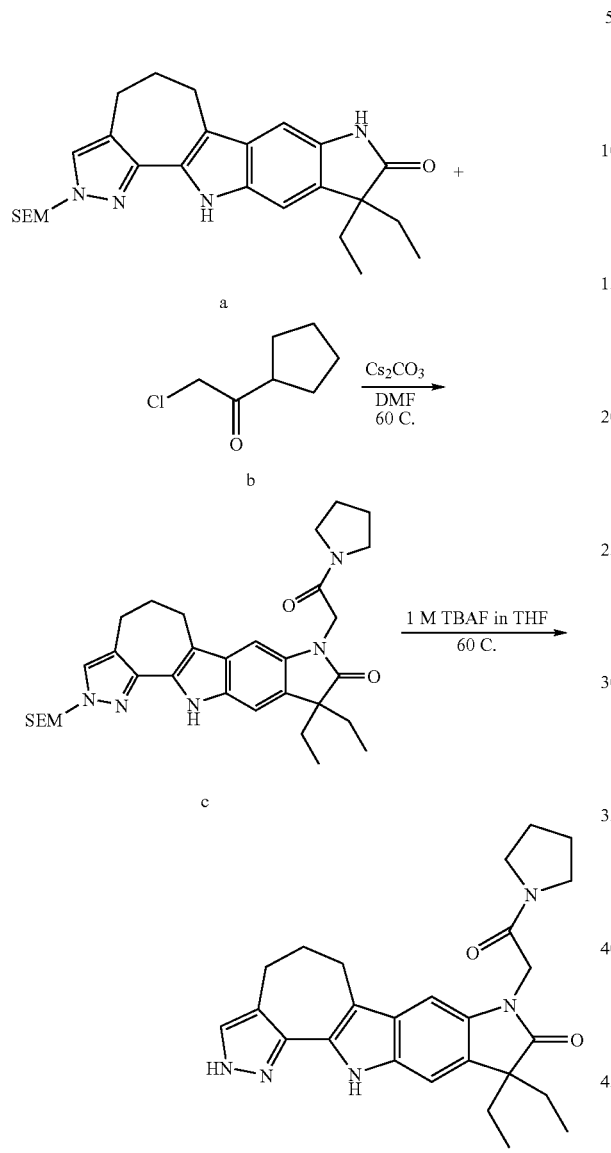

Compound a from the synthesis of compound 74 (215 mg) was dissolved in 5.0 ml DMF and $Cs_2CO_3$ (149.9 mg) was added followed by the addition of N-(chloroacetyl) pyrrolidine b (67.9 mg). The vial was capped and the reaction was heated to 60° C. in a heat block overnight. The reaction was completed by LCMS. The reaction was diluted with 1 M HCl, extracted with EtOAc, dried over $MgSO_4$, and concentrated by vacuum to give compound c. Compound c was dissolved in 3 ml 1.0 M TBAF in THF and heated to 60° C. overnight. The reaction was completed by LCMS, diluted with $H_2O$ and 0.1 N $H_2SO_4$, extracted with EtOAc, washed with brine, dried over $MgSO_4$, concentrated under vacuum and purified by SFC to give the final compound 81.

Example 48

Synthesis of Compound 82

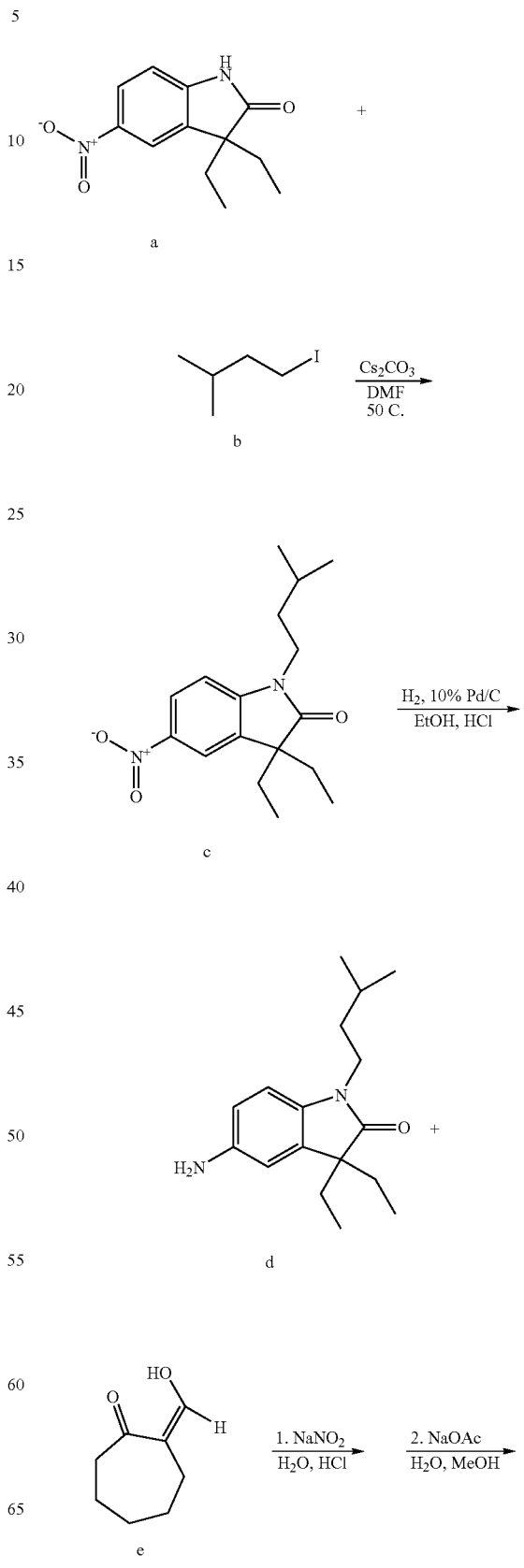

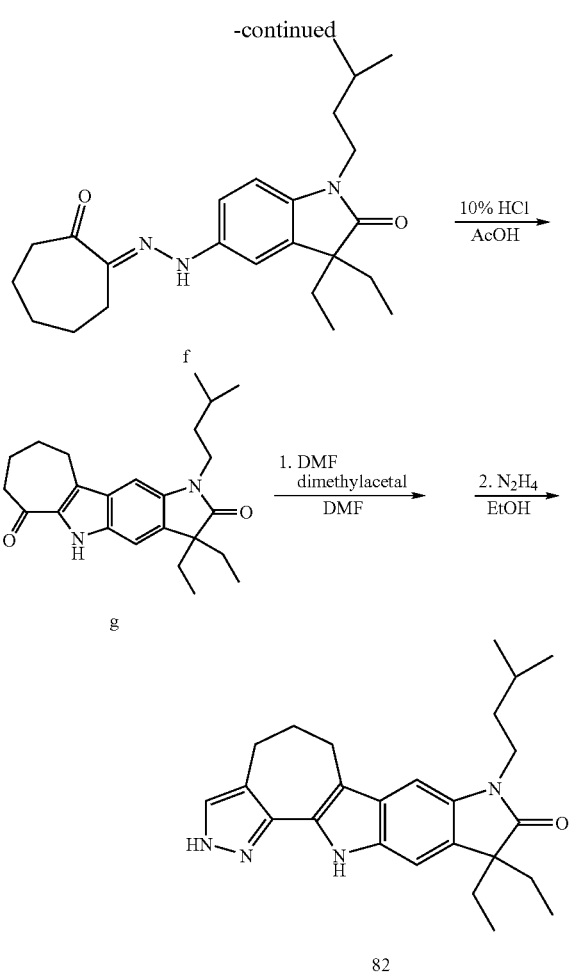

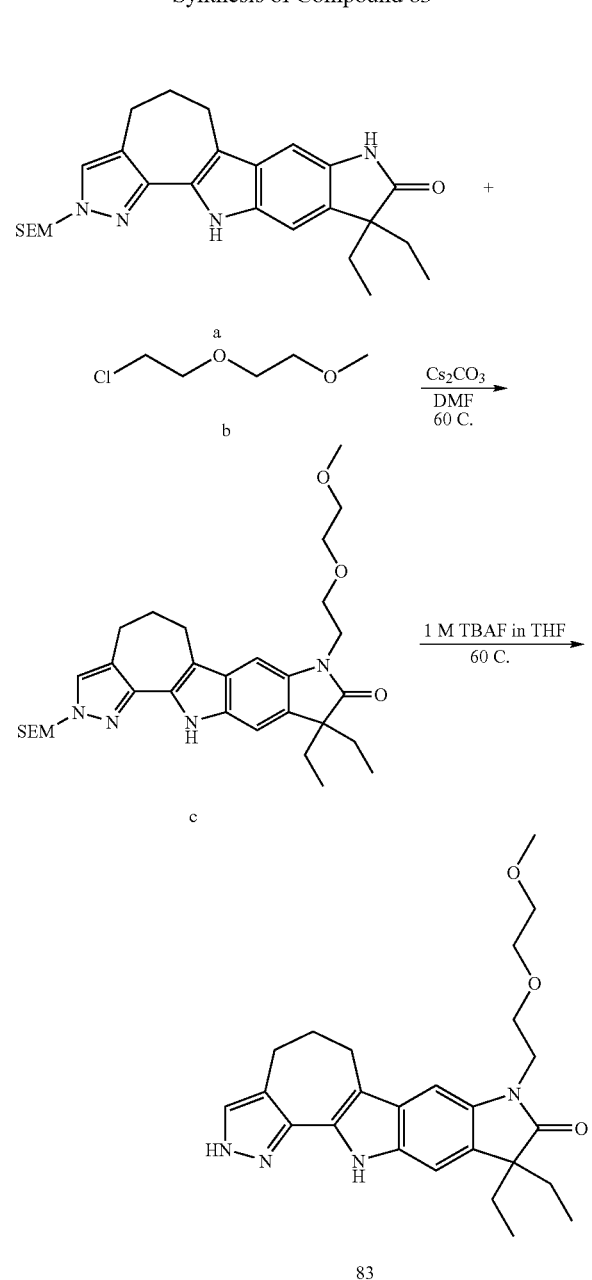

(EtOAc/hexanes) to give 2.54 g (33% yield) of compound g. Compound g was dissolved in 20 ml DMF-dimethylacetal and 20 ml DMF under N$_2$ and the reaction was heated to 110° C. with stirring for 6 hrs. The reaction was completed by TLC, cooled to room temperature and concentrated under vacuum. This intermediate was dissolved in 50 ml EtOH and 5 ml hydrazine and stirred at room temperature for 24 hrs. Completed reaction was confirmed by LCMS and the reaction mixture concentrated under vacuum and 191 mg was purified by HPLC to give the final compound 82.

Example 49

Synthesis of Compound 83

Compound a from example 8 (5.24 g) was dissolved in 40 ml of DMF. To this solution was added 26.84 g Cs$_2$CO$_3$ and 5.32 g of 1-iodo-3-methylbutane b in 10 ml DMF and the mixture was heated at 50° C. under N$_2$ with stirring for 24 hours by which time the reaction was completed by TLC. The reaction mixture was cooled and diluted with 1 M HCl, extracted with EtOAc, washed with brine, dried over MgSO$_4$, concentrated under vacuum, and flashed on the ISCO (EtOAc/hexanes) to give 6.16 g (90% yield) of compound c. Compound c (6.15 g) was dissolved in 100 ml EtOH and 1 ml of concentrated HCl and bubbled under N$_2$ for 10 minutes at which time 2 scoops of 10% Pd/C was added, an H$_2$ balloon attached and the reaction was stirred at room temperature for 48 hours. The reaction was completed by LCMS and the reaction mixture was filtered over celite and concentrated under vacuum to give 5.5 g compound d (99% yield).

Compound d (7.67 g) was dissolved in 100 ml H$_2$O and 2.67 ml concentrated HCl and cooled to 0° C. To this mixture was added 1.66 g NaNO$_2$ in 10 ml H$_2$O and the mixture was stirred for 20 minutes. This was added to 3.37 g compound e from example 2 and 7.40 g NaOAc in 100 ml H$_2$O and 100 ml MeOH at 0° C. The solution was allowed to warm up to room temperature and stir for 48 hours. The reaction was completed by LCMS and the precipitate was filtered off and confirmed to be compound f by LCMS and dried under vacuum. Compound f was dissolved in 100 ml of 1% HCl in AcOH and heated to 80° C. for 24 hours. The reaction was completed by LCMS, concentrated under vacuum and flashed by ISCO Compound a from the synthesis of compound 74 (143 mg) was dissolved in 5.0 ml DMF and Cs$_2$CO$_3$ (505 mg) was added followed by the addition of 1-bromo-2-(2-methoxy)

ethane b (280 mg). The vial was capped and the reaction was stirred at room temperature for 4 hours and at 60° C. in a heat block four hours. The reaction was completed by LCMS. Diluted the reaction mixture with 0.1N $H_2SO_4$, extracted with EtOAc, washed with brine, dried over $MgSO_4$, concentrated by vacuum and flashed on the ISCO (EtOAc/hexanes) to give compound c. Compound c was dissolved in 3 ml 1.0 M TBAF in THF and heated to 60° C. overnight. The reaction was completed by LCMS and was diluted with $H_2O$, extracted with EtOAc, washed with brine, dried over $MgSO_4$, concentrated under vacuum and purified by HPLC to give the final compound 83.

Example 50

Synthesis of Compound 84

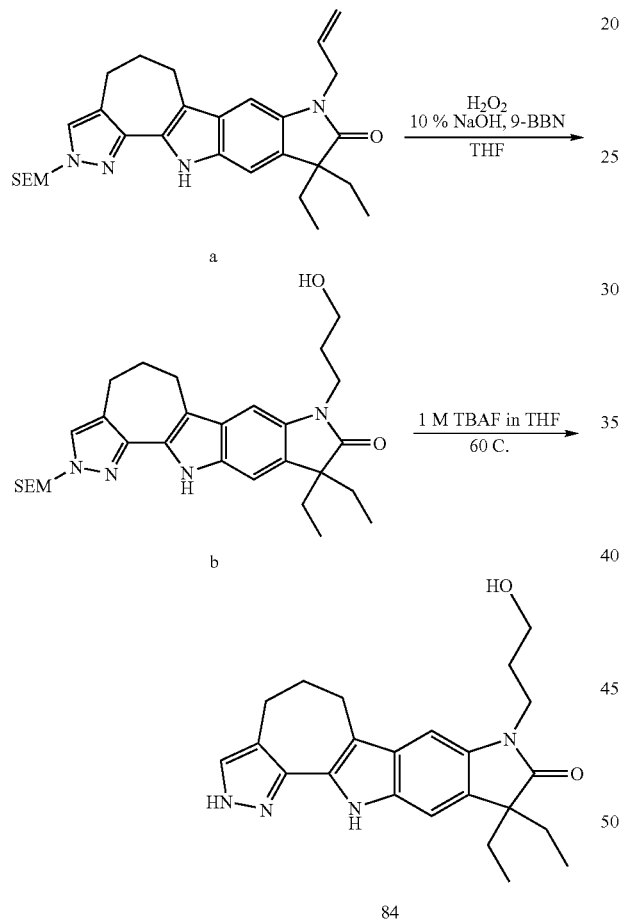

Compound a from the synthesis of compound 74 (350 mg) was dissolved in 2 ml THF and cooled to 0° C. in an ice bath. To this solution was added 0.5 M 9-BBN (12.42 ml) and the reaction was allowed to warm up to room temperature and stir for 1.5 hours. An additional 6.21 ml 9-BBN was added and the solution was stirred for another hour. The starting material was consumed as indicated by TLC and 3 ml $H_2O_2$ was added to the reaction mixture after cooling to 0° C. followed by the addition of 10% NaOH (3 ml) and the reaction was stirred at 0° C. for one hour. The reaction was completed by LCMS. The reaction mixture was diluted with brine, extracted with EtOAc, dried over $MgSO_4$, concentrated under vacuum, and flashed on the ISCO (EtOAc/hexanes) to give compound b. Compound b was dissolved in 5 ml 1 M TBAF in THF and heated at 60° C. in a capped vessel overnight. When complete by LCMS the reaction mixture was diluted with $H_2O$, extracted with EtOAc, washed with brine, dried over $MgSO_4$, concentrated under vacuum, and purified by HPLC to give the final compound 84.

Example 51

Synthesis of Compound 85

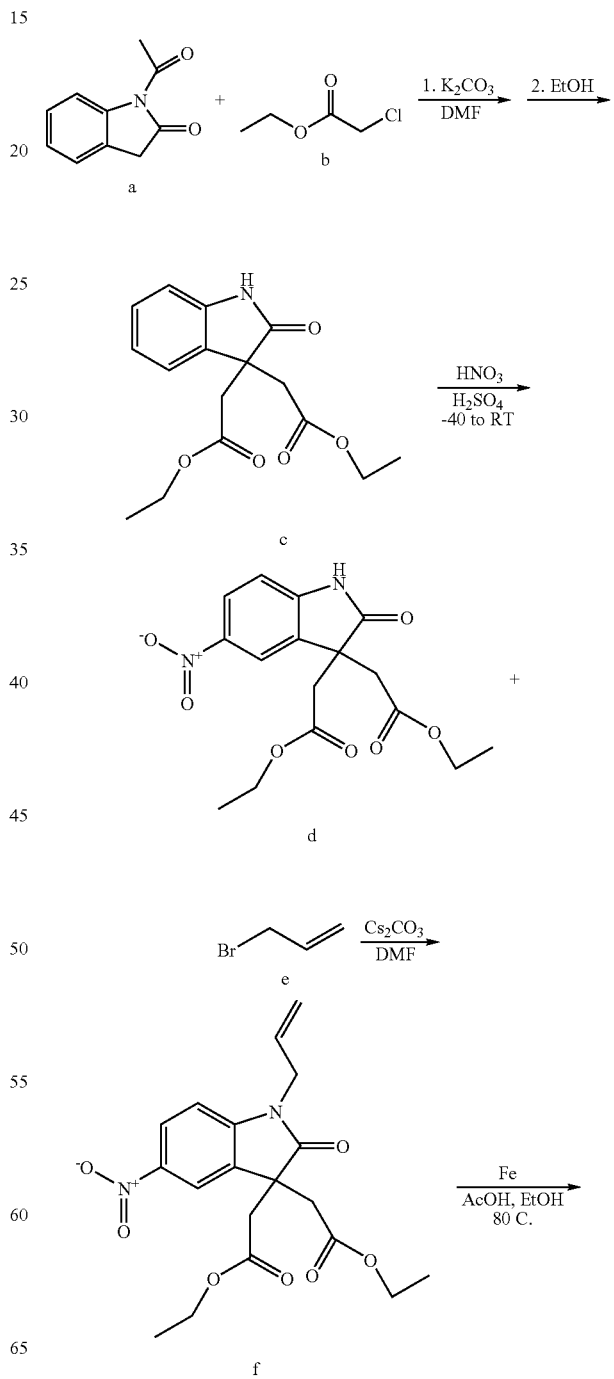

-continued
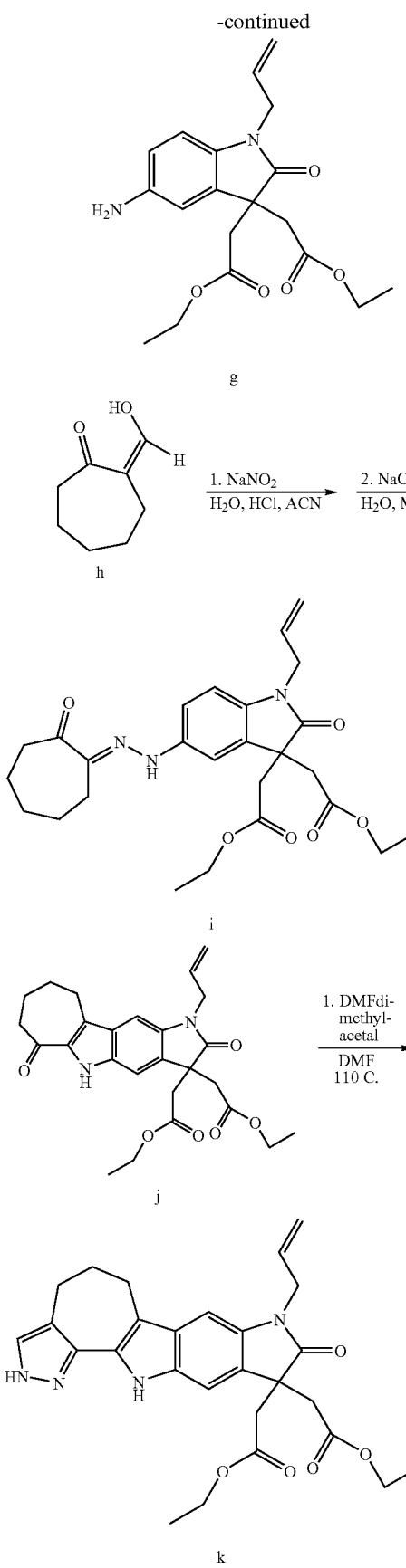
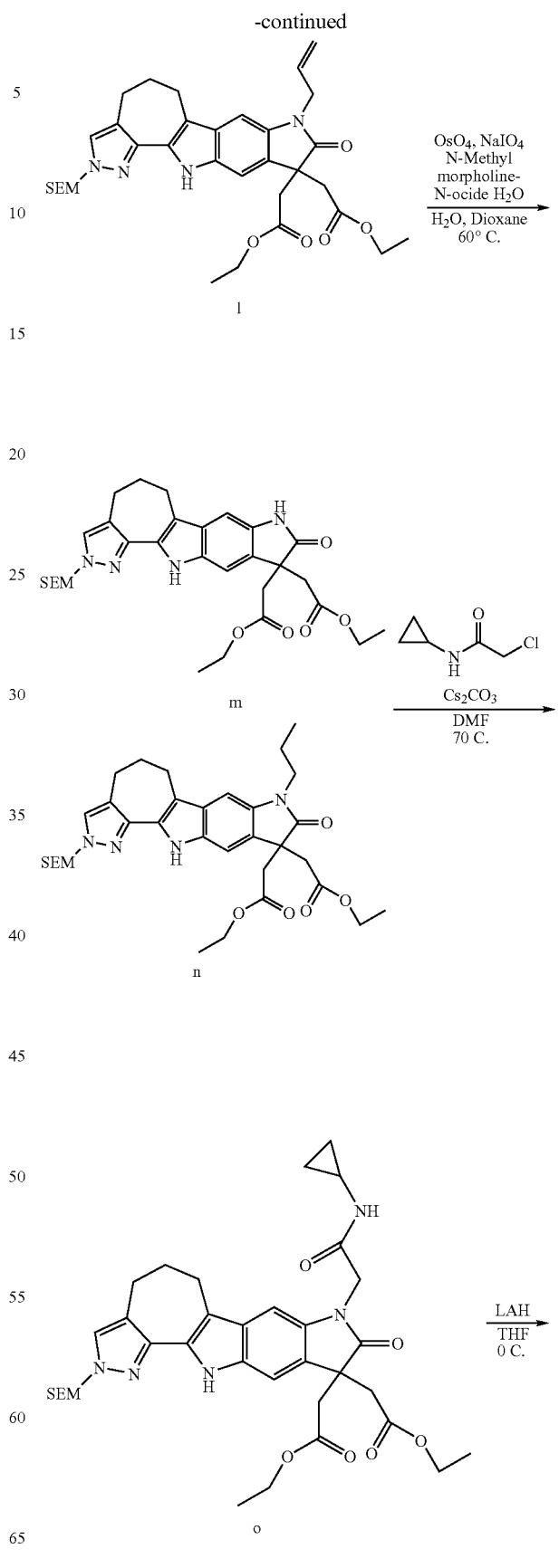

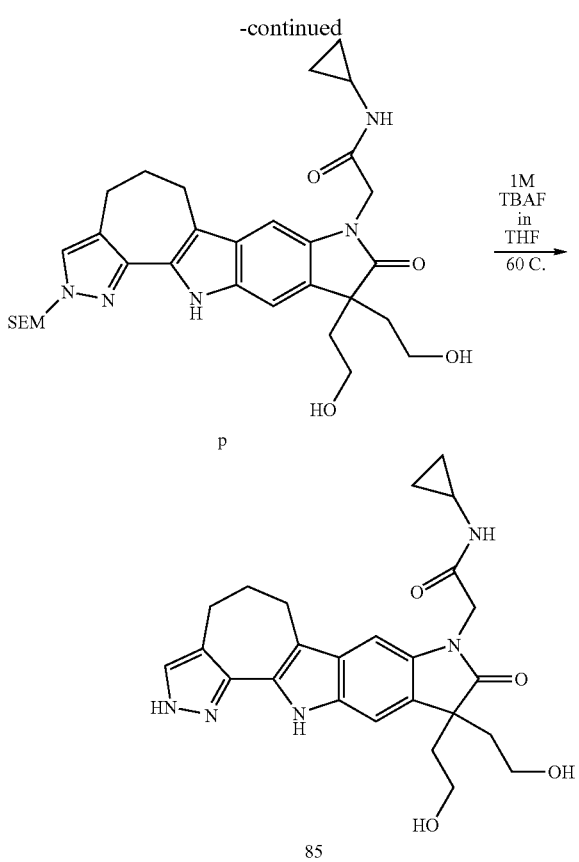

Commercially available N-acetyloxindole a (16.17 g) was dissolved in 200 ml of DMF. To this solution was added 51.03 g $K_2CO_3$ and 22.62 g of ethyl chloroacetate b and the reaction was stirred under $N_2$ for 24 hours at which time 100 ml EtOH was added and the reaction stirred for 12 hours more by which time the reaction was completed by TLC. This reaction mixture was diluted with 1 M HCl, extracted with EtOAc, washed with brine, dried over $MgSO_4$, concentrated under vacuum, and flashed on the ISCO (EtOAc/hexanes) to give compound c. Compound c (20.6 g) was dissolved in 100 ml $H_2SO_4$ and cooled to −40° C. To this solution was added 4.25 g fuming nitric acid in 10 ml $H_2SO_4$ and the reaction was allowed to warm up to room temperature and stir overnight. The reaction was completed by LCMS and the reaction mixture was slowly poured onto ice water. The filtered precipitate was filtered off and dried under vacuum to give 5.31 g compound d. Compound d was dissolved in 150 ml DMF and 9.87 g $Cs_2CO_3$ was added followed by the addition of 2.20 g allyl bromide e. The reaction was stirred overnight and confirmed to be complete by TLC. The reaction was diluted with $H_2O$ and 1 M HCl, extracted with EtOAc, washed with brine, dried over $MgSO_4$ and flashed by ISCO (EtOAc/hexanes) to give compound f.

Compound f (7.08 g) was dissolved in 129 ml AcOH and 188 ml EtOH and was purged with nitrogen for 10 minutes. To this mixture was added 6.10 g Fe and the mixture was heated to 80° C. and stirred for 3 hrs 35 minutes under $N_2$. The reaction was completed by TLC and was cooled to room temperature, diluted with EtOAc, filtered through celite and concentrated under vacuum to give compound g. Compound g (4.19 g) was dissolved in 100 ml of $H_2O$ and 1.55 ml concentrated HCl and cooled to 0° C. To this mixture was added 0.96 g $NaNO_2$ in 10 ml $H_2O$ and the reaction was stirred for 30 minutes. This reaction mixture was added to 1.95 g of compound h from example 2 and 4.29 g NaOAc in 100 ml $H_2O$ and 100 ml MeOH at 0° C. and the reaction was allowed to warm up to room temperature and stir for 72 hours. The precipitate formed was filtered off and confirmed to be compound i by LCMS. This was dissolved in 3% HCl in AcOH and heated to 80° C. for 6 hours. The reaction was completed by LCMS, concentrated under vacuum and flashed by ISCO (EtOAc/hexanes) to give 2.54 g (47% yield) of compound j. Compound j (0.94 g) was dissolved in 0.55 g DMF-dimethylacetal and 20 ml DMF under $N_2$ and the reaction was heated to 110° C. with stirring for 24 hrs. The reaction was completed by LCMS, cooled to room temperature and concentrated under vacuum. This intermediate was dissolved in 20 ml EtOH and 0.24 ml hydrazine and stirred at room temperature for 18 hrs. Completed reaction was confirmed by LCMS and the reaction mixture concentrated under vacuum and flashed by ISCO (EtOAc/hexanes) to give compound k.

Compound k (0.56 g) was dissolved in 10 ml DCM and cooled to 0° C. before adding 0.29 g SEM-Cl and 0.44 g DIPEA. The reaction was allowed to warm up to room temperature and was stirred for 2 hours. Completed reaction was confirmed by LCMS and the reaction was diluted with $H_2O$, extracted with DCM, dried over $MgSO_4$ and concentrated under vacuum to give 0.71 g compound l (100% yield). Compound l (0.71 g) was dissolved in 2 ml $H_2O$ and 8 ml dioxane and 0.40 g N-methyl morpholine N-oxide $H_2O$ was added and the reaction was stirred until everything was in solution. To this reaction mixture was added $OsO_4$ (28 mg) in a 100 mg/ml butanol solution followed by the drop wise addition of a slurry of 0.73 g sodium periodate in 4 ml $H_2O$ and subsequent heating at 60° C. in a capped vessel for 4 hrs. When complete by LCMS the reaction mixture was diluted with brine, extracted with DCM, dried over $MgSO_4$, concentrated under vacuum, and flashed by ISCO to give compounds m and n.

Compound m (148 mg) was dissolved in 5.0 ml DMF and $Cs_2CO_3$ (330 mg) was added, followed by the addition of N1-cyclopropyl-2-chloroacetamide (130 mg). The vial was capped and the reaction was heated to 70° C. in a heat block for 4 hrs. The reaction was completed by LCMS. Diluted reaction with $H_2O$, extracted with EtOAc, dried over $MgSO_4$, concentrated by vacuum, and flashed by ISCO (EtOAc/hexanes) to give compound o. Compound o was dissolved in 10 ml THF and cooled to 0° C. before adding 0.14 ml 2.5 M LAH in THF. The reaction was stirred 1 hr 35 min at 0° C. and was completed by LCMS. The reaction was quenched with 400 uL 10% NaOH and 400 uL EtOH, diluted with $H_2O$ and 1 M HCl, extracted with DCM, dried over $MgSO_4$ and concentrated under vacuum to give compound p. Compound p was dissolved in 2 ml 1.0 M TBAF in THF and 3 ml THF and heated to 60° C. overnight. Reaction was completed by LCMS and diluted with $H_2O$, extracted with EtOAc, washed with brine, dried over $MgSO_4$, concentrated under vacuum and purified by HPLC to give 18 mg of the final compound 85.

Example 52

Synthesis of Compound 86

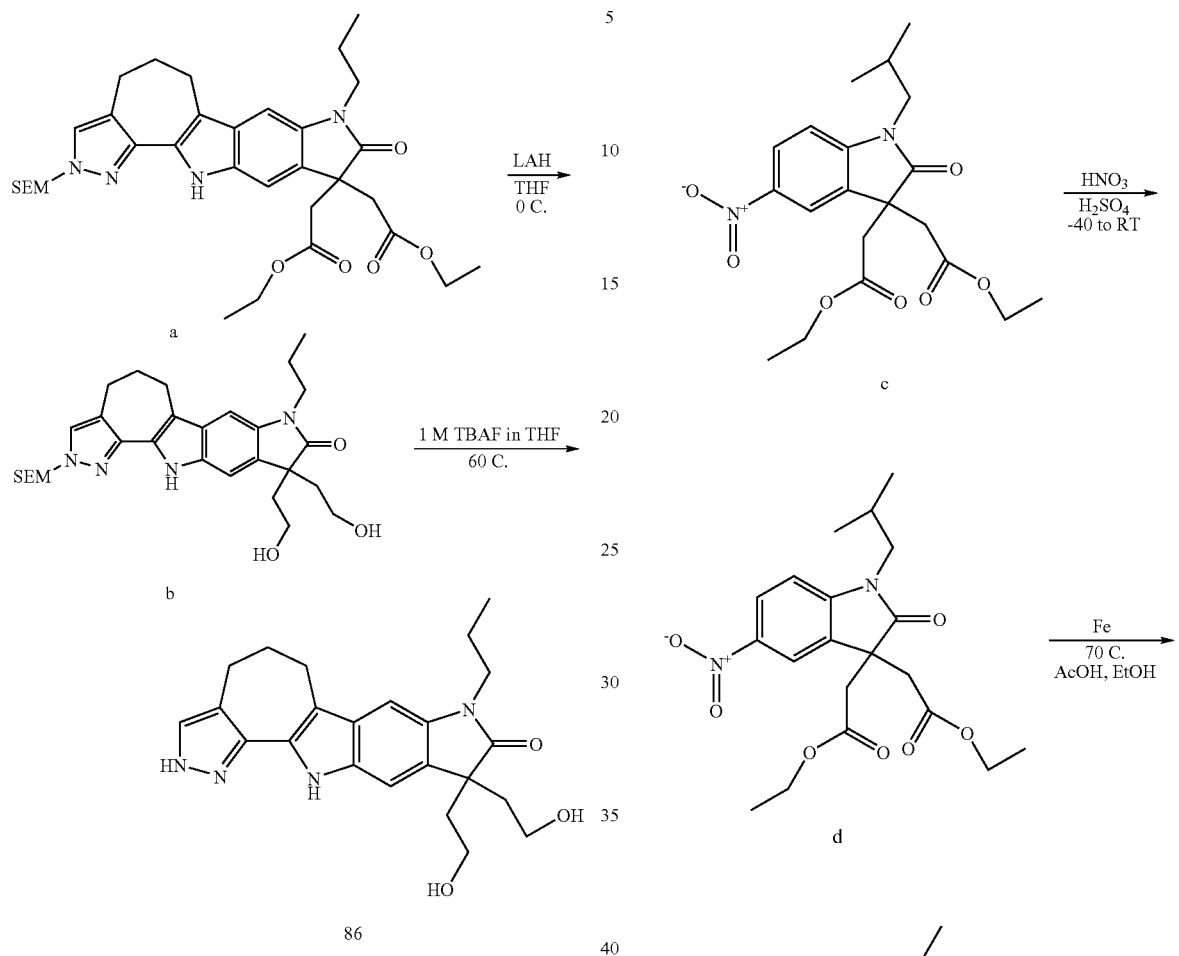

Compound a from the synthesis of compound 85 was dissolved in 15 ml THF and cooled to 0° C. before adding 0.23 ml 2.5 M LAH in THF. The reaction was stirred for 1 hr 45 min at 0° C. and was completed by LCMS. The reaction was quenched with 400 uL 10% NaOH and 400 uL EtOH, diluted with H$_2$O, extracted with EtOAc, dried over MgSO$_4$ and concentrated under vacuum to give compound b. Compound b was dissolved in 2 ml 1.0 M TBAF in THF and 3 ml THF and heated to 60° C. overnight. Reaction was completed by LCMS and diluted with H$_2$O, extracted with EtOAc, washed with brine, dried over MgSO$_4$, concentrated under vacuum and purified by HPLC to give 18 mg of the final compound 86.

Example 53

Synthesis of Compound 87

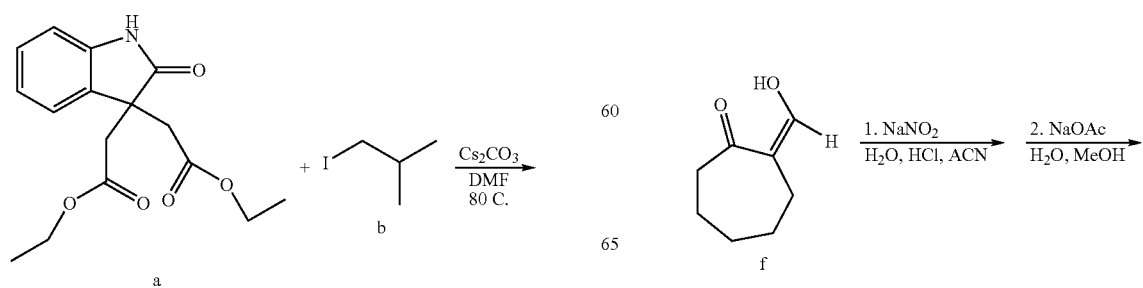

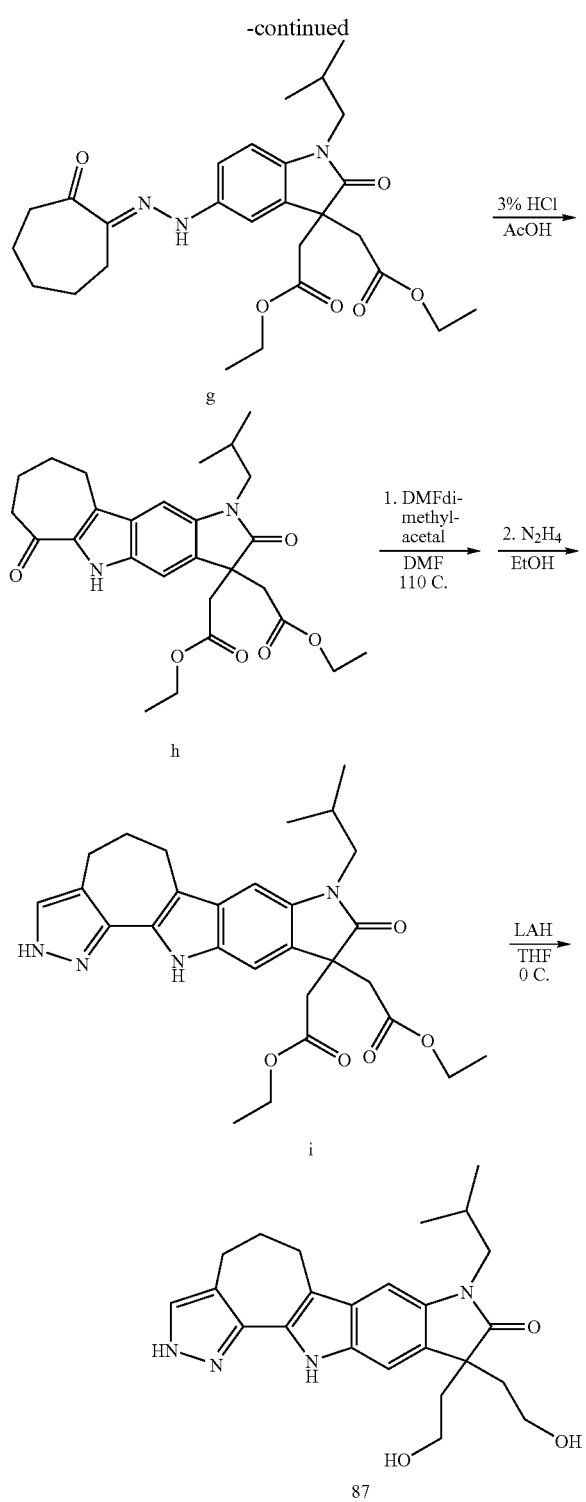

by ISCO (EtOAc/hexanes) to give 1.45 g (58% yield) of compound c. Compound c was dissolved in 20 ml $H_2SO_4$ and cooled to −40° C. at which point Fuming nitric acid (0.28 g) was added and the reaction mixture allowed to warm up to room temperature and stir 4 hrs 40 min. The reaction was completed by LCMS, cooled to room temperature, poured onto ice water, extracted with EtOAc, washed with brine, dried over $MgSO_4$, concentrated under vacuum, and flashed by ISCO (EtOAc/hexanes) to give 1.58 g compound d.

Compound d (1.58 g) was dissolved in 27 ml AcOH and 40 ml EtOH and purged with $N_2$ followed by the addition of Fe (1.31 g). This solution was heated at 70° C. for 3 hours and was completed by TLC. The reaction was cooled to room temperature, diluted with EtOAc, filtered through celite, concentrated under vacuum, and flashed by ISCO (EtOAc/hexanes) to give 1.3 g compound e. Compound e (1.3 g) was dissolved in 20 ml of $H_2O$, 2 ml ACN and 0.46 ml concentrated HCl and cooled to 0° C. To this mixture was added 0.29 g $NaNO_2$ in 5 ml $H_2O$ and the reaction was stirred for 30 minutes. This reaction mixture was added to 0.58 g of compound f from example 2 and 1.27 g NaOAc in 20 ml $H_2O$ and 20 ml MeOH at 0° C. and the reaction was allowed to warm up to room temperature and stir 72 hours. The precipitate formed was filtered off and confirmed to be compound g by LCMS. Compound g was dissolved in 50 ml of 3% HCl in AcOH and heated to 80° C. for 3 hours. The reaction was completed by LCMS, diluted with ice water, extracted with EtOAc, dried over $MgSO_4$, concentrated under vacuum and flashed by ISCO (EtOAc/hexanes) to give 0.64 g (39% yield) of compound h. Compound h (0.64 g) was dissolved in 1.33 g DMF-dimethylacetal and 30 ml DMF under $N_2$ and the reaction heated to 110° C. with stirring for 24 hrs. The reaction was completed by LCMS and cooled to room temperature. This intermediate was dissolved in 50 ml EtOH and 5 ml hydrazine and was stirred at room temperature for 24 hrs. Completed reaction was confirmed by LCMS and the reaction mixture was concentrated under vacuum and flashed by ISCO (EtOAc/hexanes) to give 276 mg compound i. Compound i (51 mg) was dissolved in 8 ml THF and cooled to 0° C. before adding 0.2 ml 2.5 M LAH in THF. The reaction was stirred for 1 hr at room temperature and was completed by LCMS. The reaction was cooled to 0° C., quenched with 400 uL 10% NaOH and 400 uL EtOH, diluted with $H_2O$, extracted with EtOAc, dried over $MgSO_4$, concentrated under vacuum, and purified by HPLC to give the final compound 87.

Example 54

Synthesis of Compound 88

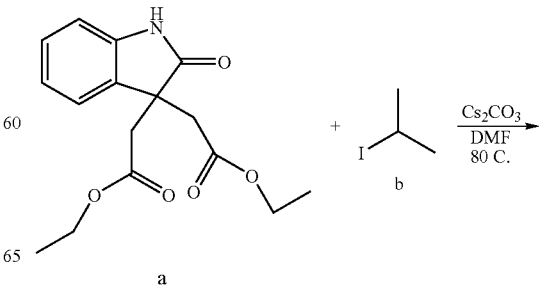

Compound a (2.10 g) from the synthesis of compound 85 was dissolved in 50 ml of DMF. To this solution was added 2.69 g $Cs_2CO_3$ and 1.38 g of 1-iodo-2-methyl propane b and the mixture was heated at 80° C. under $N_2$ with stirring for 24 hrs by which time the reaction was completed by TLC. The reaction mixture was cooled to room temperature, diluted with 1 M HCl, extracted with EtOAc, washed with brine, dried over $MgSO_4$, concentrated under vacuum, and flashed

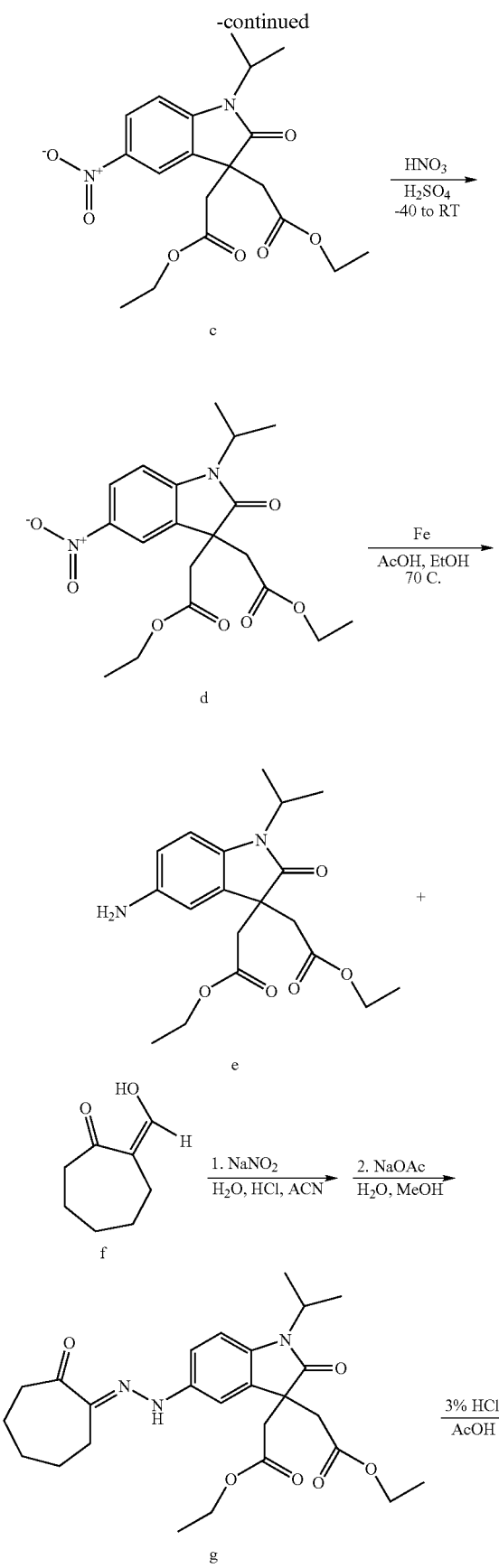
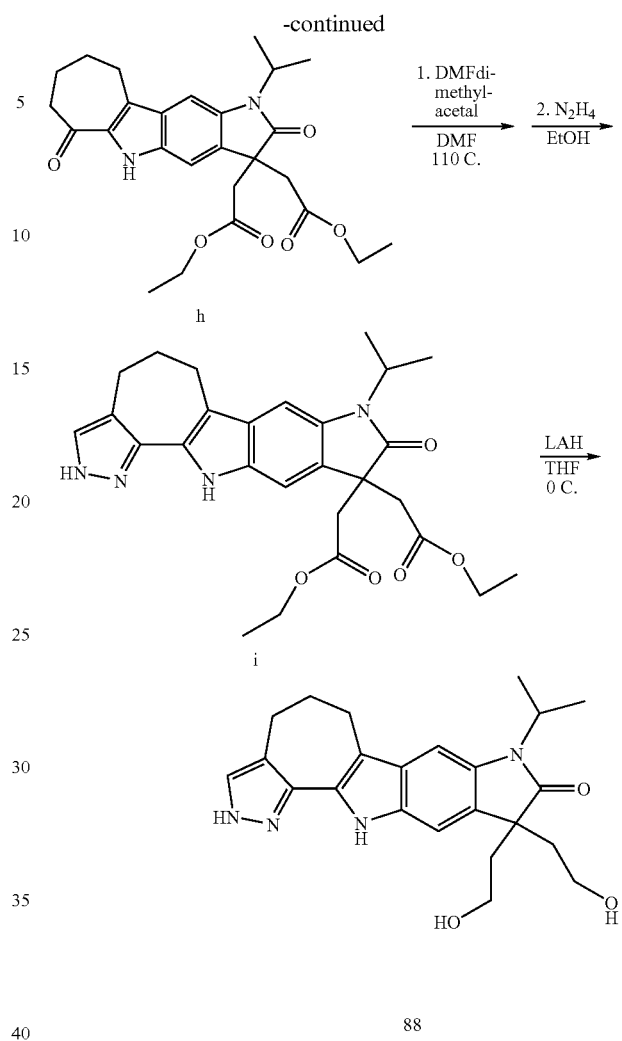

Compound a (2.02 g) from the synthesis of compound 85 was dissolved in 50 ml of DMF. To this solution was added 2.59 g $Cs_2CO_3$ and 1.22 g of isopropyl iodide b and the mixture was heated at 80° C. under $N_2$ with stirring for 24 hrs by which time the reaction was completed by TLC. The reaction mixture was cooled to room temperature, diluted with 1 M HCl, extracted with EtOAc, washed with brine, dried over $MgSO_4$, concentrated under vacuum, and flashed by ISCO (EtOAc/hexanes) to give compound c. Compound c (1.95 g) was dissolved in 20 ml $H_2SO_4$ and cooled to −40° C. at which point Fuming nitric acid (0.28 g) was added in 2 ml $H_2SO_4$ and the reaction mixture allowed to warm up to room temperature and stir overnight. The reaction was completed by LCMS, cooled to room temperature, poured onto ice water, extracted with DCM, washed with brine, dried over $MgSO_4$, concentrated under vacuum, and flashed by ISCO (EtOAc/hexanes) to give 1.31 g compound d.

Compound d (1.31 g) was dissolved in 23 ml AcOH and 34.5 ml EtOH and purged with $N_2$ followed by the addition of Fe (1.12 g). This solution was heated at 70° C. for 3 hours and was completed by TLC. The reaction was cooled to room temperature, diluted with EtOAc, filtered through celite, concentrated under vacuum, and flashed by ISCO (EtOAc/hexanes) to give 0.82 g compound e. Compound e (0.82 g) was dissolved in 20 ml of $H_2O$, 5 ml ACN and 0.30 ml concentrated HCl and cooled to 0° C. To this mixture was added 0.19 g NaNO₂ in 5 ml H₂O and the reaction was stirred for 30 minutes. This reaction mixture was added to 0.38 g of compound f from example 2 and 0.83 g NaOAc in 20 ml H₂O and 20 ml MeOH at 0° C. and the reaction was allowed to warm up to room temperature and stir overnight. The product formed was extracted with DCM, confirmed to be compound g by LCMS, dried over MgSO₄, and concentrated under vacuum. This was dissolved in 50 ml of 3% HCl in AcOH and heated to 80° C. for 3 hours. The reaction was completed by LCMS, concentrated under vacuum and flashed by ISCO (EtOAc/hexanes) to give compound h. Compound h (395 mg) was dissolved in 1.26 g DMF-dimethylacetal and 20 ml DMF under N₂ and the reaction was heated to 110° C. with stirring for 24 hrs. The reaction was completed by LCMS and cooled to room temperature. This intermediate was dissolved in 25 ml EtOH and 5 ml hydrazine and was stirred at room temperature for 72 hrs. Completed reaction was confirmed by LCMS and the reaction mixture was concentrated under vacuum to give compound i. Compound i (170 mg) was dissolved in 15 ml THF and cooled to 0° C. before adding 0.41 ml 2.5 M LAH in THF. The reaction was stirred 2 hrs 45 min at room temperature and was completed by LCMS. The reaction was cooled to 0° C., quenched with 400 uL 10% NaOH and 400 uL EtOH, diluted with H₂O, extracted with DCM, dried over MgSO₄, concentrated under vacuum, and purified by HPLC to give 37.g mg of the final compound 88.

Example 55

Synthesis of Compound 89

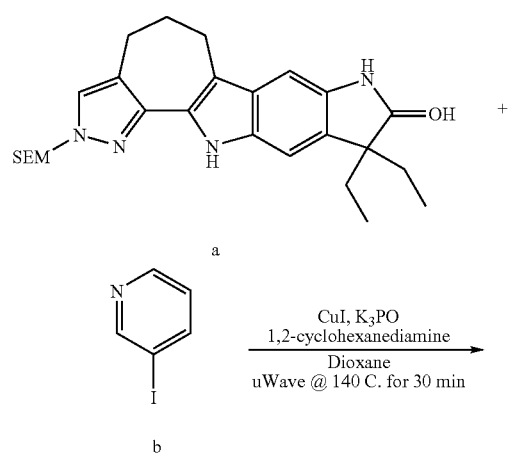

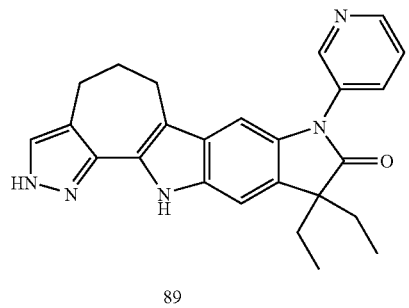

89

Compound a from the synthesis of compound 74 (920 mg) was placed in an oven dried microwave reaction vial with CuI (190 mg) and K₃PO₄ (840 mg) and purged with N₂. To this mixture was added 3-iodopyridine b and the vial purged again with N₂ followed by the addition of 1,2-cyclohexanediamine (230 mg) in 10 ml dioxane and N₂ was bubbled into the solution for 10 min and the vial crimped. The reaction vial was placed in the microwave for 30 min. at 140° C. The reaction went to half completion and was worked up by filtering off the non-product solids, concentrating under vacuum, and purifying by flash to give compound c. Compound c was dissolved in 5 ml 1.0 M TBAF in THF and heated to 60° C. overnight. The reaction was completed by LCMS and diluted with H₂O, extracted with EtOAc, washed with brine, dried over MgSO₄, concentrated under vacuum and purified by HPLC to give 117 mg of the final compound 89.1

Example 56

Synthesis of Compound 90

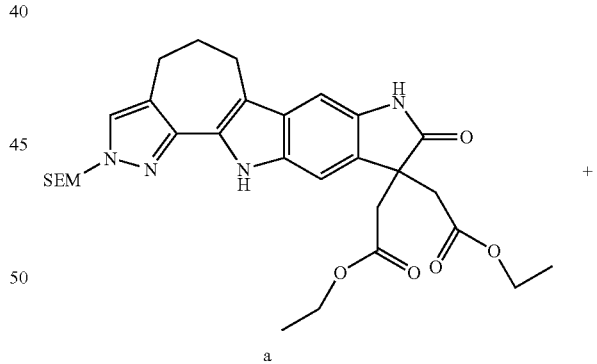

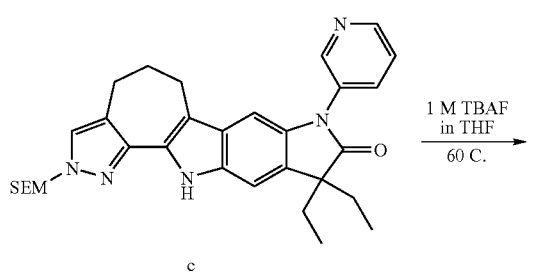

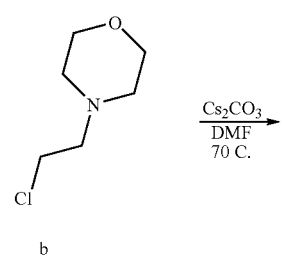

-continued

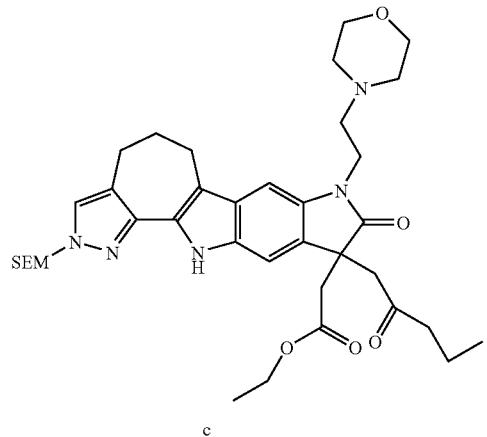

c

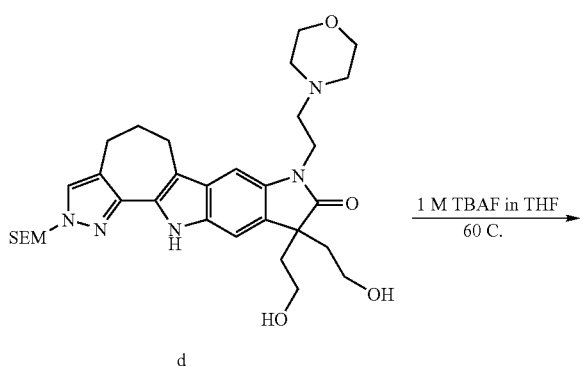

d

1 M TBAF in THF
60 C.
→

-continued

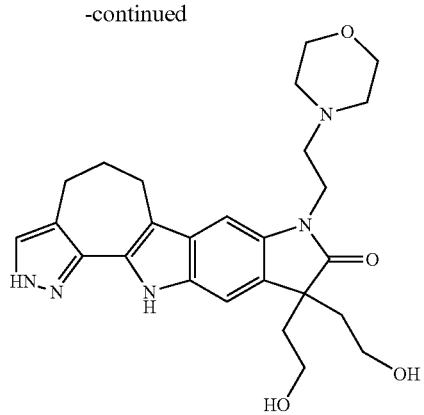

90

Compound a (148 mg) was dissolved in 5.0 ml DMF and Cs$_2$CO$_3$ (330 mg) was added, followed by the addition of 2-chloroethyl morpholine b (190 mg). The vial was capped and the reaction was heated to 100° C. in a heat block for 72 hrs. The reaction was half complete by LCMS. The reaction was diluted with H$_2$O, extracted with EtOAc, dried over MgSO$_4$, concentrated by vacuum, and flashed by ISCO (EtOAc/hexanes) to give 84.3 mg compound c. Compound c was dissolved in 10 ml THF and cooled to 0° C. before adding 0.14 ml 2.5 M LAH in THF. The reaction was stirred for 2 hr 35 min at 0° C. and was completed by LCMS. The reaction was quenched with 400 uL 10% NaOH and 400 uL EtOH, diluted with H$_2$O and 1 M HCl, extracted with DCM, dried over MgSO$_4$ and concentrated under vacuum to give compound d Compound d was dissolved in 1 ml 1.0 M TBAF in THF and 4 ml THF and heated to 60° C. overnight. The reaction was completed by LCMS and was diluted with H$_2$O, extracted with EtOAc, washed with brine, dried over MgSO$_4$, concentrated under vacuum and purified by HPLC to give 18 mg of the final compound 90.

Example 58

Synthesis of Compounds 91 to 111

Compounds 91 to 111 were prepared using the procedures in examples 1 and 2 using the appropriate alkyl halide.

| compound no. | | alkyl halide |
|---|---|---|
| 91 | 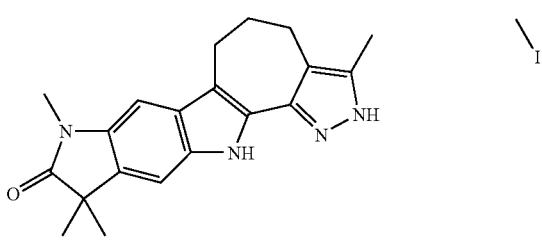 | |

-continued

| compound no. | | alkyl halide |
|---|---|---|
| 92 | | |
| 93 | | |
| 94 | | |
| 95 | | |
| 96 | | |
| 97 | | |

-continued

| compound no. | | alkyl halide |
|---|---|---|
| 98 | (structure) | (structure) |
| 99 | (structure) | (structure) |
| 100 | (structure) | (structure) |
| 101 | (structure) | (structure) |
| 102 | (structure) | (structure) |

-continued

| compound no. | | alkyl halide |
|---|---|---|

103

(structure)

(bromo-PEG-methyl ether)

104

(structure)

(bromoacetonitrile)

105

(structure)

(benzyl bromide)

106

(structure)

(2-chlorobenzyl bromide)

107

(structure)

(2-(diethylamino)ethyl bromide)

-continued
| compound no. | | alkyl halide |
|---|---|---|
| 108 | 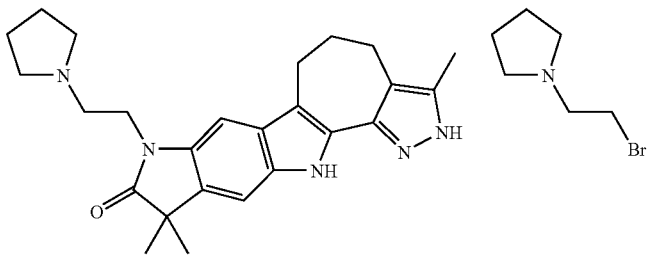 | |
| 109 | 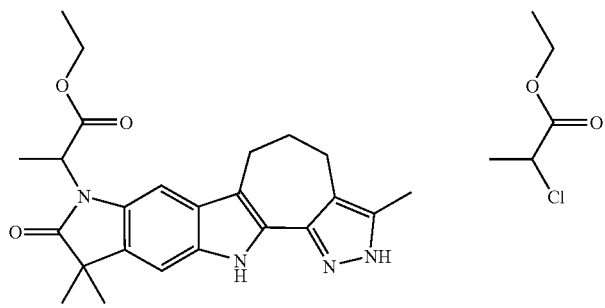 | |
| 110 | 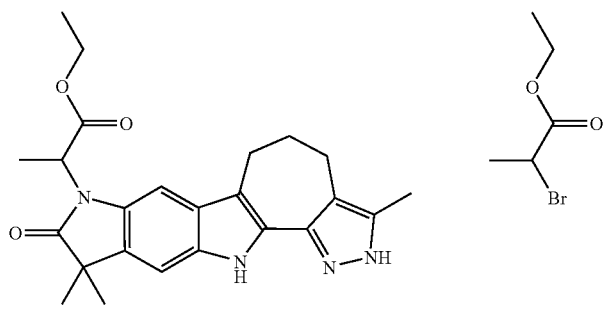 | |
| 111 | 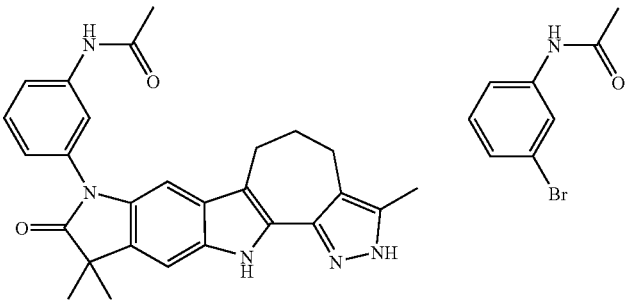 | |

Example 59

Synthesis of Compound 112

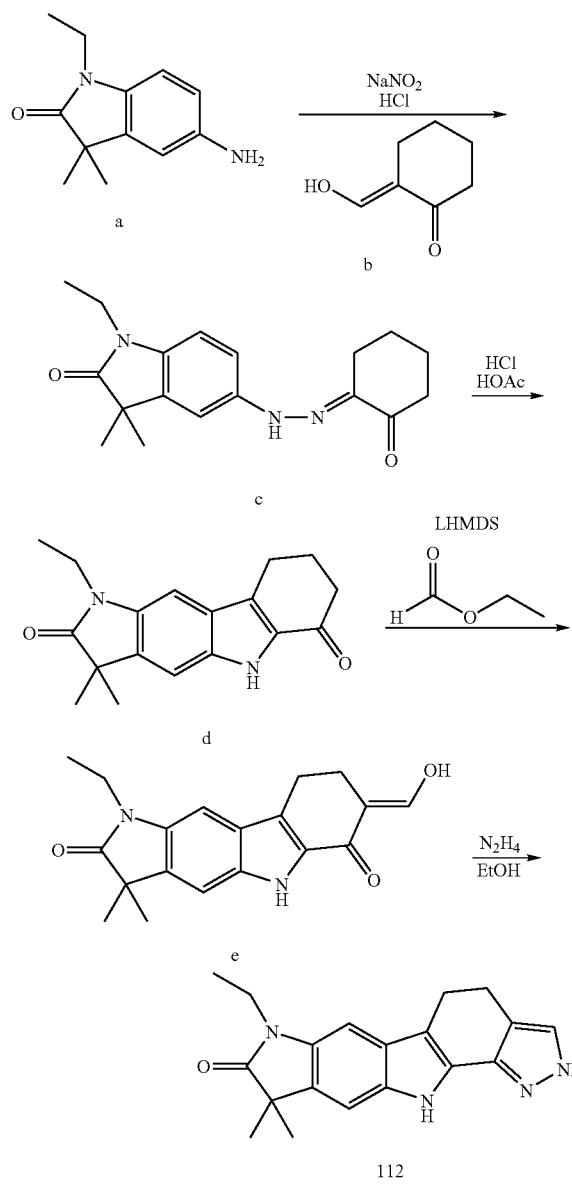

Compound a from example 1 (1.72 g) was dissolved in 30 ml of water and 1.05 ml of 37% HCl and cooled to 0° C. with stirring. A solution of sodium nitrite (700 mg) in 15 ml of water was added over 10 minutes. This diazonium salt solution a was slowly added to a suspension of b (1.17 g) in 100 ml of water, 30 ml of methanol and 3.11 g of sodium acetate with stirring at 0° C. After 2 hours, the reaction mixture was partitioned between ethyl acetate and water. The organic phase was dried and concentrated to give the crude compound c.

Compound c was dissolved in 30 ml of acetic acid and 10 ml of 37% HCl added. The reaction mixture was heated to 95° C. for 30 minutes, cooled and poured into 300 ml of water. The mixture was extracted with ethyl acetate and the separated organic phase was washed with brine, dried over sodium sulfate, filtered and concentrated. Purification by automated flash chromatography on silica gave 606 mg of compound d.

Compound d (58 mg) was dissolved in 4 ml of THF and stirred at room temperature. 0.59 ml of lithium bis trimethylsilylamide (1M in THF) was added and reaction mixture stirred for 10 minutes. Ethyl formate (0.048 ml) was added and the mixture stirred for 5 hours, then poured into 10% citric acid water solution and extracted with ethyl acetate. The organic phase was washed with water, brine, dried over sodium sulfate, filtered and concentrated. The residue (compound e) was dissolved in 30 ml of ethanol and 0.6 ml of hydrazine hydrate and the reaction stirred for 6 hours. Then concentrated and partitioned between ethyl acetate and water. The organic phase was washed with brine, dried, and concentrated. Purification of the residue by HPLC gave 15 mg of compound 112.

Example 60

Synthesis of Compound 113

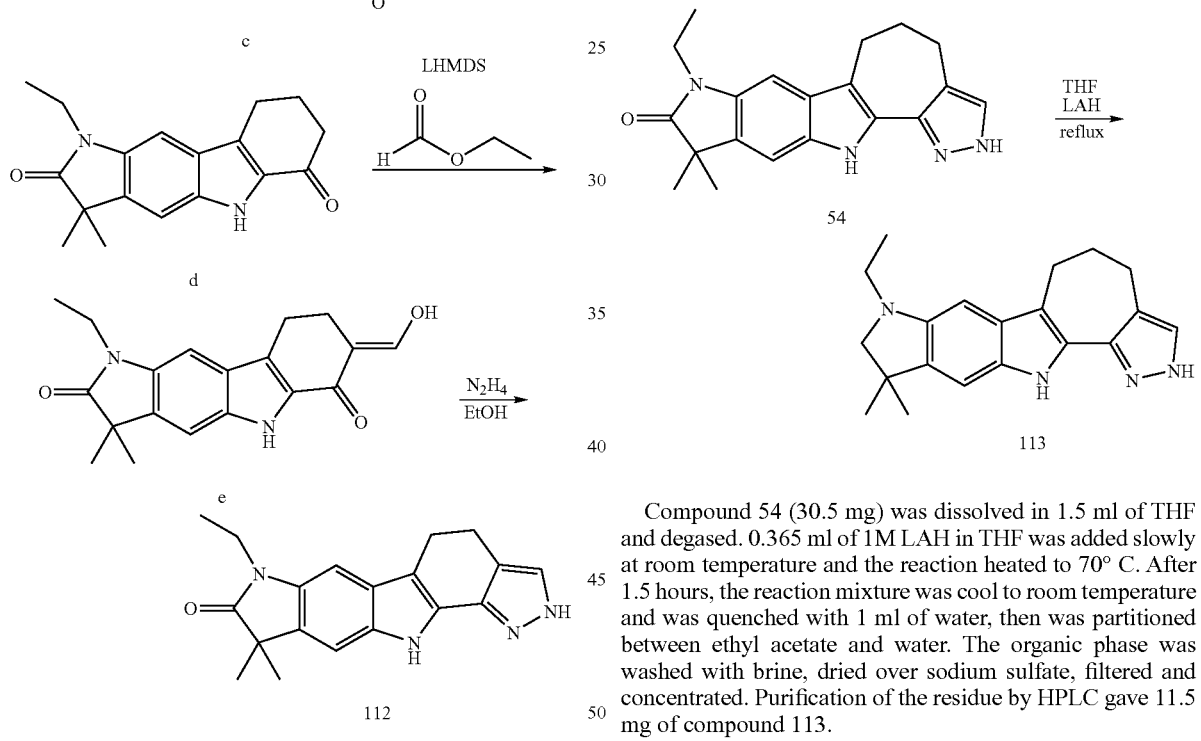

Compound 54 (30.5 mg) was dissolved in 1.5 ml of THF and degased. 0.365 ml of 1M LAH in THF was added slowly at room temperature and the reaction heated to 70° C. After 1.5 hours, the reaction mixture was cool to room temperature and was quenched with 1 ml of water, then was partitioned between ethyl acetate and water. The organic phase was washed with brine, dried over sodium sulfate, filtered and concentrated. Purification of the residue by HPLC gave 11.5 mg of compound 113.

Example 61

Synthesis of Compounds 114 to 117

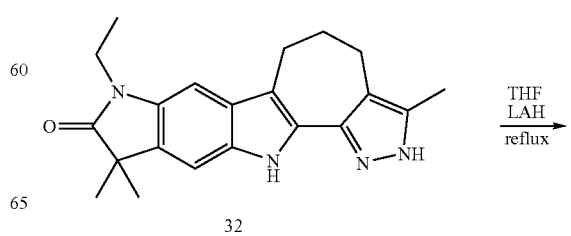

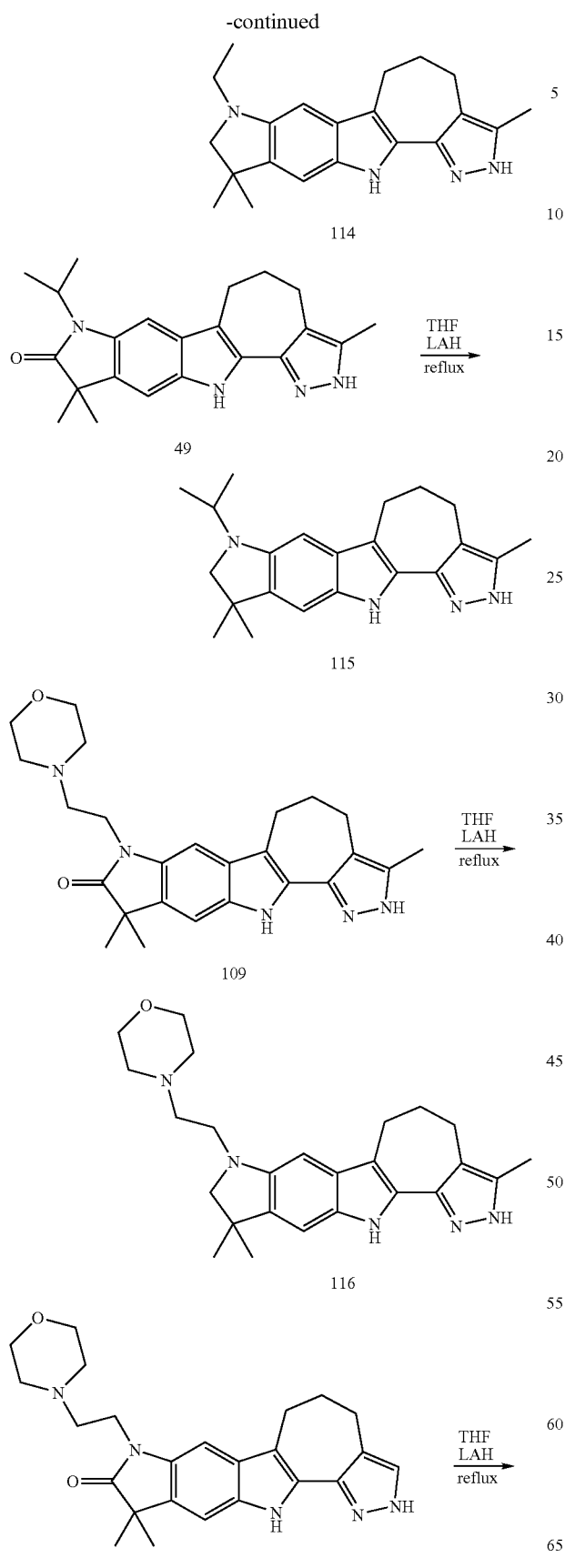
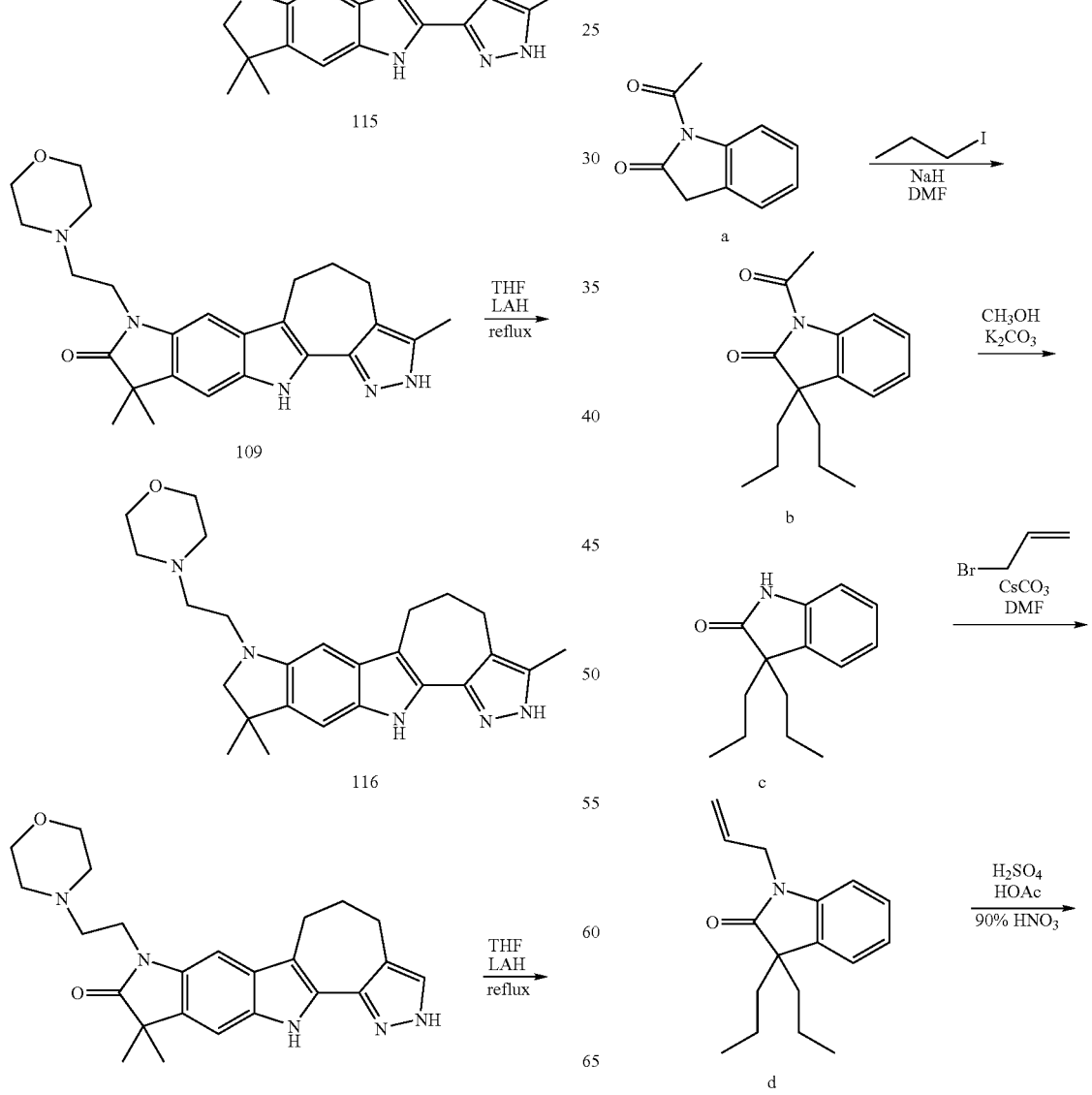
Compounds 114 to 117 were prepared in a similar manner to the procedures of example 60 in which the lactam starting compounds were reduced with LAH in THF.
Example 62
Synthesis of Compound 118

-continued

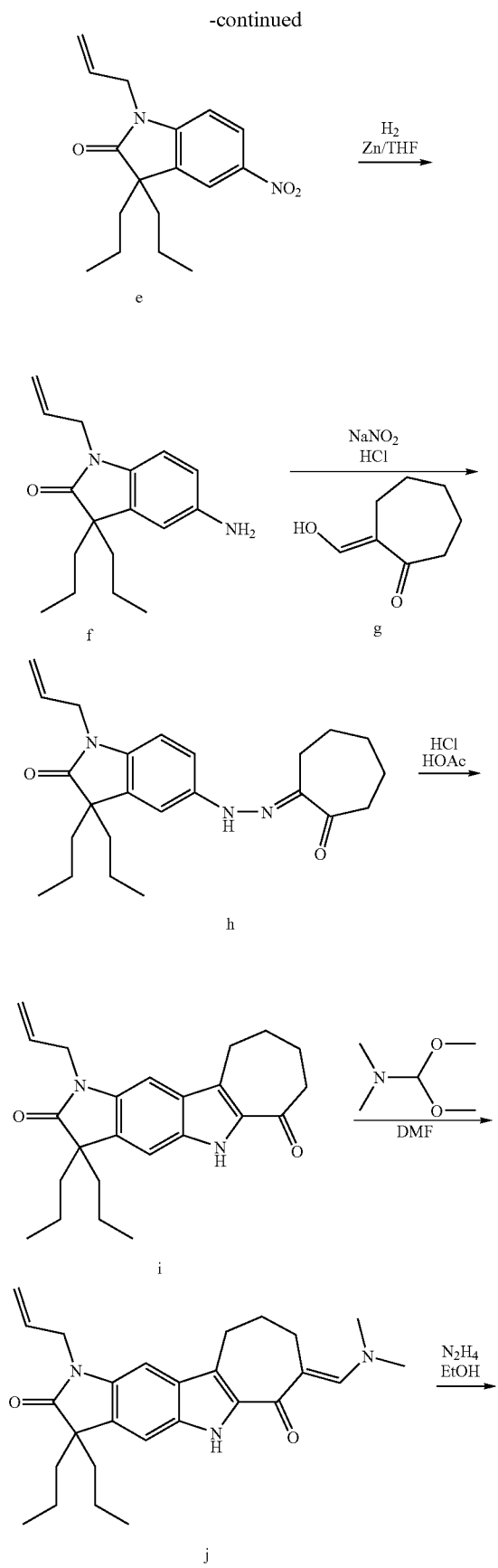

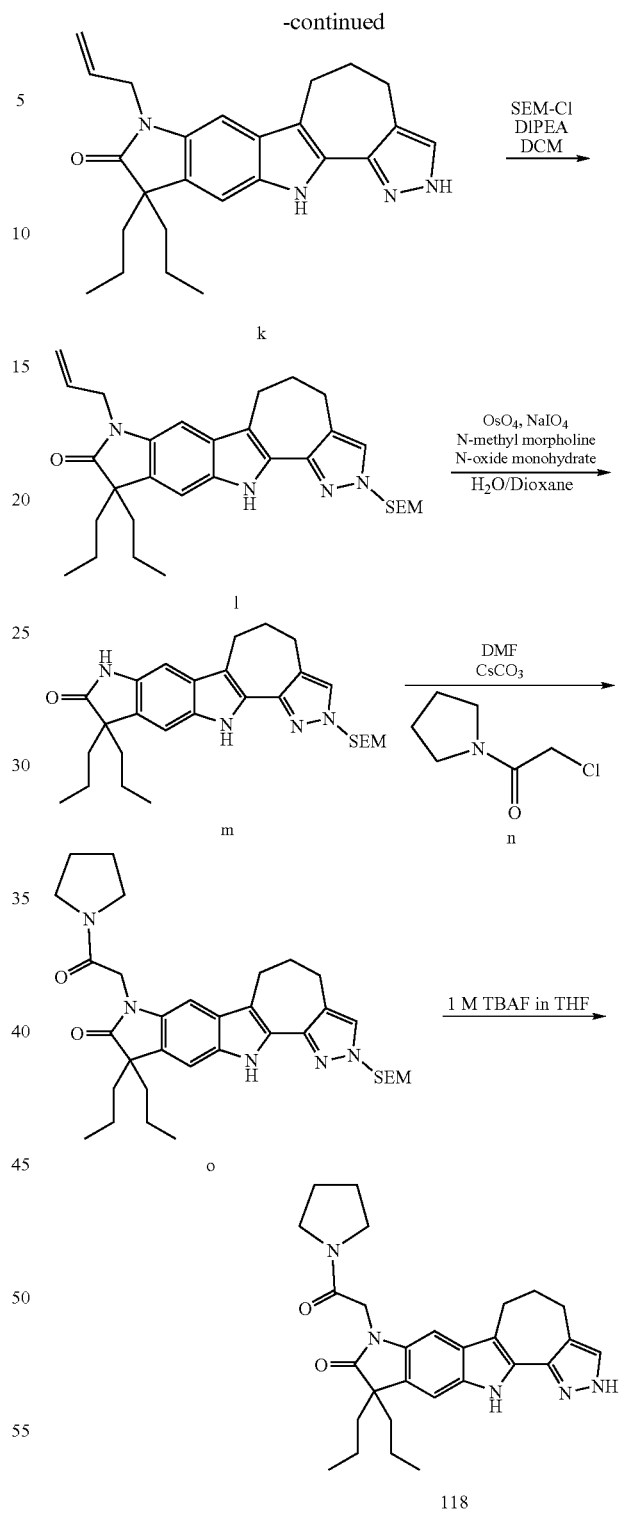

Sodium hydride (11.8 g) was added to 100 ml DMF and cooled to 0° C. N-acetyloxindole a (25.67 g) in 500 ml of DMF was added to this solution for 30 mins. then 30 ml of 1-iodopropane was added, warmed to room temperature and the reaction stirred for 24 hours. The reaction mixture was concentrated under vacuum, then partitioned between water and ethyl acetate. The organic phase was washed with brine, dried over sodium sulfate, filtered and concentrated under vacuum, and flashed on the ISCO (EtOAc/Hexanes) to give compound b (15.98 g).

Compound b (15.98 g) was dissolved in 150 ml $CH_3OH$ and $K_2CO_3$ (17.04 g) was added at room temperature. The reaction was stirred for 2 hours, then poured into 10% citric acid water solution and extracted with ethyl acetate. The organic phase was washed with brines, dried over sodium sulfate, filtered and concentrated under vacuum. Purification by automated silica gel chromatography gave 12.60 g of compound c.

Compound c (12.60 g) was dissolved in 250 ml DMF and 37.82 g $CsCO_3$ was added followed by 9.32 g allyl bromide. The reaction was stirred 18 hours and confirmed to be complete by TLC. The reaction was slowly poured into 10% citric acid water and extracted with ethyl acetate, washed with brine, dried over sodium sulfate and concentrated under vacuum to give crude compound d (15.21 g).

A mechanically stirred solution of d (15.20 g) in 140 ml of conc. sulfuric acid and 15 ml HOAc was cooled to −35° C. To this solution was added 2.66 ml fuming nitric acid in 50 ml $H_2SO_4$ and the reaction was allowed to warm up to room temperature. The reaction was completed by TLC after 1 hour. The reaction mixture was slowly poured into ice water and extracted with ethyl acetate, washed with brine, dried over sodium sulfate, concentrated under vacuum and flashed by ISCO to gave 13.91 g of compound e.

Compound e (12.76 g) was reduced under a balloon of hydrogen in the slurry of Zn dust (13.74 g) in 70 ml of THF and 70 ml of HOAc for 3 hours. The catalyst was filtered off and the filtrate concentrated under vacuum and flashed by ISCO to gave 8.41 g compound f.

Compound f (3.97 g) was dissolved in 30 ml of ACN and 20 ml HOAc, added 50 ml $H_2O$ and 1.82 ml concentrated HCl and cooled to 0° C. To this mixture was added 1.21 g $NaNO_2$ in 20 ml $H_2O$ and the reaction was stirred for 5 minutes. To this reaction mixture was added to 2.45 g of compound g 5.38 g, NaOAc in 200 ml $H_2O$ and 15 ml ACN at 0° C. and the reaction was allowed to warm up to room temperature and stirred for 2.5 hours. The precipitate formed was filtered off and confirmed to be compound h by LCMS. Purification by automated silica gel chromatography gave 4.56 g of compound h.

Compound h (4.56 g) was dissolved in 50 ml HOAc and 1.15 ml HCl and heated to 90° C. with stirring for 40 mins. The reaction was completed by LCMS and cooled to room temperature. The reaction mixture was slowly poured into ice water and extracted with ethyl acetate/hexane (2:1), washed with brine, dried over sodium sulfate and concentrated under vacuum and flashed by ISCO to give 3.30 g of compound i.

Compound i (3.30 g) was heated to 95° C. in a mixture of 25 ml of DMF and 25 ml of DMF dimethylacetal for 24 hours. The reaction mixture was concentrated under vacuum. The residue, compound j, was dissolved in 200 ml of ethanol, 1.27 ml of hydrazine hydrate added and the reaction stirred for 3.5 hours. The reaction mixture was concentrated to gave the crude compound k under vacuum at 20° C. The crude compound k was dissolved in 220 ml DCM and cooled to 0° C. before adding 2.31 ml SEM-Cl and 4.56 ml DIPEA. The reaction was stirred for 2 hours at 0° C. The reaction was diluted with 10% citric acid $H_2O$, extracted with DCM, dried over $Na_2SO_4$, concentrated under vacuum and flashed by ISCO to give 4.51 g of compound l.

Compound l (4.51 g) was dissolved in 140 ml dioxane and 14 ml $H_2O$, 2.98 g N-methyl morpholine N-oxide $H_2O$ was added and the reaction was stirred until everything was in solution.

To this reaction mixture was added $OsO_4$ (215 mg) in a 100 mg/ml butanol solution followed by the dropwise addition of a slurry of 5.44 g sodium periodate in 50 ml $H_2O$ and subsequent heating at 60° C. in a capped vessel for 80 mins. When completed by LCMS the reaction mixture was cooled to room temperature, diluted with brine, extracted with DCM, dried over $Na_2SO_4$, concentrated under vacuum, and flashed by ISCO to give compound m (1.51 g).

Compound m (51 mg) was dissolved in 2.5 ml DMF and $Cs_2CO_3$ (101 mg) was added, followed by the addition of compound n (46 mg). The vial was capped and the reaction was stirred at 40° C. for 16 hrs. The reaction was complete by LCMS. Diluted reaction with $H_2O$, extracted with EtOAc, washed with brine, dried over $Na_2SO_4$ and concentrated by vacuum to give compound o. Compound o was dissolved in 2.5 ml THF and added 0.31 ml 1.0 M TBAF in THF. The reaction was heated for 6.5 hours at 60° C. and was complete by LCMS. The reaction mixture was concentrated under vacuum, diluted with $H_2O$, extracted with EtOAc, washed with brine, dried over $Na_2SO_4$, concentrated under vacuum and flashed by ISCO to give 17 mg of compound 118.

Example 63

Synthesis of Compounds 119 and 120

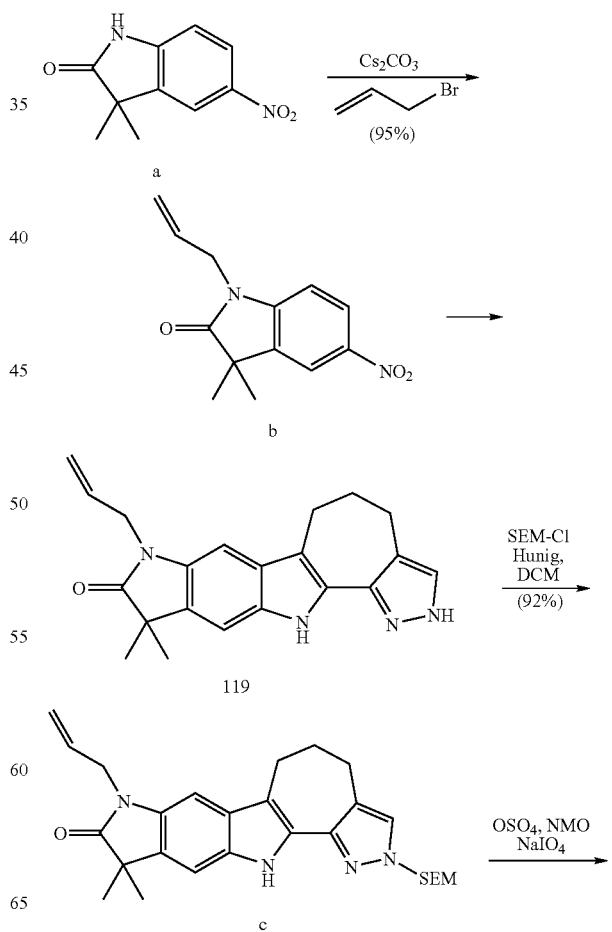

Example 64

Synthesis of Compound 121, 122 and 123

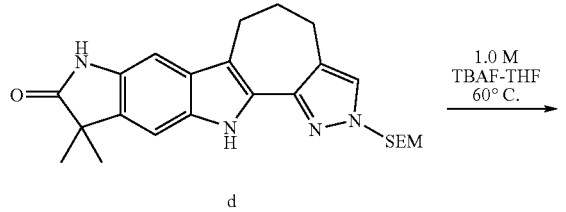

d

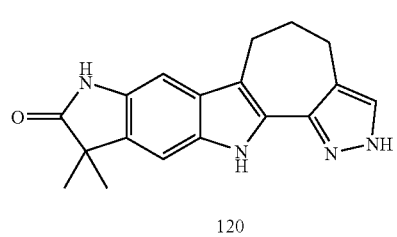

120

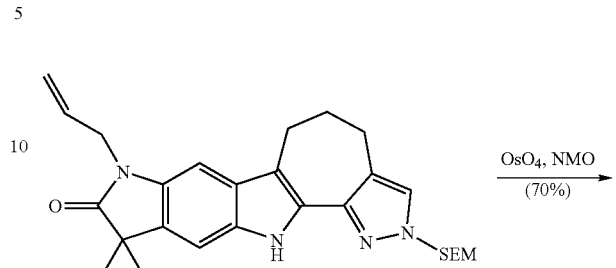

a

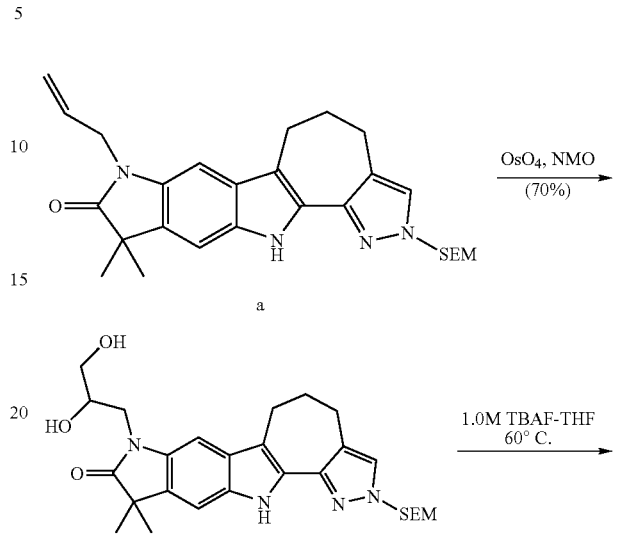

b

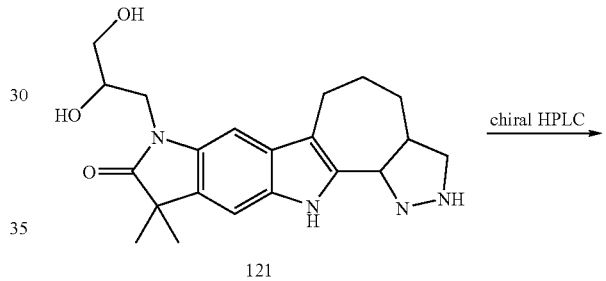

121

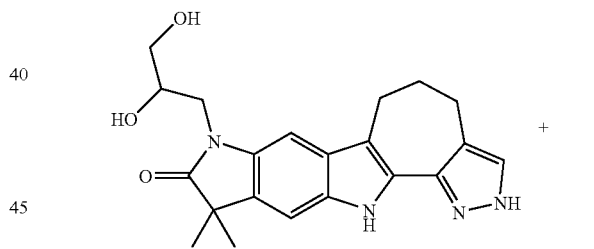

122

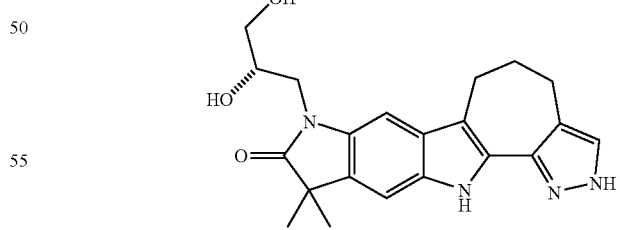

123

Compound a (40.6 g, 0.197 mol) was dissolved in DMF (500 ml) and cooled to 0° C. To this solution was added $Cs_2CO_3$ (0.22 mol, 1.1 eq) and allyl bromide (18.7 ml, 0.22 mol, 1.1 eq). The reaction mixture was allowed to warm to room temperature overnight. The reaction was then diluted with $H_2O$ (1 L) and extracted with EtOAc (0.5 L). The organic layer was further washed with $H_2O$, brine and dried over $Na_2SO_4$. The solvent was removed in vacuo to give b as a yellow solid (41 g, 85%). Compound b was treated in a similar manner to the procedures in example 21 to give 15 g of compound 119.

To a cold (0° C.) solution of compound 119 (12 g, 34.6 mmol) in DCM (175 ml) was added Hunig's base (3 eq) followed by SEM-Cl (1.5 eq) and allowed to warm to room temperature over 4 hours. The reaction mixture was diluted with 0.1 M HCl, extracted with DCM and dried over $Na_2SO_4$. The solvent was removed in vacuo and the residue was subjected to flash chromatography (silica gel, 0→50% EtOAc in hexanes, gradient elution) to afford c (15.2 g, 92%).

Compound c (0.88 g, 1.85 mmol) was dissolved in dioxane (9.0 ml) and $H_2O$ (2.0 mL). At room temperature, to this mixture was added N-methylmorpholine N-oxide monohydrate (0.750 g, 5.55 mmol, 3 eq) and a solution of $OsO_4$ (0.380 ml of a 100 mg/ml solution in t-BuOH) to give a black mixture. A slurry of $NaIO_4$ (1.2 g, 5.54 mmol, 3 eq) in $H_2O$ (4 ml) was added dropwise to the rapidly stirring mixture. The reaction vessel was then stirred at room temperature for 1 hr and then heated in a 60° C. oil bath for 2 hours. After cooling, the reaction mixture was diluted with brine, extracted with DCM and dried over $Na_2SO_4$. The solvent was removed in vacuo and the residue was subjected to flash chromatography (silica gel, 0→50% EtOAc in hexanes, gradient elution) to afford d (300 mg, 37%).

Compound d (68 mg) was dissolved in a 1.0 M solution of TBAF in THF (1.0 ml), sealed and heated to 60° C. for 5 hours. The solution was diluted with $H_2O$ and extracted with EtOAc. The organic layer was washed with $H_2O$ (3×) followed by brine and then dried over $Na_2SO_4$. The solvent was removed in vacuo and the residue subjected to purification by HPLC to afford 8 mg of compound 120.

Compound a (1.09 g, 2.29 mmol) was dissolved in tBuOH (8.0 ml), THF (2.5 ml) and $H_2O$ (0.8 mL) at room temperature. To this solution was added NMO (0.322 g, 2.85 mmol, 1.2 eq) followed by a solution of $OsO_4$ (17.5 mg, 8 mol %) in t-BuOH (0.350 ml of a 50 mg/ml solution). After 4 hours, the reaction mixture was diluted with $H_2O$, extracted with EtOAc and dried over Na$_2$SO$_4$. The solvent was removed in vacuo and the residue was subjected to flash chromatography (silica gel, 0→50% EtOAc in hexanes, gradient elution) to afford the diol b (0.810 mg, 70%). Diol b (540 mg) was treated in a manner similar to compound d in example 63 to give 410 mg of racemic compound 121.

A racemic mixture of compound 121 (21 mg) was separated by chiral HPLC to give 10 mg of compound 122 and 10 mg of compound 123.

Example 65

Synthesis of Compound 124

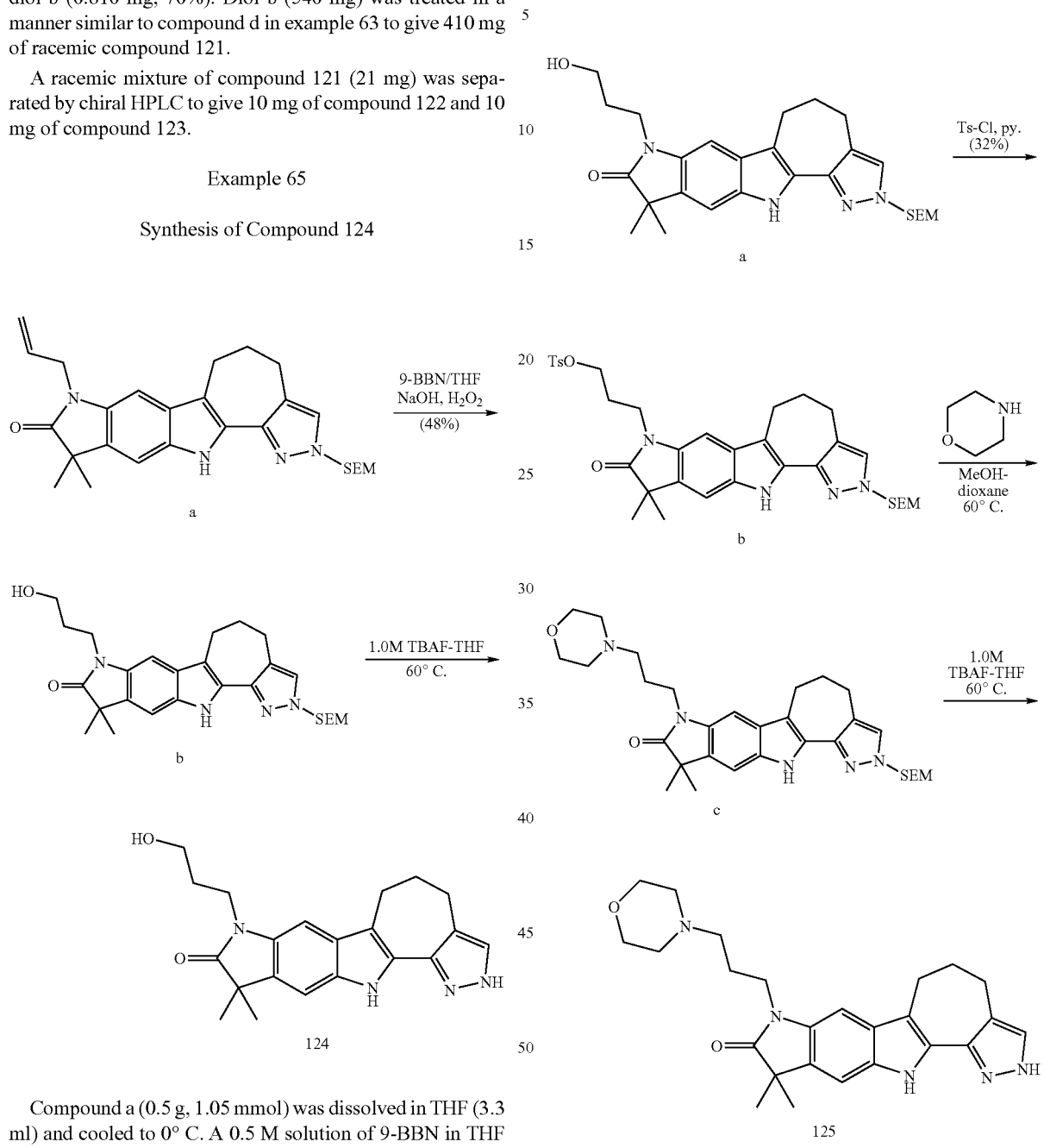

Compound a (0.5 g, 1.05 mmol) was dissolved in THF (3.3 ml) and cooled to 0° C. A 0.5 M solution of 9-BBN in THF (18.9 ml, 3.15 mmol, 9 eq,) was added to the reaction vessel and allowed to warm to room temperature. After the starting material was completely consumed, the reaction flask was cooled to 0° C., H$_2$O$_2$ (3 ml) was slowly added to the solution followed by 10% NaOH (3 mL). After stirring for an additional 20 minutes the mixture was extracted with EtOAc and dried over Na$_2$SO$_4$. The solvent was removed in vacuo and the residue was subjected to flash chromatography (silica gel, 10→80% EtOAc in hexanes, gradient elution) to afford compound b (250 mg, 48%). Compound b was treated in a similar manner to the procedures of example 63 to give 24 mg of compound 24.

Example 65

Synthesis of Compound 125

Compound a (220 mg) was dissolved in DCM (2 ml), cooled to 0° C. and treated with pyridine (0.1 ml) and tosyl chloride (300 mg). After stirring overnight the reaction was quenched under standard work up conditions and purified via flash chromatography to afford the compound b (92 mg). Compound b (92 mg) was dissolved in dioxane (2 ml) and triethylamine (0.05 ml). Morpholine was added to the solution and heated to 60° C. overnight. After the reaction was complete, the solvent was removed and the crude material containing c was treated in a similar manner to the procedures of example 63 to give 25 mg of compound 125.

Example 66

Synthesis of Compound 126

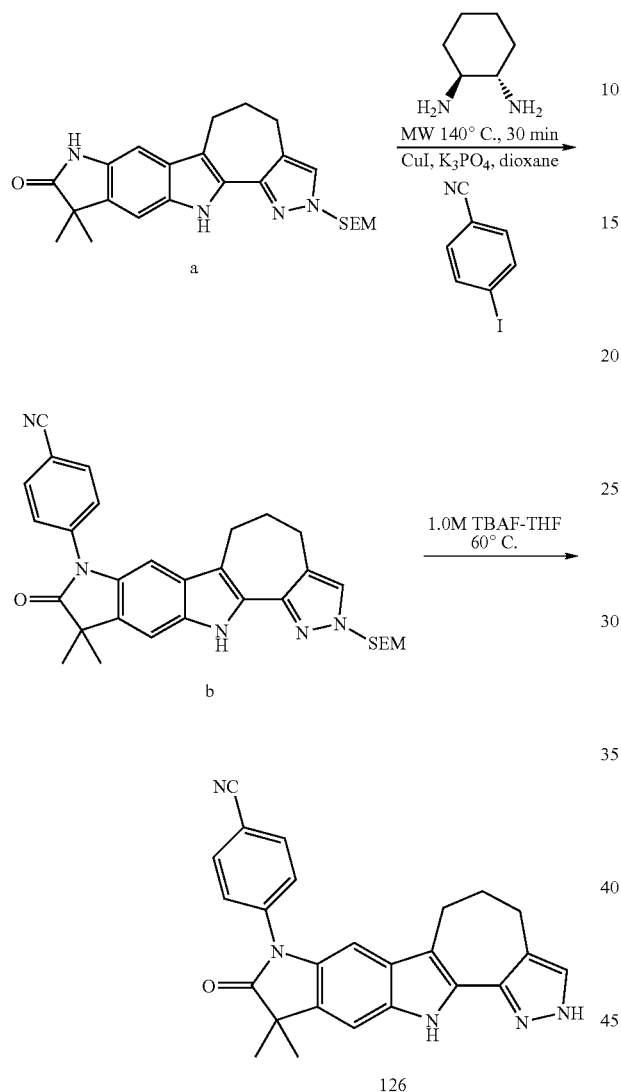

Example 67

Synthesis of Compounds 127 to 136

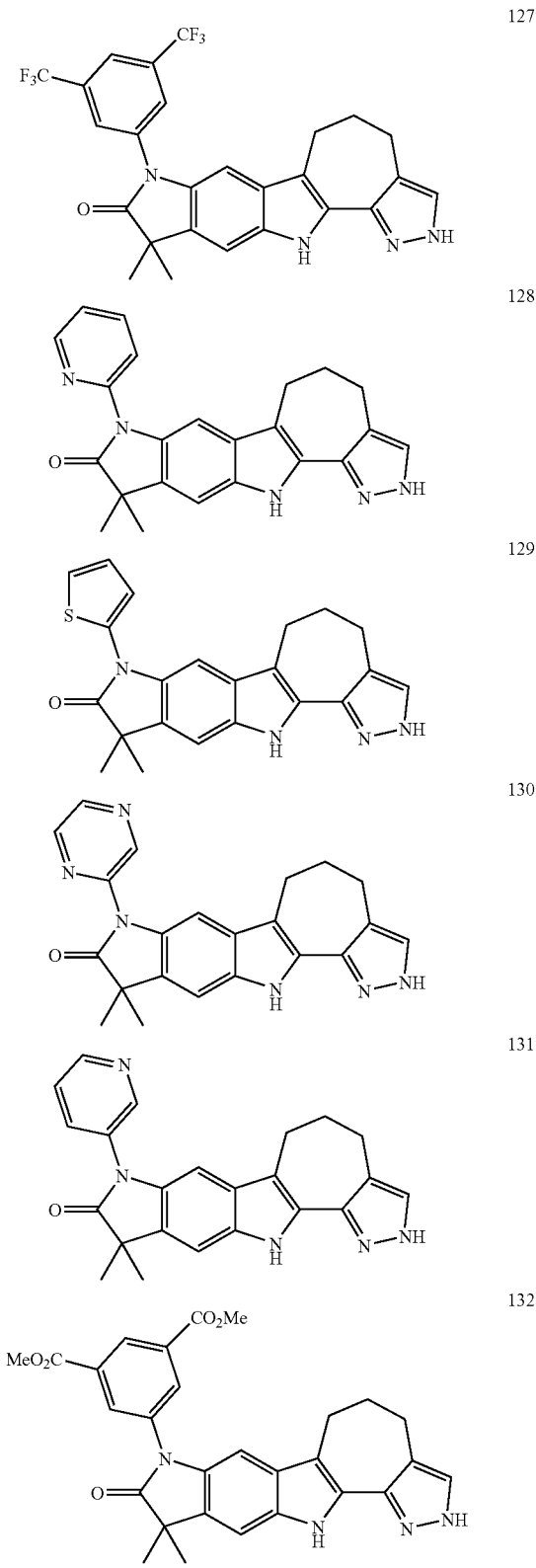

To an oven dried microwave reaction vessel and spin bar was added compound a (0.33 mmol). To this solid, CuI (0.166 mmol, 0.5 eq), 4-iodobenzonitrile (0.33 mmol, 1 eq) and $K_3PO_4$ (0.66 mmol, 2 eq) were directly added. After flushing the reaction vessel with $N_2$, a solution of trans-1,2-cyclohexanediamine (0.33 mmol, 1 eq) in dioxane (1.7 ml) was added to the mixture of solids and degassed for 15 minutes with a stream of $N_2$. The reaction vessel was then heated to 140° C. for 30 minutes under microwave conditions. After cooling to room temperature the mixture was filtered and the solvent was removed in vacuo. The residue was subjected to flash chromatography to afford the desired coupled compound b. Crude compound b was treated in a similar manner to the procedures of example 63 to give 25 mg of compound 126.

-continued

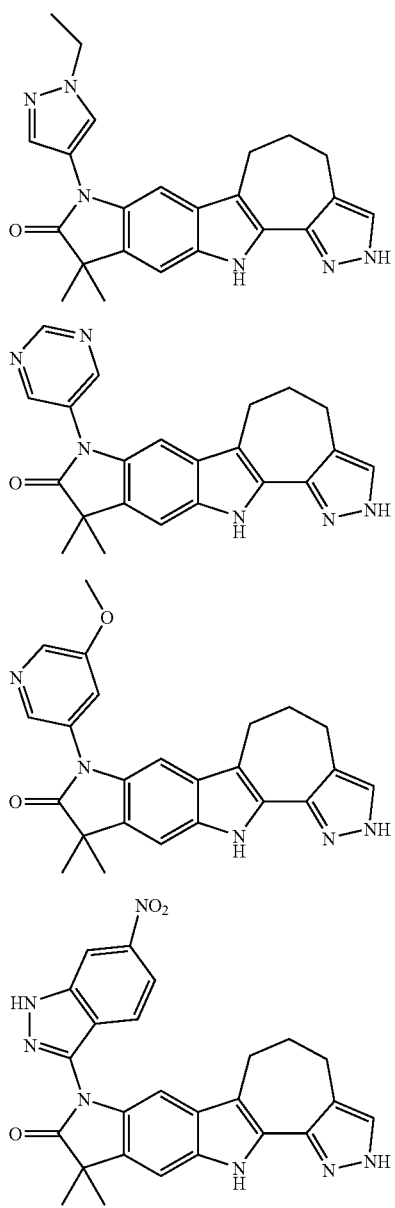

133

134

135

136

In a manner similar to the procedures of example 66, compound a was reacted with the appropriate iodo-substituted heterocycle to give:

8 mg of compound 127;
16 mg of compound 128;
11 mg of compound 129;
9 mg of compound 130;
78 mg of compound 131;
22 mg of compound 132;
25 mg of compound 133;
23 mg of compound 134;
29 mg of compound 135; and
12 mg of compound 136.

Example 68

Synthesis of Compound 137

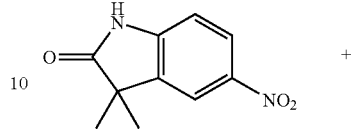

a

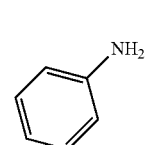

b

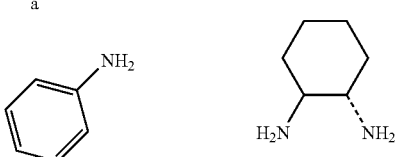

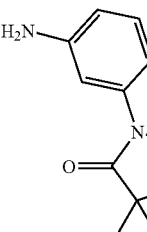

c

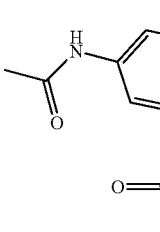

d

137

Compound a was combined with 3-iodobenzenamine b and treated in a similar manner to the procedures in example 66 in to give crude compound c. This material was dissolved in dichloromethane at room temperature and both triethylamine (2 eq) and acetic anhydride (10 eq) were added. After stirring for 3 hours the reaction mixture was concentrated and purified by flash column chromatography to give 120 mgs of compound d. Compound d was treated in a similar manner to the applicable procedures in examples 1, 2 and 21 to give 11 mg of compound 137.

Example 69

Synthesis of Compound 138

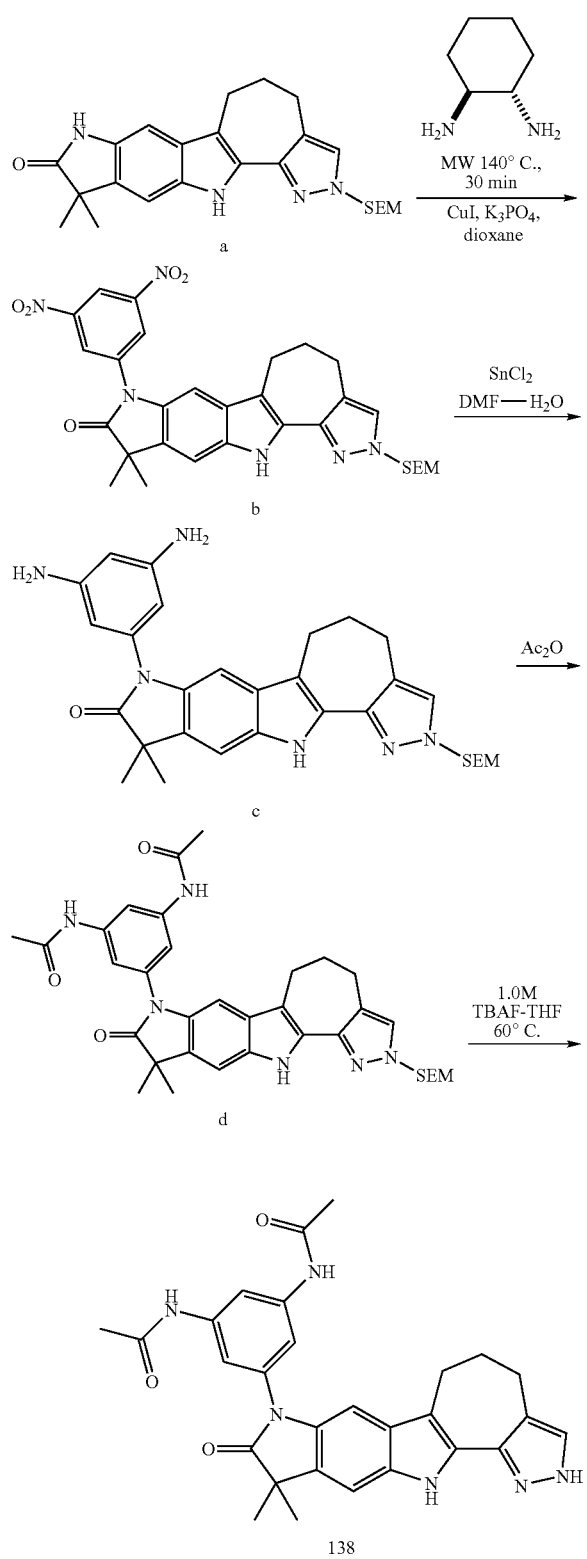

Compound a was combined with the appropriate coupling partner and treated in a similar manner to the procedures of example 66 to give 295 mg compound b. Compound b (214 mg) was heated to 60° C. in a solution of DMF (0.2 M)/H$_2$O (5 eq) and SnCl$_2$ (6 eq). After 5 hours, the reaction mixture was cooled to room temperature, diluted with EtOAc and washed with 10% citric acid, dried and concentrated to give compound c as a crude oil. This material was dissolved in dichloromethane, triethylamine (2 eq) and acetic anhydride (10 eq) was added at room temperature. After stirring for 3 hours the reaction mixture was concentrated and purified by flash column chromatography to give compound d. Compound d was treated in a similar manner to the procedures in example 63 to give 7 mg of compound 138.

Example 70

Synthesis of Compound 139

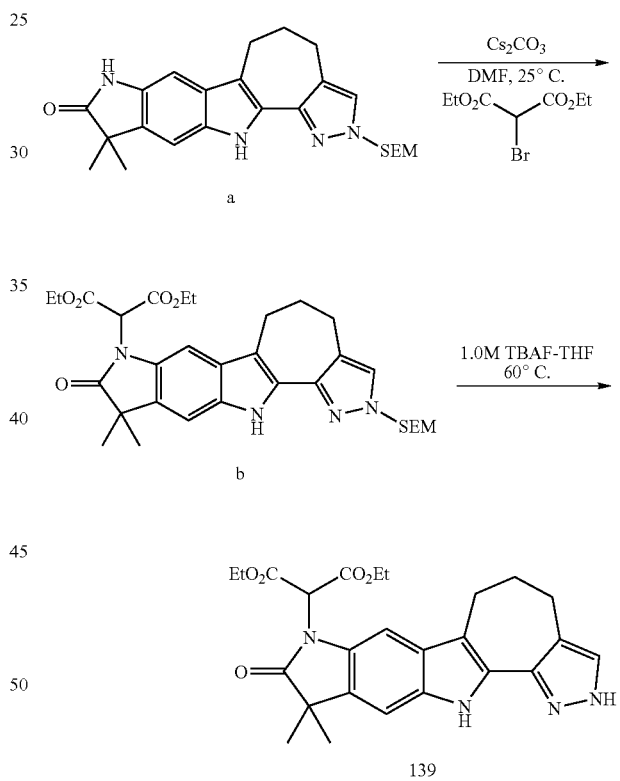

Compound a (0.2 mmol) was dissolved in DMF (1.0 ml) at room temperature. To this solution was added Cs$_2$CO$_3$ (1.0 mmol) and diethyl bromomalonate (1.0 mmol). The reaction mixture was then stirred at 60° C. for 8 hours. After complete consumption of the starting material, the mixture was diluted with H$_2$O and extracted with EtOAc. The organic layer was washed with H$_2$O (2x) followed by brine and then dried over Na$_2$SO$_4$. The residue was subjected to flash chromatography

Example 71
Synthesis of Compounds 140 to 163
140
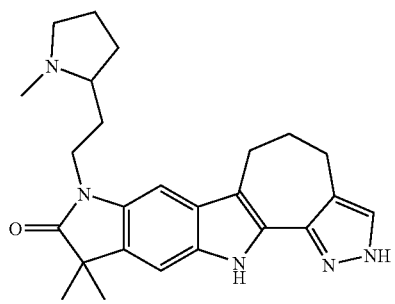
141
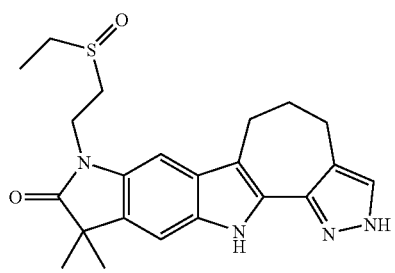
142
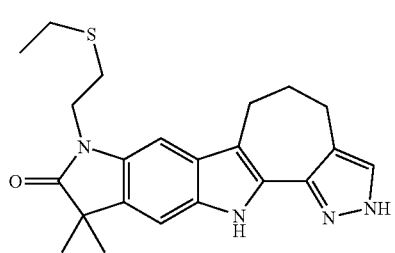
143
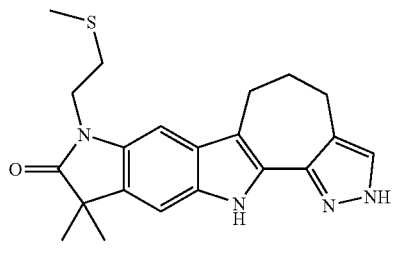
144
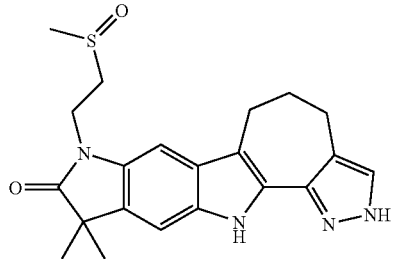
145
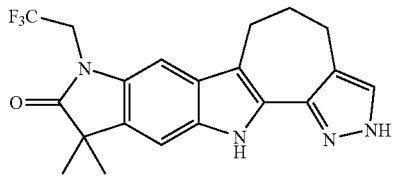
-continued
146
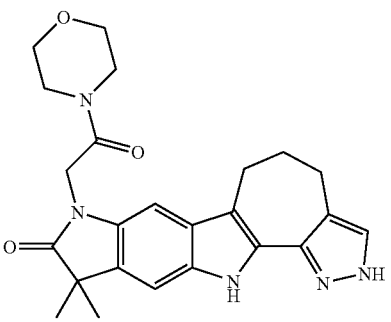
147
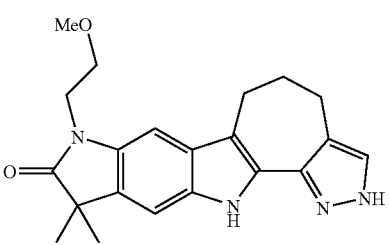
148
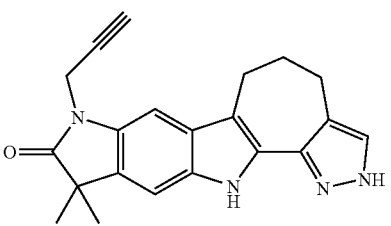
149
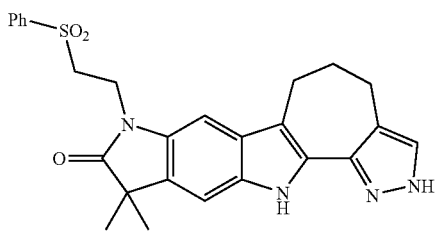
150
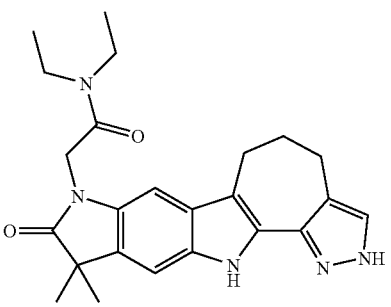

-continued
151 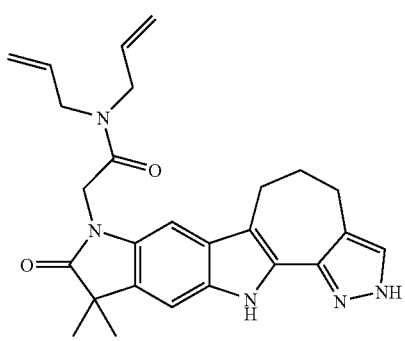
152 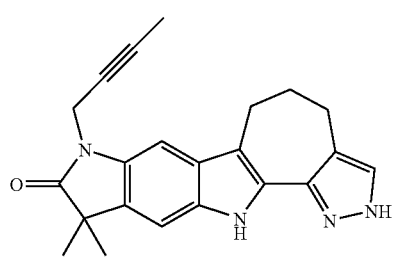
153 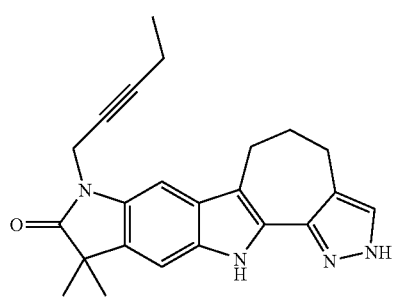
154 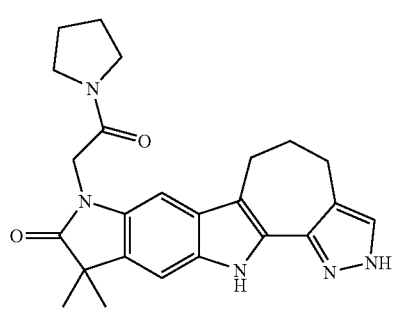
155 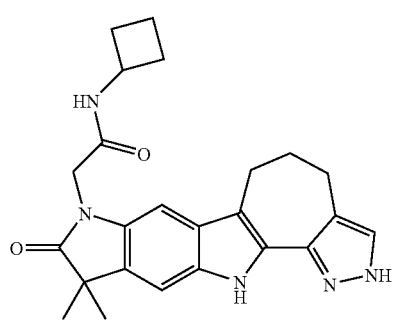
-continued
156 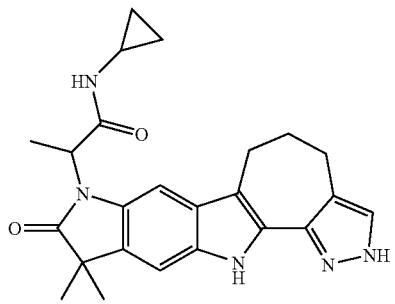
157 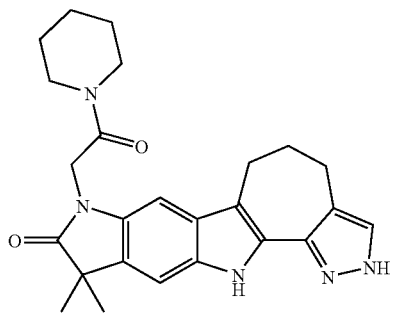
158 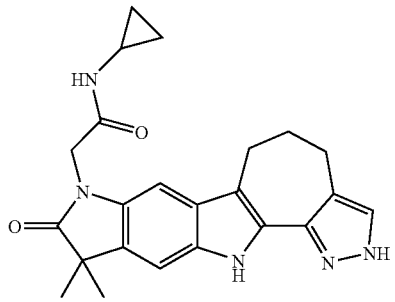
159 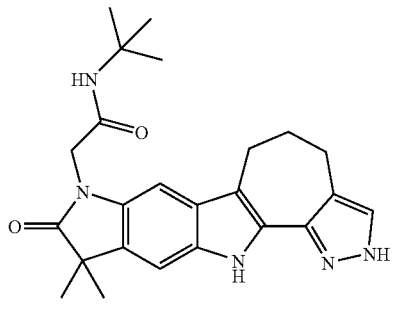
160

-continued

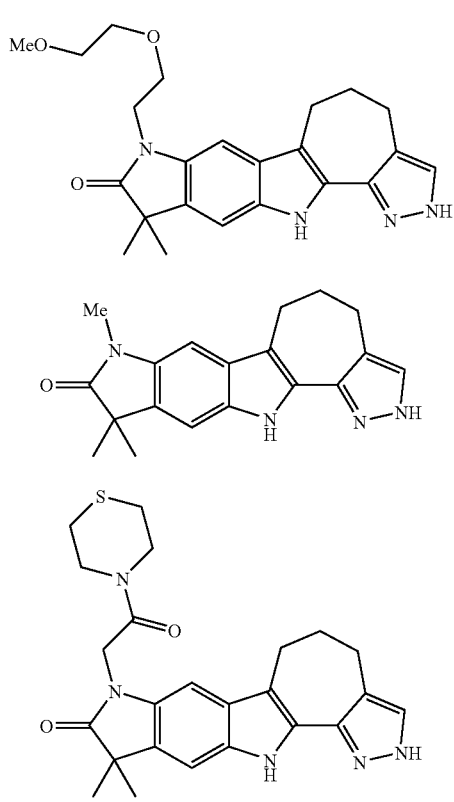

161

162

163

In a manner similar to the procedures of example 70, compound a was reacted with the appropriate bromo- or chloro-substituted heterocycle to give:

12 mg of compound 140;
9 mg of compound 141;
1 mg of compound 142;
6 mg of compound 143;
15 mg of compound 144;
1 mg of compound 145;
52 mg of compound 146;
54 mg of compound 147;
25 mg of compound 148;
15 mg of compound 149;
11 mg of compound 150;
12 mg of compound 151;
15 mg of compound 152;
11 mg of compound 153;
65 mg of compound 154;
24 mg of compound 155;
40 mg of compound 156;
38 mg of compound 157;
28 mg of compound 158;
6 mg of compound 159;
20 mg of compound 160;
47 mg of compound 161;
5 mg of compound 162; and
26 mg of compound 163.

Example 72

Synthesis of Compound 164

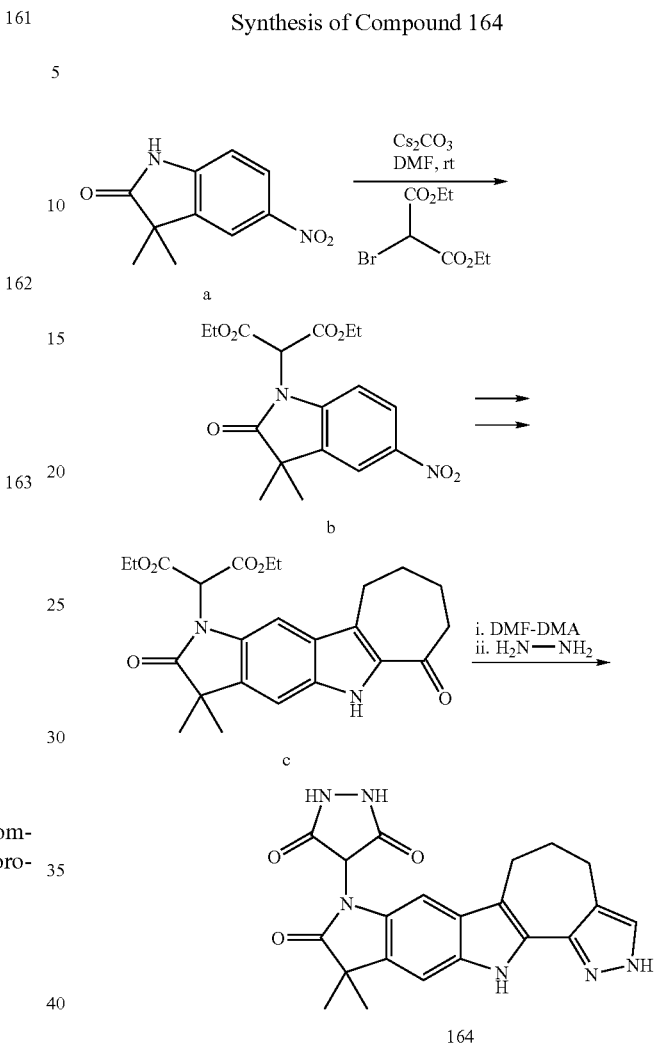

Compound a (5 g) was combined with diethyl 2-bromomalonate and treated in a similar manner to the procedures of example 70 to give 5.78 g of compound b. Compound b (5.78 g) was treated in a similar manner to the applicable procedures of examples 1 and 2 to give 2.5 g or compound c. Compound c was treated with DMF-dimethylacetal and hydrazine in a similar manner to the procedures of example 21 to give compound 164.

Example 73

Synthesis of Compound 165

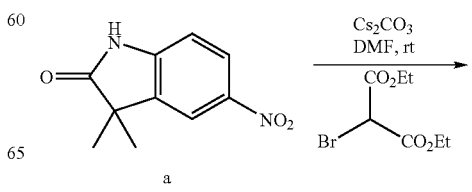

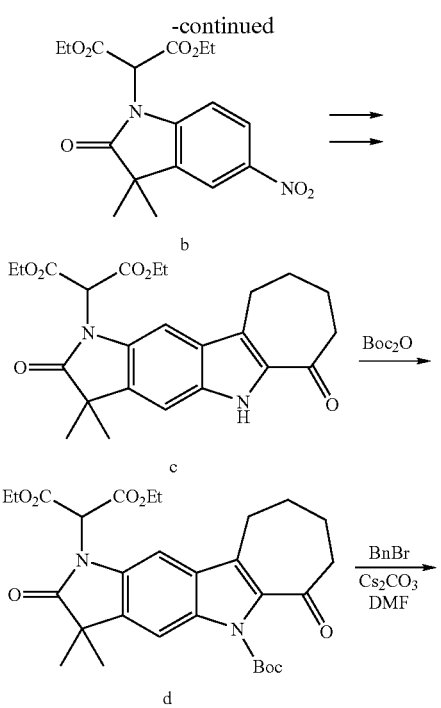

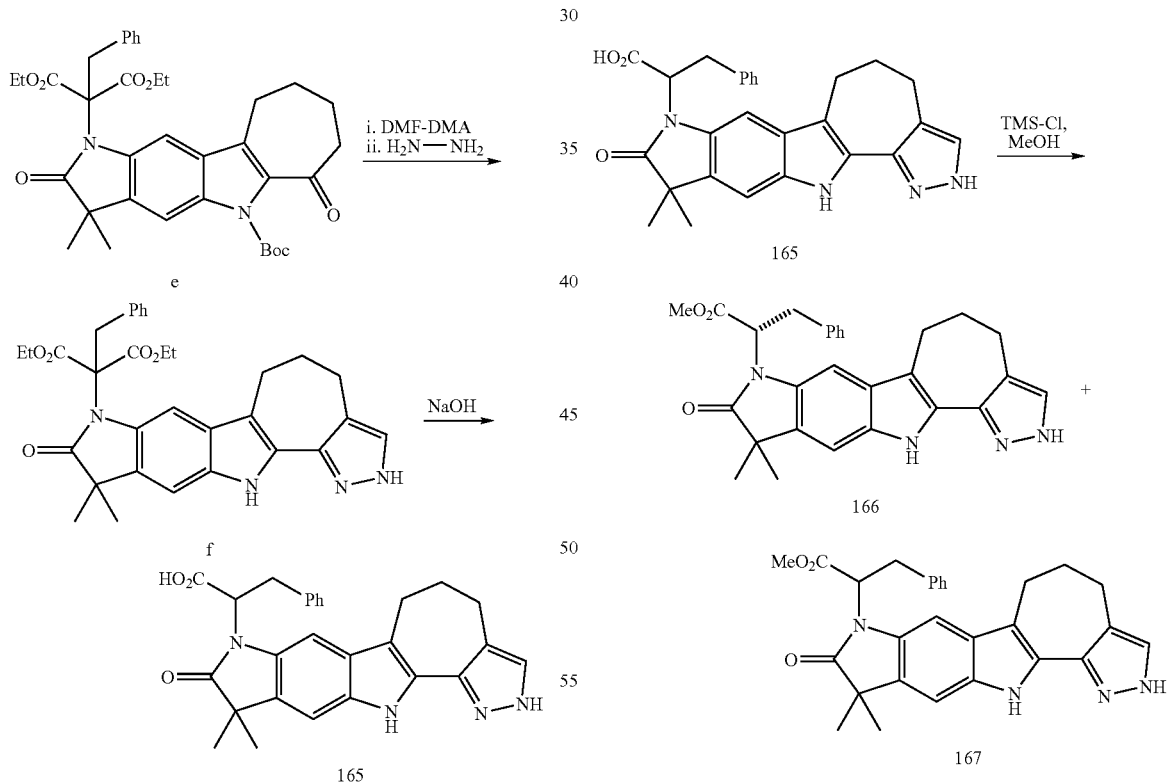

Example 74

Synthesis of Compounds 166 and 167

Compound a (5 g) was combined with diethyl 2-bromomalonate and treated in a similar manner to the procedures of example 70 to give 5.78 g of compound b. Compound b (5.78 g) was treated in a similar manner to the applicable procedures of examples 1 and 2 to give 2.5 g of compound c. Compound c (400 mg) was treated with 4-DMAP (0.25 eq) and Boc anhydride (3 eq) in dichloromethane at room temperature and allowed to stir overnight. Upon quenching with 0.1M HCl the organic layer was separated from the aqueous layer and washed with brine. The organic layer was then dried, concentrated and purified by flash column chromatography to afford 320 mg of compound d.

Compound d (220 mg) was heated to 60° C. in a mixture of DMF containing $Cs_2CO_3$ (3 eq) and benzyl bromide (2 eq) for 3 hours. The reaction mixture was quenched with $H_2O$, then extracted with EtOAc and subsequently washed with additional $H_2O$ (3×). The organic layer was dried, concentrated and purified by flash column chromatography to give 191 mg of compound d.

Compound d (191 mg) was treated in a similar manner to the applicable procedures for example 21 to give 150 mg of compound e. Compound e (33 mg) was dissolved in a 1:1 mixture of EtOH/$H_2O$ and cooled to 0° C. To this solution was added 2N KOH (2.5 eq) and allowed to stir overnight while warming to room temperature. A 1N HCl solution was added to the reaction and extracted with ethyl ether, dried, concentrated and purified by HPLC to afford 8 mg of compound 165.

Compound 165 (25 mg) was dissolved in MeOH (5 mL) and added to this solution was TMS-Cl (0.20 ml). The reaction was allowed to stir overnight and then concentrated in vacuo and diluted with EtOAc. The crude reaction was washed with $NaHCO_3$ and the organic layer was dried, concentrated and then purified by chiral HPLC to afford 10 mg of each enantiomer 166 and 167.

Example 75

Synthesis of Compound 168

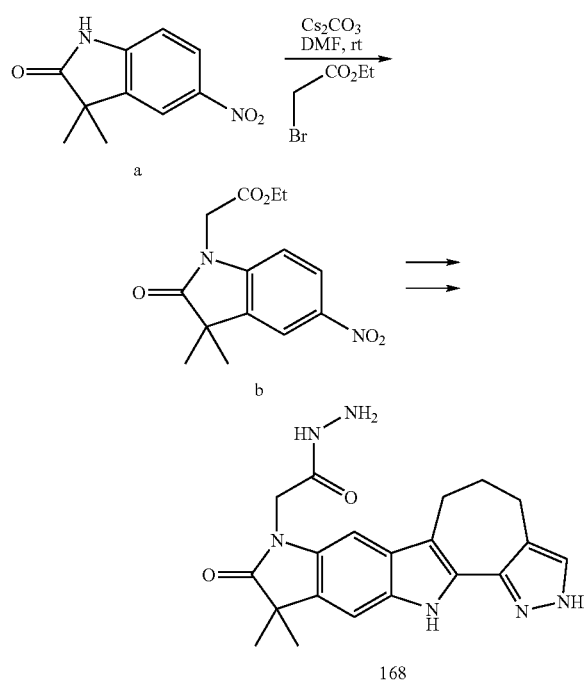

Compound a (5.0 g) was treated in a similar manner to the applicable procedures in examples 1, 2 and 21 to give 2.6 g of compound 168.

Example 76

Synthesis of Compound 169

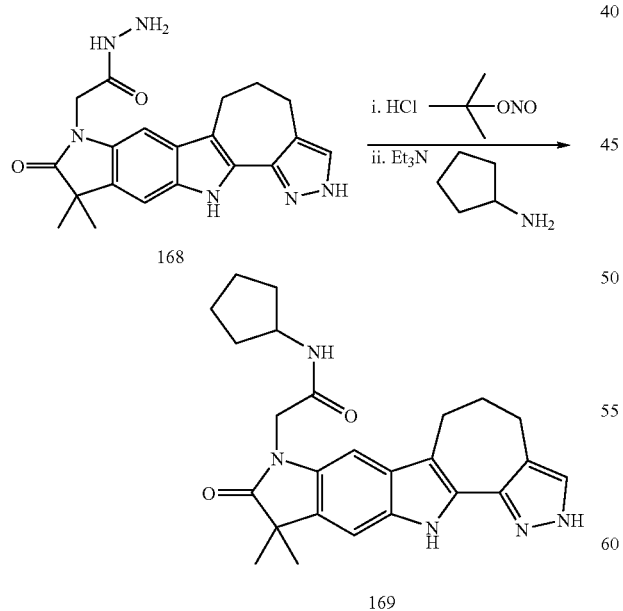

A solution of compound 168 (424 mg) in DMF was cooled to −40° C. and con HCl was added slowly and then allowed to warm to −20° C. To this mixture was added t-butyl nitrite dropwise and the reaction mixture was gradually warmed to −15° C. Cyclopentylamine (0.9 eq) was then added dropwise to the cold solution, followed by triethylamine (3 eq). After stirring at 0° C. overnight, the reaction mixture was quenched with AcOH and concentrated under vacuum. The crude mixture was diluted with $H_2O$ and extracted with EtOAc and the separated organic layer subsequently washed with $H_2O$ (2×). The organic layer was then dried, concentrated and purified by flash column chromatography to afford 156 mg of compound 169.

Example 77

Synthesis of Compound 170

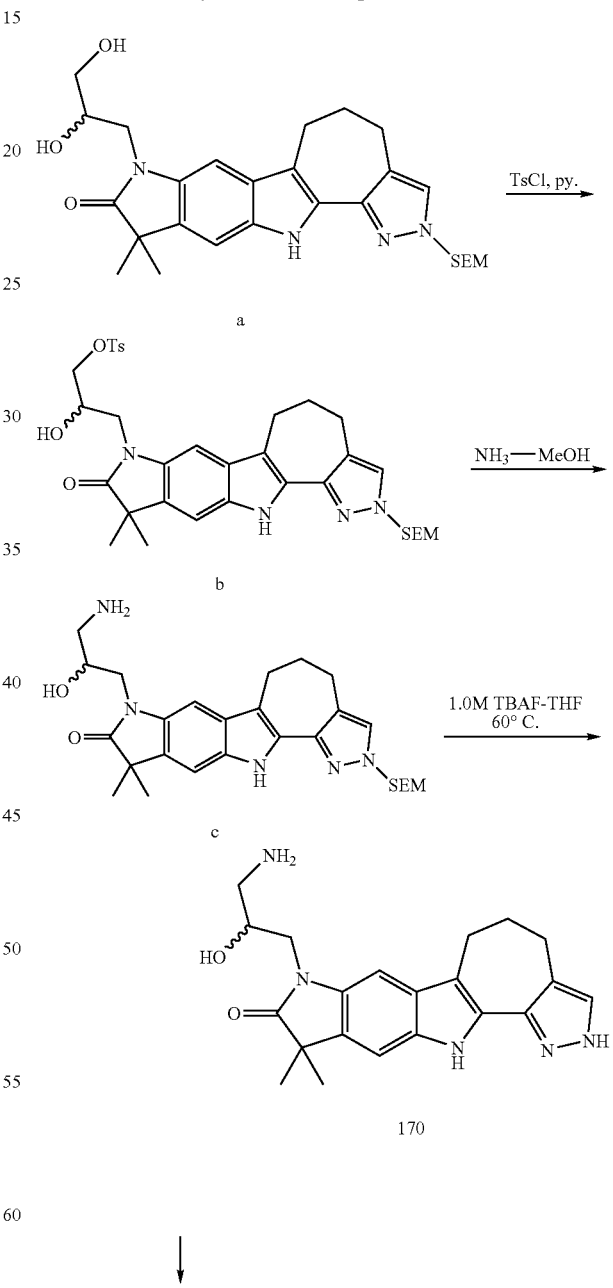

Compound a (340 mg) was dissolved in dichloromethane (0.2 M) and treated with pyridine (3 eq) at room temperature. To this solution was added tosyl chloride (1.1 eq) and the reaction was allowed to stir overnight. The reaction was then diluted with 1N HCl and extracted with DCM. The organic layer was further washed with H₂O, brine and dried over Na₂SO₄. The solvent was removed in vacuo and purified by column chromatography to give 176 mg of compound b.

Compound b was heated to 60° C. in a sealed tube containing 2.0M of NH₃/MeOH. After 6 hours the solution was concentrated in vacuo to give compound c as a crude oil. Compound c was treated in a similar manner to the procedures in example 63 to afford 12 mg of compound 170.

Example 78

Synthesis of Compound 171

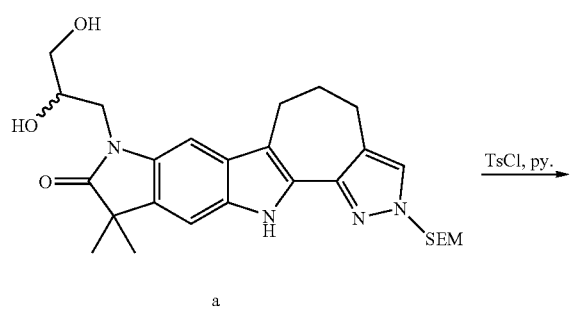

a

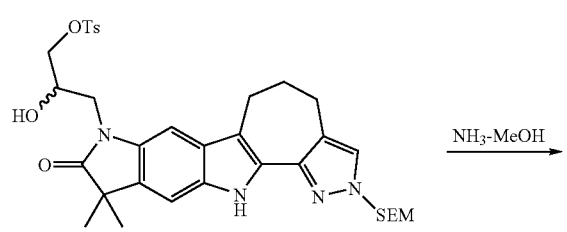

b

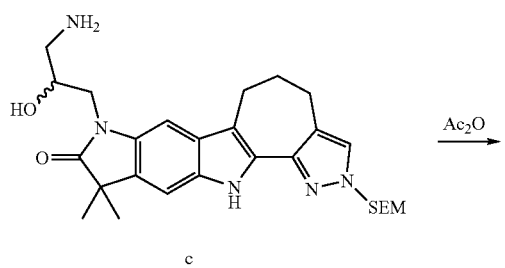

c

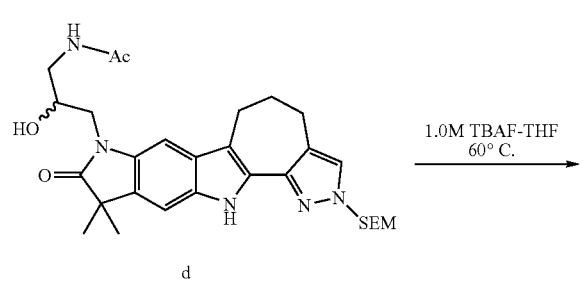

d

-continued

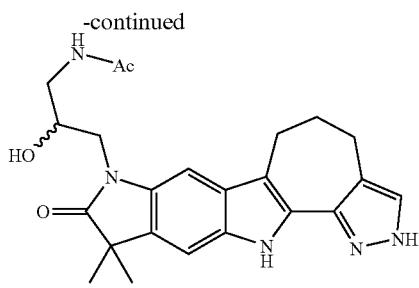

171

Compound a (340 mg) was dissolved in dichloromethane (0.2 M) and treated with pyridine (3 eq) at room temperature. To this solution was added tosyl chloride (1.1 eq) and the reaction was allowed to stir overnight. The reaction was then diluted with 1N HCl and extracted with DCM. The organic layer was further washed with H₂O, brine and dried over Na₂SO₄. The solvent was removed in vacuo and purified by column chromatography to give 176 mg of compound b.

Compound b was heated to 60° C. in a sealed tube containing 2.0M of NH₃/MeOH. After 6 hours the solution was concentrated in vacuo to give compound c as a crude oil. Compound c was dissolved in dichloromethane, triethylamine (2 eq) and acetic anhydride (10 eq) at room temperature. After stirring for 3 hours the reaction mixture was concentrated to afford compound d as a crude oil. Compound d was treated in a similar manner to the procedures in example 63 to afford 2 mg of compound 171.

Example 79

Synthesis of Compound 172

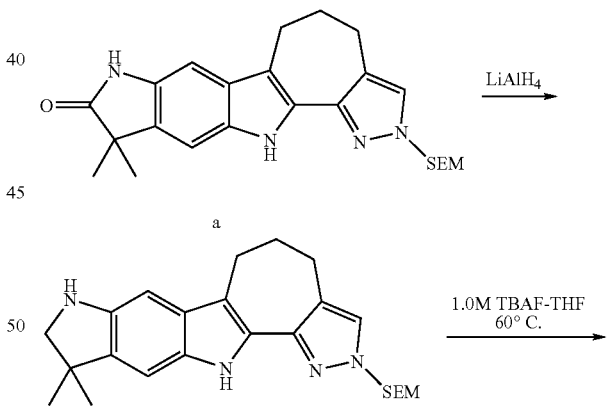

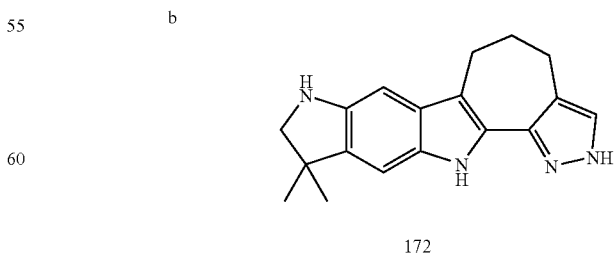

172

Compound a (219 mg) was dissolved in THF and a 1.0M solution of lithium aluminum hydride (3 eq) was added at room temperature. The reaction mixture was heated to 70° C. for 5 hours and then allowed to cool to room temperature. The reaction was quenched with H₂O and NaOH and filtered through Celite. Upon extracting with EtOAc, the organic layer was further washed with H₂O, brine and dried over Na₂SO₄. The solvent was removed in vacuo and purified by column chromatography to give 158 mg of compound b. Compound b (100 mg) was treated in a similar manner to the procedures in example 63 to give 5 mg of compound 172.

Example 79

Synthesis of Compound 173

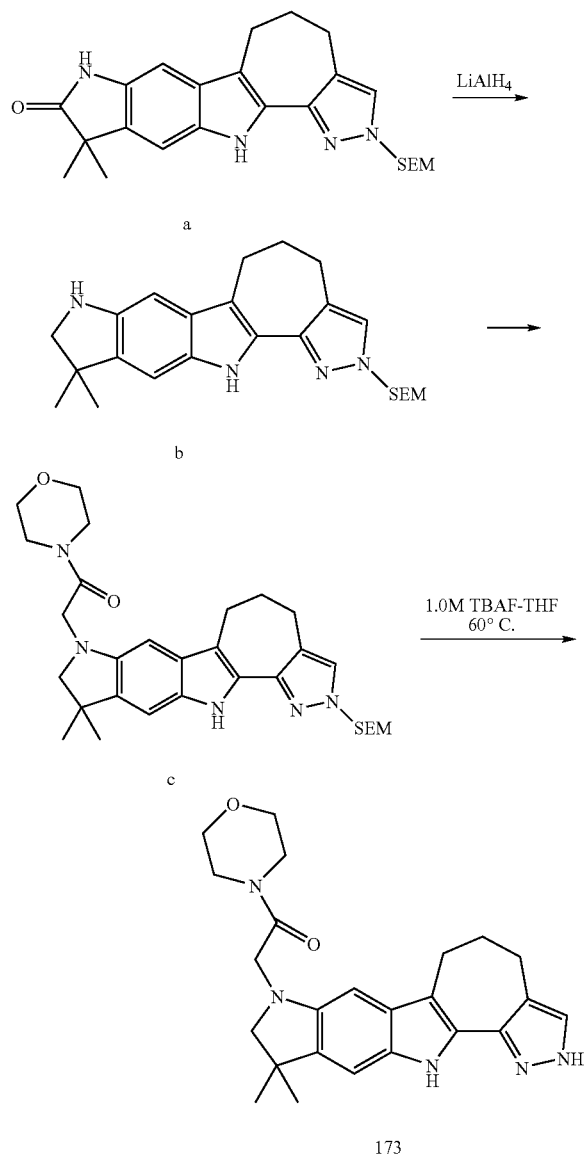

Compound a (219 mg) was dissolved in THF and a 1.0M solution of lithium aluminum hydride (3 eq) was added at room temperature. The reaction mixture was heated to 70° C. for 5 hours and then allowed to cool to room temperature. The reaction was quenched with H₂O and NaOH and filtered through Celite. Upon extracting with EtOAc, the organic layer was further washed with H₂O, brine and dried over Na₂SO₄. The solvent was removed in vacuo and purified by column chromatography to give 158 mg of compound b. Compound b (58 mg) was combined with the appropriate halide in a similar manner to the procedures in example 70 to give compound c as a crude oil. Compound c was treated in a similar manner to the procedures in example 63 to give 19 mg of compound 173.

Example 80

Synthesis of Compound 174

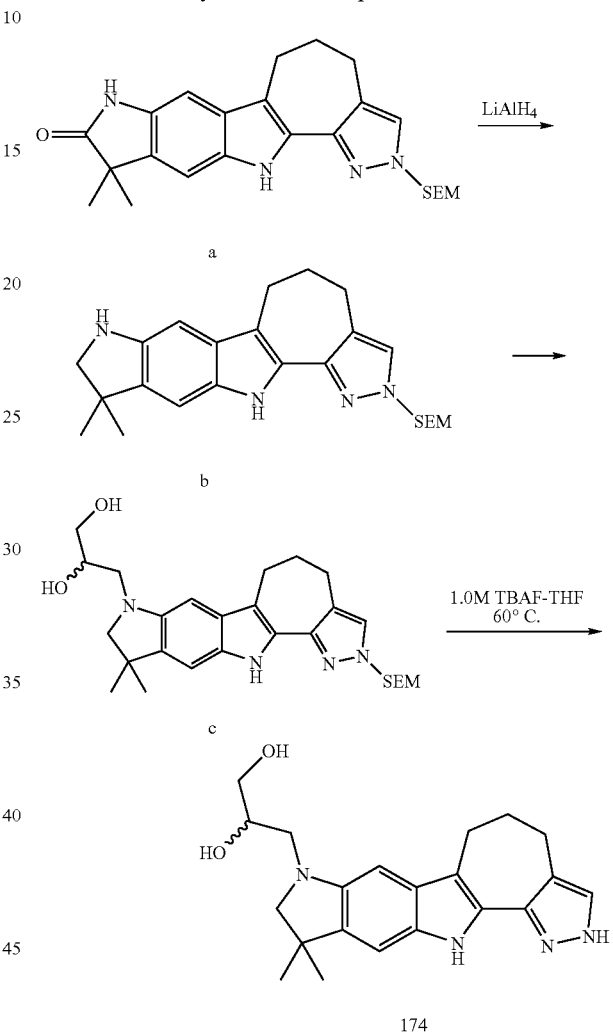

Compound 174 was prepared in a similar manner to the procedures in example 70 using the appropriate halide. Yield 20 mg compound 174.

Example 81

Synthesis of Compound 175

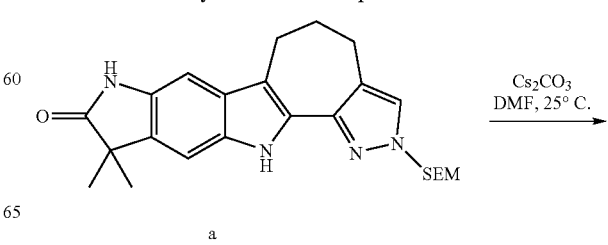

-continued

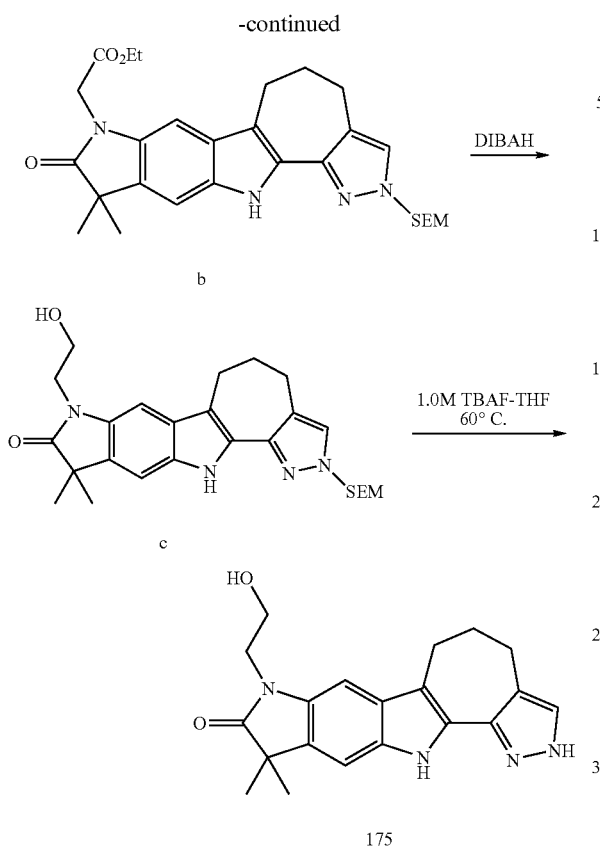

175

-continued

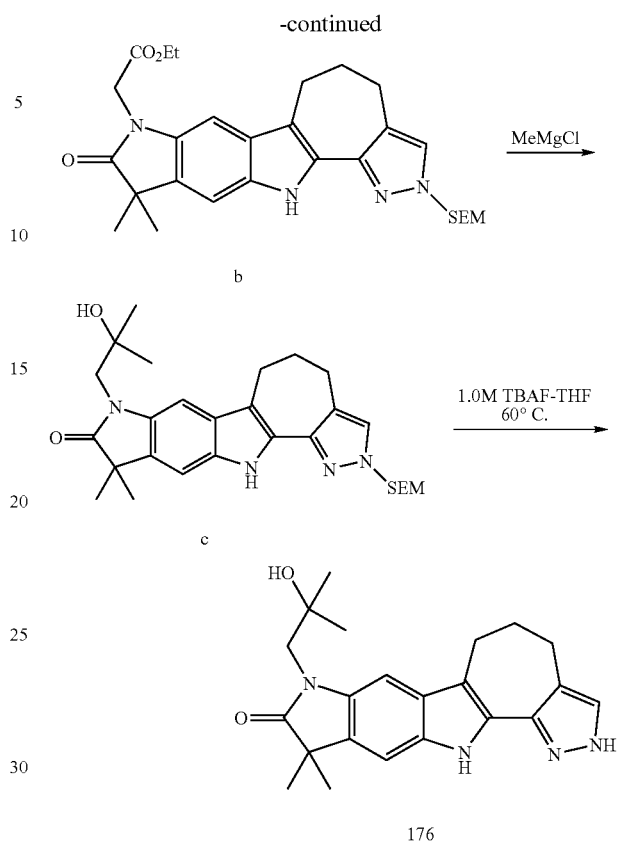

176

Compound a (127 mg) was treated in a similar manner to the procedures in example 70 to give 100 mg of compound b. Compound b (50 mg) was dissolved in THF and a 1.0M solution of diisobutyl aluminum hydride (6 eq) was added at 0° C. The reaction mixture was allowed to stir for 2 hours and then warmed to room temperature. The reaction was quenched with MeOH and filtered through Celite. Upon extracting with EtOAc, the organic layer was further washed with H$_2$O, brine and dried over Na$_2$SO$_4$. The solvent was removed in vacuo and the crude material containing compound c was subjected to the next reaction. Crude compound c was treated in a similar manner of the procedures in example 63 to give 2 mg of compound 175.

Compound a (127 mg) was treated in a similar manner to the procedures in example 70 to give 100 mg of compound b. Compound b (63 mg) was dissolved in THF and a 1.0M solution of methyl magnesium chloride (6 eq) was added at 0° C. The reaction mixture was allowed to stir for 2 hours and then warmed to room temperature. The reaction was quenched with NH$_4$Cl and filtered through Celite. Upon extracting with EtOAc, the organic layer was further washed with H$_2$O, brine and dried over Na$_2$SO$_4$. The solvent was removed in vacuo and the crude material c was subjected to the next reaction. Crude compound c was treated in a similar manner to the procedures in example 63 to give 6 mg of compound 176.

Example 82

Synthesis of Compound 176

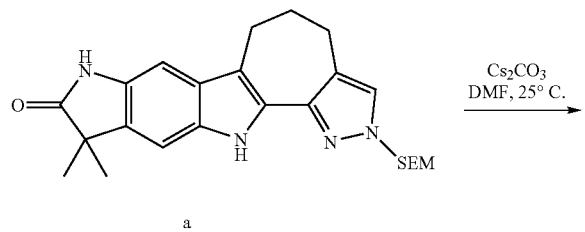

Example 83

Synthesis of Compound 177

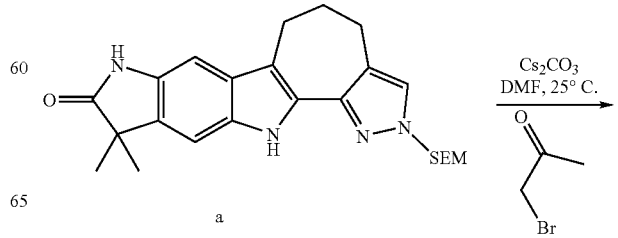

-continued

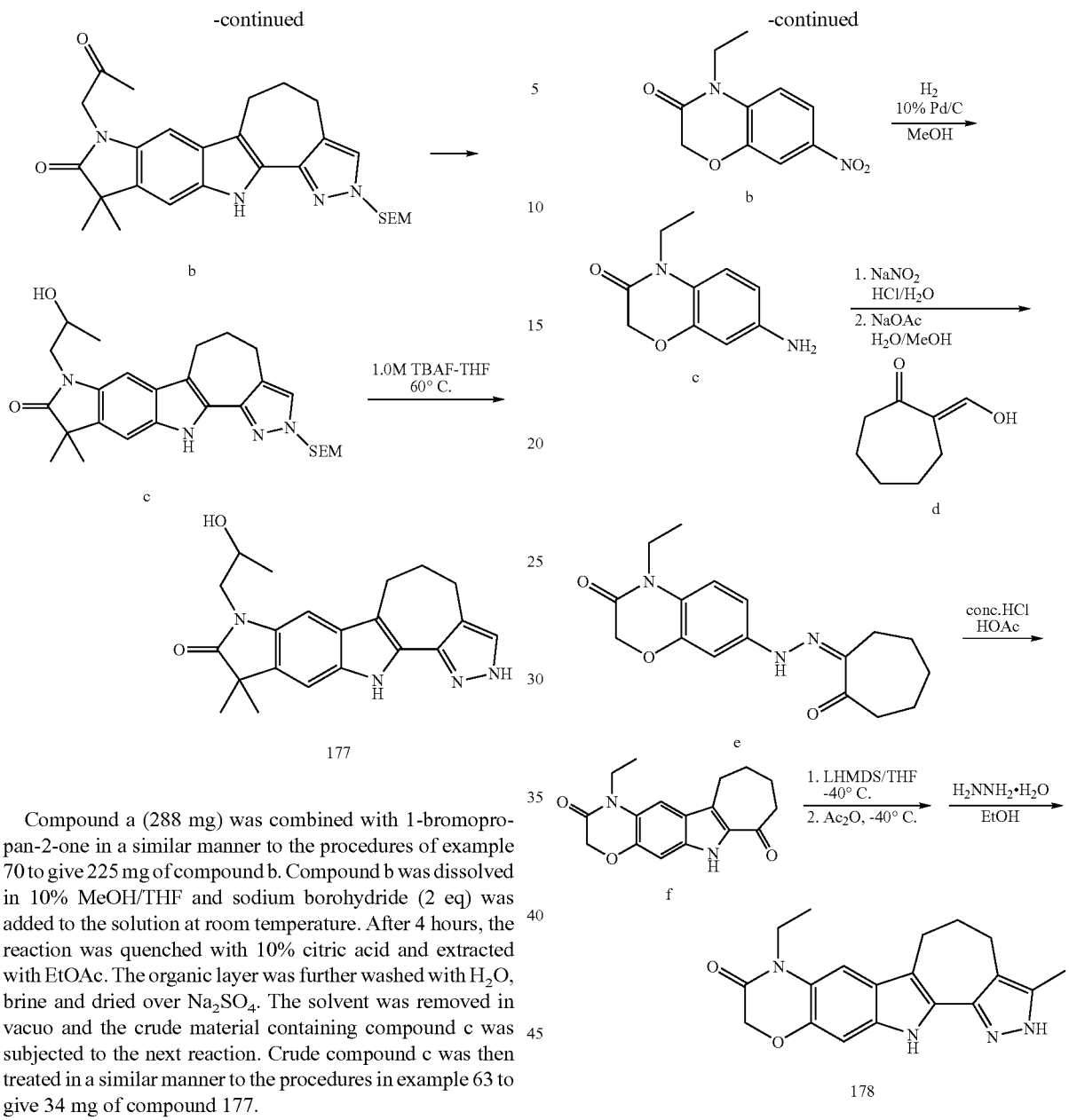

Compound a (288 mg) was combined with 1-bromopropan-2-one in a similar manner to the procedures of example 70 to give 225 mg of compound b. Compound b was dissolved in 10% MeOH/THF and sodium borohydride (2 eq) was added to the solution at room temperature. After 4 hours, the reaction was quenched with 10% citric acid and extracted with EtOAc. The organic layer was further washed with H₂O, brine and dried over Na₂SO₄. The solvent was removed in vacuo and the crude material containing compound c was subjected to the next reaction. Crude compound c was then treated in a similar manner to the procedures in example 63 to give 34 mg of compound 177.

Example 84

Synthesis of Compound 178

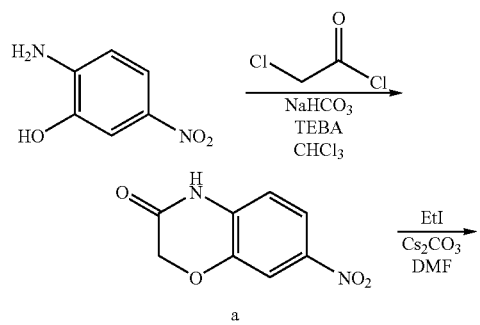

A mixture of 2-amino-5-nitrophenol (8.377 g), triethylbenzylammonium chloride (11.36 g) in CHCl₃ (125 mL) was stirred for 10 min. Finely ground NaHCO₃ (16.80 g) was added. The mixture was cooled with ice bath. A solution of chloroacetyl chloride (4.78 mL) in CHCl₃ (25 mL) was added over 20 min. Stirring continued at 0 C for 1 h. The mixture was then heated at 60 C for 5 h. After cooling to rt, solvents were rotary evaporated. The residue was suspended in water (200 mL) and stirred for 30 min. Solid was collected by filtration, washed with water (2×). The solid was resuspended in water (100 mL), stirred rigorously for 2 h. Solid was collected by filtration, washed with water (2×), and dried under vacuum. The solid product a (10.26 g) was used directly for the next step.

To a mixture of compound a (1.94 g) and cesium carbonate (3.95 g) in DMF (10 mL) was added EtI (0.96 mL) and placed in an ice bath. The mixture was stirred at 0 C for 1 h, then at rt for 2 h. To the mixture was added water (150 mL) and EtOAc (150 mL). The contents were mixed well until solid dissolved. The aqueous layer was separated and extracted with EtOAc (50 mL) The combined EtOAc solutions were washed with brine (3×100 mL), and dried (MgSO4). Filtration and evaporation of solvents gave compound c (2.01 g).

A solution of compound c (2.01 g) in MeOH (270 mL) was vacuumed and flushed with nitrogen (3×). 10% Pd/C (0.45 g) was added. The mixture was vacuumed and flushed with hydrogen (3×) and stirred under hydrogen for 2 h. The mixture was filtered through a pad of Celite and washed with MeOH. Concentration gave compound c (1.758 g).

To a mixture of compound c (1.758 g), conc. HCl (1.14 mL) in water (45 mL) at 0 C was added a solution of sodium nitrite (0.63 g) in water (15 mL) dropwise. The mixture was stirred at 0 C for 30 min, then transferred into a mixture of compound d (1.283 g), NaOAc (5.6 g) in MeOH (30 mL) and water (15 mL) over 20 min. The mixture was stirred at 0 C for 1 h. MeOH was mostly removed by rotary evaporation. The remaining suspension was diluted with water (50 mL) and EtOAc (250 mL). EtOAc layer was separated and washed with brine (150 mL) and dried (Na$_2$SO$_4$). Filtration and evaporation gave compound e (3.19 g) which was used directly for the next step.

To a suspension of compound e (2.98 g) in HOAc (42 mL) was added conc. HCl (0.79 mL) dropwise. The mixture was heated at 80 C for 2 h. Solvents were removed by rotary evaporation. The residue was suspended in EtOAc and stirred for 1 h. then stayed at rt overnight. Solid was collected by filtration, washed with EtOAc and EtAc/hexane (1:1), and dried in vacuum. The crude was purified by flash chromatography to give compound f (0.941 g). Compound f was treated in a similar manner to the applicable procedures in example 2 to give 43 mg of TFA salt of compound 178.

Example 85

Synthesis of Compound 179

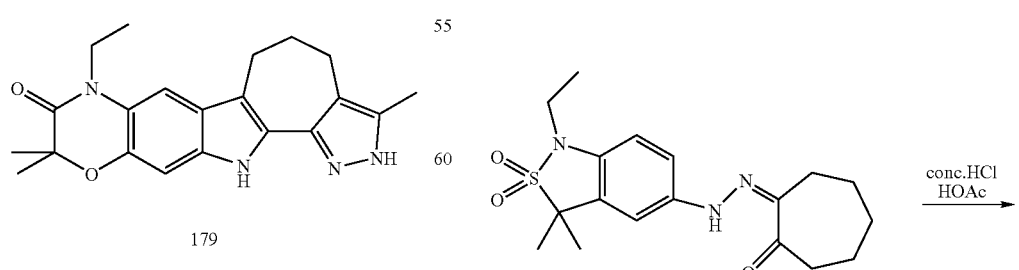

Compound 179 was prepared from 2-amino-5-nitropenol in a similar manner to compound 178 in Example 84.

Example 86

Synthesis of Compound 180

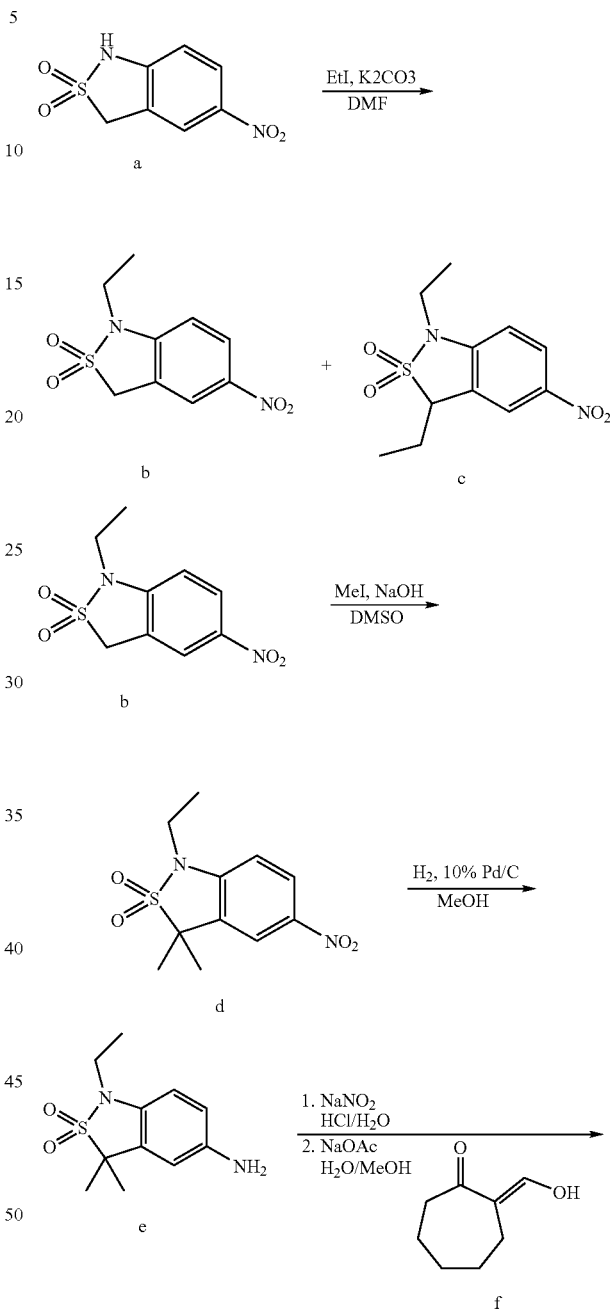

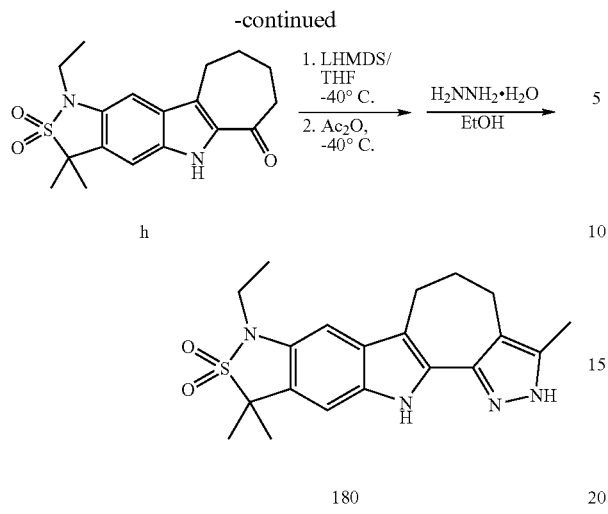

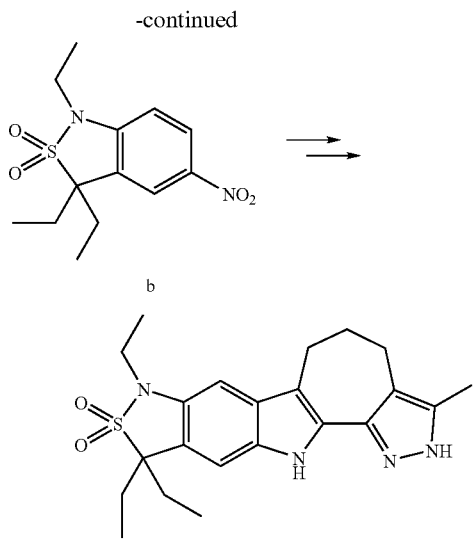

Compound a was prepared following procedures in reference: Petry et al, in PCT patent application publication no. WO2005116003. To a solution of compound a (727 mg) in DMF (10 mL) at 0 C was added potassium carbonate (955 mg). After 10 min, EtI (0.184 mL) was added dropwise. After 30 min at 0 C, the mixture was stirred at rt for 16 h. More potassium carbonate (1.91 g), DMF (10 mL) and EtI (0.92 mL) was added. The mixture was stirred for 6 h before concentrated under vacuum. The residue was treated with EtOAc (60 mL) and water (30 mL). Citric acid solution (10%) was added until pH=7. EtOAc layer was separated. The aqueous layer was saturated with sodium sulfate and extracted with EtOAc (2×). The combined EtOAc solutions were washed with brine and dried (Na$_2$SO$_4$). Chromatography gave compound b (132 mg) and compound c (114 mg).

To a solution of compound b (111 mg) in DMSO (9 mL) was added MeI (0.14 mL) and ground NaOH (364 mg). The mixture was stirred for 30 min then poured into saturated ammonium chloride solution (50 mL). The mixed solution was saturated with sodium sulfate and extracted with EtOAc. The extract was dried (Na$_2$SO$_4$). The crude was purified with flash chromatography to give compound d (89 mg). Compound 180 was prepared from compound d in a similar manner to the applicable procedures in examples 1 and 2. Yield 14 mg of compound 180.

To a solution of compound a (132 mg) from example 86 in DMF (1.9 mL) at rt was added cesium carbonate (477 mg). After 5 min, EtI (0.117 mL) was added. The mixture was stirred at rt for ca. 70 h. Citric acid solution (10%) was added until no more gas evolving. The contents were diluted with EtOAc and water. The aqueous layer was separated and extracted with EtOAc. The combined EtOAc solutions were washed with saturated NaHCO$_3$ and brine, and dried (Na$_2$SO$_4$). The crude product was purified with flash chromatography to give compound b (132 mg). Compound 181 was prepared from compound b in a similar manner to the applicable procedures in examples 1 and 2. Yield 4 mg of compound 181.

Example 88

Synthesis of Compound 182

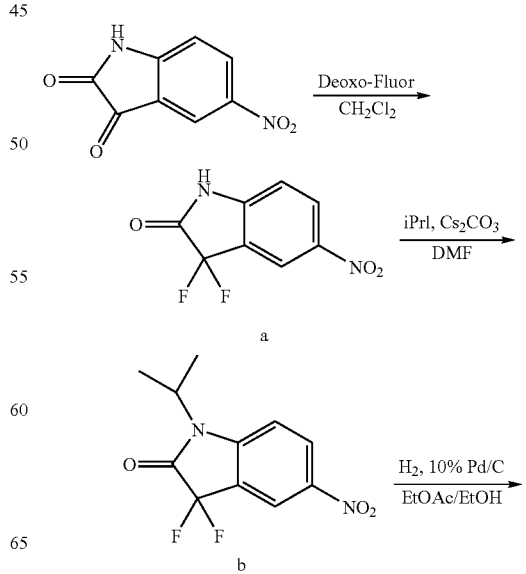

Example 87

Synthesis of Compound 181

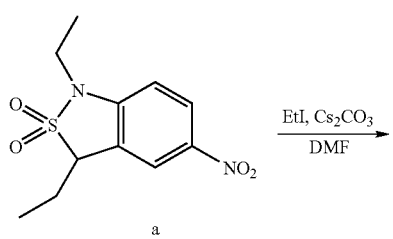

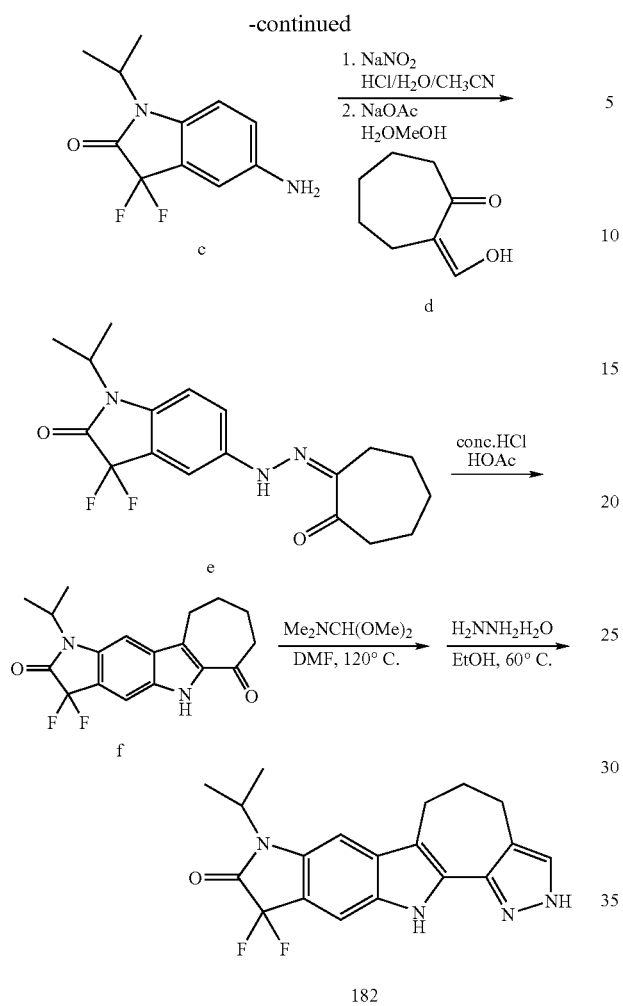

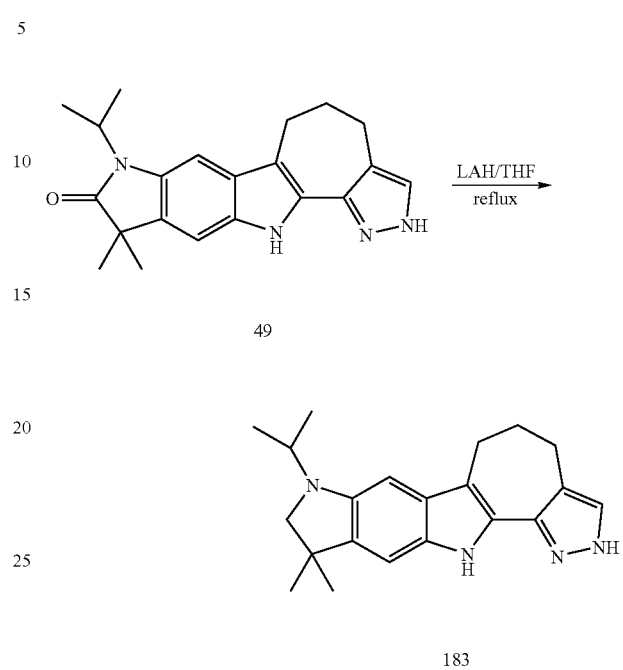

Example 89

Synthesis of Compound 183

A suspension of compound 49 (174 mg) in THF (10 mL) at 0 C was added LAH (1.5 mL, 1.0 M in THF). The mixture was stirred at 0 C for 15 min then at rt for 4 h. THF (10 mL) was added. The mixture was stirred at rt for 16 h then at 70 C for 5 h. LAH (2.5 mL, 1.0 M in THF) was added and the contents were heated at 70 C for 4 h. To the mixture were added subsequently: water (0.3 mL), 10% NaOH (0.6 mL), and water (0.9 mL). Filtration and concentration gave crude compound 183, part of which was purified with reverse-phase chromatography to afford compound 183 as TFA salt (21 mg).

A mixture of 5-nitroisatin (3 g) and Deoxo-Fluor™ (5.76 mL) in dichloromethane (100 mL) was stirred at rt for 16 h. MeOH (5 mL) was added slowly. After 30 min, water (200 mL) was added. The organic layer was separated. The aqueous layer was extracted with dichloromethane. The combined organic solutions were dried (Na$_2$SO$_4$). The crude was purified with flash chromatography to give compound a (2.115 g).

To a solution of compound a (2.10 g) in DMF (20 mL) at 0 C was added cesium carbonate (3.834 g) and isopropyl iodide (1.01 mL). The mixture was stirred at 0 C for 30 min then at rt for 9 h. Solvents were removed in vacuum, The residue was partitioned between EtOAc and water. The organic layer was separated and washed with saturated NaHCO$_3$ and brine, and dried (Na$_2$SO$_4$). The crude was purified with flash chromatography to give compound b (1.47 g).

A mixture of compound b (1.458 g), 10% Pd/C (142 mg), EtOAc (28.5 mL) and EtOH (5.7 mL) was stirred under hydrogen for 2 h. Filtered through a pad of Celite and concentration gave crude compound c (1.339 g) which was used in next step directly. Compound c was treated in a similar manner to the applicable procedures in examples 2 and 21 to give 33 mg of compound 182.

Example 90

Synthesis of Compound 184

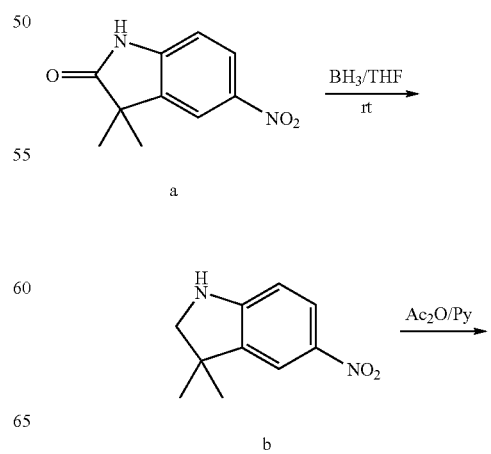

-continued

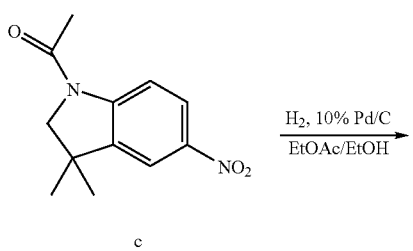

c

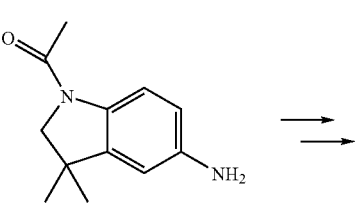

d

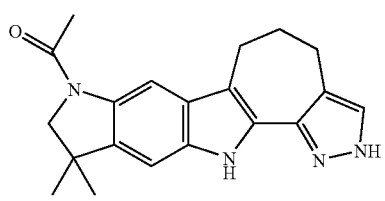

184

To a suspension of compound a (1.072 g) in THF (40 mL) at 0 C was added borane (15.6 mL, 1.0 M in THF). The mixture was stirred at 0 C for 30 min then at rt for 16 h and more borane (11 mL, 1.0 M in THF) was added. The mixture was stirred at rt for 4 h and then dry MeOH (2 mL) was added. After 30 min, the mixture was concentrated under vacuum. The residue was partitioned between EtOAc (150 mL) and water (50 mL). The organic layer was separated and washed with saturated NaHCO$_3$ and brine, and dried (Na$_2$SO$_4$). The crude compound b (1.297 g) was use directly.

To a solution of crude compound b (633 mg) in pyridine (12.7 mL) at 0 C was added acetyl chloride (0.54 mL). The mixture was stirred at 0 C for 30 min then at rt for 16 h before being cooled to 0 C. Water (1 mL) was added dropwise and the mixture was stirred for 30 min and concentrated under vacuum. The residue was partitioned between EtOAc (100 mL) and 0.5 M citric acid (50 mL). The organic layer was separated and washed with saturated NaHCO$_3$ and brine, and dried (Na$_2$SO$_4$). The crude was purified with flash chromatography to afford compound c (459 mg).

A mixture of compound c (457 mg), 10% Pd/C (49 mg) in EtOAc (20 mL) and EtOH (10 mL) was stirred under hydrogen for 16 h. More 10% Pd/C (49 mg) was added. The mixture was stirred for 20 h. Filtration and concentration gave crude compound d (404 mg). Compound d was treated in a similar manner to the applicable procedures of examples 2 and 21 to give 40 mg of compound 184.

Example 91

Synthesis of Compound 185

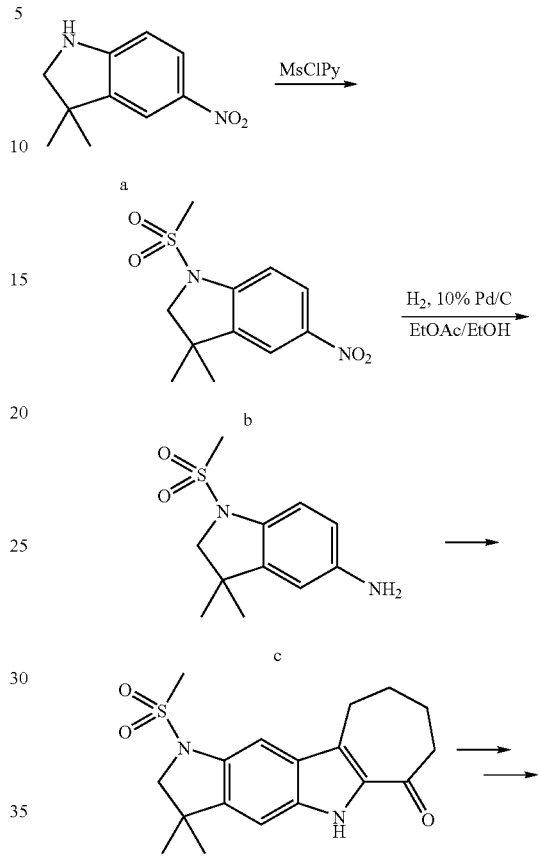

To a solution of crude compound a (0.657 g) in pyridine (13.9 mL) at 0 C was added MsCl (0.65 mL). The mixture was stirred at 0 C for 30 min, then at rt for ca. 40 h. The contents were concentrated. The residue was partitioned between EtOAc and 0.5 M citric acid. The organic layer was separated, washed with saturated NaHCO$_3$ and brine, and dried (Na$_2$SO$_4$). The crude was purified by flash chromatography to afford compound b (0.596 g).

A mixture of compound b (0.595 g), 10% Pd/C (110 mg) in EtOAc (22 mL) and EtOH (11 mL) was stirred under hydrogen for 16 h. Filtration and concentration gave compound c (0.527 g) which was treated in a similar manner to the applicable procedures of examples 2 to give 388 mg of compound d which in turn was treated in a similar manner to the applicable procedures of example 21 with DMF-dimethylacetal and hydrazine to give 126 mg of compound 185.

Example 92

Synthesis of Compound 186

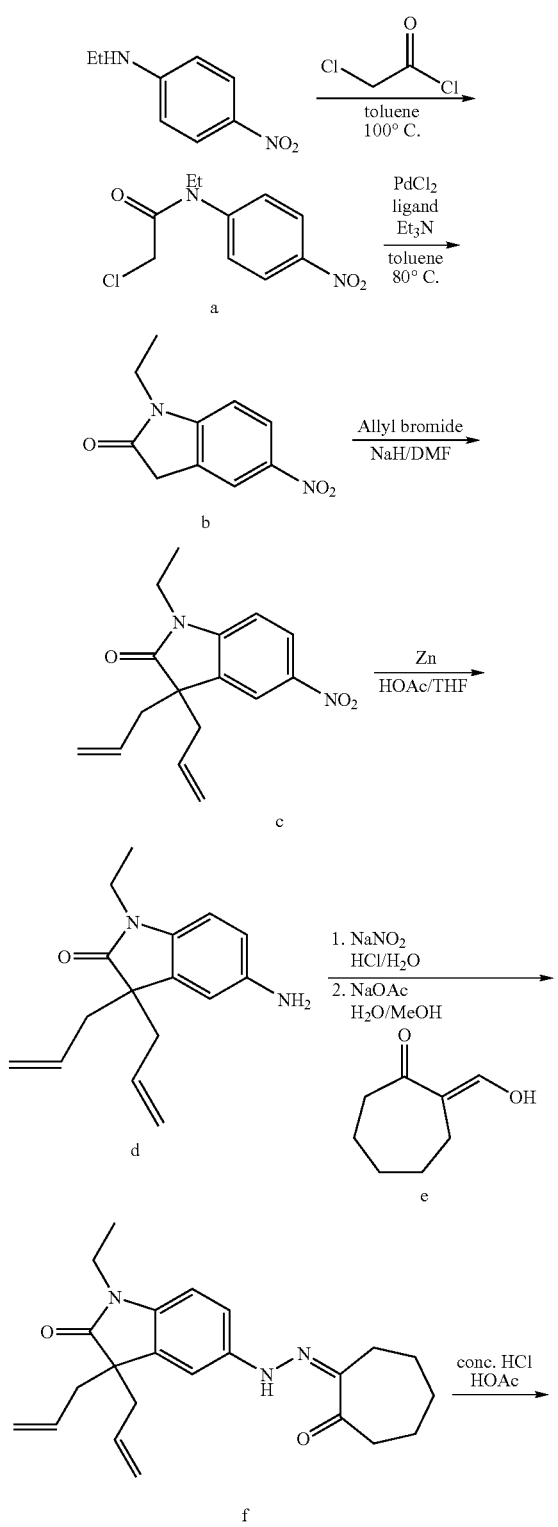

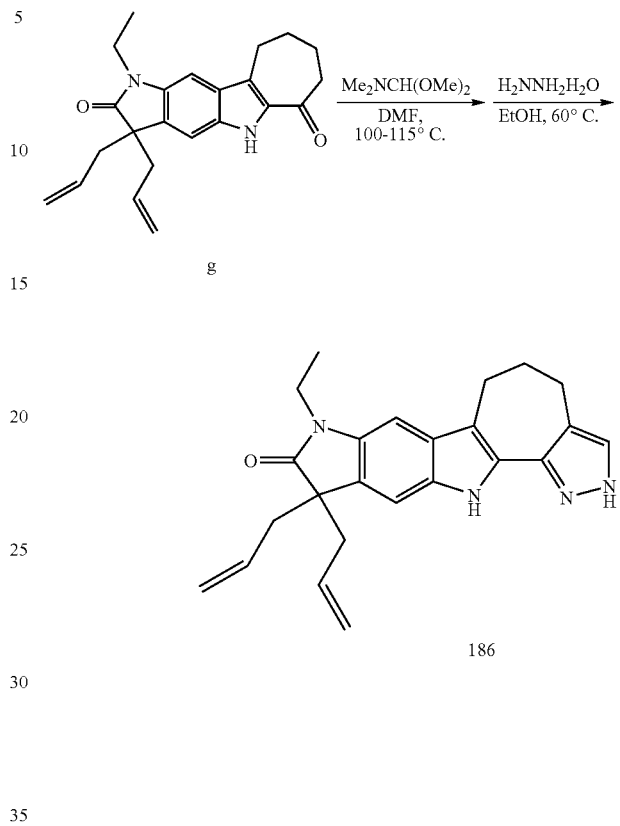

To a suspension of N-ethyl-4-nitroaniline (5.2 g) in toluene (31 mL) was added chloroacetyl chloride (3.7 mL). The mixture was stirred at rt for 15 min and heated at 100° C. for 1 h. The contents were cooled to rt then to ca. 4 C. Solvents were decanted. The solid was re-crystallized from ethanol to give compound a (6.7 g).

A mixture of compound a (2.43 g), palladium acetate (67 mg), bis(biphenyl)di(t-butyl)phosphine (179 mg), and triethylamine (2.1 mL) in toluene (10 mL) was heated at 80 C under nitrogen for 3 h. After being cooled to rt, the mixture was diluted with EtOAc and filtered. Concentration gave compound b (1.78 g).

To a mixture of compound b (317 mg) and DMF (4.5 mL) at 0 C was added NaH (154 mg, 60% in oil). After 10 min, allyl bromide (0.333 mL) was added dropwise. The mixture was stirred at 0 C for 10 min then at rt for 2 h before diluted with water and EtOAc. The organic layer was separated, washed with water, brine, and dried ($Na_2SO_4$). The crude was purified with flash chromatography to afford compound c (450 mg).

To a solution of compound c (2.441 g) in THF (12 mL) was added zinc powder. HOAc (3 mL) was added slowly. A cold water bath was used. After 1 h, more HOAc (3 mL) was added. The mixture was stirred for 1 h before being diluted with EtOAc (200 mL) and filtered. The filtrate was washed with water (2×), saturated $NaHCO_3$, brine, and dried ($Na_2SO_4$). The crude was purified with flash chromatography to give compound d (1.158 g). Compound d was treated in a similar manner to the applicable procedures of examples 2 and 21 to give 520 mg of compound 186.

Example 93

Synthesis of Compound 187

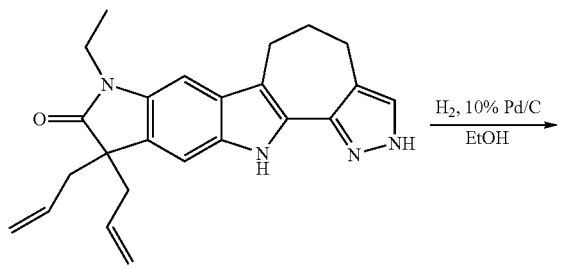

A mixture of compound 186 (120 mg), 10% Pd/C (16 mg) in EtOH (6 mL) was stirred under hydrogen for 4 h. Filtration and concentration gave compound 187 (120 mg).

Example 94

Synthesis of Compound 188

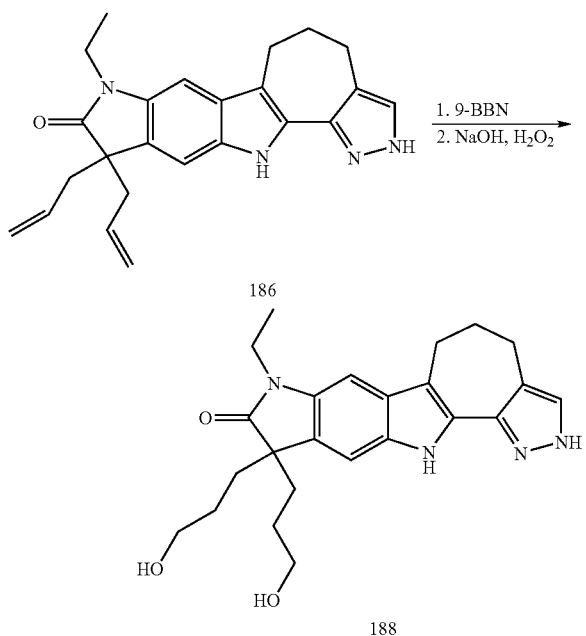

To a solution of compound 186 (90 mg) in THF (4.6 mL) at 0 C was added 9-BBN (4.6 mL, 0.5 M in THF) dropwise. After 15 min at 0 C, the mixture was stirred at rt for 2 h. Cooled to 0 C, to the mixture was added 3 M NaOH (1.5 mL) and $H_2O_2$ (1.5 mL, 31%). The mixture was stirred at 0 C for 15 min then at rt for 3 h before diluted with EtOAc and water. The aqueous layer was separated and extracted with EtOAc. The combined EtOAc solutions were washed with brine and dried ($Na_2SO_4$). The crude was purified with flash chromatography to afford compound 188 (88 mg).

Example 95

Synthesis of Compound 189

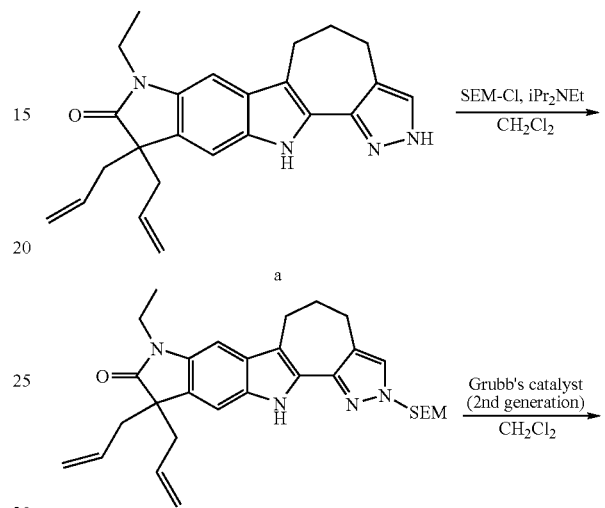

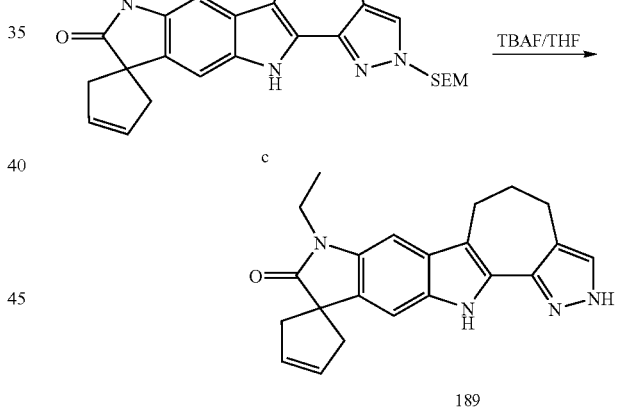

To a solution of compound a (240 mg) in $CH_2Cl_2$ (4 mL) at 0 C was added Hunig's base (0.308 mL) and SEM-Cl (0.164 mL). The mixture was stirred at 0 C for 10 min then at rt for 18 h. Water (4 mL) was added after the contents were cooled to 0 C. After stirring for 1 h, aqueous layer was separated. The organic layer was washed with saturated $NaHCO_3$, brine and dried ($Na_2SO_4$). The crude was purified with flash chromatography to give compound b (270 mg).

To a solution of compound b (55 mg) in $CH_2Cl_2$ (4 mL) at rt was added Grubb's catalyst $2^{nd}$ generation (11 mg). The mixture was stirred for 2 h. Concentrated with silica gel, the crude was purified with flash chromatography to give compound c (27 mg).

A mixture of compound c (133 mg), TBAF (0.82 mL, 1.0 M in THF), and THF (1.5 mL) was heated at 60 C for 20 h before being diluted with EtOAc and water. The organic layer was separated and washed with brine and dried (Na$_2$SO$_4$). The crude was purified with flash chromatography to afford compound 189 (75 mg).

Example 96

Synthesis of Compound 190

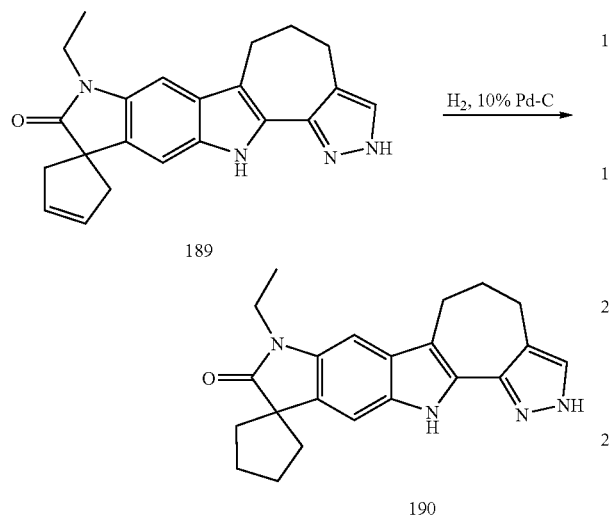

A mixture of compound 189 (45 mg), 10% Pd/C (20 mg) in MeOH (9 mL) and EtOAc (9 mL) was stirred under hydrogen for 2 h. Filtration and concentration gave the crude which was purified with reverse-phase chromatography to afford compound 190 as TFA salt (28 mg).

Example 97

Synthesis of Compound 191

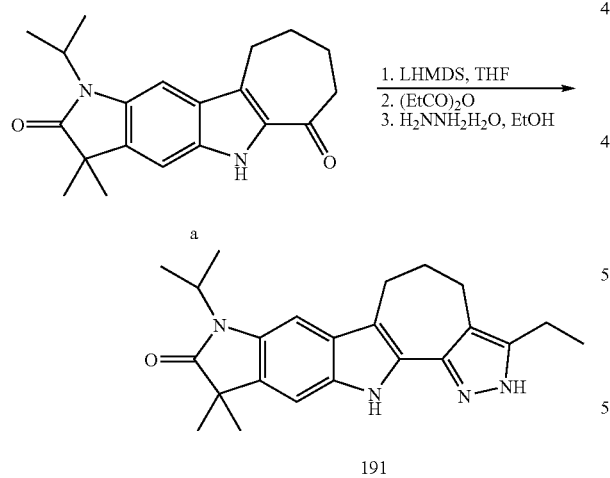

A solution of compound a (100 mg) in THF (6.2 mL) was cooled to ca. −75 C. LHMDS (1.54 mL, 1.0 M in THF) was added dropwise. Temperature was gradually raised to −50 C and maintained for 30 min. The mixture was re-cooled to −75 C. Propionic anhydride (0.24 mL) was added dropwise. The temperature was raised to −30 C and gradually to 0 C over 30 min. The mixture was transferred to a solution of hydrazine hydrate (0.30 mL) in ethanol (6.2 mL) at 0 C. The mixture was stirred at 0 C to rt and at rt for 16 h. The mixture was concentration under vacuum. The residue was partitioned between EtOAc and water. The organic layer was separated and washed with NaHCO$_3$ and brine, and dried (Na$_2$SO$_4$). The crude was purified with reverse-phase chromatography to give compound 191 as TFA salt (55 mg).

Example 98

Synthesis of Compound 192

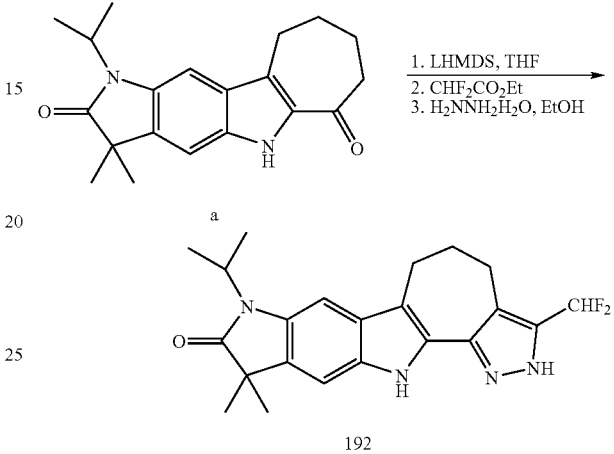

Compound a was treated in a similar manner to the applicable procedures of example 2 to give 15 mg of compound 192 TFA salt.

Example 99

Synthesis of Compound 193

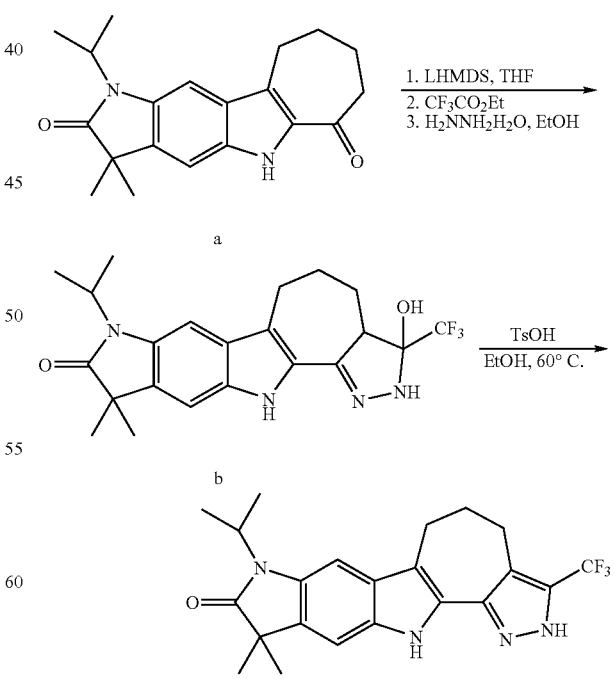

Compound b was prepared from compound a in a similar manner to applicable procedures in example 2. The crude was purified with flash chromatography. A mixture of compound b (70 mg) and 4-toluenesulfonic acid hydrate (31 mg) in ethanol (3 mL) was heated at 70 C for 30 min. The contents were concentrated under vacuum. The residue was partitioned between EtOAc and saturated NaHCO$_3$. The organic layer was separated and washed with brine, and dried (Na$_2$SO$_4$). The crude was purified with flash chromatography to give compound 193 (28 mg).

Example 100

Synthesis of Compound 194

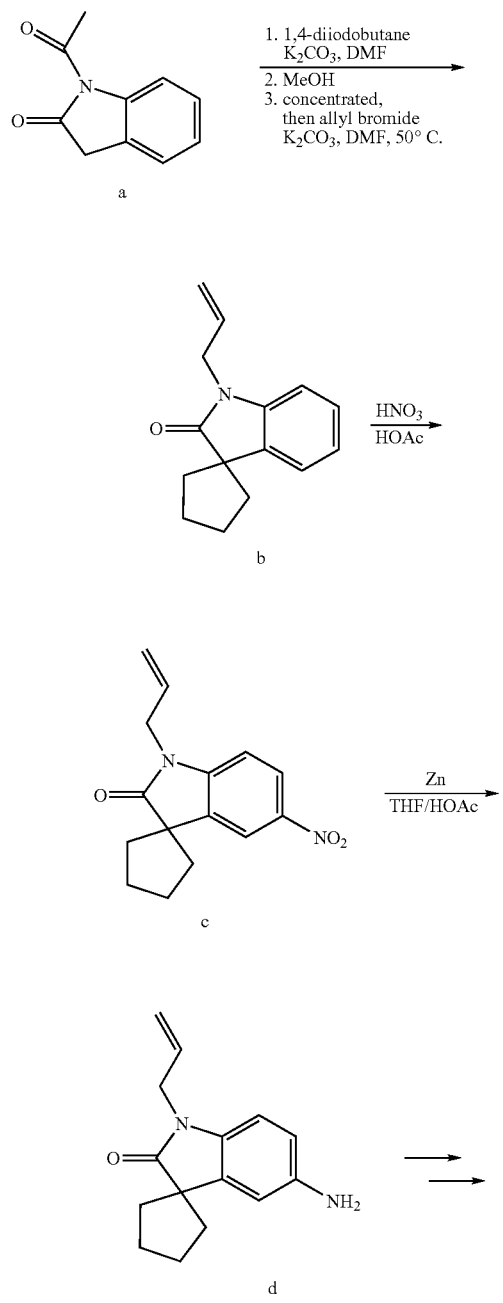

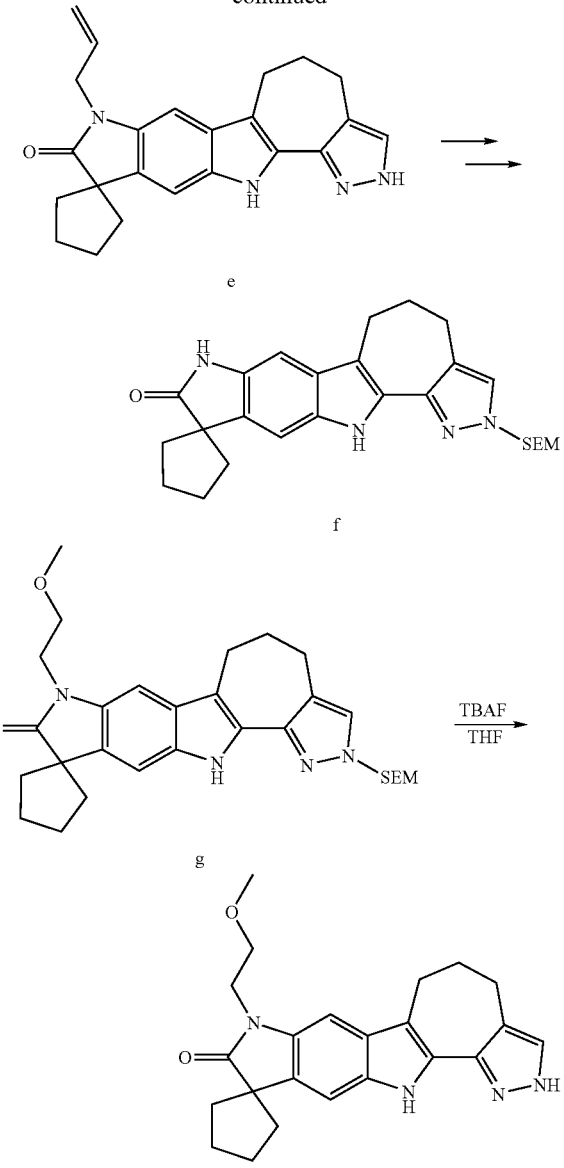

To a mixture of compound a (23.90 g) and K$_2$CO$_3$ (56.56 g) in DMF (400 mL) was added 1,4-diiodobutane (18.89 mL). The mixture was stirred at rt for 5 h. MeOH (100 mL) was slowly added. The mixture was stirred overnight before concentrated under vacuum. To the residue was added DMF (400 mL), K$_2$CO$_3$ (37.70 g) and allyl bromide (23.61 mL). The mixture was stirred at rt overnight. More K$_2$CO$_3$ (18.85 g) and allyl bromide (11.81 mL) were added. The mixture was heated at 50 C for 5 h. After concentration, the residue was suspended in EtOAc and filtered. The filtrate was washed with water, half saturated NaHCO$_3$, half saturated brine and brine, and dried (Na$_2$SO$_4$). The crude was purified with flash chromatography to afford compound b (11.88 g).

To a solution of compound b (13.604 g) in HOAc (60 mL) cooled with cold water was added nitric acid (11.2 mL, 90% fuming). After 30 min, the mixture was cooled to 0 C and diluted with water slowly, followed by extraction with EtOAc (2×). The combined EtOAc extracts were washed with saturated NaHCO$_3$ and brine, and dried (Na$_2$SO$_4$). The crude was purified with flash chromatography to give compound c (6.677 g).

To a solution of compound c (6.677 g) in THF (100 mL) and HOAc (100 mL) cooled with cold tap water was added zinc dust (8.015 g) in portions. The mixture was stirred for 16 h. The mixture was diluted with EtOAc (300 mL) and filtered through a pad of Celite. The filtrate was concentrated under vacuum to give crude compound d (ca. 6 g) which was used without further purification. Compound d was treated in a similar manner to the applicable procedures of example 62 to give 62 mg of compound 194.

Example 101

Synthesis of Compound 195

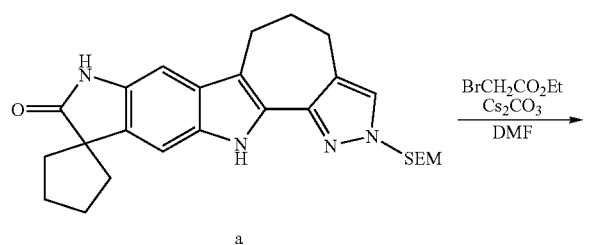

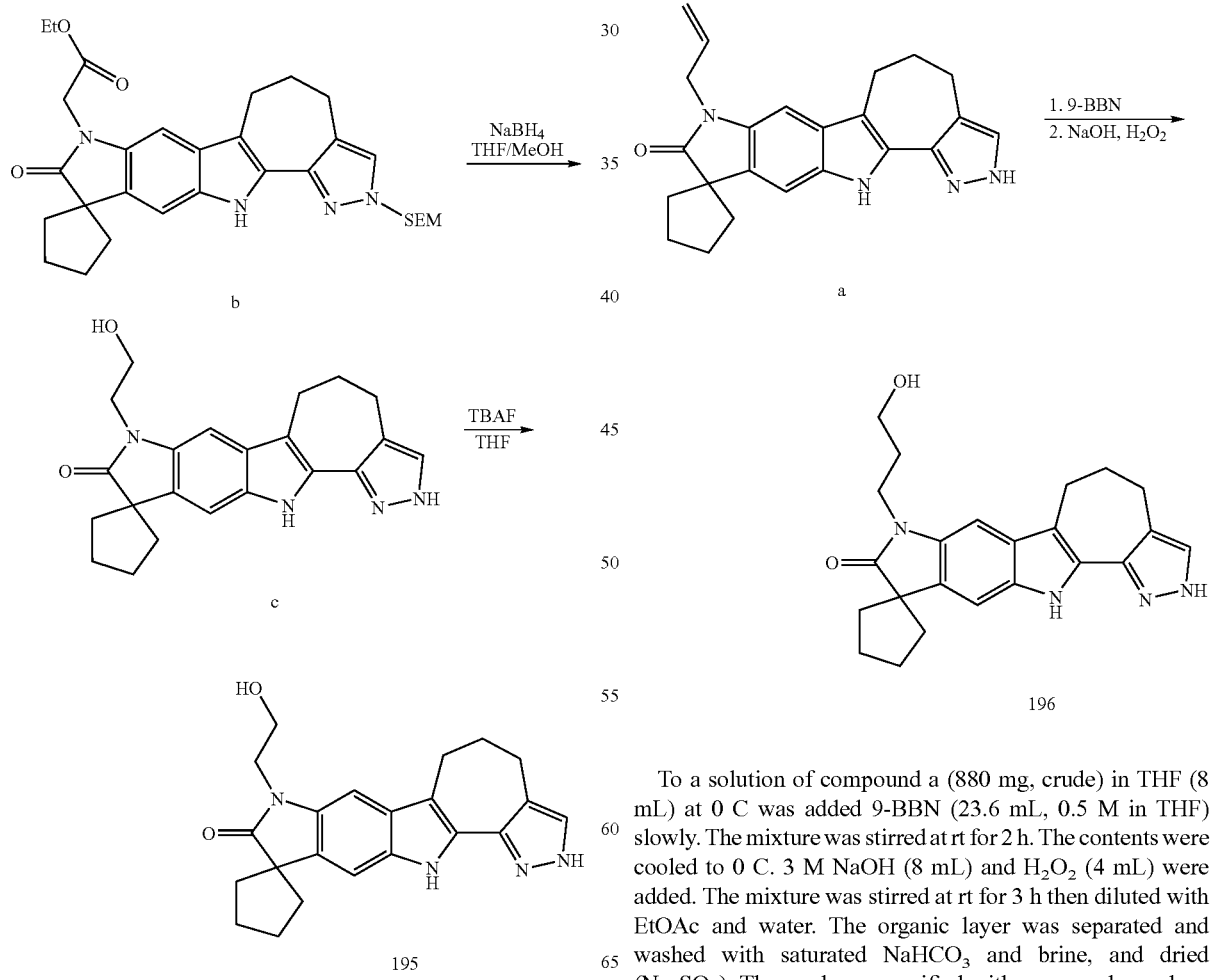

Compound b was prepared from compound a in a similar manner to the applicable procedures in example 62. To a suspension of compound b (80 mg) and NaBH$_4$ (55 mg) in THF (2 mL) at 50 C was added MeOH (0.2 mL) dropwise. The mixture was heated at 50 C overnight. After cooled to rt, the mixture was diluted with saturated NH$_4$Cl solution and stirred for 1 h. Organic solvents were evaporated under vacuum. The remaining contents were partitioned between EtOAc and water. The organic layer was separated and washed with saturated NaHCO$_3$ and brine, dried (Na$_2$SO$_4$). The crude compound c was mixed with TBAF (0.44 mL, 1.0 M in THF) and THF (1.5 mL). The mixture was heated at 60 C overnight. After concentration, the residue was partitioned between EtOAc and water. The EtOAc solution was separated and washed with water (2×) and brine, and dried (Na$_2$SO$_4$). The crude was purified with reverse-phase chromatography to give compound 195 as TFA salt (29 mg).

Example 102

Synthesis of Compound 196

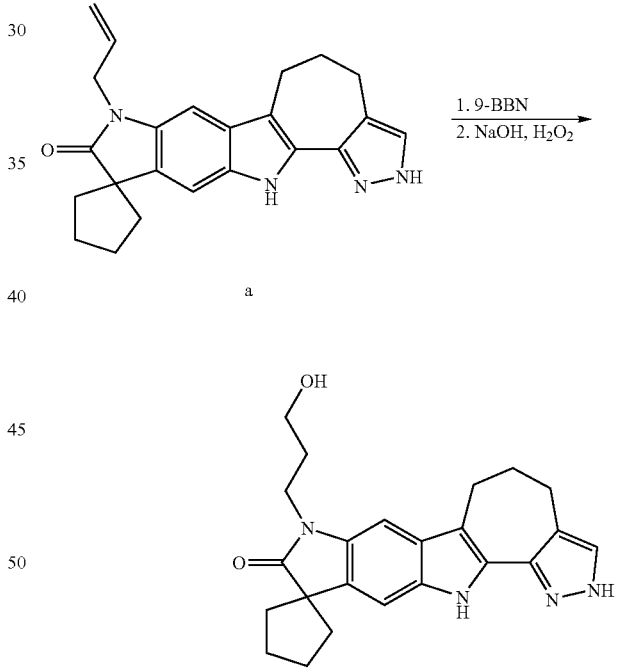

To a solution of compound a (880 mg, crude) in THF (8 mL) at 0 C was added 9-BBN (23.6 mL, 0.5 M in THF) slowly. The mixture was stirred at rt for 2 h. The contents were cooled to 0 C. 3 M NaOH (8 mL) and H$_2$O$_2$ (4 mL) were added. The mixture was stirred at rt for 3 h then diluted with EtOAc and water. The organic layer was separated and washed with saturated NaHCO$_3$ and brine, and dried (Na$_2$SO$_4$). The crude was purified with reverse-phase chromatography to give compound 196 as TFA salt (37 mg).

Example 103

Synthesis of Compound 197

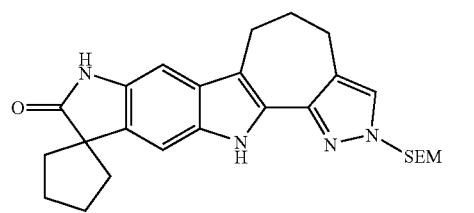

a

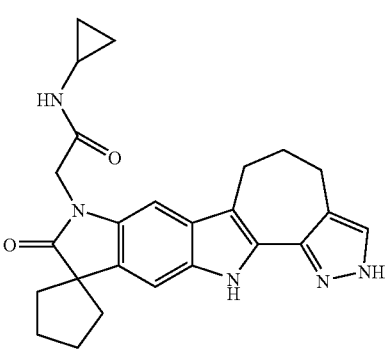

197

Compound a was treated in a similar manner to the applicable procedures of example 62 to give 62 mg of compound 197.

Example 104

Synthesis of Compound 198

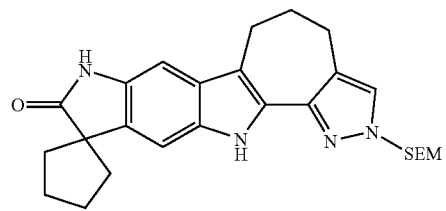

a

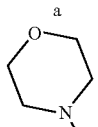

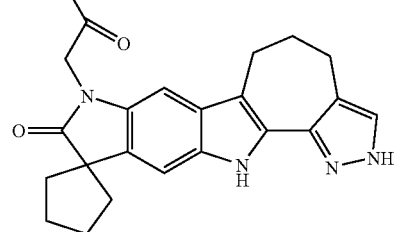

198

Compound a was treated in a similar manner to the applicable procedures of example 62 to give 76 mg of compound 198.

Example 105

Synthesis of Compound 199

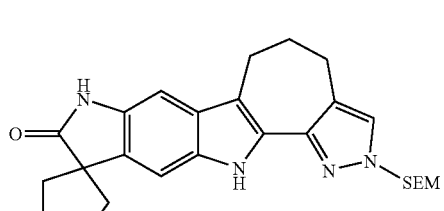

a

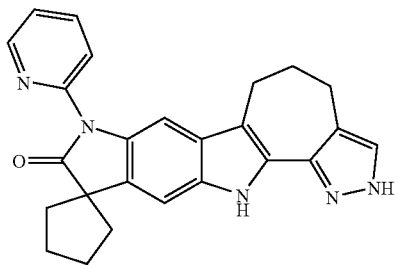

199

Compound a was treated in a similar manner to the applicable procedures of example 62 to give 7 mg of the TFA salt of compound 199.

Example 106

Synthesis of Compound 200

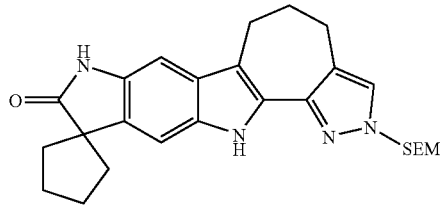

a

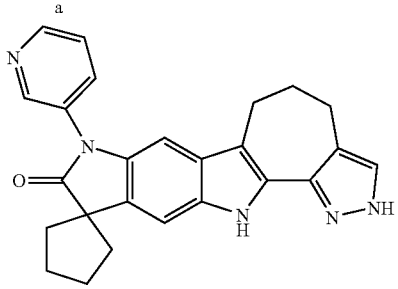

200

Compound a was treated in a similar manner to the applicable procedures of example 62 to give 11 mg of the TFA salt of compound 200.

Example 107

Synthesis of Compound 201

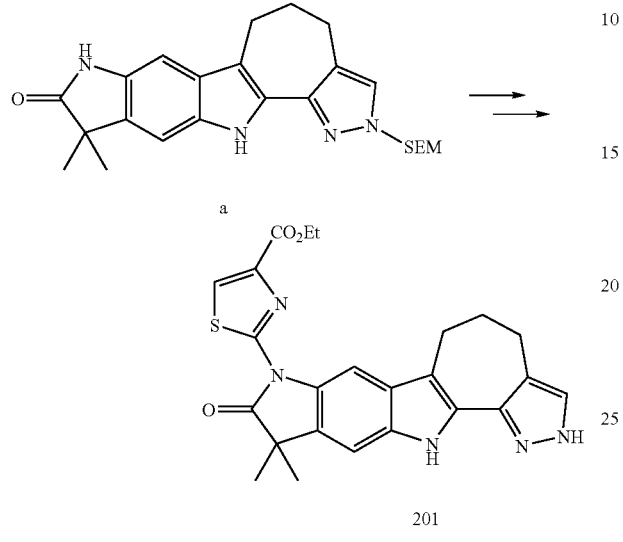

Compound a was treated in a similar manner to the applicable procedures of example 62 to give 10 mg of the TFA salt of compound 201.

Example 108

Synthesis of Compound 202

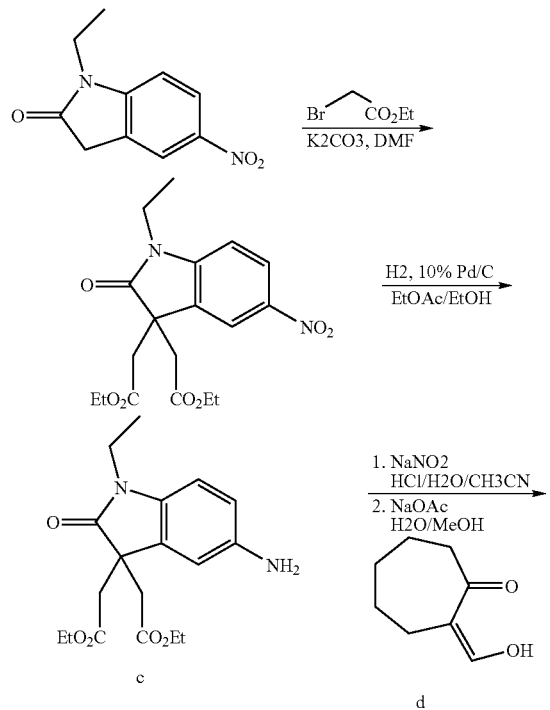

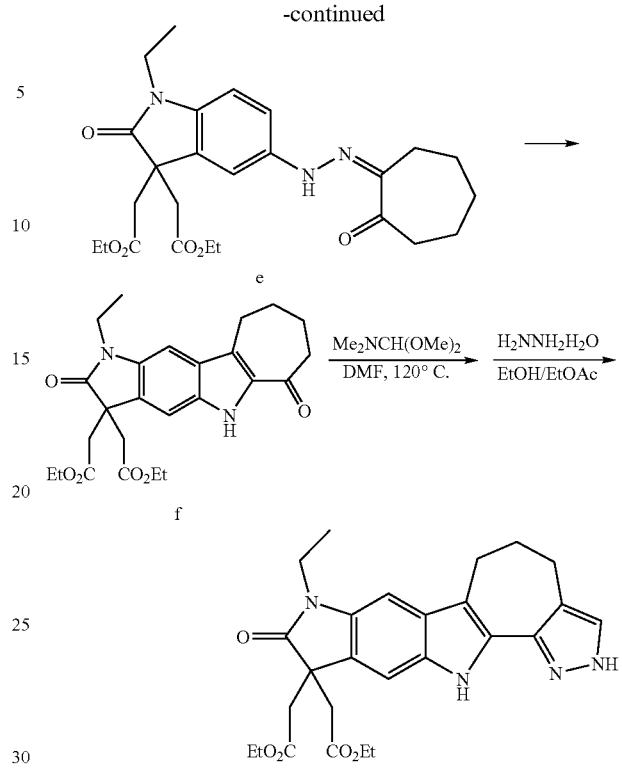

A solution of compound a (206 mg) in DMF (4 mL) at 0 C was added $K_2CO_3$. After 10 min, ethyl bromoacetate (0.277 mL) was added. The mixture was stirred at 0 C for 10 min then at rt for ca. 16 h. After diluted with EtOAc (15 mL), the mixture was filtered. The filtrate was concentrated under vacuum. The residue was purified with flash chromatography to give compound b (299 mg).

Compound c was treated in a similar manner to the applicable procedures in example 2 to give compound f. A mixture of compound f (3.55 g), DMF dimethyl acetal (15.6 mL) and DMF (3.9 mL) was heated at 110 C for ca. 20 h. The contents were concentrated under vacuum. To the residue was added EtOH (78 mL), hydrazine hydrate (1.9 mL) and EtOAc (117 mL). The mixture was stirred at rt for ca. 16 h. After the contents were concentrated to a thick slurry, solid was collected by filtration, washed with EtOH, and dried under vacuum to give compound 202 (3.55 g).

Example 109

Synthesis of Compound 203

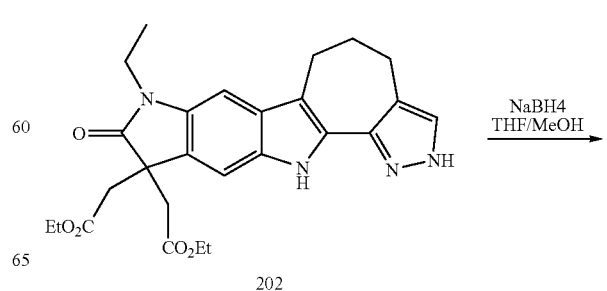

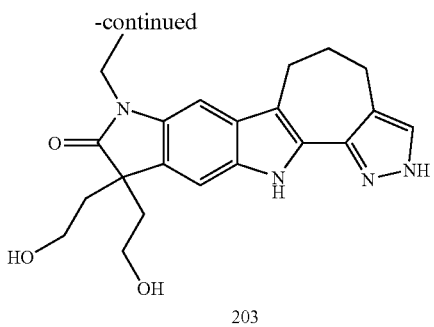

203

To a solution of compound 202 (1.26 g) from example 108 in THF (20 mL) was added NaBH₄ (0.783 g). The mixture was heated at 50 C. MeOH was added dropwise. The resulting mixture was kept at 50 C for 4 h. The mixture was cooled to rt. 10% HOAc was slowly added until gas evolving ceased. Diluted with EtOAc and water. 3 M NaOH was added slowly until aqueous pH is neutral. The aqueous phase was separated and extracted with EtOAc. The combined EtOAc solutions were washed with saturated NaHCO₃ and brine, and dried (Na₂SO₄). Flash chromatography afforded compound b (0.661 g).

Example 110

Synthesis of Compound 204

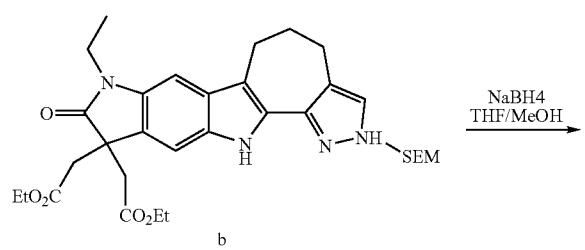

202

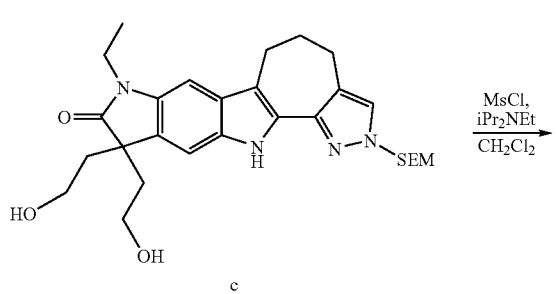

b

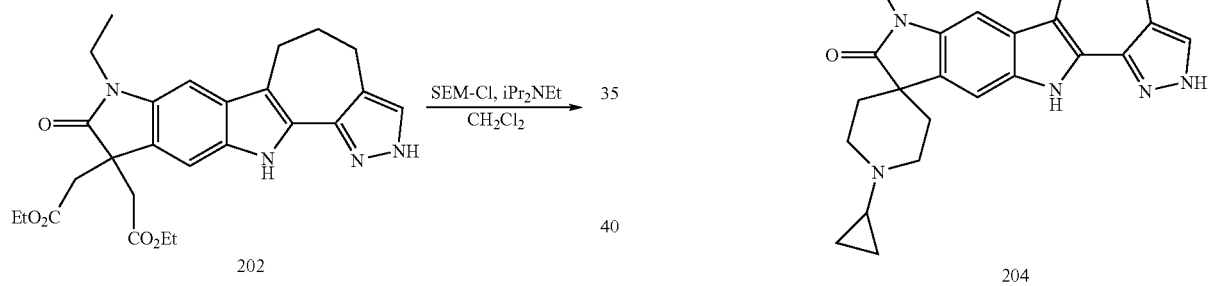

Compound b was prepared from compound 202 in a similar manner to the applicable procedures in example 63. The crude was purified with flash chromatography to give compound b. Compound c was prepared from compound b in a similar manner to the procedures described in example 109.

A mixture of compound c (420 mg), DIPEA (0.397 mL), MsCl (0.124 mL) in CH₂Cl₂ (8 mL) was stirred at 0 C then gradually raised to rt overnight. The contents were diluted with CH₂Cl₂, washed with water (2×), and concentrated. The crude was purified with flash chromatography to afford compound d (456 mg).

A mixture of compound d (58 mg), cyclopropylamine (0.5 mL) and EtOH (1.7 mL) was heated at 50 C overnight. The contents were concentrated. The residue was partitioned between CH₂Cl₂ and water. The organic layer was separated and concentrated. The crude compound e was combined with TBAF (0.26 mL, 1.0 M in THF) and THF (0.6 mL). The resulting mixture was heated at 60 C for 18 h before diluted with EtOAc and water. The organic layer was separated and washed with water. After concentration, the crude was purified with reverse-phase chromatography to give compound 204 (456 mg) as TFA salt.

Example 111

Synthesis of Compound 205

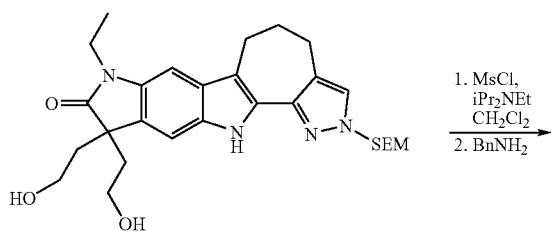

A mixture of compound a (123 mg), DIPEA (0.232 mL), MsCl (0.036 mL) in CH$_2$Cl$_2$ (2.3 mL) was stirred at 0 C for 2 h. Solvents were removed under vacuum. BnNH$_2$ (2 mL) was added. The mixture was heated at 80 C for 1 h and concentrated under vacuum. The residue was partitioned between EtOAc and water. The EtOAc solution was separated and washed with saturated NH$_4$Cl solution, water and brine, and dried (Na$_2$SO$_4$).

The crude compound b was mixed with TBAF (0.7 mL, 1.0 M in THF) and THF (1.6 mL). The mixture was heated at 60 C for 15 h before diluted with EtOAc and washed with water (2×). The EtOAc solution was concentrated and purified with reverse-phase chromatography to afford compound 59 mg of the TFA salt of compound 205.

Example 112

Synthesis of Compound 206

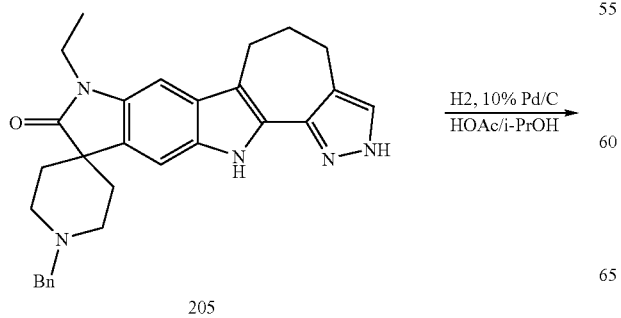

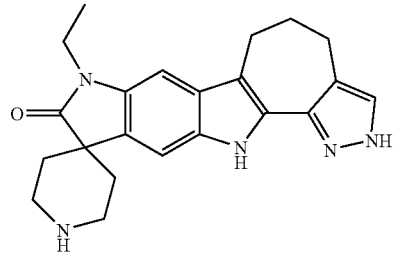

A mixture of compound 205 TFA salt (30 mg), 10% Pd/C (15 mg), HOAc (4 mL) and isopropanol (1 mL) was heated at 70 C under hydrogen for 5 h. After concentration, the residue was partitioned between CH$_2$Cl$_2$/isopropanol (4:1) and 1 N NaOH. The organic phase was separated and concentrated. The crude was purified with reverse-phase chromatography to give compound b as TFA salt (14 mg).

Example 113

Synthesis of Compound 207

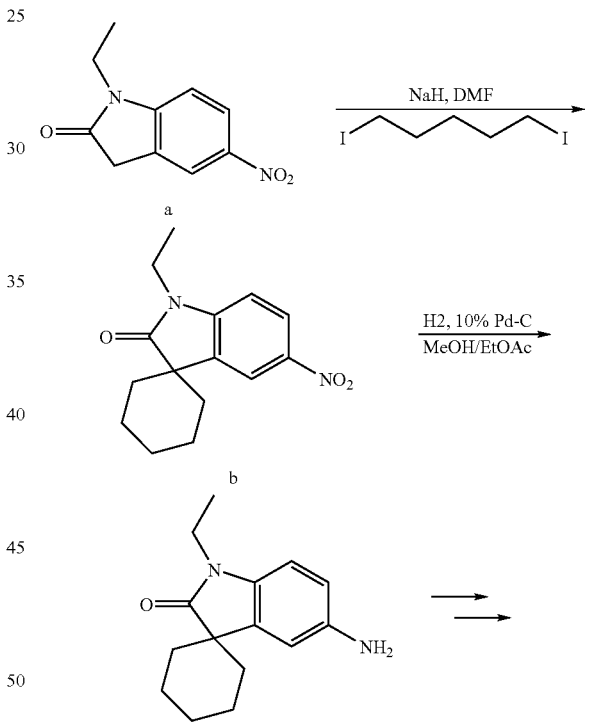

To a solution of compound a (150 mg) in DMF (3 mL) at 0 C was added NaH (150 mg, 60% in oil). After 10 min, 1,5-diiodopentane (0.135 mL) was added. The mixture was stirred at rt for 2 h. The contents were diluted with EtOAc and half saturated NaHCO₃. The organic layer was separated and washed with half saturated brine (2×) and brine, and dried (Na₂SO₄). The crude was purified with flash chromatography to give compound b (161 mg).

A mixture of compound b (160 mg), 10% Pd/C (29 mg), MeOH (12 mL) and EtOAc (6 mL) was stirred under hydrogen for 2 h. The mixture was diluted with EtOAc and stirred overnight. Filtration and concentration gave crude compound c (154 mg) which was used directly in further steps. Compound c was treated in a similar manner to the applicable procedures in example 23 to give 17 mg of the TFA salt of compound 207.

Example 114

Synthesis of Compound 208

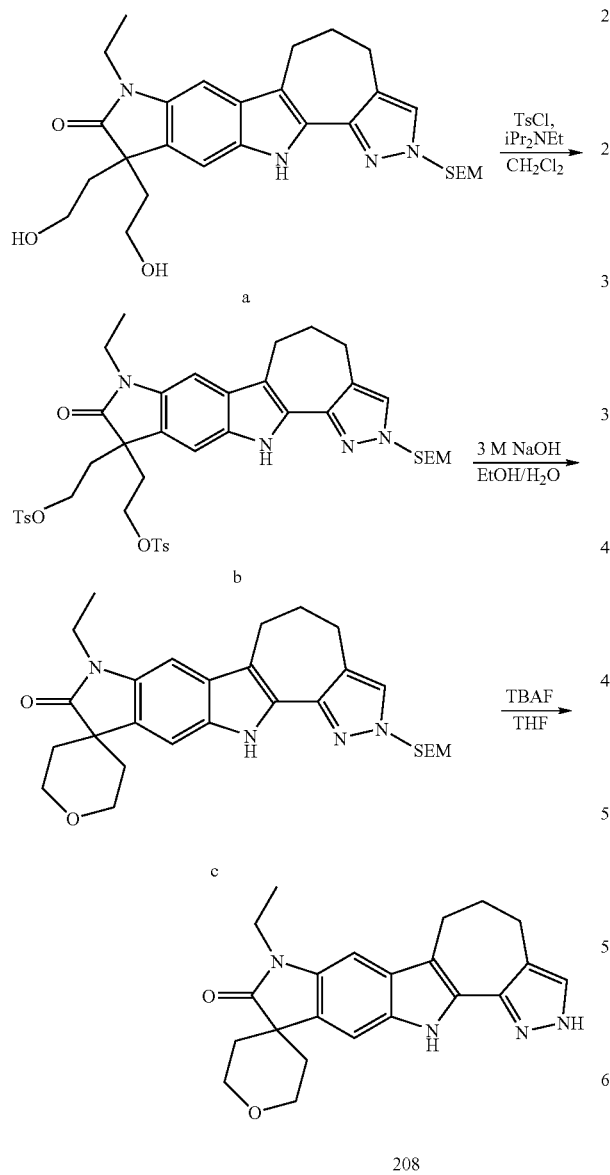

A mixture of compound a (108 mg), DIPEA (0.272 mL), and TsCl (159 mg) in CH₂Cl₂ (2 mL) was stirred at rt for ca.

2 weeks. Water (1 mL) was added. After 1 h, organic layer was separated and washed with saturated NH4Cl, water and brine, and dried (Na₂SO₄).

The crude compound b was combined with 3 M NaOH (2 mL) and dioxane (2 mL). The mixture was heated at 60 C for 20 h. More 3 M NaOH (2 mL) was added. The mixture was heated at 80 C for 24 h. Solvents were evaporated under vacuum. The residue was partitioned between CH₂Cl₂/isopropanol (4:1) and water. The organic layer was separated and washed with water and concentrated.

The crude compound c was mixed with TBAF (2 mL, 1.0 M in THF) and THF (2 mL). The mixture was heated at 60 C overnight. After diluted with EtOAc, the mixture was washed with water (2×) and brine, and dried (Na₂SO₄). The crude was purified with reverse-phase chromatography to give compound 208 as TFA salt (17 mg).

Example 115

Synthesis of Compound 209

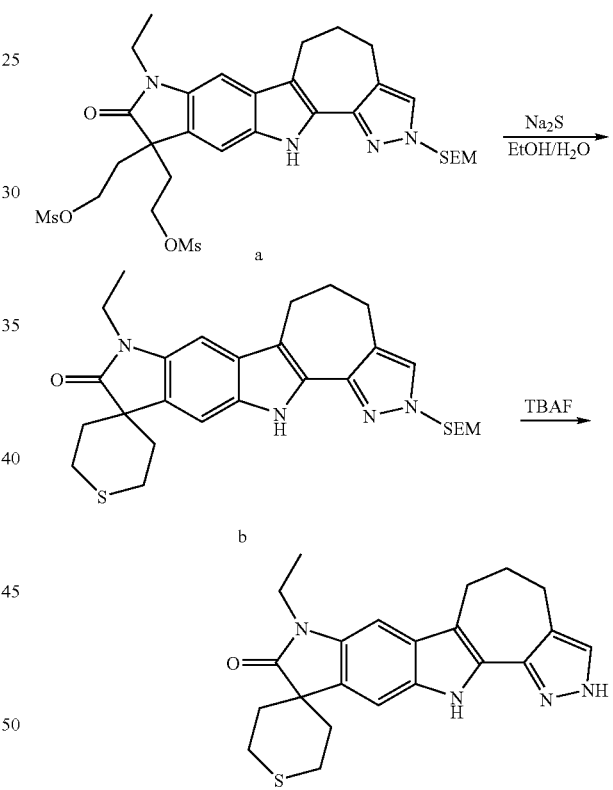

A mixture of compound a (64 mg), sodium sulfide (37 mg), EtOH (1.88 mL) and water (0.94 mL) was heated at 60 C for 5 h. After concentration, the residue was partitioned between CH₂Cl₂ and water. The organic phase was separated and concentrated.

The crude compound b was mixed with TBAF (0.28 mL, 1.0 M in THF) and THF (0.66 mL) and heated at 60 C for 18 h. The mixture was diluted with EtOAc and water. The EtOAc solution was separated, washed with water, and concentrated. Compound 209 (9 mg) was obtained by reverse-phase chromatography as TFA salt.

Example 116

Synthesis of Compound 210

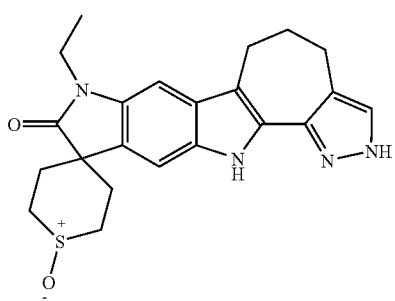

Compound 210 TFA salt (5 mg) was obtained as a byproduct of the synthesis of compound 209 in example 115.

Example 117

Synthesis of Compound 211

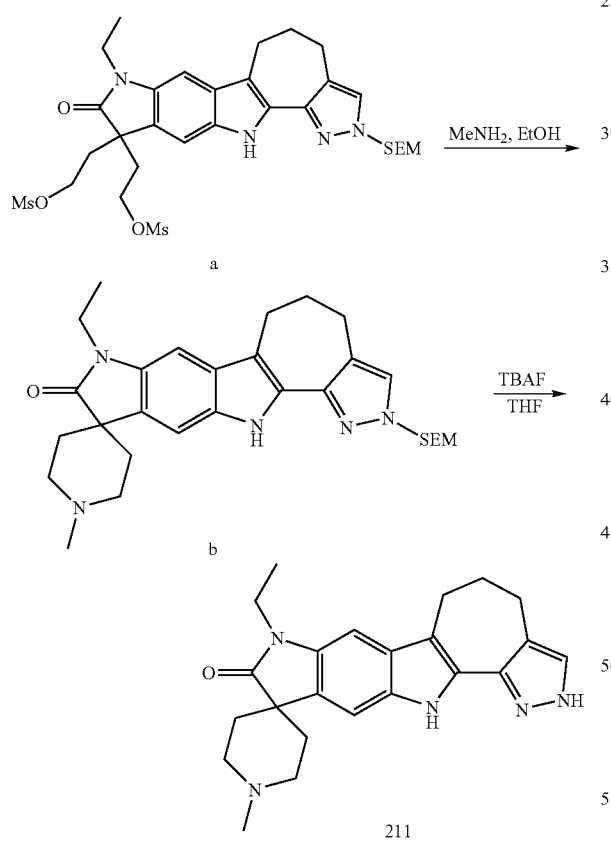

A mixture of compound a (80 mg), methylamine (0.205 mL, 10% in H₂O) and EtOH (1.2 mL) was heated at 60 C for 4 h. The contents were concentrated. The residue was partitioned between EtOAc and water. The aqueous layer was separated and extracted with EtOAc. The combined EtOAc solutions were washed with water and brine, and dried (Na₂SO₄).

The crude compound b was mixed with TBAF (0.28 mL, 1.0 M in THF) and THF (0.66 mL) and heated at 60 C for 16 h. More TBAF (0.7 mL, 1.0 M in THF) was added, and the mixture was heated at 60 C for 16 h. The contents were concentrated. The residue was partitioned between EtOAc and water. The EtOAc layer was separated and washed with dilute NaOH solution, and concentrated. The crude was purified with reverse-phase chromatography to give compound 211 as TFA salt (44 mg).

Example 118

Synthesis of Compound 212

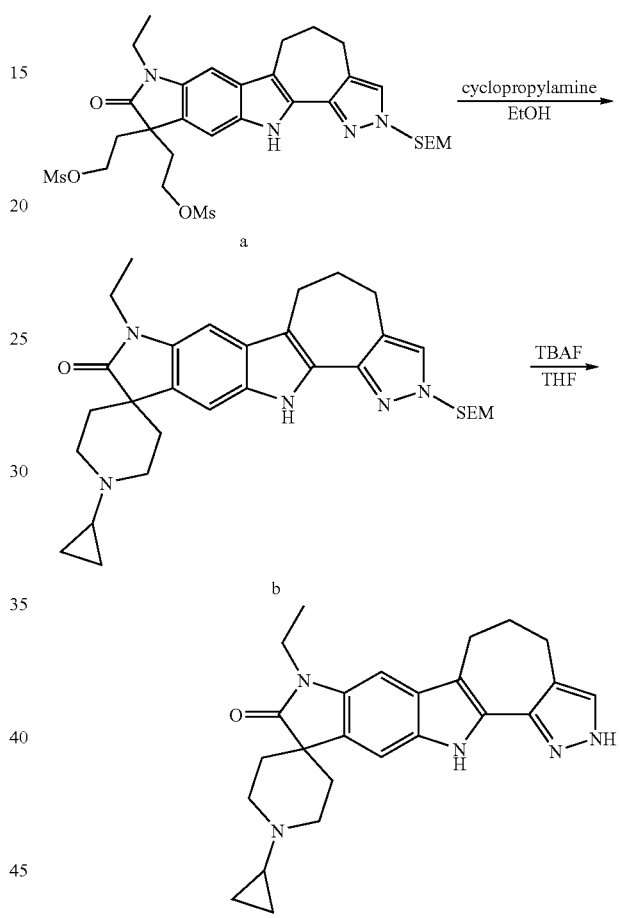

Compound 212 TFA salt (21 mg) was prepared in a similar manner to the procedures in example 117.

Example 119

Synthesis of Compound 213

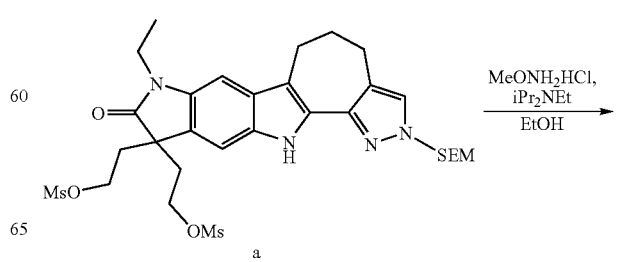

-continued

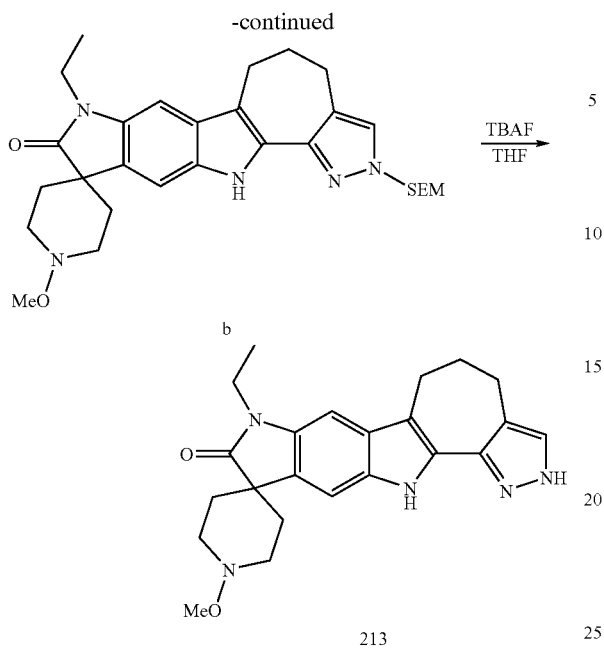

213

A mixture of compound a (80 mg), O-methylhydroxylamine hydrochloride (87 mg), DIPEA (0.348 mL) and EtOH (1.2 mL) was heated at 60° C. for 16 h. The contents were concentrated and the residue was partitioned between EtOAc and water. The aqueous layer was separated and extracted with EtOAc. The combined EtOAc solutions were washed with water and brine, and dried ($Na_2SO_4$). The crude was purified with flash chromatography to give compound b (32 mg).

Compound b (32 mg) was mixed with TBAF (0.5 mL, 1.0 M in THF) and THF (1.5 mL) and heated at 60° C. for 6 h. The contents were concentrated. The residue was partitioned between EtOAc and water. The EtOAc layer was separated and washed with dilute NaOH solution, and concentrated. The crude was purified with reverse-phase chromatography to give compound 213 as TFA salt (9 mg).

Example 120

Synthesis of Compound 214

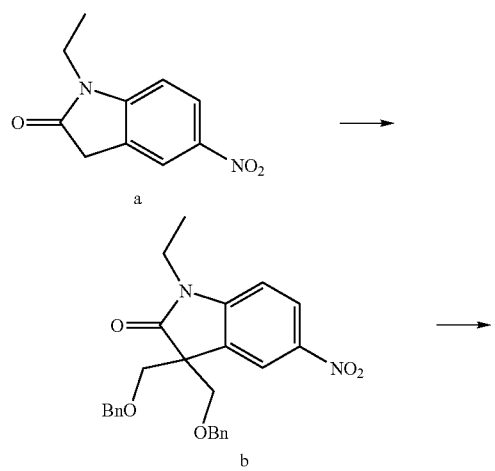

-continued

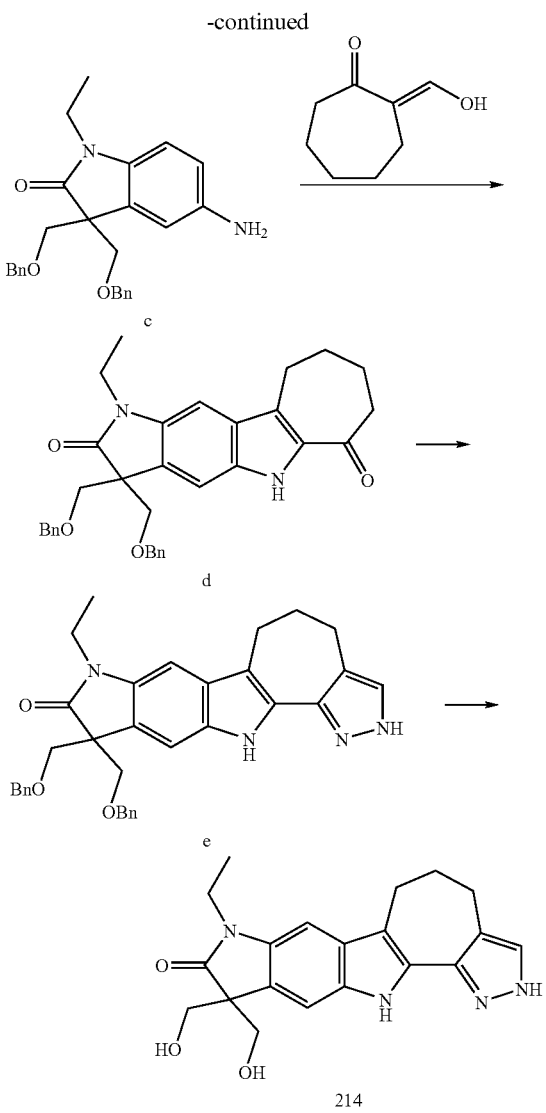

Nitrolactam a (206 mg, 0.999 mmol) was added into a round bottom flask under an atmosphere of nitrogen, followed by tetrahydrofuran (5 mL, 60 mmol). The mixture was cooled to −78° C. and lithium hexamethyldisilazide (0.35 g, 2.1 mmol) was added dropwise to give a deep red solution. The mixture was stirred at −78° C. for 15 minutes. The freshly filtered benzyl chloromethyl ether (620 mg, 2.4 mmol) was added dropwise at −78° C. The mixture was stirred at −78° C. for 30 minutes and allowed to warm to at 23° C. overnight. The mixture was diluted with 20 ml sat. $NH_4Cl$ and extracted with 20 ml ethyl acetate and hexanes (1/1). The organic layer was dried over $Na_2SO_4$, concentrated via rotavap, and purified via column chromatography (0-50% ethyl acetate/hexanes) to give 206 mg of pure compound b.

Nitrolactam b was added into a round bottom flask under an atmosphere of nitrogen, followed by acetic acid (4 mL, 60 mmol) and ethyl acetate. Then iron (130 mg, 2.3 mmol) was added in one portion to give a light yellow suspension. The mixture was heated to 70° C. for 2 hours. Monitoring the reaction by LCMS showed complete conversion. The mixture was diluted with 20 ml ethyl acetate and was filtered through Celite. The filtrate was concentrated via rotavap, and purified via column chromatography (0-80% ethyl acetate/hexanes) to give pure amine compound c (120 mg).

Amine compound c was added into a Round bottom flask under an atmosphere of nitrogen, followed by acetonitrile and water. The mixture was cooled to 0° C. and 0.013 ml conc. HCl was added dropwise, followed by sodium nitrite (2.0 ml mg, 0.29 mmol) was added in one portion to give a deep red solution. The mixture was stirred at 0° C. for 30 min. Into a round bottom flask was charged 60 mg of the enol (E)-2-(hydroxymethylene)cycloheptanone, 240 mg sodium acetate and 0.5 ml water, 0.5 ml ethanol. The resulting pale yellow suspension was cooled at 0° C., and the diazo mixture was added dropwise over 5 min, to give an orange suspension. The mixture was stirred at 0° C. for 30 min and then warmed to 23° C. for 1 hour. The mixture was diluted with 10 ml of water and extracted with 10 ml ethyl acetate. The organics were dried over Na$_2$SO$_4$ and concentrated via rotavap. The resulting yellow oil was dissolved in 6 ml acetic acid followed by 0.01 ml conc. HCl. The mixture was heated at 70° C. for 1 hour when monitoring the reaction with LCMS showed complete conversion. The mixture was concentrated via rotavap, dissolved in 10 ml ethyl acetate, and washed with 10 ml H$_2$O. Removal of solvent via rotavap gave a deep red oil, which was purified by column chromatography (0-100% ethyl acetate/hexanes) to provide pure compound d.

Compound d was added into a round bottom flask under an atmosphere of nitrogen followed by 300 mg dimethyl acetal and 0.2 ml DMF. The mixture was heated at 100° C. for 2 hours when LCMS showed disappearance of starting material and the mixture was concentrated via rotavap. The resulting black oil was dissolved in 4 ml of anhy. ethanol, and 70 mg hydrazine was added in one portion. The mixture was stirred at 23° C. for 1 hour when LCMS showed complete conversion. The mixture was then concentrated to dryness, diluted with 10 ml of sat. NH$_4$Cl and extracted with 10 ml ethyl acetate. The organics were dried over Na$_2$SO$_4$, concentrated via rotavap. The resulting yellow oil was purified by column chromatography (0-100% ethyl acetate/hexanes) to provide pure compound e.

Compound e was added to a round bottom flask under an atmosphere of nitrogen followed by 2 ml anhy. ethanol. Addition of 2 ml of anhy. methanol was added to give a pale yellow solution. 20 mg palladium on carbon (10%) was added under an atmosphere of nitrogen. The mixture was degassed and filled with H$_2$ three times, before being stirred under a H$_2$ balloon overnight at 23° C., when LCMS showed complete deprotection. The mixture was filtered through a plug of silica gel, concentrated via rotavap and purified via column chromatography (0-15% methanol/CH$_2$Cl$_2$) to give compound 214.

Example 121

Synthesis of Compound 215

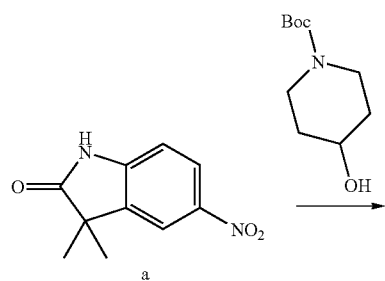

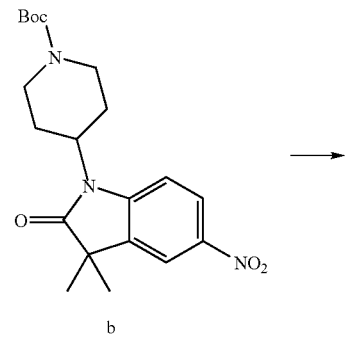

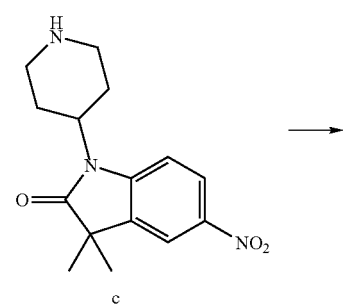

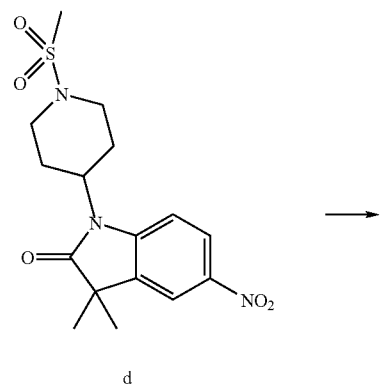

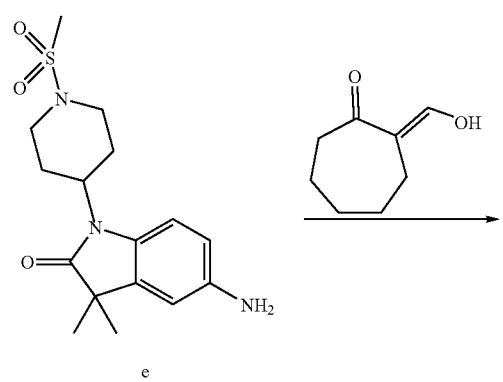

-continued

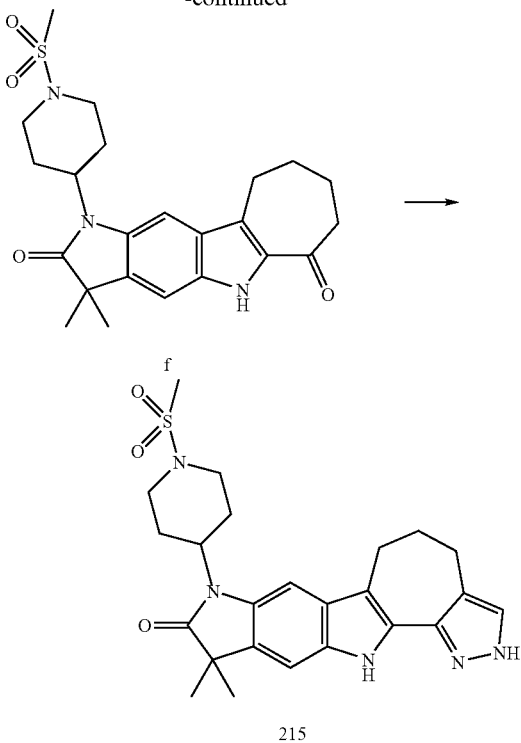

To a 10 ml round bottom flask was added 120 mg of nitro lactam a, followed by 351 mg tert-butyl 4-hydroxypiperidine-1-carboxylate, 520 mg Ph₃P, and 4.0 ml anhy. THF. Then 275 μl DEAD was added dropwise over 5 min, giving rise to a yellow solution instantly. After 1 hr at 23° C., LCMS showed complete conversion. The mixture was diluted with 10 ml sat. NH₄Cl, and extracted with 10 ml EtOAc. The crude product b was purified by column chromatography (0-50% EtOAc/hexanes).

To a 100 ml round bottom flask was added 200 mg of compound b followed by 10 ml CH₂Cl₂, and 2.0 ml TFA. The mixture was heated at 40° C. for 3 hr when LCMS showed complete conversion. The mixture was concentrated via rotavap and azeotroped from 2×20 ml anhy. toluene. The crude product c was directly carried to the next reaction.

To a 100 ml round bottom flask was added 0.6 g compound c followed by 10.0 ml anhy. CH₂Cl₂, 1.08 ml DIPEA. The mixture was cooled at 0° C. and 1.08 g Ms₂O was added dropwise. The mixture was stirred at 0° C. for 30 min. and warmed at 23° C. The mixture was diluted with 40 ml sat. NH₄Cl and extracted with 40 ml EtOAc/hexanes (1/1). The crude mixture of d was dried over Na₂SO₄, concentrated via rotavap, and directly carried to the next step.

Compound d was added to a round bottom flask under an atmosphere of nitrogen, followed by acetic acid (10.00 mL, 175.9 mmol) and 10.0 ml ethanol. Then iron (694 mg, 12.4 mmol) was added in one portion to give a light yellow suspension. The mixture was heated to 70° C. for 2 hours. Monitoring the reaction by LCMS showed complete conversion. The mixture was diluted with 80 ml ethyl acetate and was filtered through Celite. The filtrate was concentrated via rotavap, and purified via column chromatography (0-100% ethyl acetate/hexanes) to give compound e.

Compound e was added into a round bottom flask under an atmosphere of nitrogen, followed by acetonitrile and water. The mixture was cooled to 0° C. and 75 μl 4N HCl was added dropwise followed by addition of sodium nitrite (13.7 mg, 0.199 mmol) in 0.33 ml of dH₂O in one portion to give a deep red solution. The mixture was stirred at 0° C. for 30 min. Into a round bottom flask was charged 56 mg of the enol (E)-2-(hydroxymethylene)cycloheptanone, 162 mg sodium acetate, 1.0 ml water and 1.0 ml ethanol. The resulting pale yellow suspension was cooled at 0° C., and the diazo mixture was added dropwise over 5 min, to give an orange suspension. The mixture was stirred at 0° C. for 30 min. and warmed to at 23° C. for 1 hour. The mixture was diluted with 20 ml of water, and extracted with 2×20 ml EtOAc give crude hydrazone. The crude hydrazone was dissolved in 4.0 ml acetic acid, followed by 40 μl conc. HCl. The mixture was heated to 70° C. for 1 hour when monitoring the reaction with LCMS showed complete conversion. The mixture was concentrated via rotavap, dissolved in 10 ml ethyl acetate and was washed with 10 ml sat. brine. The aqueous layer was extracted with another 10 ml ethyl acetate. Removal of solvent via rotavap gave a deep black oil, which was purified by column chromatography (0-100% ethyl acetate/hexanes) to provide pure compound f.

Compound f was added into a round bottom flask under an atmosphere of nitrogen followed by 0.36 ml DMF-dimethyl acetal and 0.2 ml DMF. The mixture was heated to 100° C. for 4 hours when LCMS showed disappearance of starting material. The mixture was concentrated via rotavap. The resulting black oil was dissolved in 4 ml of anhy. ethanol and 85 μl hydrazine was added in one portion. The mixture was stirred at 23° C. for 1 hour when LCMS showed complete conversion. The mixture was concentrated to dryness, diluted with 10 ml of sat. NH₄Cl, extracted with 2×10 ml ethyl acetate. The organics were dried over Na₂SO₄ and concentrated via rotavap. The resulting yellow oil was purified by column chromatography (0-100% ethyl acetate/hexanes) to provide pure compound 215.

Example 122

Synthesis of Compound 216

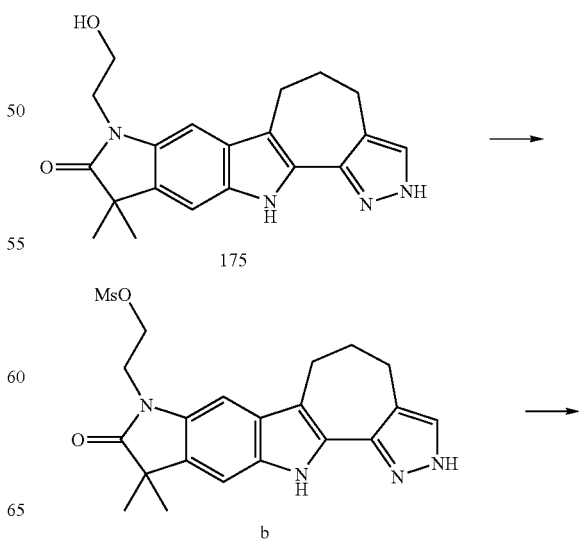

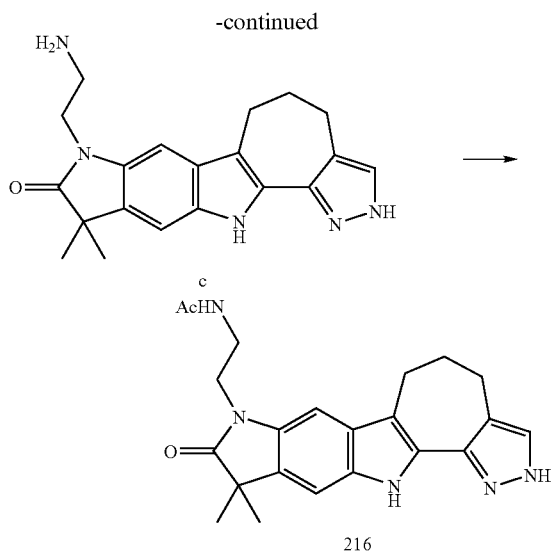

To a 100 ml RM flask was added 1.0 g of compound 175 followed by 20 ml anhy. CH$_2$Cl$_2$ and 1.49 ml DIPEA. The mixture was cooled to −10° C. with a NaCl/ice bath and 331 μl MsCl was added dropwise. After 30 min at −10° C., the mixture was carefully diluted with 50 ml EtOAc/hexanes (1/1), and washed with 50 ml sat. NH$_4$Cl. The crude mixture of mesylate b was dried over Na$_2$SO$_4$, concentrated and directly carried onto the next step.

To a 10 ml round bottom flask was added 60 mg of mesylate b followed by 2.0 ml 1,4-dioxane and 1.0 ml ammonia hydroxide. The mixture was heated to 60° C. for 2 hr when LCMS showed incomplete conversion. Additional 1.0 ml ammonia hydroxide was introduced every 1 hr for another 3 hr, when LCMS showed complete conversion. The mixture was cooled and diluted with 6 ml dH$_2$O, and extracted with 2×6 ml EtOAc. The organics were dried over Na$_2$SO$_4$, concentrated via rotavap to give amine c which was directly carried to the next step.

To a 10 ml round bottom flask was added crude amine c followed by 2.0 ml any. THF. The resulting yellow solution was cooled at 0° C. and 58 μl NEt$_3$ and 13 μl Ac$_2$O were added sequentially. After 30 min at 0° C., LCMS showed complete conversion. The mixture was quenched with 6 ml sat. NH$_4$Cl, and extracted with 2×6 ml EtOAc. The crude product was purified by column chromatography (EtOAc, then 0-10% MeOH/CH$_2$Cl$_2$) to give compound 216.

Example 123

Synthesis of Compound 217

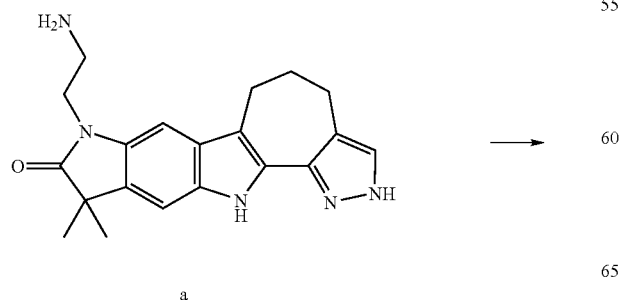

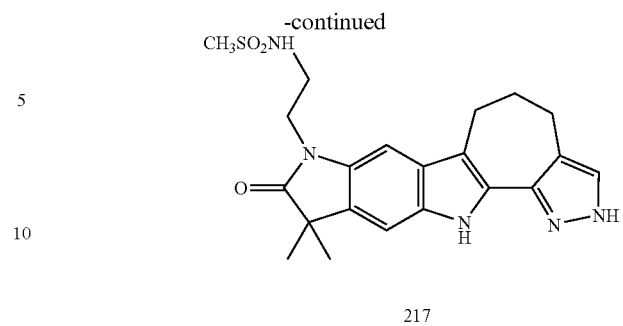

To a 10 ml round bottom flask was added crude amine a from example 122 followed by 2.0 ml anhy. THF. The resulting yellow solution was cooled at 0° C. and 58 μl NEt$_3$ and 11 μl MsCl were added sequentially. After 30 min at 0° C., LCMS showed complete conversion. The mixture was quenched with 6 ml sat. NH$_4$Cl, and extracted with 2×6 ml EtOAc. The crude product was purified by column chromatography (50-100% EtOAc/hexanes, then 0-10% MeOH/CH$_2$Cl$_2$) to give compound 217.

Example 124

Synthesis of Compound 218

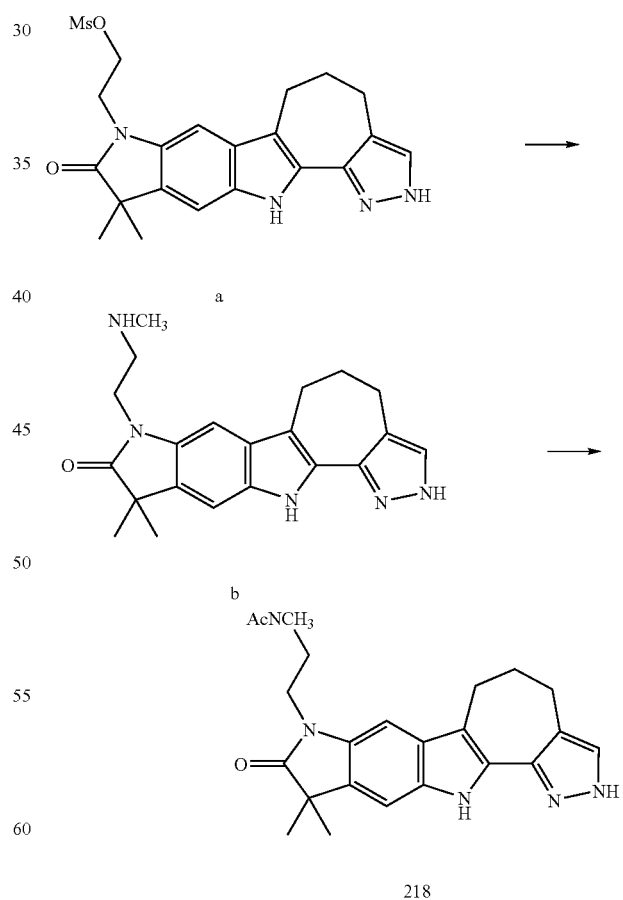

To a 10 ml round bottom flask was added 100 mg of mesylate a from example 122 followed by 2.0 ml 2M MeNH$_2$/THF solution. The mixture was heated at 60° C. for 2 hr when LCMS showed incomplete conversion. Additional 5×2 ml 2M MeNH₂/THF solution was added and the mixture was stirred at 60° C. for 2 days. The mixture was cooled and concentrated to dryness. The resulting yellow oil was diluted with 6 ml dH₂O, and extracted with 2×6 ml EtOAc. The organics were dried over Na₂SO₄, concentrated via rotavap to give secondary amine b which was directly carried to the next step.

To a 10 ml round bottom flask was added crude secondary amine b followed by 2.0 ml anhy. THF. The resulting yellow solution was cooled at 0° C. and 58 µl NEt₃ and 13 µl Ac₂O were added sequentially. After 30 min at 0° C., LCMS showed complete conversion. The mixture was quenched with 6 ml sat. NH₄Cl, and extracted with 2×6 ml EtOAc. The crude product was purified by column chromatography (0-20% MeOH/CH₂Cl₂) to give compound 218.

Example 125

Synthesis of Compound 219

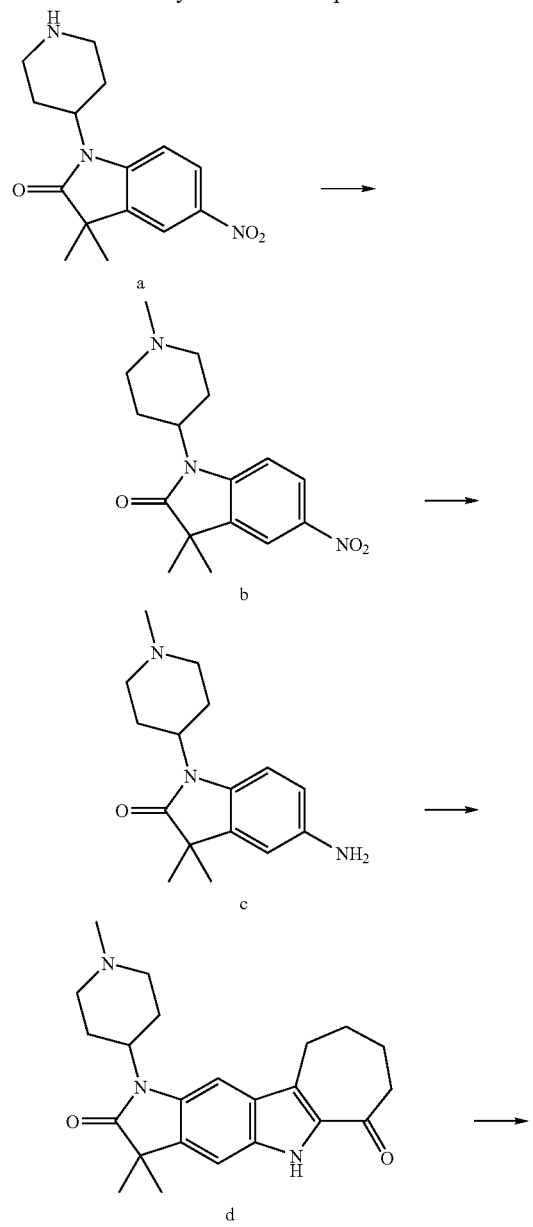

-continued

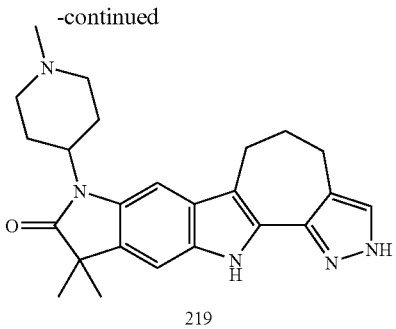

219

To a 25 ml round bottom flask was added 100 mg of compound a from example 121 followed by 0.4 ml acetic acid and 4.0 ml DMF. Then 93 mg paraformaldehyde was added and the resulting white suspension was stirred at 23° C. for 15 min before 220 mg of Na(OAc)₃BH was added in one portion. The mixture was stirred for 4 hr when LCMS showed complete conversion. The mixture was diluted with 20 ml sat. NaHCO₃, and extracted with 2×20 ml EtOAc. The crude mixture was purified via column chromatography (0-100% EtOAc/hexanes, then 0-20% MeOH/CH₂Cl₂) to give pure compound b.

To a 250 ml round bottom flask was added 100 mg of compound b followed by 10 ml ethanol. The flask was flushed with nitrogen and 50 mg Pd/C (10%) was added in one portion. The mixture was evacuated and filled with H₂ three times before being stirred at 23° C. for 4 hr when LCMS showed complete conversion. The black mixture was filtered through celite and the cake was washed with 2×10 ml MeOH. Combined filtrate was concentrated to dryness via rotavap to give compound c which was directly carried to the next step.

Compound c was added into a round bottom flask under an atmosphere of nitrogen, followed by acetonitrile and water. The mixture was cooled at 0° C. and 75 µl 12 N HCl was added dropwise, followed by sodium nitrite (41.2 mg, 0.597 mmol) in 1.0 ml of dH₂O was added in one portion to give a deep red solution. The mixture was stirred at 0° C. for 30 min. Into a round bottom flask was charged 167 mg of enol (E)-2-(hydroxymethylene)cycloheptanone, 488 mg sodium acetate and 1.0 ml water, 1.0 ml ethanol. The resulting pale yellow suspension was cooled to 0° C., and the diazo mixture was added dropwise over 5 min, to give an orange suspension. The mixture was stirred at 0° C. for 30 min, warmed to at 23° C. for 1 hour. The mixture was diluted with 20 ml of water, and extracted with 2×20 ml EtOAc to give crude hydrazone. The crude hydrazone was dissolved in 10.0 ml acetic acid, followed by 0.1 ml conc. HCl. The mixture was heated at 70° C. for 1 hour when monitoring the reaction with LCMS showed complete conversion. The mixture was concentrated via rotavap, dissolved in 10 ml ethyl acetate, and washed with 10 ml sat. brine. The aqueous layer was extracted with another 10 ml ethyl acetate. Removal of solvent via rotavap gave a deep black oil, which was purified by column chromatography (0-25% MeOH/CH₂Cl₂) to provide pure compound d.

Compound d was added into a round bottom flask under an atmosphere of nitrogen, followed by 0.63 ml DMF-dimethyl acetal and 0.36 ml DMF. The mixture was heated at 100° C. for 4 hours, when LCMS showed disappearance of starting material. The mixture was concentrated via rotavap. The resulting black oil was dissolved in 8.0 ml of anhy. ethanol, and 149 µl hydrazine was added in one portion. The mixture was stirred at 23° C. for 1 hour when LCMS showed complete conversion. The mixture was concentrated to dryness, diluted with 10 ml of dH$_2$O, extracted with 2×10 ml ethyl acetate. The organics were dried over Na$_2$SO$_4$, concentrated via rotavap. The resulting yellow oil was purified by column chromatography (0-25% MeOH/CH$_2$Cl$_2$) to provide pure compound 219.

Example 126

Synthesis of Compound 220

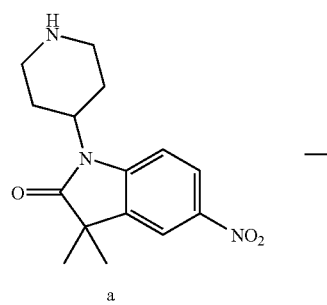

a

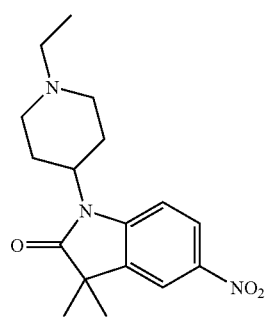

b

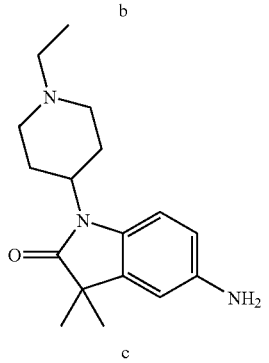

c

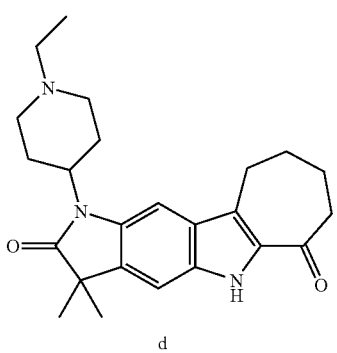

d

-continued

220

To a 25 ml round bottom flask was added 100 mg of compound a from example 121 followed by 0.4 ml acetic acid and 4.0 ml DMF. Then 58 mg acetaldehyde was added and the resulting yellow solution was stirred at 23° C. for 15 min before 220 mg of Na(OAc)$_3$BH was added in one portion. The mixture was stirred for 4 hr when LCMS showed complete conversion. The mixture was diluted with 20 ml sat. NaHCO$_3$, and extracted with 2×20 ml EtOAc. The crude mixture was purified via column chromatography (0-100% EtOAc/hexanes then 0-20% MeOH/CH$_2$Cl$_2$) to give pure compound b.

To a 250 ml round bottom flask was added 100 mg of compound b followed by 10 ml ethanol. The flask was flushed with nitrogen and 50 mg Pd/C (10%) was added in one portion. The mixture was evacuated and filled with H$_2$ three times before being stirred at 23° C. for 4 hr when LCMS showed complete conversion. The black mixture was filtered through celite and the cake was washed with 2×10 ml MeOH. Combined filtrate was concentrated to dryness via rotavap to give amine compound c which was directly carried to the next step.

Amine compound c was added to a round bottom flask under an atmosphere of nitrogen, followed by acetonitrile and water. The mixture was cooled to 0° C. and 75 μl 12 N HCl was added dropwise followed by sodium nitrite (41.2 mg, 0.597 mmol) in 1.0 ml of dH$_2$O added in one portion to give a deep red solution. The mixture was stirred at 0° C. for 30 min. Into a round bottom flask was charged 167 mg of enol (E)-2-(hydroxymethylene)cycloheptanone, 488 mg sodium acetate, 1.0 ml water and 1.0 ml ethanol. The resulting pale yellow suspension was cooled at 0° C., and the diazo mixture was added dropwise over 5 min, to give an orange suspension. The mixture was stirred at 0° C. for 30 min and warmed to 23° C. for 1 hour. The mixture was diluted with 20 ml of water and extracted with 2×20 ml EtOAc to give crude hydrazone. The crude hydrazone was dissolved in 10.0 ml acetic acid followed by 0.1 ml conc. HCl. The mixture was heated to 70° C. for 1 hour when monitoring the reaction with LCMS showed complete conversion. The mixture was concentrated via rotavap, dissolved in 10 ml ethyl acetate and washed with 10 ml sat. brine. The aqueous layer was extracted with another 10 ml ethyl acetate. Removal of solvent via rotavap gave a deep black oil, which was purified by column chromatography (0-25% MeOH/CH$_2$Cl$_2$) to provide pure compound d.

Compound d was added into a round bottom flask under an atmosphere of nitrogen, followed by 0.67 ml DMF-dimethyl acetal and 0.39 ml DMF. The mixture was heated at 100° C. for 4 hours, when LCMS showed disappearance of starting material. The mixture was concentrated via rotavap. The resulting black oil was dissolved in 8.0 ml of anhy. ethanol, and 160 μl hydrazine was added in one portion. The mixture was stirred at 23° C. for 1 hour when LCMS showed complete conversion. The mixture was concentrated to dryness, diluted with 10 ml of dH$_2$O and extracted with 2×10 ml ethyl acetate. The organics were dried over Na$_2$SO$_4$ and concentrated via rotavap. The resulting yellow oil was purified by column chromatography (0-25% MeOH/CH$_2$Cl$_2$) to provide pure compound 220.

Example 127

Synthesis of Compound 221

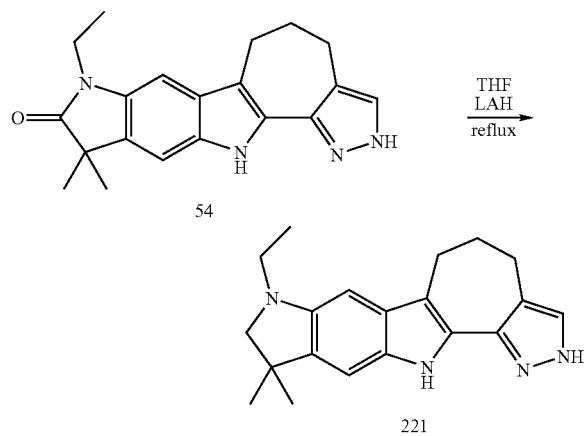

Compound 54 (30.5 mg) was dissolved in 1.5 ml of THF and degassed. 0.365 ml of 1M LAH in THF was added slowly at room temperature and the reaction heated to 70° C. After 1.5 hours, the reaction mixture was cooled to room temperature and was quenched with 1 ml of water, then was partitioned between ethyl acetate and water. The organic phase was washed with brine, dried over sodium sulfate, filtered and concentrated. Purification of the residue by HPLC gave 11.5 mg of compound 221.

Example 128

Synthesis of Compound 222

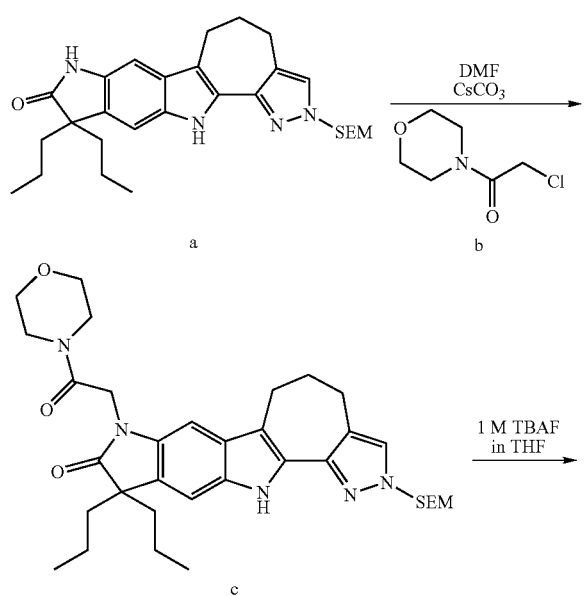

-continued

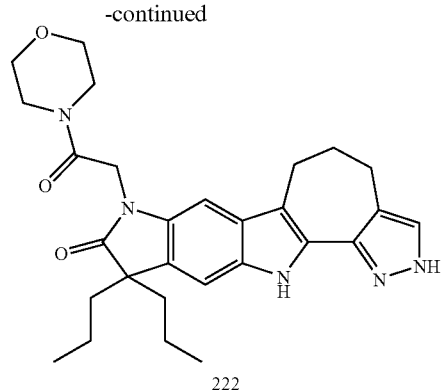

Compound a from example 62 (51 mg) was dissolved in 2 ml DMF and Cs$_2$CO$_3$ (101 mg) was added, followed by the addition of compound b (51 mg). The vial was capped and the reaction was stirred at room temperature for 18 hrs. The reaction was completed by LCMS. Diluted reaction with H$_2$O, extracted with EtOAc, washed with brine, dried over Na$_2$SO$_4$ and concentrated by vacuum to give compound c. Compound c was dissolved in 2.5 ml THF and added 0.31 ml 1.0 M TBAF in THF. The reaction was heated for 5 hours at 60° C. and was completed by LCMS. The reaction mixture was concentrated under vacuum, diluted with H$_2$O, extracted with EtOAc, washed with brine, dried over Na$_2$SO$_4$ concentrated under vacuum and purified by HPLC to give compound 222 (28.9 mg).

Example 129

Synthesis of Compounds 223 and 224

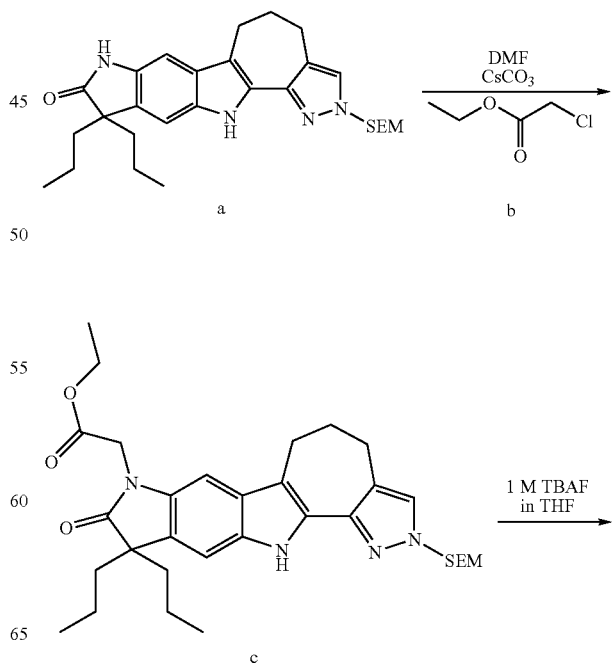

-continued

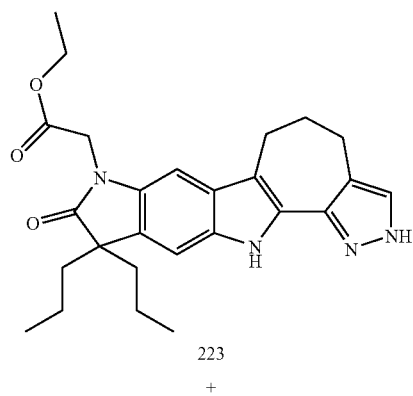

223

+

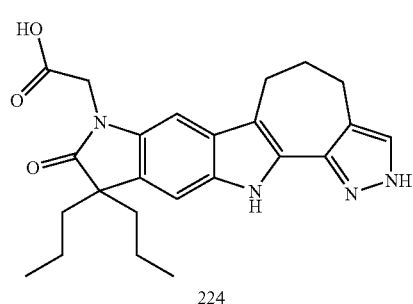

224

Compound a from example 62 (56 mg) was dissolved in 2.5 ml DMF and Cs$_2$CO$_3$ (111 mg) was added followed by the addition of compound b (42 mg). The vial was capped and the reaction was stirred at room temperature for 21 hrs. The reaction was completed by LCMS. The reaction was diluted with H$_2$O, extracted with EtOAc, washed with brine, dried over Na$_2$SO$_4$ and concentrated by vacuum to give compound c. Compound c was dissolved in 2.5 ml THF and 0.34 ml 1.0 M TBAF in THF was added. The reaction was heated for 28 hours at 60° C. and was completed by LCMS. The reaction mixture was concentrated under vacuum, diluted with H$_2$O, extracted with EtOAc, washed with brine, dried over Na$_2$SO$_4$, concentrated under vacuum and purified by HPLC to give compound 223 (12.2 mg) and 224 (11.8 mg).

Example 130

Synthesis of Compound 225

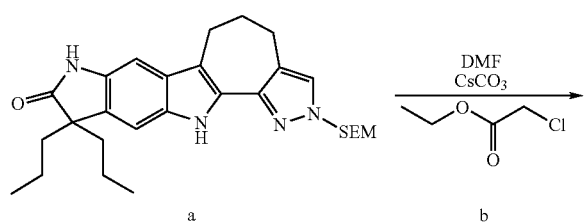

a     b

-continued

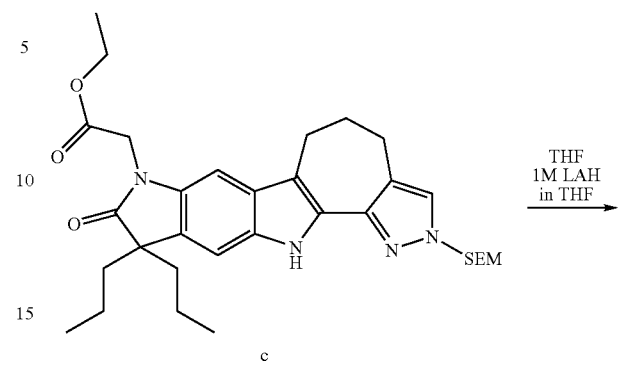

c

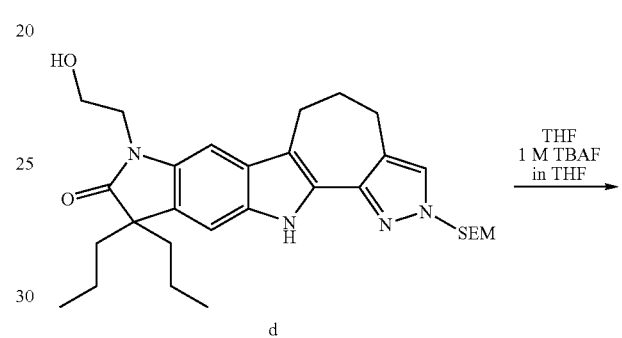

d

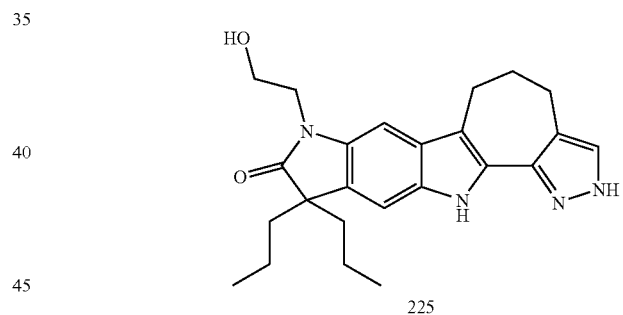

225

Compound a from example 62 (112 mg) was dissolved in 4 ml DMF and Cs$_2$CO$_3$ (223 mg) was added followed by the addition of compound b (84 mg). The vial was capped and the reaction was stirred at room temperature for 24 hrs. The reaction was completed by LCMS. The reaction was diluted with H$_2$O, extracted with EtOAc, washed with brine, dried over Na$_2$SO$_4$ and concentrated by vacuum to give compound c. Compound c was dissolved in 4 ml THF and 1.14 ml 1.0 M LAH in THF at 0° C. was added. The reaction was completed by LCMS. The reaction mixture was quenched with water and extracted with EtOAc, washed with brine, dried over Na$_2$SO$_4$, concentrated under vacuum to give compound d. Compound d was dissolved in 4 ml THF and 0.68 ml 1.0 M TBAF in THF at room temperature was added. The reaction was heated to 70° C. and stirred overnight. It was completed by LCMS, diluted with H$_2$O, extracted with EtOAc, washed with brine, dried over Na$_2$SO$_4$, concentrated under vacuum and purified by HPLC to give compound 225 (44.9 mg).

Example 131

Synthesis of Compound 226

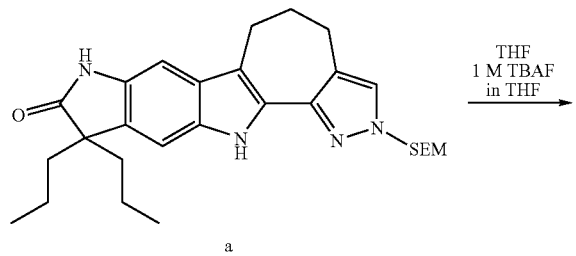

a $\xrightarrow{\text{THF} \atop \text{1 M TBAF in THF}}$

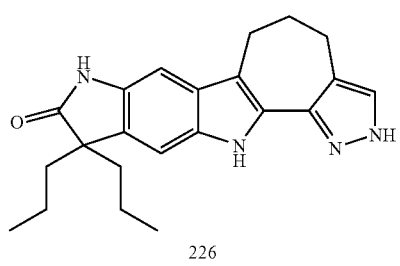

226

Compound a from example 62 (140 mg) was dissolved in 7 ml THF and added 0.85 ml 1.0 M TBAF in THF. The reaction was heated for 23 hours at 50° C. and was completed by LCMS. The reaction mixture was diluted with H$_2$O, extracted with EtOAc, washed with brine, dried over Na$_2$SO$_4$, concentrated under vacuum and flashed by ISCO to give compound 226 (55.5 mg).

Example 132

Synthesis of Compound 227

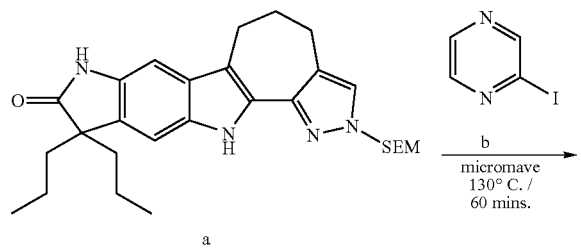

a $\xrightarrow[\text{microwave} \atop \text{130° C. / 60 mins.}]{b}$

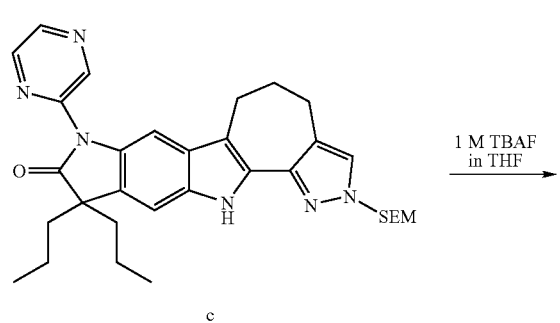

c $\xrightarrow{\text{1 M TBAF in THF}}$

-continued

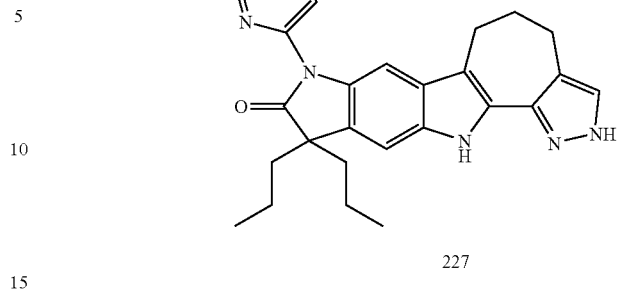

227

Compound a from example 62 (50 mg) was added to an oven dried microwave reaction vessel with spin bar. To this solid 1.7 ml DMF, CuI (10 mg), K$_3$PO$_4$ (43 mg) and compound b (25 mg) were directly added. After flushing the reaction vessel with N$_2$, a solution of trans-1,2-cyclohexanediamine (12 mg) in dioxane was added to the mixture of solids and the vessel was sealed. Then it was heated to 130° C. for 60 minutes under microwave conditions. After cooling to room temperature the mixture was diluted with H$_2$O, extracted with EtOAc, washed with brine, dried over Na$_2$SO$_4$ and concentrated by vacuum and flashed by ISCO to give compound c (35 mg). Compound c was dissolved in 2.0 ml THF and added 0.184 ml 1.0 M TBAF in THF. The reaction was heated for 2.5 hours at 60° C. and was completed by LCMS. The reaction mixture was diluted with H$_2$O, extracted with EtOAc, washed with brine, dried over Na$_2$SO$_4$, concentrated under vacuum and flashed by ISCO to give compound 227 (21 mg).

Example 133

Synthesis of Compound 228

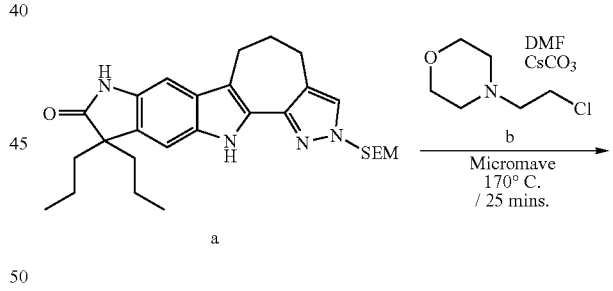

a $\xrightarrow[\text{Microwave} \atop \text{170° C. / 25 mins.}]{\text{DMF, CsCO}_3, b}$

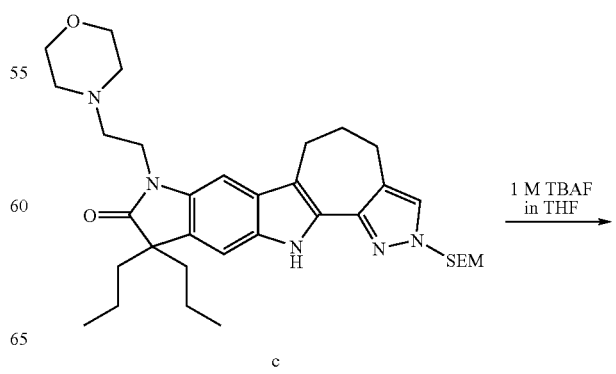

c $\xrightarrow{\text{1 M TBAF in THF}}$

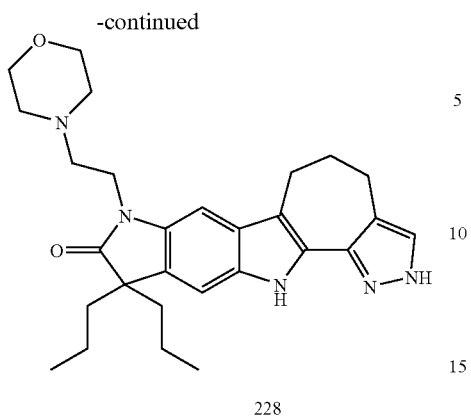

228

Compound a from example 62 (48 mg) was added to an oven dried microwave reaction vessel with spin bar. To this solid 9 ml DMF, K₂CO₃ (403 mg) and compound b (109 mg) were directly added. The reaction vessel was flashed with N₂ and sealed. Then it was heated to 170° C. for 25 minutes under microwave conditions. After cooling to room temperature the mixture was diluted with H₂O, extracted with EtOAc, washed with brine, dried over Na₂SO₄ and concentrated by vacuum to give compound c. Compound c was dissolved in 3.0 ml THF and 0.29 ml 1.0 M TBAF in THF was added. The reaction was heated for 3 hours at 55° C. and was completed by LCMS. The reaction mixture was diluted with H₂O, extracted with EtOAc, washed with brine, dried over Na₂SO₄, concentrated under vacuum and flashed by ISCO to give compound 228 (10 mg).

Example 134

Synthesis of Compound 229

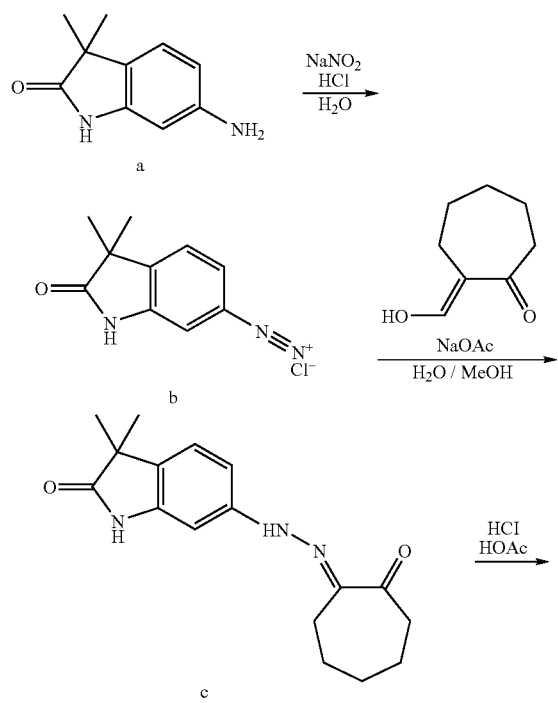

Compound a was prepared according to procedures described by Holck et al (U.S. Pat. No. 4,963,686 1990). A solution of compound a (540 mg) in 10 ml of water acidified with 0.4 ml of 37% HCl was cooled on an ice bath and a solution of sodium nitrite (254 mg) in 3 ml of water was added over 10 minutes. The deep red solution of b was stirred 0.5 hr then added slowly to a suspension of sodium acetate (1.9 g), water (50 ml), methanol (10 ml) and enol (E)-2-(hydroxymethylene)-cycloheptanone (477 mg, prepared as in example 2). After stirring for 30 minutes, the yellow precipitate of compound c was collected by filtration, washed with water and air dried. Yield=0.85 g.

A solution of compound c (0.85 g) in 180 ml of acetic acid and 18 ml of 37% HCl was heated to 90° C. for 45 min. then cooled and partially concentrated under vacuum. The concentrate was partitioned between ethyl acetate and water, washed with saturated sodium bicarbonate then brine, dried over sodium sulfate, filtered and concentrated. The product crystallized from ethyl acetate and was filtered to give 394 mg of compound d.

Compound d (510 mg) was dissolved in 100 ml of dry THF and cooled on an ice water bath. LHMDS (7.23 ml of 1M solution in THF) was added over 5 minutes. After 20 minutes, acetic anhydride (0.68 ml) was added and the reaction stirred for 1 hr. This reaction mixture containing compound e was poured into a cold solution of hydrazine hydrate (20 ml) and ethanol (100 ml) and stirred overnight. The reaction mixture was concentrated and partitioned between ethyl acetate and 10% citric acid. The organic phase was washed with water, brine, dried over sodium sulfate, filtered and concentrated to give 590 mg of crude compound. Purification by silica flash column gave 130 mg of compound 229.

Example 135

Synthesis of Compounds 230 and 231

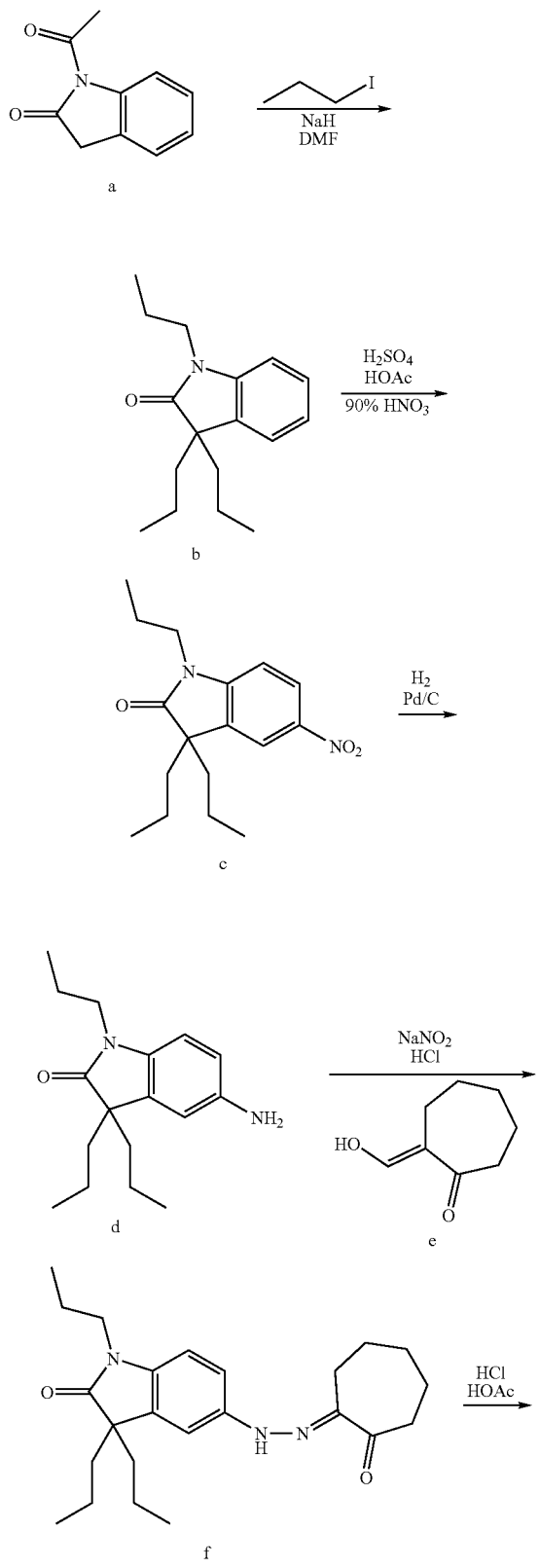

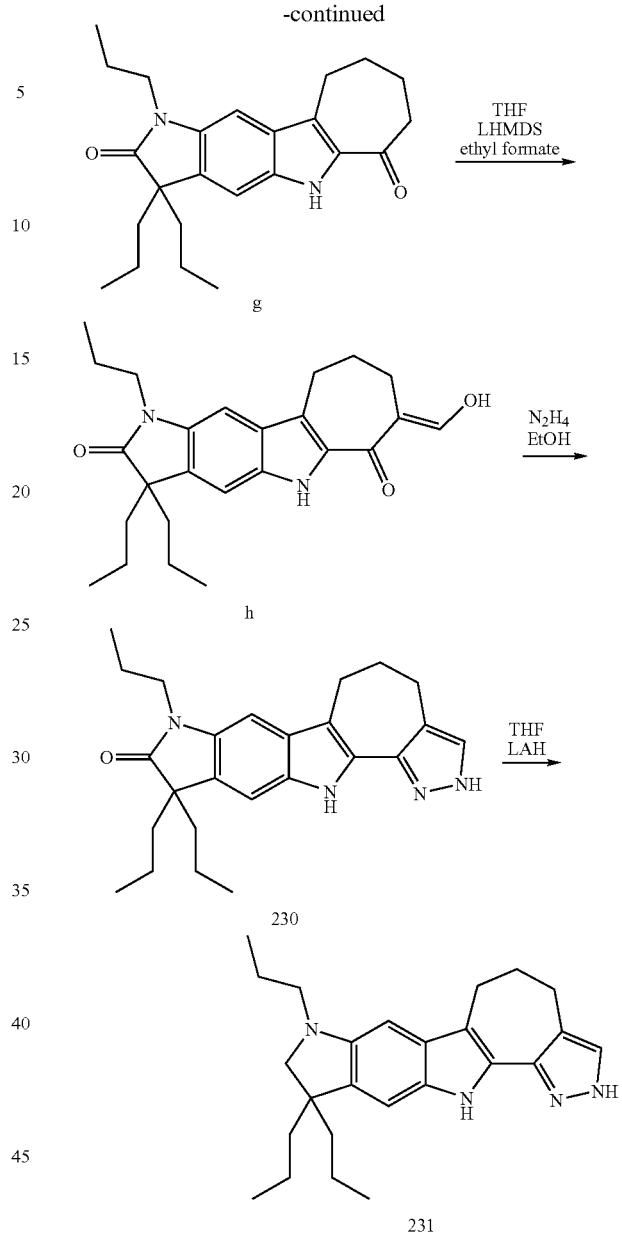

Sodium hydride (10.08 g) was added to 400 ml DMF and cooled to 0° C. N-acetyloxindole a (24.50 g) in 100 ml of DMF was added to this solution for 15 mins followed by 40.96 ml of 1-iodopropane and warmed to room temperature and the reaction stirred for 24 hours. The reaction mixture was concentrated under vacuum then partitioned between water and ethyl acetate. The organic phase was washed with brine, dried over sodium sulfate, filtered and concentrated under vacuum and flashed by ISCO (EtOAc/Hexanes) to give compound b (23.67 g).

A mechanically stirred solution of b (5.12 g) in 80 ml of conc. sulfuric acid and 5 ml HOAc was cooled to −35° C. To this solution was added 0.921 ml fuming nitric acid in 40 ml $H_2SO_4$ and the reaction was allowed to warm up to room temperature. The reaction was completed by TLC after 75 minutes. The reaction mixture was slowly poured into ice water and extracted with ethyl acetate, washed with brine, dried over sodium sulfate, concentrated under vacuum to give 5.98 g of compound c. Compound c (5.98 g) was reduced under a balloon of hydrogen with 10% Pd/C in 10/1 methanol/acetic acid for 4.5 hours. The catalyst was filtered off and the filtrate concentrated under vacuum and flashed by ISCO to give 5.15 g compound d.

Compound d (3.97 g) was dissolved 120 ml $H_2O$/2.35 ml concentrated HCl and cooled to 0° C. To this mixture was added 1.56 g $NaNO_2$ in 40 ml $H_2O$ and the reaction was stirred for 5 minutes. This reaction mixture was added to 2.89 g of enol (E)-2-(hydroxymethylene)-cycloheptanone and 6.94 g NaOAc in 200 ml $H_2O$ and 20 ml methanol at 0° C. and the reaction was allowed to warm to room temperature and stirred for 1.5 hours. The precipitate formed was filtered off and confirmed to be compound f by LCMS.

Compound f was dissolved in 100 ml HOAc and 2.0 ml HCl and heated to 95° C. with stirring for 1.5 hours. The reaction was completed by LCMS and cooled to room temperature. The reaction mixture was slowly poured into ice water and extracted with ethyl acetate/hexane (2:1), washed with brine, dried over sodium sulfate and concentrated under vacuum and flashed by ISCO to give 1.47 g of compound g.

Compound g (208 mg) was dissolved in THF (5 ml) and lithium-bis-trimethylsilylamide (2.19 ml of 1M solution in THF) was added. The reaction was stirred for 10 minutes then 0.18 ml of ethyl formate was added. This reaction was stirred for 4.5 hours then poured into water and extracted with ethyl acetate, washed with brine, dried over sodium sulfate and concentrated under vacuum to gave the crude compound h. Compound h was dissolved in ethanol (25 ml) then hydrazine hydrate (0.5 ml) was added and stirred at room temperature for 22 hours. The solvents were evaporated and purified by HPLC to give compound 230 (25.4 mg).

Compound 230 (12.7 mg) was dissolved in 1.5 ml of THF and degassed. 0.126 ml of 1M LAH in THF was added slowly at room temperature and the reaction heated to 70° C. After 1 hour, the reaction mixture was cooled to room temperature, quenched with 1 ml of water and then partitioned between ethyl acetate and water. The organic phase was washed with brine, dried over sodium sulfate, filtered and concentrated. Purification of the residue by HPLC gave 2.8 mg of compound 231.

Example 136

Synthesis of Compounds 232

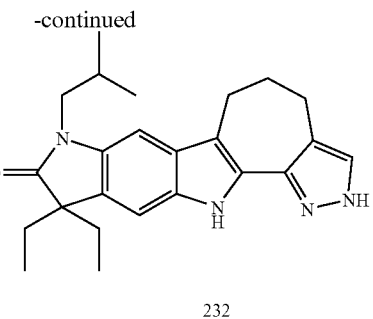

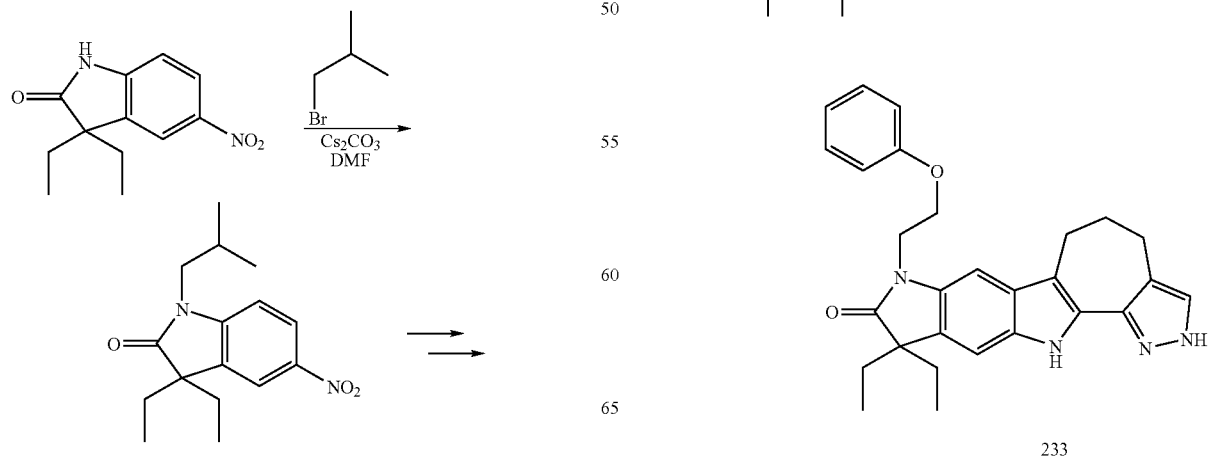

232

Compound 232 (17 mg) was prepared using the procedures described in example 22 and alkylating with 1-bromo-2-methylpropane.

Example 137

Synthesis of Compounds 233

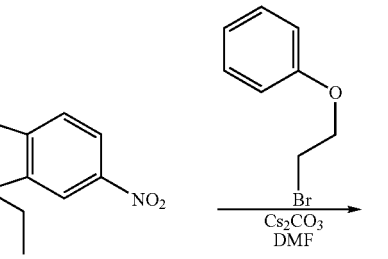

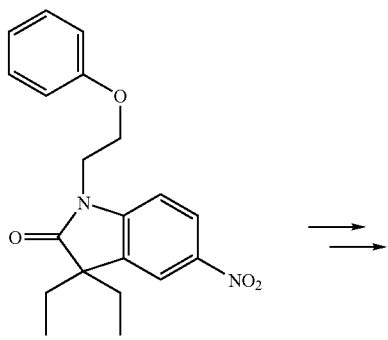

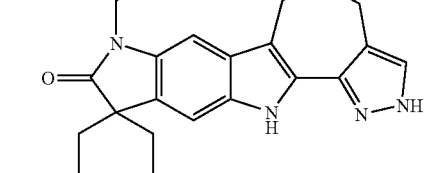

233

Compound 233 (5.3 mg) was prepared using the procedures described in example 22 and alkylating with 1-bromo-2-phenoxyethane.

Example 138

Synthesis of Compounds 234

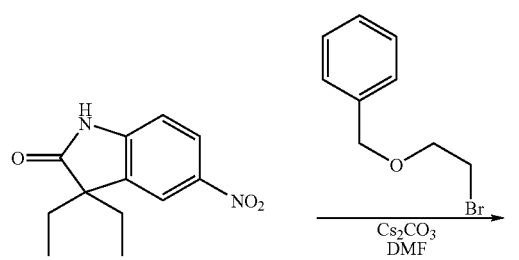

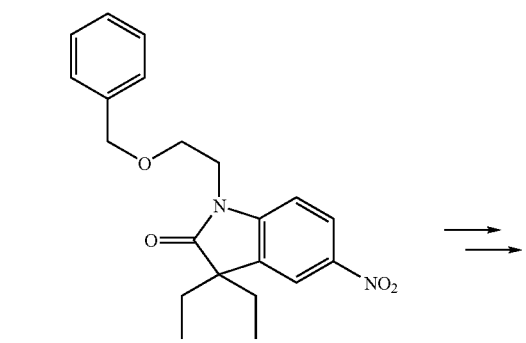

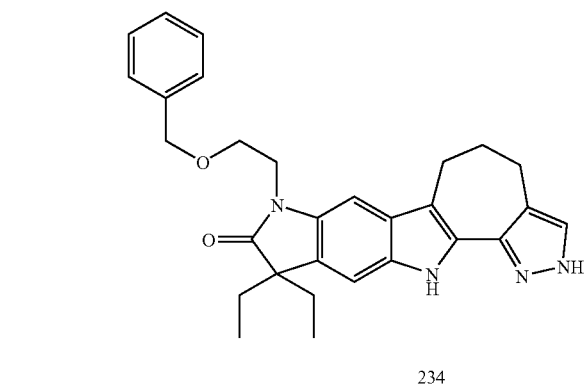

234

Compound 233 (27 mg) was prepared using the procedures described in example 22 and alkylating with 1-bromo-2-benzyloxyethane.

Example 139

Synthesis of Compounds 235

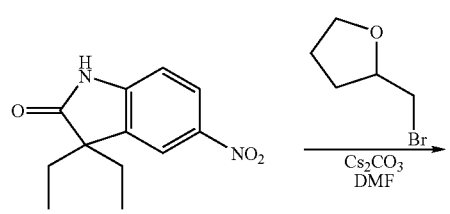

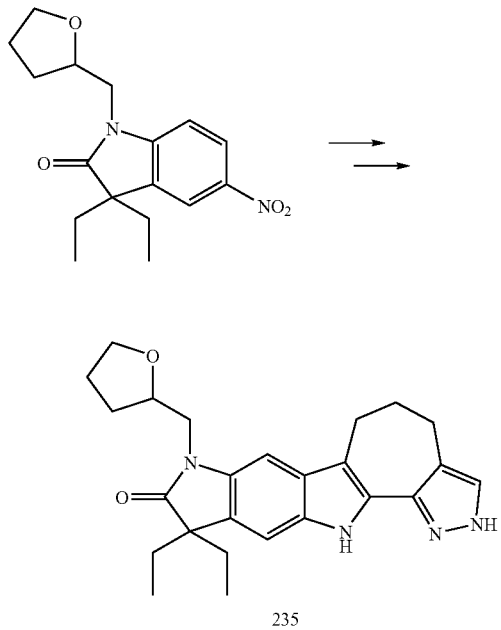

235

Compound 233 (30 mg) was prepared using the procedures described in example 22 and alkylating with 2-(bromomethyl)-tetrahydrofuran.

Example 140

Synthesis of Compounds 236

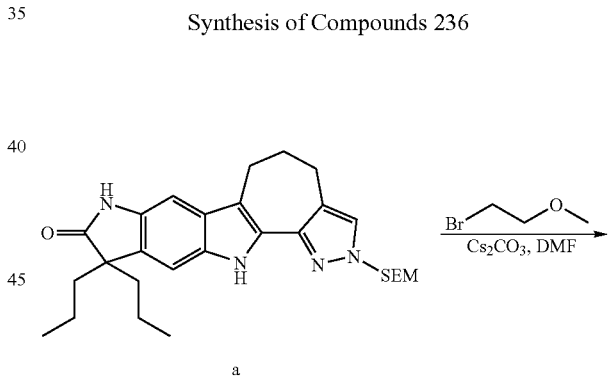

a b

261

-continued

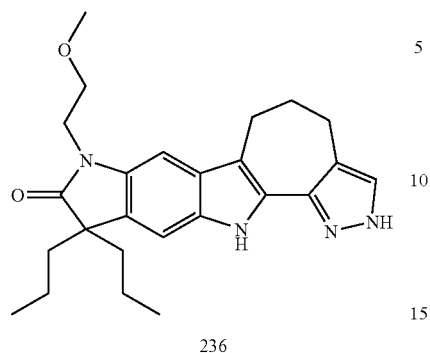

236

Compound a (40 mg, 0.08 mmol) from example 62 was dissolved in DMF (0.8 mL). To this solution was added $Cs_2CO_3$ (53 mg, 0.16 mmol) and 2-bromoethyl methyl ether (22 mg, 0.16 mmol). The reaction mixture was then stirred at 60° C. and monitored by LCMS. After complete consumption of starting material, the mixture was diluted with $H_2O$ and extracted with EtOAc. The organic layer was washed with brine, dried over $Na_2SO_4$, filtered and concentrated. The residue was dissolved in 1 M TBAF in THF (1 mL) and heated at 60° C. for 1 hour. The mixture was diluted with EtOAc and washed with $H_2O$ (3×) followed by brine and then dried over $Na_2SO_4$. The solvent was removed in vacuo and the residue was subjected to purification by HPLC to afford 16 mg of compound 236.

Example 141

Synthesis of Compounds 237

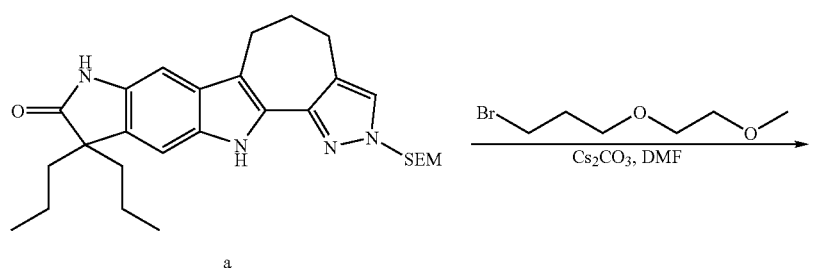

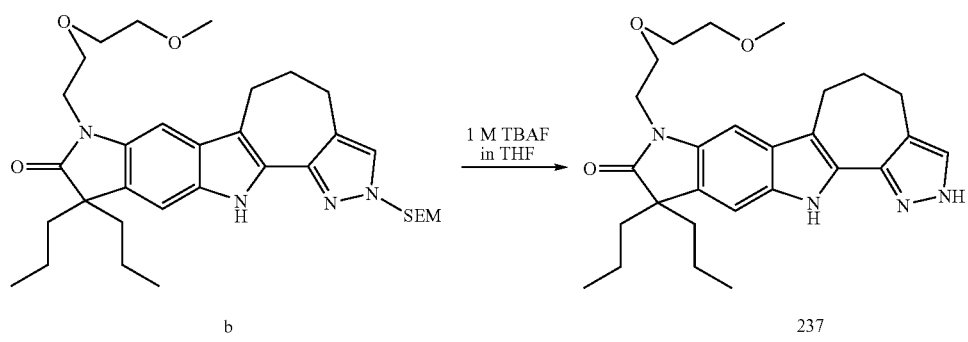

262

Compound 237 (10 mg) was prepared using the procedures described in example 140 and alkylating with 1-(2-methoxy-ethoxy)-3-bromopropane.

Example 142

Synthesis of Compounds 238

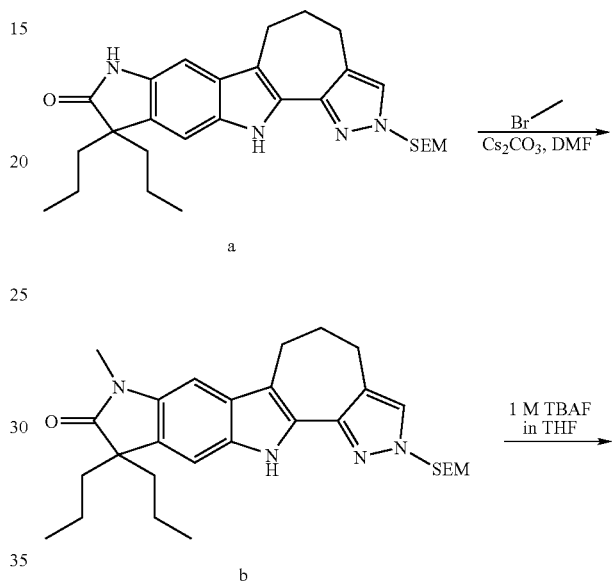

-continued

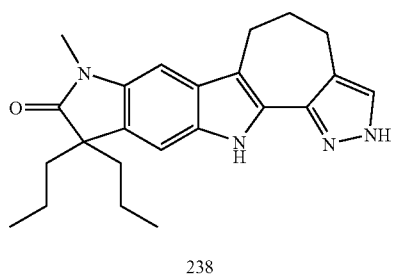

238

Compound 238 (14 mg) was prepared using the procedures described in example 140 and alkylating with bromomethane.

Example 143

Synthesis of Compounds 239

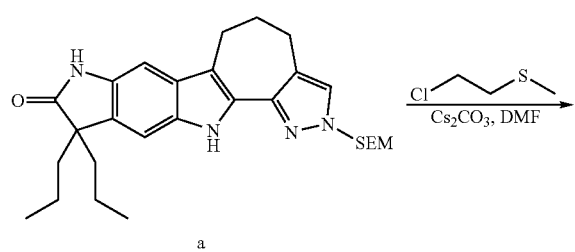

a

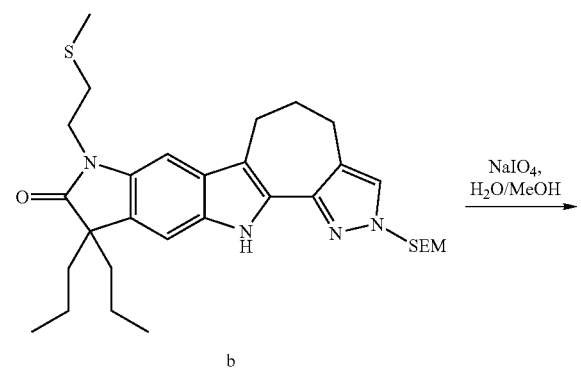

b

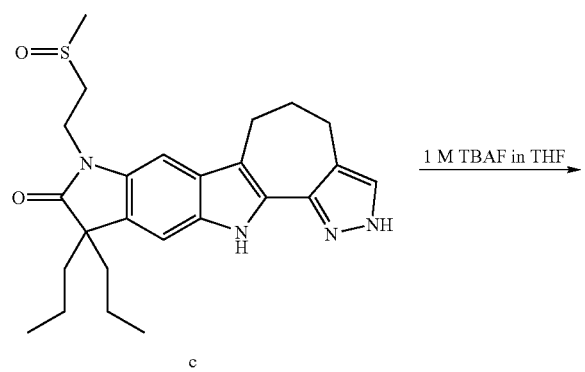

c

-continued

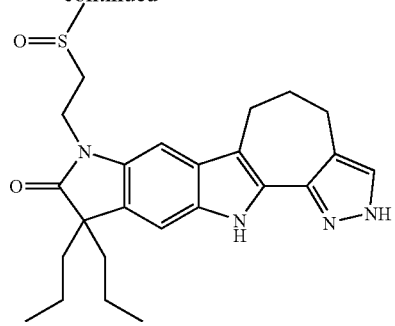

239

Compound a (60 mg, 0.12 mmol) from example 62 was dissolved in DMF (1.2 mL). To this solution was added $Cs_2CO_3$ (260 mg, 0.8 mmol) and 2-chloroethyl methyl thioether (220 mg, 2.0 mmol). The reaction mixture was then stirred at 80° C. and monitored by LCMS. After complete consumption of starting material, the mixture was diluted with $H_2O$ and extracted with EtOAc. The organic layer was washed with brine, dried over $Na_2SO_4$, filtered and concentrated. The residue was subjected to flash chromatography (EtOAc/Hexane) to afford 43 mg of compound b. Compound b (43 mg, 0.076 mmol) was dissolved in MeOH (1 mL), $H_2O$ (1 mL) and EtOAc (1 mL). To this solution was added $NaIO_4$ (33 mg, 0.15 mmol). The reaction mixture was then stirred at room temperature for 5 hours. The mixture was then diluted with EtOAc, washed with sat. $Na_2S_2O_3$ (2×), brine, dried over $Na_2SO_4$, filtered and concentrated to give compound c. The residue was dissolved in 1 M TBAF in THF (1 mL) and heated at 60° C. for 1 hour. The mixture was diluted with EtOAc and washed with $H_2O$ (3×) followed by brine and then dried over $Na_2SO_4$. The solvent was removed in vacuo and the residue was subjected to purification by HPLC to afford 21 mg of compound 239.

Example 144

Synthesis of Compounds 240

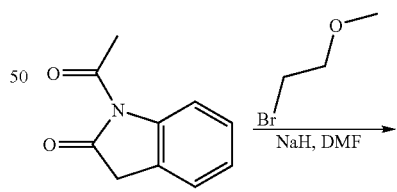

a

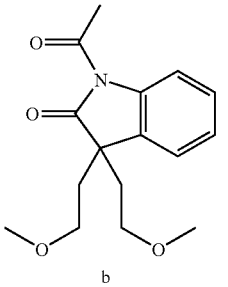

b

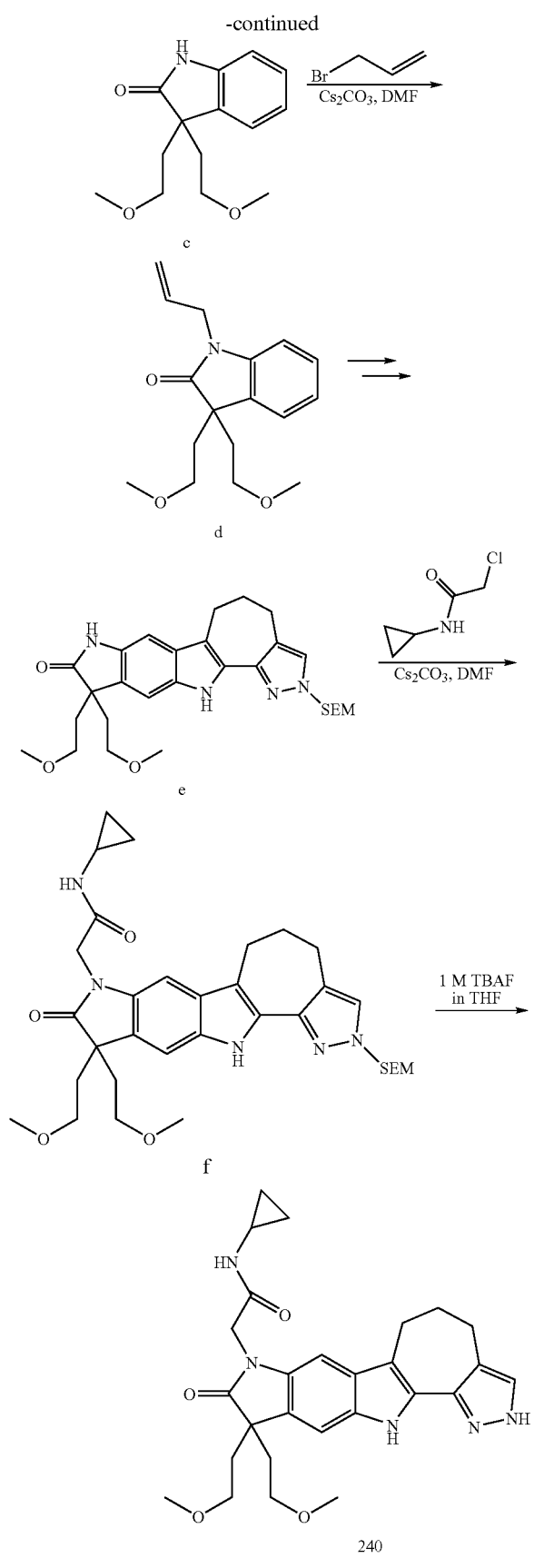

To a suspension of NaH (95%, 3.42 g) in anhydrous DMF (100 mL) at −35° C. was added dropwise a solution of N-acetyl oxindole a (10.0 g, 57.1 mmol) in DMF (100 mL) over 2 hours. The resulting slurry was then stirred at −35° C. for 15 min. A solution of 2-bromoethyl methyl ether (19.84 g, 142.7 mmol) in DMF (40 mL) was then added dropwise over 45 min. The mixture was then warmed up to room temperature and stirred for 4 hours before pouring into ice containing 25 mL of acetic acid. The mixture was extracted with EtOAc (4×). The combined organic phases were dried over $Na_2SO_4$, filtered and concentrated. The residue was subjected to flash chromatography (silica gel, EtOAc/hexane) to afford 7.19 g of compound b in 43% yield.

Compound b (8.34 g, 28.6 mmol) was dissolved in MeOH (55 mL), potassium carbonate (3.95 g, 28.6 mmol) was added. The reaction mixture was stirred at room temperature for 1 hour. The mixture was then diluted with sat. $NH_4Cl$, extracted with DCM (3×). The combined organic phases were dried over $MgSO_4$, filtered and concentrated to afford 7.06 g of compound c.

Compound c (7.33 g, 29.4 mmol) was dissolved in DMF (60 mL). To this solution was added $Cs_2CO_3$ (10.52 g, 32.3 mmol) and cooled to 0° C. Allyl bromide (3.91 g, 32.3 mmol) was then added in one portion. The reaction mixture was stirred at 0° C. for 30 min, warmed to room temperature and stirred for 18 hours. The mixture was diluted with EtOAc and washed with sat. $NH_4Cl$. The aqueous phase was extracted with EtOAc (2×). The combined organic phases were dried over $Na_2SO_4$, filtered and concentrated. The residue was subjected to flash chromatography (silica gel, EtOAc/hexane) to afford 7.36 g of compound d in 87% yield.

Compound d (7.36 g, 25.5 mmol) was treated in a similar manner to the applicable procedures in a example 62 to afford 2.35 g of compound e. Compound e (150 mg, 0.286 mmol) was combined with the appropriate halide 2-chloro-N-cyclopropylacetamide and treated in a manner similar to the applicable procedures in example 140 to give 14 mg of compound 240.

Example 145

Synthesis of Compounds 241

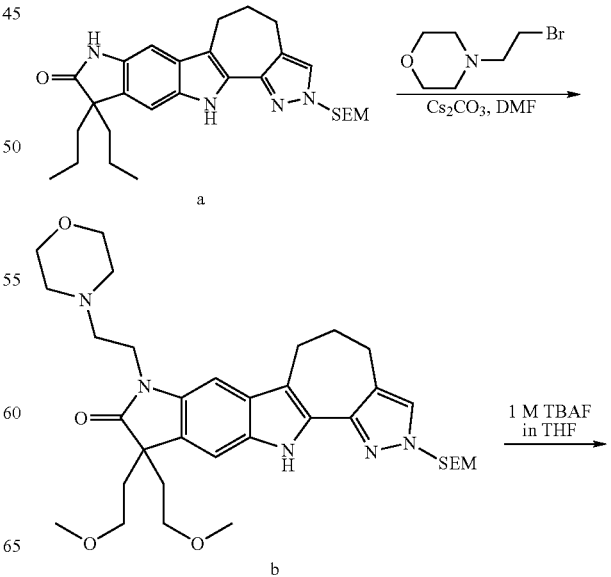

-continued

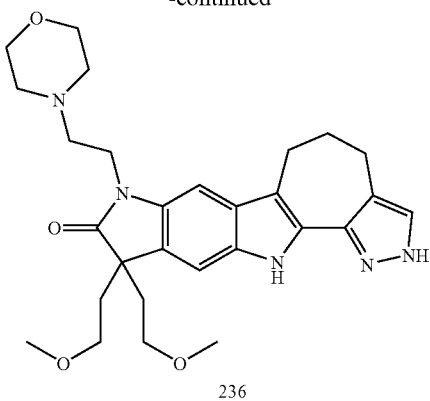

236

Compound a (104 mg, 0.2 mmol) from example 144 was combined with the appropriate halide and treated in a manner similar to the procedures in example 140 to give 38 mg of compound 241.

Example 146

Synthesis of Compounds 242

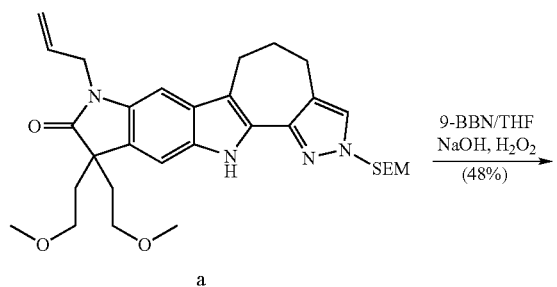

a

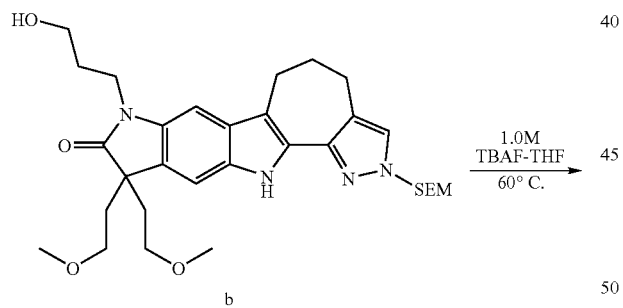

b

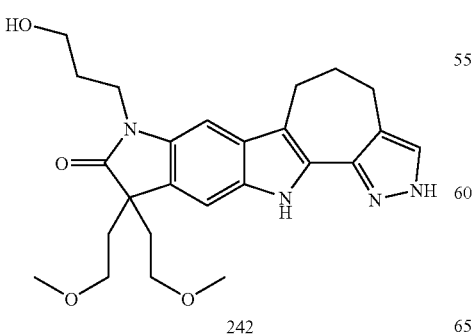

242

Compound a (150 mg, 0.27 mmol) was treated in a manner similar to the procedures of example 65 to give 17 mg of compound 242.

Example 147

Synthesis of Compounds 243

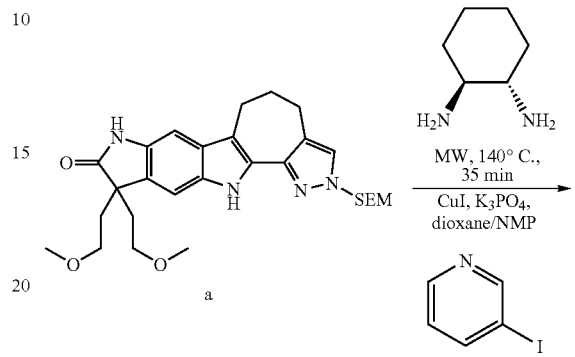

a

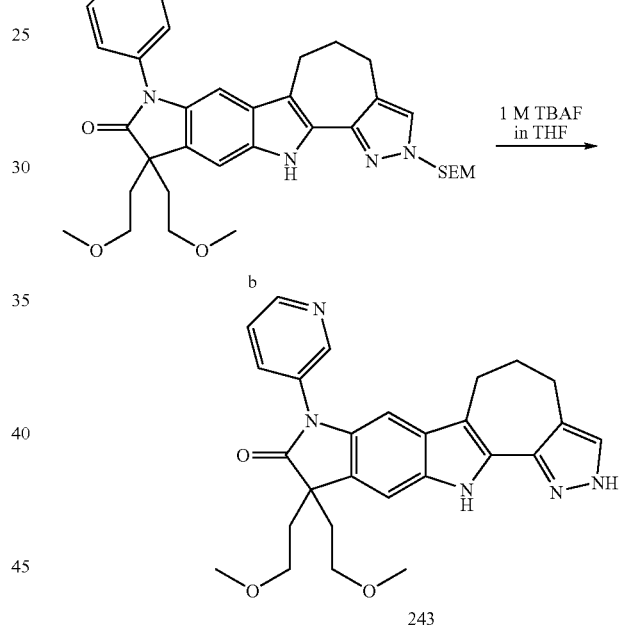

243

A microwave reaction vessel was charged with compound a (105 mg, 0.2 mmol), CuI (19 mg, 0.1 mmol), $K_3PO_4$ (85 mg, 0.4 mmol), 3-iodopyridine (82 mg, 0.4 mmol) and dioxane/NMP (4 mL/0.8 mL). After degassing for 15 min with a stream of $N_2$, trans-1,2-cyclohexanediamine (23 mg, 0.2 mmol) was added and the vessel was sealed. The reaction was then heated at 140° C. for 35 min. under microwave conditions. After cooling to room temperature the mixture was filtered through celite and washed with EtOAc. The organic phase was washed with sat. $NH_4Cl$, dried over $Na_2SO_4$ and concentrated. The residue was subjected to flash chromatography (silica gel, EtOAc/hexane) to afford 140 mg of compound b in 78% yield.

Compound b (140 mg, 0.233 mmol) was dissolved in 1 M TBAF in THF (3 mL) and heated at 60° C. for 3 h. The mixture was diluted with EtOAc and washed with $H_2O$ (3×) followed by brine and then dried over $Na_2SO_4$. The solvent was removed in vacuo and the residue was subjected to purification by HPLC to afford 66 mg of compound 243.

Example 148

Synthesis of Compounds 244

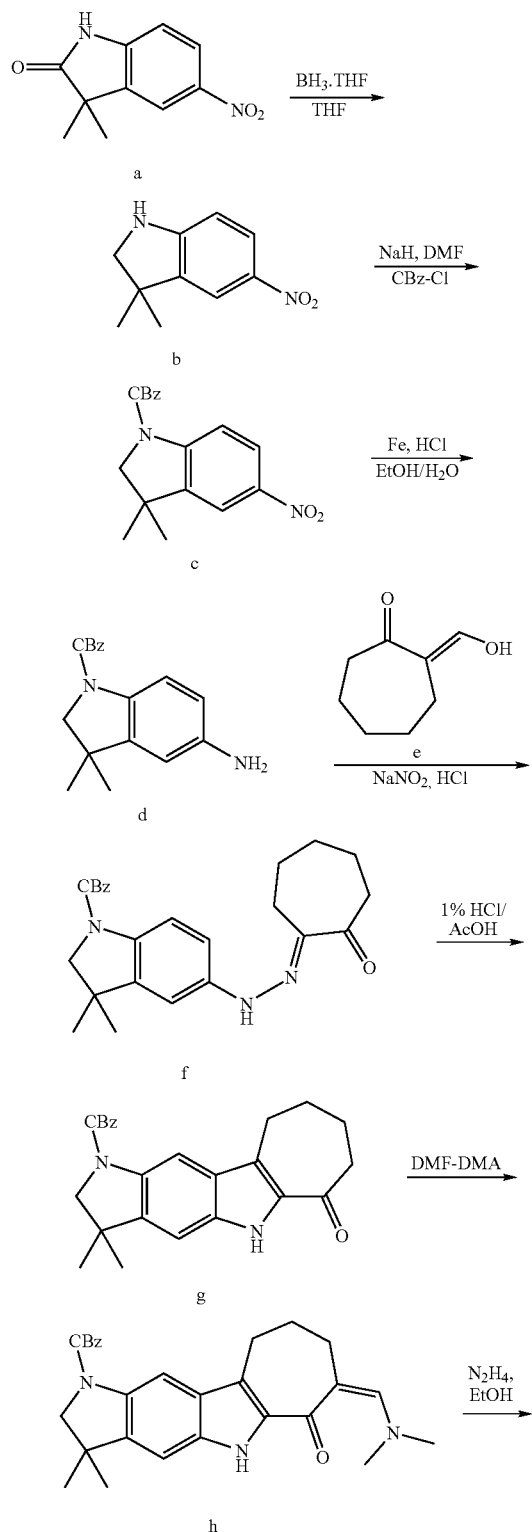

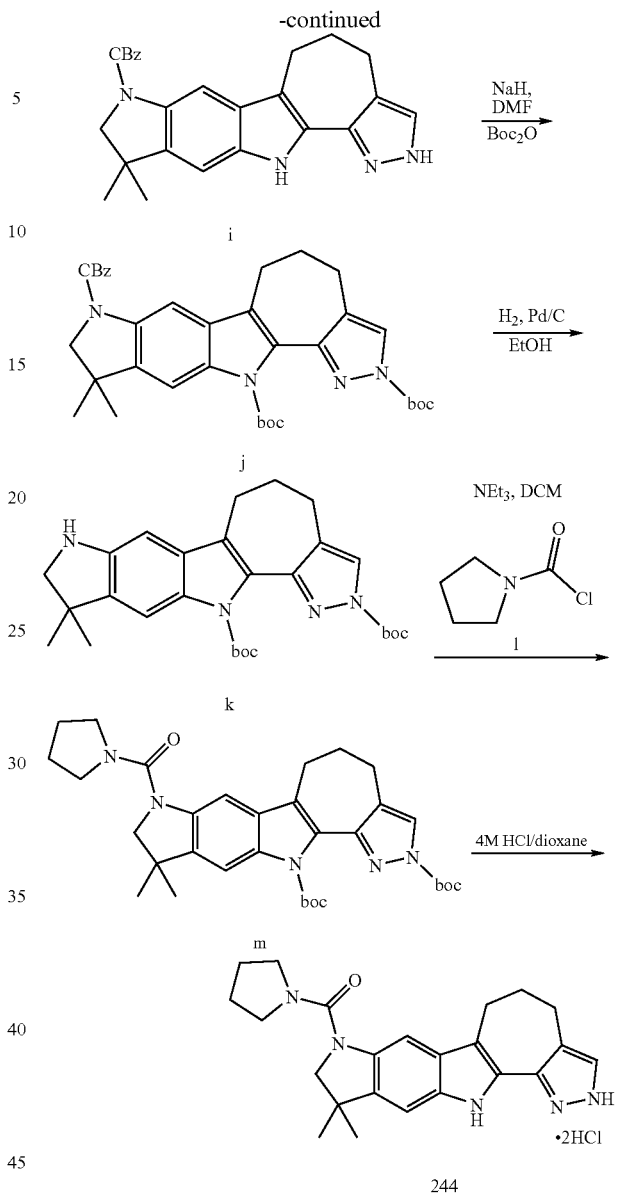

Borane.THF complex (800 ml, 1M solution) was added drop-wise over an hour to a stirred solution of 3,3-dimethyl-5-nitro-1,3-dihydro-indol-2-one a (40 g, 0.2 mol). The resulting solution was stirred at room temperature for 24 hours before being quenched by cautious drop-wise addition of methanol (200 ml), followed by water (200 ml). The resulting solution was extracted with ethyl acetate (2×1l), the organic layers were combined, washed with brine (500 ml) before being dried ($MgSO_4$), filtered and concentrated. The residue was triturated with heptane to afford compound b (35.5 g, 95% yield) as an orange solid.

Compound b (18 g, 0.09 mol) was dissolved in DMF (300 ml) and the mixture cooled to 0° C. To this was added NaH (60%, 4.12 g, 0.1 mol) portion wise. The mixture was stirred at room temperature for 30 minutes then benzyl chloroformate (14.1 ml, 0.1 mol) was added drop-wise over 15 minutes. The reaction mixture was stirred for 2 hours whereupon LCMS showed complete consumption of starting material. The DMF was removed under vacuum and the resulting crude material was partitioned between ethyl acetate (300 ml) and water (300 ml). The organic layer was washed with brine (100 ml), dried (MgSO$_4$), filtered and concentrated. The resulting residue was then triturated with heptane and ether, to afford compound c (18 g, 58% yield) as a yellow solid.

Compound c (9.1 g, 0.028 mol) was dissolved in a 5:1 mixture of ethanol and water (150 ml). To this solution was added iron powder (4.1 g, 0.073 mol) and concentrated hydrochloric acid (1 ml), the mixture was heated to 80° C. for three hours. After this time, the reaction mixture was cooled to room temperature and filtered through a pad of celite®, the celite® was washed with ethanol (100 ml), and the solution was concentrated under vacuum to give compound d (8.1 g, 97% yield) as a brown oil.

Compound d (13.5 g, 0.049 mol) was dissolved in a 1:1 solution of acetonitrile/water (250 ml) and the mixture was cooled to 0° C. Concentrated HCl (5.4 ml) was added dropwise, followed by the drop-wise addition of a solution of sodium nitrite (2.96 g, 0.049 mol) in water (70 ml). After stirring for 15 minutes, this diazonium salt solution was added slowly to a stirred solution of enol e (12.0 g, 0.086 mol) and sodium acetate (17.6 g, 0.214 mol) in a 1:1 solution of ethanol/water (200 ml) at 0° C. After stirring for 16 hours, the suspension was filtered under vacuum to afford compound f (17.8 g, 99% yield) as a red solid.

Compound f (17.8 g, 0.049 mol) was dissolved in acetic acid (100 ml) and concentrated HCl (1 ml) was added. The resulting mixture was heated to 100° C. for 30 minutes before being cooled to room temperature. The solvent was removed under vacuum and the resulting residue was subjected to flash column chromatography (30% ethyl acetate/heptane) to afford compound g (5.2 g, 26% yield) as an orange solid.

Compound g (5.0 g, 0.012 mol) was dissolved in DMF (40 ml). DMF-DMA (40 ml) was added and the solution heated to 100° C. for 16 hours. The mixture was then cooled and the solvent removed under vacuum. The resulting residue (compound h) was then taken on to the next step without further purification.

Compound h was dissolved in ethanol (40 ml), hydrazine hydrate (7 ml) was added and the reaction mixture stirred for 16 hours. After this time the mixture was diluted with water (50 ml) and extracted with ethyl acetate (2×100 ml). The organic layers were combined, dried (MgSO$_4$), filtered and concentrated to afford compound i (5.0 g, 99% yield) as a yellow solid.

Compound i (5.0 g, 0.012 mol) was dissolved in DMF (50 ml) and the mixture cooled to 0° C. To this was added NaH (60%, 1.55 g, 0.04 mol) portion wise. The mixture was stirred at room temperature for 30 minutes then boc anhydride (8.72 g, 0.04 mol) was added portion wise over 15 minutes. The reaction mixture was heated to 70° C. for 16 hours, whereupon LCMS showed complete consumption of starting material. The DMF was removed under vacuum and the resulting crude material was partitioned between ethyl acetate (100 ml) and water (100 ml). The organic layer was washed with brine (100 ml) before being dried (MgSO$_4$), filtered and concentrated. The resulting residue was subjected to flash column chromatography (heptane to 10% ethyl acetate/heptane) and subsequent trituration with heptane to afford compound j (2.85 g, 35% yield) as a white solid.

Compound j (2.85 g, 0.0045 mol) was dissolved in ethanol (30 ml) and 10% Pd/C (0.3 g) was added. The mixture was then stirred vigorously under an atmosphere of hydrogen for 3 hours. After this time, the catalyst was removed by filtration through celite, and concentration of the filtrate afforded compound k (1.74 g, 79% yield) as a white solid.

Compound k (0.1 g, 0.2 mmol) was dissolved in DCM (5 ml), triethylamine (0.03 ml, 0.2 mmol) was added in one portion, followed by pyrrolidine carbonyl chloride l (0.02 ml, 0.2 mmol) in one portion and the mixture was stirred at room temperature for 16 hours. After this time, the mixture was diluted with DCM (5 ml) and washed with water (5 ml). The organic layer was dried (MgSO$_4$), filtered and concentrated to afford compound m as a brown oil. The crude residue was then dissolved in 4M HCl in dioxane (5 ml), and the mixture stirred for 16 hours. The solid precipitate was then collected by filtration and washed with ether (5 ml) before being dried under vacuum to afford compound 244 (25 mg, 32% yield) as a white solid.

Example 149

Synthesis of Compounds 245 to 254

Compounds 245 to 254 were prepared using the procedures in example 148:

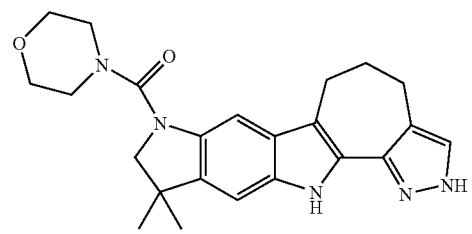

245

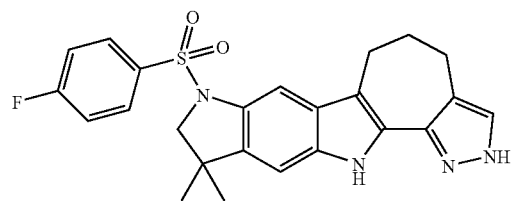

246

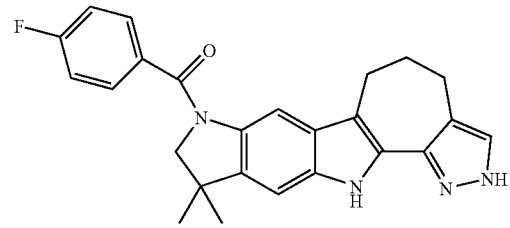

247

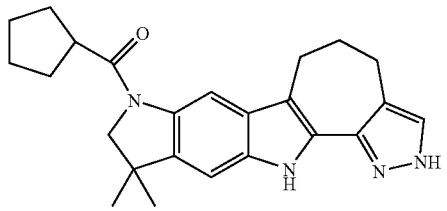

248

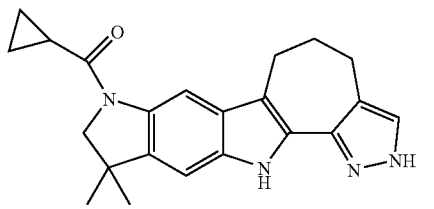

249

Example 150

Synthesis of Compounds 255 and 256

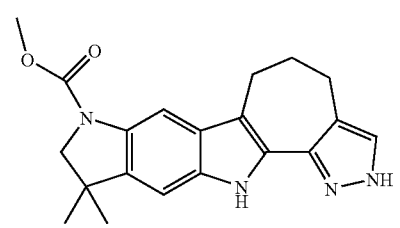

250

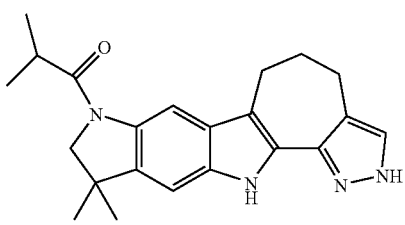

251

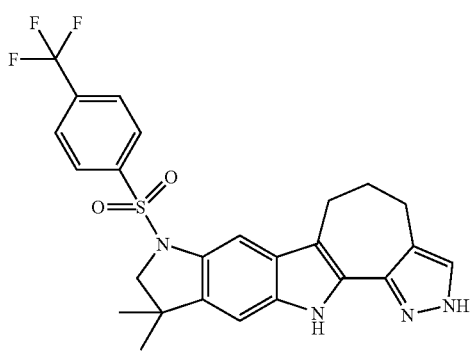

252

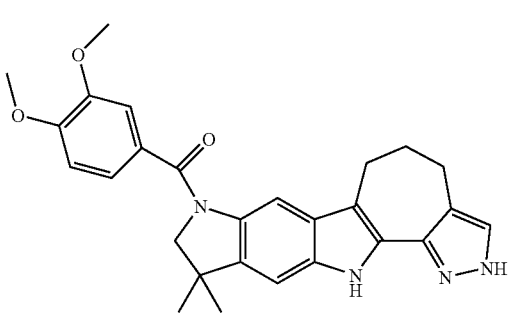

253

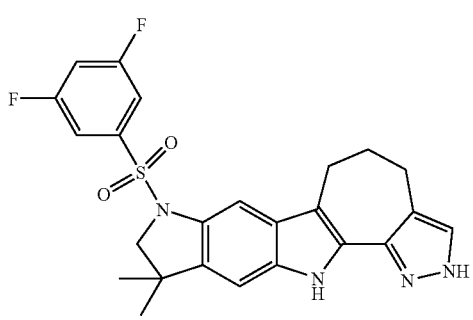

254

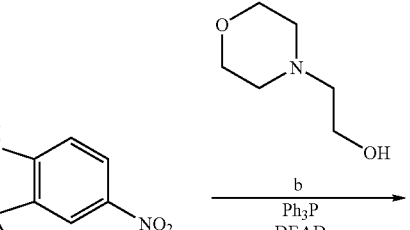

a

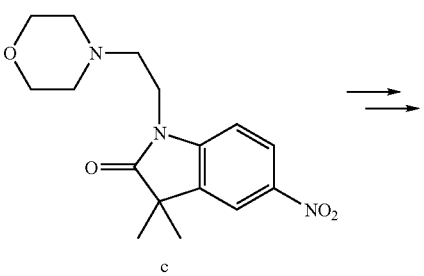

c

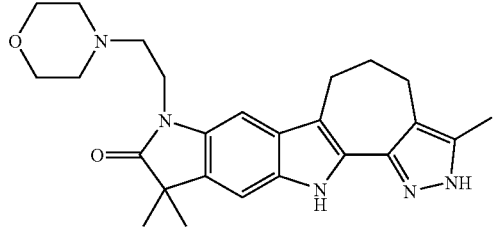

255

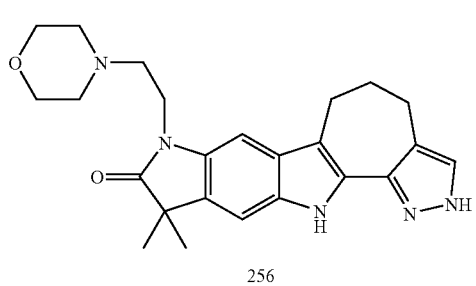

256

A mixture of compound a (2.6 g), 2-morpholinoethanol b (3.31 g), triphenylphosphine (6.62 g) and 180 ml of THF was stirred at ambient temperature while 4.4 g of DEAD was added over 15 minutes. The reaction was stirred an additional 15 minutes then concentrated under vacuum. The residue was partitioned between water and methylene chloride and the organic phase concentrated under vacuum. The product was purified by automated silica gel chromatography using methylene chloride and ethyl acetate to give 5.0 g of compound c. One gram of compound c was reacted similarly to the applicable procedures in example 8 to give 59 mg of compound 253. One gram of compound c was reacted similarly to the applicable procedures in example 23 to give 61 mg of compound 254.

Example 151
Synthesis of Compounds 257 to 258
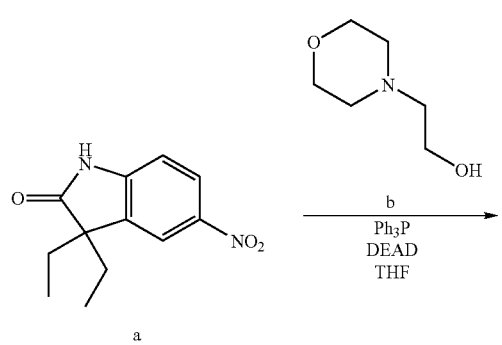
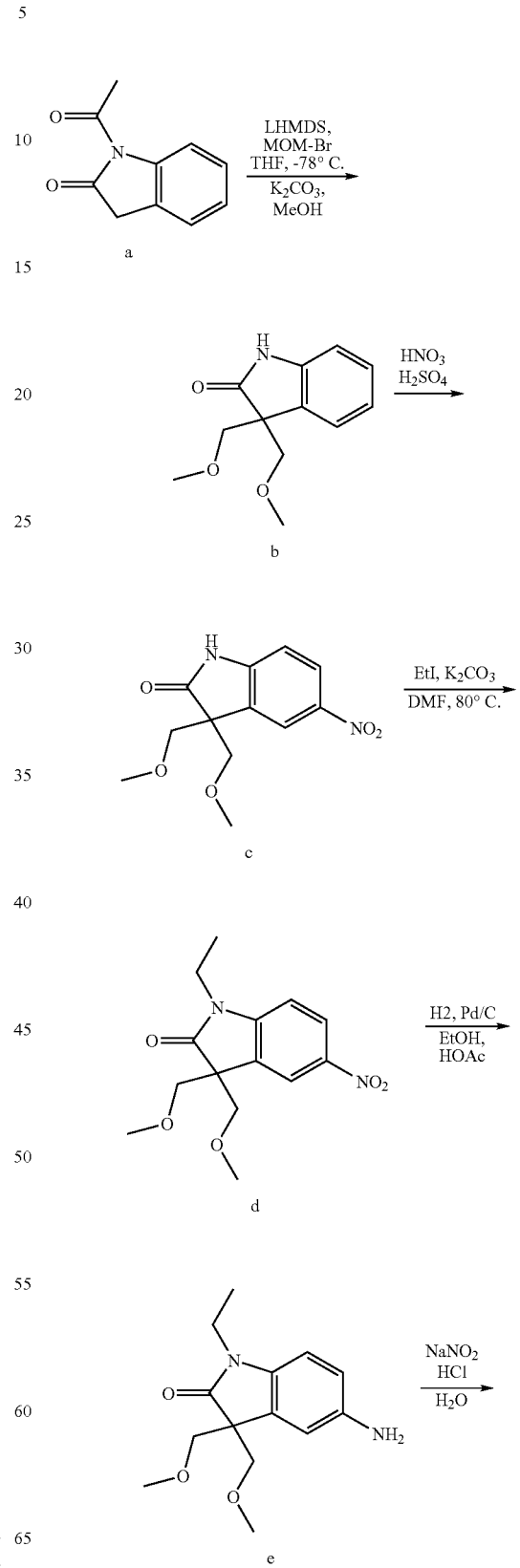
Compound a from example 8 was reacted similarly to the applicable procedures in example 150 and then example 8 to give 71 mg of compound 255. Compound a from example 8 was reacted similarity of the applicable procedures in example 150 and then example 23 to give 65 mg of compound 256.
Example 152
Synthesis of Compounds 259

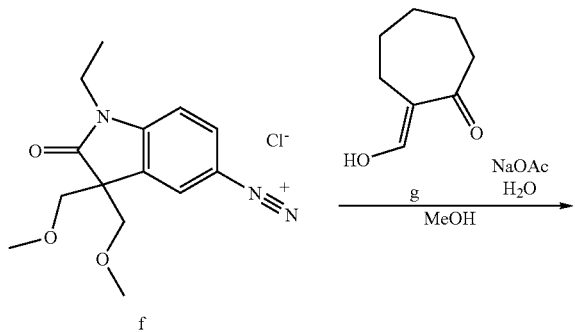

f

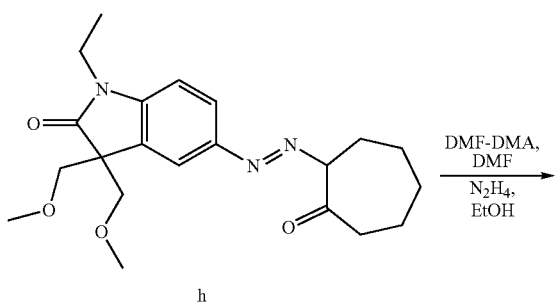

h

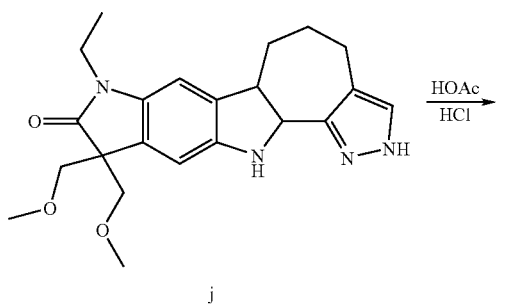

j

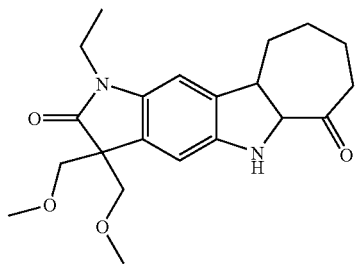

259

Compound a (37.4 g,) was dissolved in 600 mL THF in a 2 L round bottom flask and cooled to −78° C. under a nitrogen atmosphere. Once cool, LHMDS (1M in THF, 450 mL) was slowly added over 1 hour under nitrogen. After addition was complete, the reaction was stirred for an additional 1 hour at −78° C. A solution of MOM-Br (40.65 mL) in 100 mL THF was added slowly over 30 minutes to the cold solution. After addition the reaction was stirred over night warming to room temperature. The reaction was checked by TLC (4:1 Hexanes:EtOAc) showing consumption of starting material and generation of 2 new major spots that corresponded to product with and with out the acetyl group. To the reaction was added 100 mL MeOH and 6 g of $K_2CO_3$. The reaction was stirred at room temperature with occasional checking by TLC. After approximately 4 hours the reaction was complete. The mixture was concentrated and the resulting oil was partitioned between EtOAc and water twice. The aqueous layer was back extracted and the combined organic layers washed with brine, dried with $MgSO_4$ and concentrated to a semi-solid (53.6 g). The crude product was vigorously triturated with 5% EtOAc in hexanes, filtered and dried to yield 31.06 g compound b. The filtrate was concentrated and flashed on silica gel to yield an additional 7.8 g material for a combined total of 38.86 g of compound b. This material was carried on to the next step with out further purification.

Compound b (31.06 g) was suspended in 300 ml of sulfuric acid and cooled to −40° C. with mechanical stirring on a dry ice/acetonitrile bath. A solution of 5.7 ml of fuming nitric acid in 100 ml of sulfuric acid was added over 60 minutes. The reaction was allowed to warm to room temperature. After 6 hrs., the reaction mixture was poured into ice and the precipitated product collected by vacuum filtration. The product was washed with water 2× and vacuum dried to give 30.0 g of compound c.

Compound c (38 g) was combined with 39.4 g of cesium carbonate and 17.12 ml of iodoethane in 500 ml of DMF and stirred at 80° C. overnight. The reaction was cooled and filtered then partitioned between ethyl acetate and water, washed with brine, dried over magnesium sulfate, filtered and concentrated to give a yellow solid which was purified on silica gel to give 20 g of compound d.

Compound d (20 g) was reduced under 50 psi of hydrogen over 10% Pd/C in ethanol (200 ml) and acetic acid (20 ml) for 2 hrs. The catalyst was removed by filtration and the concentrated product recrystallized from hexane and ethyl acetate to give 11.35 g of compound e as a tan solid.

Compound e (11.35 g) was dissolved in 50 ml of water and 5.4 ml of 37% HCl. This solution was cooled to 0° C. and stirred while a solution of sodium nitrite (3.5 g) in 10 ml of water was added over 5 min. This cold diazonium salt solution f was then added to a stirred suspension of enol g (7.21 mg) in 50 ml of water, 50 ml of methanol and 17.6 g of sodium acetate. After one hour, the red oily product i was allowed to settle and the yellow supernatant decanted off. The red oil was triturated twice with water and twice decanted. The red oil was dissolved in 250 ml of acetic acid and 25 ml of 37% HCl and warmed to 70° C. for 20 min. The reaction mixture was cooled and partitioned between ethyl acetate and water. The organic phase was washed with sat. sodium bicarbonate, brine, dried over magnesium sulfate and concentrated. Purification by flash chromatography on silica gave 3.8 g of compound i.

To a solution of compound i (3.3 g) dissolved in 15 ml DMF was added 15 ml of DMF-DMA and the reaction heated to 60° C. overnight. The reaction mixture was concentrated to an oil and added to a solution of hydrazine (8.1 ml) in 50 ml of ethanol and stirred overnight at room temperature. After concentration, the mixture was partitioned between ethyl acetate and water twice. The combined organic layers were washed once with brine, concentrated and purified on silica gel to yield 3.1 g of the compound 259.

Example 153

Synthesis of Compound 260

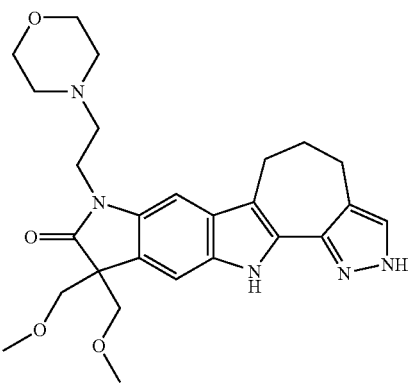

Compound 260 was prepared from 3,3-bis(methoxymethyl)indolin-2-one of example 152 treated in a similar manner to the procedures in example 56.

Example 154

Synthesis of Compounds 261

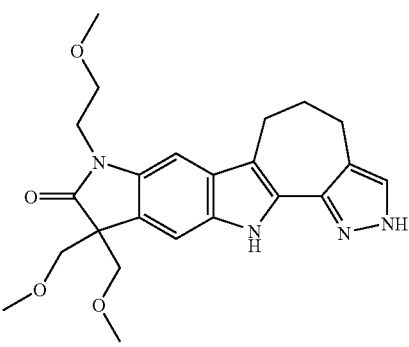

Compound 261 was prepared from 3,3-bis(methoxymethyl)indolin-2-one of example 152 treated in a similar manner to the procedures in example 22.

Example 155

Synthesis of Compounds 262

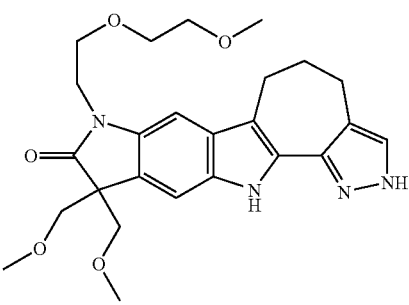

Compound 262 was prepared from 3,3-bis(methoxymethyl)indolin-2-one of example 152 treated in a similar manner to the procedures in example 49.

Example 156

Synthesis of Compounds 263

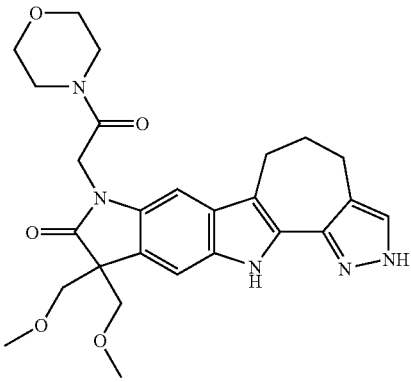

Compound 263 was prepared from 3,3-bis(methoxymethyl)indolin-2-one of example 152 treated in a similar manner to the procedures in example 70.

Example 157

Synthesis of Compounds 264

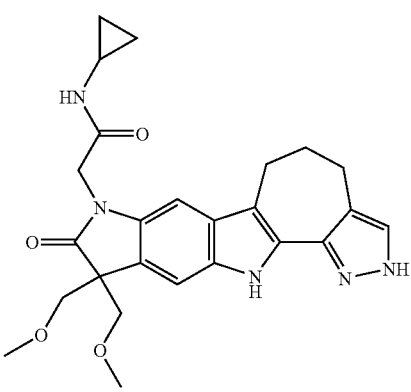

Compound 264 was prepared from 3,3-bis(methoxymethyl)indolin-2-one of example 152 treated in a similar manner to the procedures in example 70.

Example 158

Synthesis of Compounds 265

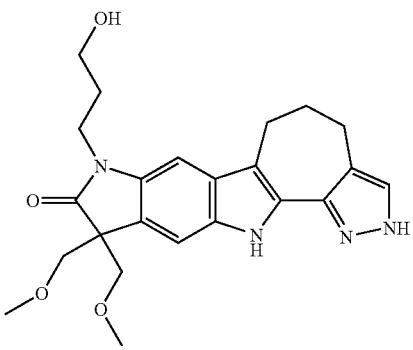

Compound 265 was prepared from 3,3-bis(methoxymethyl)indolin-2-one of example 152 treated in a similar manner to the procedures in example 50.

Example 159

Synthesis of Compounds 266

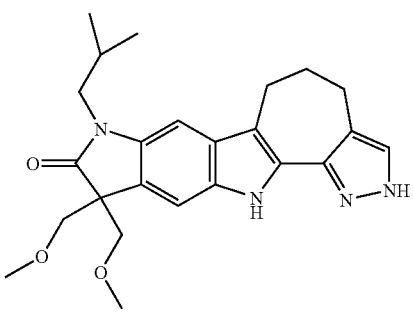

Compound 266 was prepared from 3,3-bis(methoxymethyl)indolin-2-one of example 152 treated in a similar manner to the procedures in example 70.

Example 160

Synthesis of Compounds 267

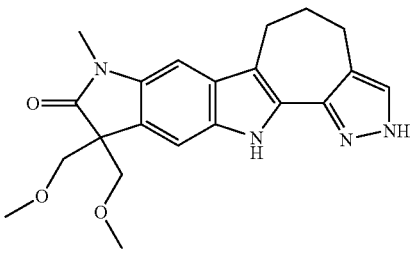

Compound 267 was prepared from 3,3-bis(methoxymethyl)indolin-2-one of example 152 treated in a similar manner to the procedures in example 70.

Example 161

Aurora A & Aurora B In Vitro Kinase Assays

Kinase activities were measured by Enzyme-Linked Immunosorbent Assay (ELISA): Maxisorp 384-well plates (Nunc) were coated with recombinant fusion protein comprising residues 1-15 of Histone H3 fused to the N-terminus of Glutathione-S-Transferase. Plates were then blocked with a solution of 1 mg/mL I-block (Tropix Inc) in phosphate-buffered saline. Kinase reactions were carried out in the wells of the ELISA plate by combining an appropriate amount of mutant Aur A and B kinases with test compound and 30 μM ATP. The reaction buffer was 1× Kinase Buffer (Cell Signaling Technologies) supplemented with 1 μg/mL I-block. Reactions were stopped after 45 minutes by addition of 25 mM EDTA. After washing, substrate phosphorylation was detected by addition of anti-phospho-Histone H3 (Ser 10) 6G3 mAb (Cell Signaling cat #9706) and sheep anti-mouse pAb-HRP (Amersham cat# NA93 IV), followed by colorimetric development with TMB. Compounds prepared according to the examples section herein where found to inhibit Aurora A and/or Aurora B kinase activity with IC50s of less than 1 micromolar.

Example 162

Cellular Proliferation/Viability Assay

Potency of test compounds in inhibiting cellular proliferation and/or cellular viability was estimated using a cellular ATP assay (Cell-Titer-Glo, Promega). Cells (HCT116, HT29 colon cancer cell lines, MCF-7 breast cancer cell line) were seeded in 384-well plates (Greiner μClear) at an appropriate density in 50:50 DMEM/Hams F-12 medium supplemented with 10% fetal calf serum, and allowed to attach overnight. Test compounds were sequentially diluted in DMSO and then culture medium, and added to the cells at appropriate concentrations. Cells were incubated with compound for 5 days. Cell number/viability was estimated using Cell-Titer-Glo reagent (Promega) according to manufacturers instructions.

Example 163

Cellular PhosphoHistone/Mitosis Assay

Efficacy of compounds in inhibiting progression through mitosis and Aurora B-dependent Histone H3 phosphorylation was estimated by automated microscopy and image analysis. HT29 colon cancer cells were seeded at an appropriate density in 384-well plates (Greiner μClear) in 50:50 DMEM/Hams F-12 medium supplemented with 10% fetal calf serum and allowed to attach overnight. Test compounds were sequentially diluted in DMSO and then culture medium, and added to the cells at appropriate concentrations. After 16 hours of incubation with compounds, cells were processed for immunofluorescent microscopy. Cells were fixed with 4% paraformaldehyde, then wells are blocked with 5% fish gelatin (Sigma), then incubated with anti-phospho-Histone H3 (Ser10) rabbit polyclonal antibody (Cell Signaling) and anti-MPM2 monoclonal antibody (Cell Signaling), followed by incubation with goat anti-rabbit-AlexaFluor 555 and sheep anti-mouse AlexaFluor 488 (Invitrogen) and nuclear counterstaining with Hoechst 33342. Images were acquired using a Discovery-1 automated microscopy system (Molecular Devices), and analyzed using MetaMorph software (Molecular Devices) to calculate the percentage of cells scoring positive for MPM2 and for Phospho-Histone H3.

We claim:

1. A compound of formula I:

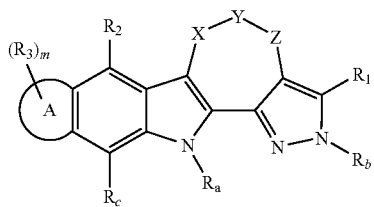

I wherein ring A is a 5, 6 or 7 member ring carbocycle or heterocycle;

X, Y and Z are independently absent, $CR_4R_{4'}$, $NR_5$, S, SO, $SO_2$ or O; wherein at least one of X, Y and Z is not absent; or X and Y together are $CR_4=CR_4$; or Y and Z together are $CR_4=CR_4$;

$R_a$ and $R_b$ are independently H or a protecting group;

$R_c$ is H, hydroxyl, halogen, alkyl, haloalkyl;

$R_1$ is H, hydroxyl, halogen, amino, or is alkyl, acyl, alkoxy or alkylthio optionally substituted with hydroxyl, halogen, carbonyl, thiocarbonyl, amino, carboxyl and alkoxy;

$R_2$ is H, halogen, hydroxyl, mercapto, amino, alkyl, a carbocycle or a heterocycle, wherein said alkyl, carbocycle and heterocycle are optionally substituted with halogen, hydroxyl, mercapto, amino, carboxyl, alkyl, a carbocycle or a heterocycle and wherein one or more $CH_2$ groups of an alkyl group is optionally replaced with —O—, —S—, —S(O)—, —S(O)$_2$—, —N($R_5$)—, —C(O)—, —C(S)—, —C(O)—$NR_5$—, —$NR_5$—C(O)—, —SO$_2$—$NR_5$—, —$NR_5$—SO$_2$—, —$NR_5$—C(O)—$NR_5$—, —C(O)—O— or —O—C(O)—;

$R_3$ is hydroxyl, mercapto, halogen, amino, nitro, cyano, carbonyl, thiocarbonyl, alkyl, a carbocycle or a heterocycle, or two $R_3$ groups together form a carbocycle or a heterocycle; wherein said alkyl, carbocycles and heterocycles are optionally substituted with halogen, hydroxyl, mercapto, carboxyl, carbonyl, thiocarbonyl, amino, nitro, cyano, alkyl, haloalkyl, a carbocycle or a heterocycle and wherein one or more $CH_2$ groups of an alkyl group is optionally replaced with —O—, —S—, —S(O)—, —S(O)$_2$—, —N($R_5$)—, —C(O)—, —C(O)—$NR_5$—, —$NR_5$—C(O)—, —SO$_2$—$NR_5$—, —$NR_5$—SO$_2$—, —$NR_5$C(O)—$NR_5$—, —C(O)—O— or —O—C(O)—;

$R_4$ and $R_4'$ are independently H, hydroxyl, halogen, amino, carbonyl, thiocarbonyl, alkyl, a carbocycle or a heterocycle, or $R_4$ and $R_{4'}$ together form a carbocycle or heterocycle, wherein said alkyl, carbocycles and heterocycles are optionally substituted with halogen, hydroxyl, carboxyl, amino, alkyl, a carbocycle or a heterocycle and wherein one or more $CH_2$ groups of an alkyl group is optionally replaced with —O—, —S—, —S(O)—, —S(O)$_2$—, —N($R_5$)—, —C(O)—, —C(O)—$NR_5$—, —$NR_5$—C(O)—, —SO$_2$—$NR_5$—, —$NR_5$—SO$_2$—, —$NR_5$—C(O)—$NR_5$—, —C(O)—O— or —O—C(O)—;

$R_5$ is H, alkyl, a carbocycle or a heterocycle wherein one or more $CH_2$ or CH groups of said alkyl is optionally replaced with —O—, —S—, —S(O)—, —S(O)$_2$—, —NH—, or —C(O)—; and said alkyl, carbocycle and heterocycle is optionally substituted with hydroxyl, alkoxy, acyl, halogen, mercapto, carbonyl, carboxyl, acyl, halo-substituted alkyl, amino, cyano nitro, amidino, guanidino an optionally substituted carbocycle or an optionally substituted heterocycle;

m is 0 to 10;

or a salt thereof.

2. The compound of claim 1, wherein ring A is selected from the group consisting of:

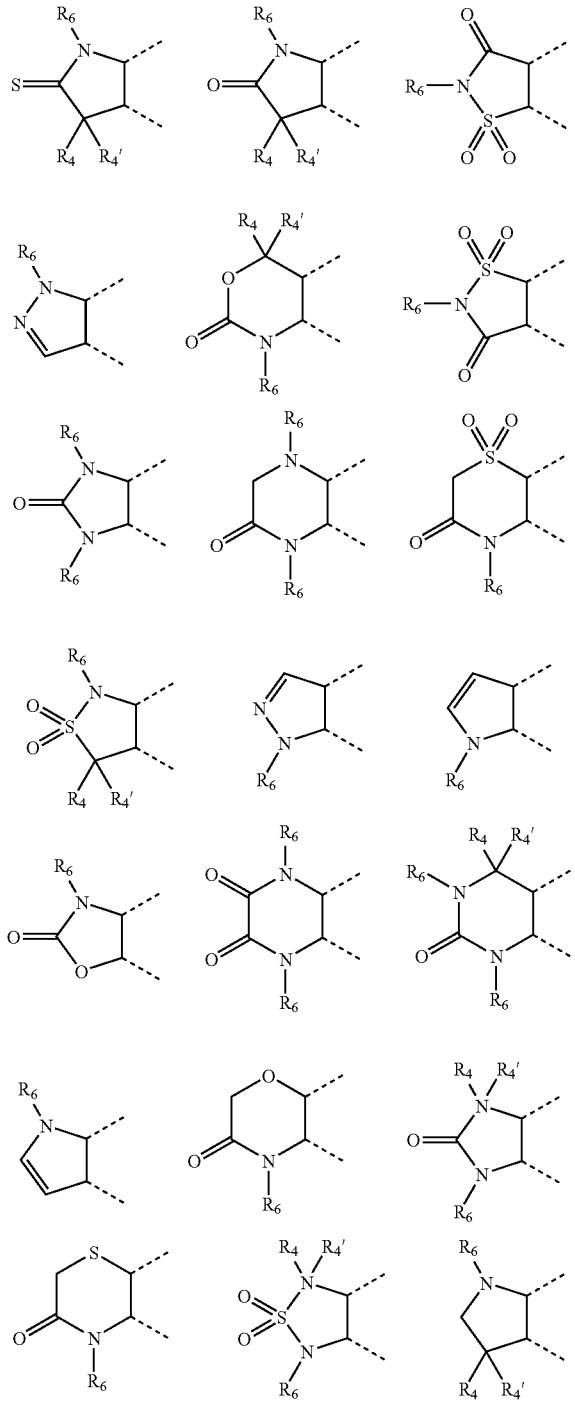

-continued

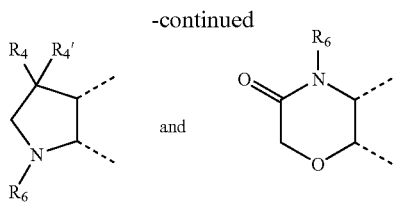

and wherein
$R_4$ and $R_4'$ are independently H, hydroxyl, halogen, amino, carbonyl, thiocarbonyl, alkyl, a carbocycle or a heterocycle, or $R_4$ and $R_4'$ together form a carbocycle or heterocycle, wherein said alkyl, carbocycles and heterocycles are optionally substituted with halogen, hydroxyl, carboxyl, amino, alkyl, a carbocycle or a heterocycle and wherein one or more $CH_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—;

$R_5$ is H, alkyl, a carbocycle or a heterocycle wherein one or more $CH_2$ or CH groups of said alkyl is optionally replaced with —O—, —S—, —S(O)—, —S(O)$_2$—, —NH—, or —C(O)—; and said alkyl, carbocycle and heterocycle is optionally substituted with hydroxyl, alkoxy, acyl, halogen, mercapto, carbonyl, carboxyl, acyl, halo-substituted alkyl, amino, cyano nitro, amidino, guanidino an optionally substituted carbocycle or an optionally substituted heterocycle; and $R_6$ is alkyl, a carbocycle or a heterocycle, wherein said alkyl, carbocycle and heterocycle are optionally substituted with halogen, hydroxyl, mercapto, carboxyl, carbonyl, thiocarbonyl, amino, nitro, cyano, substituted or unsubstituted alkyl, a substituted or unsubstituted carbocycle or heterocycle and wherein one or more $CH_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—.

3. The compound of claim 1, wherein X, Y and Z are independently CR$_4$R$_4'$.

4. The compound of claim 1, wherein Ra, Rb and Rc are each H.

5. The compound of claim 1, wherein $R_1$ is H, alkyl, hydroxyalkyl, alkylthio, alkoxycarbonyl or aminocarbonyl.

6. The compound of claim 1, wherein $R_1$ is methyl.

7. The compound of claim 1, wherein $R_2$ is H, or an optionally substituted alkyl, carbocycle or heterocycle wherein the substituents are halogen, hydroxyl, amino or mercapto and wherein one or more $CH_2$ groups of said alkyl group is optionally replaced with —O—, —S—, —S(O)—, —S(O)$_2$—, —N(R$_5$)—, —C(O)—, —C(S)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—.

8. The compound of claim 1, wherein $R_3$ is alkyl wherein one or more $CH_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—.

9. The compound of claim 1, wherein $R_3$ is alkyl optionally substituted with carbonyl, thiocarbonyl, amino, hydroxyl, carboxyl or aminocarbonyl.

10. The compound of claim 1, wherein two $R_3$ groups together form a spiro carbocycle or heterocycle.

11. The compound of claim 1, wherein said compound has the general formula II

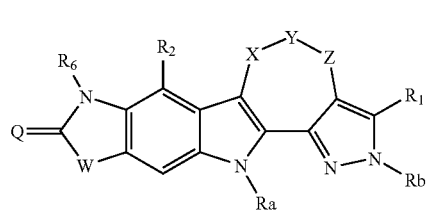

II wherein
Q is H$_2$, O or S;
W is CR$_4$R$_4'$, NR$_5$, O, S, SO or SO$_2$;
$R_6$ is alkyl, a carbocycle or a heterocycle, wherein said alkyl, carbocycle and heterocycle are optionally substituted with halogen, hydroxyl, mercapto, carboxyl, carbonyl, thiocarbonyl, amino, nitro, cyano, substituted or unsubstituted alkyl, a substituted or unsubstituted carbocycle or heterocycle and wherein one or more $CH_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$——NR$_5$—SO$_2$—, —NR$_5$—C(O)—NR$_5$—, —, C(O)—O— or —O—C(O)—.

12. The compound of claim 11, wherein Q is O.

13. The compound of claim 11, wherein W is CR$_4$R$_4'$.

14. The compound of claim 11, wherein $R_6$ is alkyl optionally substituted with halogen, hydroxyl, amino, a carbocycle or a heterocycle and wherein one or more $CH_2$ groups of an alkyl group is optionally replaced with —O—, —S—, —S(O)—, —S(O)$_2$—, —N(R$_5$)—, —C(O)—, —C(O)—NR$_5$—, —NR$_5$—C(O)—, —SO$_2$—NR$_5$—, —NR$_5$—SO$_2$—, —NR$_5$—C(O)—NR$_5$—, —C(O)—O— or —O—C(O)—.

15. A method for treating a disease or condition in a mammal associated with the Aurora kinase signalling, comprising administering to said mammal an effective amount of a compound of claim 1.

16. A method for treating a disease or condition in a mammal associated with the Aurora kinase signalling, comprising administering to said mammal an effective amount of a compound of claim 11.

17. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,749,994 B2 |
| APPLICATION NO. | : 11/503405 |
| DATED | : July 6, 2010 |
| INVENTOR(S) | : Rawson et al. |

It is certified that error appears in the above-identified patent and that said Letters Patent is hereby corrected as shown below:

Column 283, line 26 reads "$R_c$ is H, hydroxyl, halogen, alkyl, haloalkyl;" should read
-- $R_c$ is H, hydroxyl, halogen, alkyl, or haloalkyl; --

Column 283, line 27 reads "$R_1$ is H, hydroxyl, halogen, amino, or is alkyl, acyl, alkoxy" should read
-- $R_1$ is H, hydroxyl, halogen, or amino, or is alkyl, acyl, alkoxy --

Column 285, line 37 reads "unsubstituted alkyl, a substituted or unsubstituted car-" should read
-- unsubstituted alkyl, or a substituted or unsubstituted car- --

Signed and Sealed this

Twenty-sixth Day of October, 2010

David J. Kappos
*Director of the United States Patent and Trademark Office*